US011548893B2

(12) United States Patent
Plewe et al.

(10) Patent No.: US 11,548,893 B2
(45) **Date of Patent: *Jan. 10, 2023**

(54) ENANTIOMERICALLY PURE ADAMANTANE CARBOXAMIDES FOR THE TREATMENT OF FILOVIRUS INFECTION

(71) Applicant: Arisan Therapeutics, Inc., San Diego, CA (US)

(72) Inventors: Michael Bruno Plewe, San Diego, CA (US); Kenneth McCormack, Oceanside, CA (US); Gregory Henkel, Carlsbad, CA (US); Nadezda V. Sokolova, San Diego, CA (US); Eric Brown, Santee, CA (US); Vidyasagar Reddy Gantla, San Diego, CA (US)

(73) Assignee: Arisan Therapeutics Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/629,882

(22) PCT Filed: Jul. 11, 2018

(86) PCT No.: PCT/US2018/041715

§ 371 (c)(1),
(2) Date: Jan. 9, 2020

(87) PCT Pub. No.: WO2019/018185

PCT Pub. Date: Jan. 24, 2019

(65) Prior Publication Data

US 2021/0171521 A1 Jun. 10, 2021

Related U.S. Application Data

(60) Provisional application No. 62/533,029, filed on Jul. 15, 2017.

(51) Int. Cl.

| | |
|---|---|
| *C07D 471/10* | (2006.01) |
| *C07D 471/08* | (2006.01) |
| *C07D 205/12* | (2006.01) |
| *C07D 209/54* | (2006.01) |
| *C07D 211/58* | (2006.01) |

(Continued)

(52) U.S. Cl.

CPC ............ *C07D 471/10* (2013.01); *A61K 45/06* (2013.01); *C07C 235/40* (2013.01); *C07D 205/12* (2013.01); *C07D 209/54* (2013.01); *C07D 211/58* (2013.01); *C07D 295/192* (2013.01); *C07D 471/08* (2013.01); *C07D 487/04* (2013.01)

(58) Field of Classification Search

CPC .. C07D 471/10; C07D 471/08; C07D 205/12; C07D 209/54; C07D 211/58; C07D 295/192; C07D 487/04; A61K 45/06; A61K 31/015; A61K 31/13; A61K 31/165; A61K 31/397; A61K 31/445; A61K 31/4468; A61K 31/496; A61K 31/4965; A61K 31/53; A61K 31/7056; C07C 487/10; C07C 453/02; C07C 295/03; C07C 243/08; C07C 223/12; C07C 211/56; C07C 207/14; C07C 233/62; C07C 209/96; C07C 221/20; C07C 235/40; C07C 2603/74

See application file for complete search history.

(56) References Cited

U.S. PATENT DOCUMENTS

| | | | |
|---|---|---|---|
| 3,300,480 | A | 1/1967 | Narayanan |
| 3,352,912 | A | 11/1967 | Prichard |

(Continued)

FOREIGN PATENT DOCUMENTS

| | | | |
|---|---|---|---|
| CN | 104610112 | A | 5/2015 |
| CN | 104693039 | A | 6/2015 |

(Continued)

OTHER PUBLICATIONS

PCT International Search Report for PCT International Application No. PCT/US2017/013560.

Supplementary Partial European Search Report for Application No. EP 17741793.

De Clercq, Ebola virus (EBOV) infection: Therapeutic strategies, Biochemical Pharmacology, 2015, pp. 1-10, vol. 93, Elsevier, Netherlands.

Côté et al., Small molecule inhibitors reveal Niemann-Pick C1 is essential for Ebola virus infection, Nature, 2011, pp. 344-348, vol. 477, Nature Research, UK.

(Continued)

*Primary Examiner* — Sun Jae Yoo

(74) *Attorney, Agent, or Firm* — Karl Neidert

(57) ABSTRACT

The compounds of the invention as shown by general structure I, as shown below, are effective in treating filovirus infections.

I

X is selected from the group consisting of O and H;

$R^1$ is selected from ($C_6$ to $C_{10}$) aryl and ($C_2$ to $C_9$) heteroaryl, and $R^2$ is selected from ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, and $NR^{3a}R^{3b}$ is defined in the specification.

These compounds are effective in treating filovirii infections including Ebolavirus and Marburg virus.

52 Claims, No Drawings

(51) Int. Cl.
*C07D 295/192* (2006.01)
*C07D 487/04* (2006.01)
*A61K 45/06* (2006.01)
*A61K 31/015* (2006.01)
*A61K 31/13* (2006.01)
*A61K 31/165* (2006.01)
*A61K 31/397* (2006.01)
*A61K 31/445* (2006.01)
*A61K 31/4468* (2006.01)
*A61K 31/496* (2006.01)
*A61K 31/4965* (2006.01)
*A61K 31/53* (2006.01)
*A61K 31/7056* (2006.01)
*C07C 235/40* (2006.01)
*C07C 243/08* (2006.01)
*C07C 211/56* (2006.01)
*C07C 233/62* (2006.01)

(56) References Cited

U.S. PATENT DOCUMENTS

| | | |
|---|---|---|
| 3,383,423 A | 5/1968 | Moore |
| 3,663,565 A | 5/1972 | Krimmel |
| 3,816,509 A | 6/1974 | Krimmel |
| 4,052,439 A | 10/1977 | Herrin |
| 4,087,522 A | 5/1978 | Von Esch |
| 4,100,170 A | 7/1978 | Shetty |
| 4,351,847 A | 9/1982 | Griffith |
| 4,357,351 A | 11/1982 | Fancher |
| 4,386,105 A | 5/1983 | Kinsolving |
| 4,486,601 A | 12/1984 | Kinsolving |
| 4,537,908 A | 8/1985 | Griffith |
| 4,829,086 A | 5/1989 | Bodor |
| 4,910,190 A | 3/1990 | Bergeson |
| 5,124,473 A | 6/1992 | Shroot |
| 5,135,926 A | 8/1992 | Bodor |
| 5,424,414 A | 6/1995 | Mattingly |
| 5,486,597 A | 1/1996 | Kalindjian |
| 5,498,795 A | 3/1996 | Song |
| 5,506,256 A | 4/1996 | Kobayashi |
| 5,658,923 A | 8/1997 | Takahashi |
| 5,670,526 A | 9/1997 | Dodd |
| 5,696,267 A | 12/1997 | Reichard |
| 5,872,138 A | 2/1999 | Naylor-Olsen |
| 5,914,339 A | 6/1999 | Sum |
| 6,057,364 A | 5/2000 | Jasys |
| 6,191,165 B1 | 2/2001 | Ognyanov |
| 6,207,665 B1 | 3/2001 | Bauman |
| 6,235,737 B1 | 5/2001 | Styczynski |
| 6,462,064 B1 | 10/2002 | Pfahl |
| 7,338,961 B2 | 3/2008 | Smith |
| 7,511,175 B2 | 3/2009 | Patel |
| 7,803,559 B1 | 9/2010 | Diamond |
| 8,030,296 B2 | 10/2011 | Potter |
| 8,063,248 B2 | 11/2011 | Smith |
| 8,557,800 B2 | 10/2013 | Smith |
| 9,301,950 B2 | 4/2016 | Degrado |
| 9,452,992 B2 | 9/2016 | Cunningham |
| 9,974,800 B2 | 5/2018 | Fathi |
| 2002/0115883 A1 | 8/2002 | Ogata |
| 2002/0197285 A1 | 12/2002 | Bonda |
| 2003/0186967 A1 | 10/2003 | Kees |
| 2003/0229065 A1 | 12/2003 | Levy |
| 2004/0048847 A1 | 3/2004 | Lino |
| 2004/0087658 A1 | 5/2004 | Moebius |
| 2004/0116423 A1 | 6/2004 | Nivorozhkin |
| 2004/0204379 A1 | 10/2004 | Cheng |
| 2004/0209858 A1 | 10/2004 | Bennani |
| 2005/0113458 A1 | 5/2005 | Gupta |
| 2005/0124678 A1 | 6/2005 | Levy |
| 2005/0192358 A1 | 9/2005 | Georgiev |
| 2006/0149070 A1 | 7/2006 | Rohde |
| 2006/0241187 A1 | 10/2006 | Chern |
| 2006/0270630 A1 | 11/2006 | Smith |
| 2006/0270631 A1 | 11/2006 | Smith |
| 2006/0287317 A1 | 12/2006 | Smith |
| 2007/0135388 A1 | 6/2007 | Makriyannis |
| 2007/0225283 A1 | 9/2007 | Hammock |
| 2007/0249621 A1 | 10/2007 | Wolf |
| 2008/0021088 A1 | 1/2008 | Dalavalle |
| 2008/0206548 A1 | 8/2008 | Enoki |
| 2008/0234249 A1 | 9/2008 | Ye |
| 2009/0143390 A1 | 6/2009 | Cincotta |
| 2009/0163545 A1 | 6/2009 | Goldfarb |
| 2009/0192198 A1 | 7/2009 | Bitner |
| 2009/0218935 A1 | 9/2009 | Sotoyama |
| 2009/0264401 A1 | 10/2009 | Gill |
| 2010/0160250 A1 | 6/2010 | Douglass |
| 2010/0216785 A1 | 8/2010 | Lazzari |
| 2010/0226943 A1 | 9/2010 | Brennan |
| 2010/0298352 A1 | 11/2010 | Prochownik |
| 2011/0014699 A1 | 1/2011 | Wender |
| 2011/0028510 A1 | 2/2011 | Altmeyer |
| 2011/0065762 A1 | 3/2011 | Wang |
| 2011/0065766 A1 | 3/2011 | Wang |
| 2011/0136861 A1 | 6/2011 | Rao |
| 2011/0244472 A1 | 10/2011 | Prochownik |
| 2011/0306552 A1 | 12/2011 | Rao |
| 2011/0319459 A1 | 12/2011 | Gupta |
| 2012/0020922 A1 | 1/2012 | Jordan |
| 2012/0022080 A1 | 1/2012 | Miyata |
| 2012/0059162 A1 | 3/2012 | Kusakabe |
| 2012/0095004 A1 | 4/2012 | Smith |
| 2012/0135954 A1 | 5/2012 | Schang |
| 2012/0157494 A1 | 6/2012 | Harris |
| 2012/0202756 A1 | 8/2012 | Franklin |
| 2012/0252799 A1 | 10/2012 | Yu |
| 2012/0264708 A1 | 10/2012 | Mitchell |
| 2012/0289500 A1 | 11/2012 | Brown |
| 2013/0040953 A1 | 2/2013 | Paller |
| 2013/0072553 A1 | 3/2013 | Xu |
| 2013/0108964 A1 | 5/2013 | Ohsawa |
| 2013/0203775 A1 | 8/2013 | Yeung |
| 2013/0231391 A1 | 9/2013 | Shetty |
| 2013/0338145 A1 | 12/2013 | Mitchell |
| 2013/0345127 A1 | 12/2013 | Boehme |
| 2014/0045779 A1 | 2/2014 | Xu |
| 2014/0073631 A1 | 3/2014 | Shetty |
| 2014/0243544 A1 | 8/2014 | Wang |
| 2014/0271996 A1 | 9/2014 | Prakash |
| 2014/0275263 A1 | 9/2014 | Wassel |
| 2014/0357611 A1 | 12/2014 | Palczewski |
| 2015/0018326 A1 | 1/2015 | Jiang |
| 2015/0025041 A1 | 1/2015 | Lindsley |
| 2015/0056165 A1 | 2/2015 | Or |
| 2015/0166532 A1 | 6/2015 | Gray |
| 2015/0175648 A1 | 6/2015 | Kalayanov |
| 2020/0017514 A1* | 1/2020 | Plewe .............. C07D 207/12 |

FOREIGN PATENT DOCUMENTS

| | | |
|---|---|---|
| CN | 104693085 A | 6/2015 |
| EP | 0392059 A1 | 10/1990 |
| WO | 9429329 A1 | 12/1994 |
| WO | 0134610 A1 | 5/2001 |
| WO | 0134619 A1 | 5/2001 |
| WO | 2004056745 A2 | 7/2004 |
| WO | 2006048750 A2 | 5/2006 |
| WO | 2007112914 A2 | 10/2007 |
| WO | 2007113634 A1 | 10/2007 |
| WO | 2009072643 A1 | 6/2009 |
| WO | 2010111713 A2 | 3/2010 |
| WO | 2010097641 A1 | 9/2010 |
| WO | 2010129954 A1 | 11/2010 |
| WO | 2011014009 A2 | 2/2011 |
| WO | 2011058582 A1 | 5/2011 |
| WO | 2011068927 A2 | 6/2011 |
| WO | 2011160024 A2 | 12/2011 |
| WO | 2012136859 A1 | 10/2012 |
| WO | 2013022550 A2 | 2/2013 |

(56) References Cited

FOREIGN PATENT DOCUMENTS

| WO | 2015057068 A1 | 4/2015 |
|---|---|---|
| WO | 2016051396 A1 | 4/2016 |
| WO | 2017127306 A1 | 7/2017 |

OTHER PUBLICATIONS

Office communication for U.S. Appl. No. 16/033,636.
CAS Registry No. 377770-50-8 (2001) (Year: 2001).
CAS Abstract of E. Boreka et al., Mol. Biol. Virusov, Khimioter. Khimioprofil. Virusn. Infekts., Mater. Ob'edin. Sess. Otd. Gig., Microbiol. Epidemiol. Akad. Med. Nauk SSSR Beloruss Inst. Epidemiol. Microbiol. (1974) (Year: 1974).
CAS Registry No. 1317582-53-8 (2011) (Year: 2011).
PCT International Search Report for PCT International Application No. PCT/US18/41715.
Search History for PCT Application No. PCT/US18/41715.
Handa et al., Synthesis of 3-Aryl-1-adamantanemethylamines, Journal of Chemical and Engineering Data, 1984, pp. 223-225, vol. 29, No. 2, American Chemical Society, USA.
Šlhar et al., Evaluation of adamantane hydroxamates as botulinum neurotoxin inhibitors: Synthesis, crystallography, modeling, kinetic and cellular based studies, Bioorganic & Medicinal Chemistry, 2013, pp. 1344-1348, vol. 21, Elsevier, Netherlands.
Shokova et al., p-(3-Carboxy- and 3-carboxymethyl-1-adamantyl)calix[4]arenes: synthesis and arming with amino acid units, Tetrahedron Letters, 2004, pp. 6465-6469, vol. 45, Elsevier, Netherlands.
Safonova et al., Synthesis and Biological Activity of 5-(Adamant-1-Yl)Salicylic Acid, 3-(4-Hydroxyphenyl)Adamantanecarboxylic Acid and Some of Their Derivatives, Pharmaceutical Chemistry Journal, 1989, pp. 760-765, vol. 23, No. 9, Kluwer Academic/Plenum Publishers, USA.
Graf et al., Targeting Ceramide Metabolism with a Potent and Specific Ceramide Kinase Inhibitor, Molecular Pharmacology, 2008, pp. 925-932, vol. 74, No. 4, The American Society for Pharmacology and Experimental Therapeutics, USA.
Min et al., A novel class of highly potent multidrug resistance reversal agents: Disubstituted adamantyl derivatives, Bioorganic & Medicinal Chemistry Letters, 2009, pp. 5376-5379, vol. 19, Elsevier, Netherlands.
Gadhe et al., Various Partial Charge Schemes on 3D-QSAR Models for P-gp Inhibiting Adamantyl Derivatives, Bull. Korean Chem. Soc, 2011, pp. 1604-1612, vol. 32, No. 5, Korean Chemical Society, Korea.
Koperniku et al., Synthesis and trypanocidal action of new adamantane substituted imidazolines, Med. Chem. Commun., 2013, pp. 856-859, vol. 4, The Royal Society of Chemistry, UK.
Webster et al., Discovery and biological evaluation of adamantyl amide 11b-HSD1 inhibitors, Bioorganic & Medicinal Chemistry Letters, 2007, pp. 2838-2843, vol. 17, Elsevier, Netherlands.
Danilenko et al., Synthesis and biological activity of adamantane derivatives. IV. Viral inhibiting activity of some adamantylamines, Pharmaceutical Chemistry Journal, 1976, pp. 737-741, vol. 10, No. 6, Kluwer Academic/Plenum Publishers, USA.
Danilenko et al., Synthesis and biological activity of adamantane derivatives V. virus-inhibiting action of arylamides of adamantane carboxylic acids, Pharmaceutical Chemistry Journal, 1976, pp. 901-904, vol. 10, No. 7, Kluwer Academic/Plenum Publishers, USA.
Ogawa et al., 3'-Functionalized Adamantyl Cannabinoid Receptor Probes, Journal of Medicinal Chemistry 2015, pp. 3104-3116, vol. 58, American Chemical Society, USA.
Lee et al., Inhibition of Ebola Virus Infection: Identification of Niemann-Pick C1 as the Target by Optimization of a Chemical Probe, ACS Med. Chem. Lett., 2013, pp. 239-243, vol. 4, American Chemical Society, USA.
Adamczyc et al., Synthesis of hapten-phosphoramidites from 2'-deoxyuridine, Tetrahedron, 2003, pp. 5749-5761, vol. 59, Elsevier Science, Netherlands.
Aldrich et al., Antiviral Agents. 2.' Structure-Activity Relationships of Compounds Related to 1-Adamantanamine, Journal of Medicinal Chemistry, 1971, pp. 535-543, vol. 14, No. 6, American Chemical Society, USA.
Badarau et al., Development of Potent and Selective Tissue Transglutaminase Inhibitors: Their Effect on TG2 Function and Application in Pathological Conditions, Chemistry & Biology, 2015, pp. 1-15, vol. 22, Elsevier, Netherlands.
Fino et al., A Convenient Method for the Preparation of Hapten Phosphoramidites, Bioconjugate Chem., 1996, pp. 274-280, vol. 7, American Chemical Society, USA.
Kennedy, A mild and general one-pot preparation of cyanoethyl-protected tetrazoles, Tetrahedron Letters, 2010, pp. 2010-2013, vol. 51, Elsevier, Netherlands.
Motornaya et al., Adamantylcalixarenes with CMPO groups at the wide rim: synthesis and extraction of lanthanides and actinides, Tetrahedron, 2007, pp. 4748-4755, vol. 63, Elsevier, Netherlands.
Shmailov et al., Synthesis of functionalized 5-(3-R-1-adamantyl)uracils and related compounds, Tetrahedron, 2010, pp. 3058-3064, vol. 66, Elsevier, Netherlands.
Danilenko et al., Synthesis and Protective Properties of Phenyladamantane With Respect To Rabies Virus, Pharmaceutical Chemistry Journal, 1998, pp. 83-85, vol. 32, No. 2, Kluwer Academic/Plenum Publishers, USA.
Prokopov et al., Models of Retention of Adamantylamidrazones in Reversed-Phase High-Performance Liquid Chromatography, Russian Journal of Physical Chemistry A, 2011, pp. 845-850, vol. 85, No. 5, Pleiades Publishing, Russia.
Popov et al., Synthesis and Properties of Carbocyclic Schiff Bases, Russian Journal of Organic Chemistry, 2002, p. 350-354, vol. 38, No. 3, Kluwer Academic/Plenum Publishers, USA.
Lavrova et al., Synthesis and Radioprotective Activity of Some Derivatives of N-(3-Aryladamant-1-Ylmethyl) Mercaptoacetamidine, Pharmaceutical Chemistry Journal, 1993, pp. 585-588, vol. 27, No. 8, Kluwer Academic/Plenum Publishers, USA.
Tseng et al., N-[(Aryl substituted adamantane)alkyl] 2-mercaptoacetamidines, their corresponding disulfides and S-phosphorothioates, Tetrahedron, 1988, pp. 1893-1904, vol. 44, Elsevier, UK.
Fan et al., Ligand-Promoted Pd(II)-Catalyzed Functionalization of Unactivated C(sp3)-H Bond: Regio- and Stereoselective Synthesis of Arylated Rimantadine Derivatives, ACS Catalysis, 2016, pp. 769-774, vol. 6, American Chemical Society, USA.
Larrosa et al., C-H Bond Arylation of Diamondoids Catalyzed by Palladium(II) Acetate, Adv. Synth. Catal., 2016, pp. 2163-2171, vol. 358, Wiley-VCH, Germany.
Chakrabarti et al., Chemistry of Adamantane. Part 1II.t The Synthesis and Reactions of 1,2-Disubstituted Adamantane Derivatives, J. Chem. SOC. (C), 1970, pp. 1303-1309, Chemical Society, UK.
Lao et al., Palladium-catalyzed methylene C(sp3)-H arylation of the adamantyl scaffold, Org. Chem. Front., 2015, pp. 1374-1378, vol. 2, Royal Society of Chemistry, UK.
Gopalan et al., Discovery of adamantane based highly potent HDAC inhibitors, Bioorganic & Medicinal Chemistry Letters, 2013, pp. 2532-2537, vol. 23, Elsevier, Netherlands.
Sorenser et al., Adamantane sulfone and sulfonamide 11-b-HSD1 Inhibitors, Bioorganic & Medicinal Chemistry Letters, 2007, pp. 527-532, 17, Elsevier, Netherlands.
Yusuff et al., Lipophilic Isosteres of a π-π Stacking Interaction: New Inhibitors of the Bcl-2-Bak Protein-Protein Interaction, ACS Med. Chem. Lett., 2012, pp. 579-583, vol. 3, American Chemical Society, USA.
Luzhkov et al., Virtual screening and bioassay study of novel inhibitors for dengue virus mRNA cap (nucleoside-2'O)-methyltransferase, Bioorganic & Medicinal Chemistry, 2007, pp. 7795-7802, vol. 15, Elsevier, Netherlands.
Shokova et al., Adamantylation and Adamantylalkylation of Amides, Nitriles and Ureas in Trifluoroacetic Acid, Synthesis, 1997, pp. 1034-1040, No. 9, Thieme Publishing Group, Germany.
Kau et al., A chemical genetic screen identifies inhibitors of regulated nudear export of a Forkhead transcription factor in PTEN-deficient tumor cells, Cancer Cell, 2003, pp. 463-476, Celt Press, USA.

(56) References Cited

OTHER PUBLICATIONS

Goode et al., Identification of Promiscuous Small Molecule Activators in High-Throughput Enzyme Activation Screens, J. Med. Chem., 2008, pp. 2346-2349, vol. 51, American Chemical Sodety, USA.

Ohta et al., Novel estrogen receptor (ER) modulators containing various hydrophobic bent-core structures, Bioorganic & Medicinal Chemistry 2014, pp. 3508-3514, vol. 22, Elsevier, Netherlands.

Puchnin et al., Calix[4]tubes: An Approach to Functionalization, Chem. Eur. J., 2012, p. 10954 -10968, vol. 18, Wiley-VCH, Germany.

Wintgens et al., Smart DNA Vectors Based on Cyclodextrin Polymers: Compaction and Endosomal Release, Pharm. Res., 2012, pp. 384-396, vol. 29, Springer, USA.

Korotkii et al., Synthesis and Antimicrobial and Antifungal Activities of Quaternary Salts of Adamantane-Containing Alkoxydialkylaminopropanols, Pharmaceutical Chemistry Journal, 2011, pp. 19-21, vol. 45, No. 1, Kluwer Academic/Plenum Publishers, USA.

Wennekes et al., Synthesis and evaluation of dimeric lipophilic iminosugars as inhibitors of glucosylceramide metabolism, Tetrahedron: Asymmetry 2009, pp. 836-846, vol. 20, Elsevier, Netherlands.

Ilies et al., Carbonic anhydrase inhibitors: aromatic and heterocyclic sulfonamides incorporating adamantyl moieties with strong anticonvulsant activity, Bioorganic & Medidnal Chemistry, 2004, p. 2717-2726, vol. 12, Elsevier, Netherlands.

Smith et al., Novel Carvedilol Analogues That Suppress Store-Overload-Induced Ca2+ Release, J. Med. Chem., 2013, pp. 8626-8655, vol. 56, American Chemical Sodety, USA.

Shiryaev et al., Synthesis and Antiviral Activity of Adamantyloxiranes and Their Derivatives, Pharmaceutical Chemistry Journal, 1990, pp. 339-343, vol. 24, No. 5, Kluwer Academic/Plenum Publishers, USA.

Wang et al., Organocatalytic asymmetric Michael addition of aldehydes and ketones to nitroalkenes catalyzed by adamantoyl L-prolinamide, RSC Adv., 2015, pp. 5863-5874, vol. 5, The Royal Society of Chemistry, UK.

Giannini et al., New retinoid derivatives as back-ups of Adarotene, Bioorganic & Medicinal Chemistry, 2012, pp. 2405-2415, vol. 20, Elsevier, Netherlands.

Šolaja et al., Novel 4-Aminoquinolines Active against Chloroquine-Resistant and Sensitive P. falciparum Strains that also Inhibit Botulinum Serotype A, J. Med. Chem., 2008, pp. 4388-4391, vol. 51, American Chemical Society, USA.

Kolocouris et al., Synthesis and Antiviral Activity Evaluation of Some Aminoadamantane Derivatives, J. Med. Chem., 1994, pp. 2896-2902, vol. 37, American Chemical Society, USA.

* cited by examiner

ENANTIOMERICALLY PURE ADAMANTANE CARBOXAMIDES FOR THE TREATMENT OF FILOVIRUS INFECTION

CROSS REFERENCES TO RELATED APPLICATIONS

This application is a continuation-in-part and claims priority to U.S. provisional patent application 62/533,029 filed on Jul. 15, 2017 and PCT application PCT/US2018/041715 filed on Jul. 11, 2018 both references are herein incorporated by reference in their entirety and for all purposes.

GOVERNMENT SUPPORT

This invention was made with government support under R43 AI118207 awarded by U.S. National Institutes of Health. The government has certain rights in the invention.

REFERENCE TO A "SEQUENCE LISTING, A TABLE, OR A COMPUTER PROGRAM LISTING APPENDIX SUBMITTED ON A COMPACT DISK

NOT APPLICABLE

FIELD OF THE INVENTION

The present invention relates to methods of inhibiting infection by viruses of the Filoviridae family (filoviruses) in humans, other mammals, or in cell culture, to treating infection by filoviruses, to methods of inhibiting the replication of filoviruses, to methods of reducing the amount of filoviruses, and to compositions that can be employed for such methods. These methods, applications, and compositions apply not only to Filoviridae viruses but also to any virus, whether naturally emerging or engineered, whose cell entry properties are determined by filovirus glycoproteins.

BACKGROUND OF THE INVENTION

The invention relates to the use of compounds for the treatment and/or prophylaxis of infection of humans or other mammals by one or more of a number of enveloped viruses of the Filoviridae family (filoviruses) or any other native or engineered enveloped virus utilizing filovirus glycoproteins to mediate cell entry. Enveloped viruses are comprised of an outer host-derived lipid membrane and an inner nucleoprotein core, which contains the viral genetic material (whether RNA or DNA). Virus-cell fusion is the means by which all enveloped viruses enter cells and initiate disease-causing cycles of replication. In all cases virus-cell fusion is executed by one or more viral surface glycoproteins that are anchored within the lipid membrane envelope. One or more glycoproteins from a given virus may form a glycoprotein complex that interacts with a number of different surface and/or intracellular receptors of infected host cells to initiate the association between virus and host cell. However, one glycoprotein is generally denoted as the protein primarily driving the fusion of viral and host cell membranes. At least three distinct classes of viral membrane fusion proteins have been determined (classes I, II, and III) [Weissenhorn, W.; Carfi, A.; Lee, K. H.; Skehel, J. J., and Wiley, D. C. *Crystal structure of the Ebola virus membrane fusion subunit, GP2, from the envelope glycoprotein ectodomain*. Mol. Cell (1998) 2:605-616; White, J. M.; Delos, S. E.; Brecher, M.; Schornberg K. *Structures and mechanisms of viral membrane fusion proteins: multiple variations on a common theme*. Crit. Rev. Biochem. Mol. Biol. (2008) 43:189-219; Igonet, S.; Vaney, M. C.; Vonrhein, C.; Bricogne, G.; Stura, E. A.; Hengartner H.; Eschli, B.; Rey, F. A. *X-ray structure of the arenavirus glycoprotein GP2 in its postfusion hairpin conformation*, Proc. Natl. Acad. Sci. (2011) 108:19967-19972], Class I fusion proteins are found in viruses from the Orthomyxoviridae, Retroviridae, Paramyxoviridae, Coronaviridae, Filoviridae, and Arenaviridae familes, Class II proteins from Togaviridae, Flaviviridae, and Bunyaviridae while Class III or other types are from $R^{6a}$ dboviridae, Herpesviridae, Poxviridae, and Hepadnaviridae.

Given that viral cell entry is an essential step in the viral replication process the identification of compounds that inhibit virus cell entry could provide attractive antivirals for viruses that are pathogenic to humans and/or other mammals. Chemical compounds that act as inhibitors of one enveloped virus may also act as inhibitors of other enveloped viruses. However, while enveloped viruses share some common

TABLE 1

Family and Genera of Envelope Viruses and Glycoprotein Classification

| Envelope Virus Family | Genera | Examples of pathogenic species | Glyco-protein Class |
|---|---|---|---|
| Orthomy-xoviridae | Influenza virus A, B, C | Influenza A virus | I |
| Filoviridae | Ebolavinis | Zaire virus; Bundibugyo; Sudan; Tai Forest | I |
|  | Marburgvirus | Marburg virus |  |
| Arenaviridae | Mammarenavirus | Lassa virus; Junin; Machupo; Guanarito | I |
| Coronaviridae | Betacoronaviruses | SARS virus; MERS; HKU-1; OC43 | I |
| Flaviviridae | Flavivirus | Dengue virus; Yellow Fever; West Nile; Japanese encephalitis | II |
| Bunyaviridae | Hantavirus | Andes virus | II |
|  | Orthobunyavirus | Bunyamwera virus |  |
|  | Phlebovirus | Rift Valley fever virus |  |
|  | Nairovirus | Crimean-Congo hemorrhagic fever virus |  |
| Togaviridae | Alphavirus | Chikungunya virus; Sindbis virus | II |
| Paramyxoviridae | Rubulavirus | Mumps virus | I |
|  | Morbillivirus | Measles virus |  |
|  | Pneumovirus | Respiratory syncitial virus |  |
|  | Henipavirus | Hendra virus; Nipah |  |
| Herpesviridae | Cytomegalovirus | Human CMV | III |
|  | Simplexvirus | HSV-1; HSV-2 |  |
|  | Varicellovirus | HHV-3 (Varicella zoster virus) |  |
|  | Roseolovirus | HHV-6; HHV-7 |  |
|  | Lymphoctyptovirus | Epstein-Barr virus |  |
|  | Rhadino virus | Kaposi's sarcoma-associated herpesvirus |  | functional and structural features with regard to glycoprotein-dependent cell entry and fusion the specific host targets and mechanisms of cell entry differ among enveloped viruses: between and even within different virus families as a function of their unique glycoprotein (GP) sequences and structures, and the cellular host proteins that they interact with [White, J. M.; Delos, S. E.; Brecher, M., Schornberg K. *Structures and mechanisms of viral membrane fusion proteins: multiple variations on a common theme*. Crit. Rev. Biochem. Mol. Biol. (2008) 43:189-219]. The invention described herein relates to the use of compounds for the treatment and/or prophylaxis of infection as mediated by the cell entry and fusion process of filovirus glycoproteins whether native or engineered.

One viral expression system that may be utilized to identify inhibitors of enveloped viruses based on their glycoprotein sequences and functional properties is the vesicular stomatitis virus (VSV) system. This approach uses VSV, a virus in the $R^{6a}$ dboviridae family (expressing Class III fusion proteins), lacking a native VSV glycoprotein. "Pseudotyped" viruses that are infective and functionally replicative in cell culture can be generated by substituting the VSV glycoprotein with a glycoprotein originating from other enveloped viruses. The cell entry properties and functions of these pseudotyped viruses are determined by the viral glycoprotein that has been introduced. The cell entry and infectivity properites of pseudotyped VSV viruses have been shown to be determined by the introduced glycoprotein from a host of envelope viruses including Ebola, Lassa, Hanta, Hepatitis B, and other viruses [Ogino, M., et al. *Use of vesicular stomatitis virus pseudotypes bearing hantaan or seoul virus envelope proteins in a rapid and safe neutralization test*. Clin. Diagn. Lab. Immunol. (2003) 10(1):154-60; Saha, M. N., et al., *Formation of vesicular stomatitis virus pseudotypes bearing surface proteins of hepatitis B virus*. J. Virol. (2005) 79(19): 12566-74; Takada, A., et al., *A system for functional analysis of Ebola virus glycoprotein*, Proc. Natl. Acad. Sci. (1997) 94:14764-69; Garbutt, M., et al., *Properties of replication-competent vesicular stomatitis virus vectors expressing glycoproteins of filoviruses and arenaviruses*. J. Virol. (2004) 78(10):5458-65]. When the pseudotype virion also expresses a reporter gene such as green fluorescent protein (GFP) or *Renilla* luciferase, virion infectivity and replication may be monitored using high-throughput optical methods in cultured mammalian cell lines, including Vero and HEK-293 cells [Cote, M.; Misasi, J.; Ren, T.; Bruchez, A., Lee, K., Filone, C. M.; Hensley, L.; Li, Q.; Ory, D.; Chandran, K.; Cunningham, J., *Small molecule inhibitors reveal Niemann-Pick C1 is essential for Ebola virus infection*, Nature (2011) 477: 344-348). While VSV does not infect humans and may not be a virus of particular interest for the development of therapeutic antivirals, VSV pseudotyped viruses expressing glycoproteins from other enveloped viruses may be used to screen chemical libraries to identify compounds that inhibit the glycoproteins, cell entry, and infectivity of enveloped viruses associated with significant human health concerns. [Cunningham, J. et al. US patent application, publication number US2013/0231332; WO 2012/031090, 8 Mar. 2012; WO2013/022550, 14 Feb. 2013; Warren, T. K., et al. Antiviral activity of a small-molecule inhibitor of Filovirus infection. Antimicrob. Agents Chemother. (2010) 54: 2152-2159; Yermolina, M., et al. *Discovery, synthesis, and biological evaluation of a novel group of selective inhibitors of filovirus entry*. J. Med. Chem. (2011) 54: 765-781; Basu, A., et al. *Identification of a small-molecule entry inhibitor for Filoviruses*. J. Virol. (2011) 85: 3106-3119; Lee, K., et al., *Inhibition of Ebola virus infection: identification of Niemann-Pick as the target by optimization of a chemical probe*. ACS Med. Chem. Lett. (2013) 4: 239-243; Madrid, P. B., et al. *A Systematic screen of FDA-approved drugs for inhibitors of biological threat agents* Plos One (2013) 8: 1-14; Elshabrawy, H. A., et al. *Identification of a broad-spectrum antiviral amall molecule against severe scute respiratory syndrome Coronavirus and Ebola, Hendra, and Nipah Viruses by using a novel high-throughput screening assay*. J. Virol. (2014) 88: 4353-4365).

Filovirus infections are associated with hemorrhagic fevers, the clinical manifestations of which may be severe and/or fatal. As described herein, for the current invention, VSV pseudotyped viruses expressing filovirus glycoproteins can be generated and screened with a collection of chemical compounds to identify those compounds that inhibit infectivity. The identification of inhibitors of filovirus glycoprotein-mediated virus cell entry may be utilized to treat infections of filoviruses to provide effective therapeutic regimens for the prophylaxis and/or treatment of filoviruses or any newly emerging virus, whether native or engineered, whose cell entry properties may be determined by filovirus glycoproteins.

The Filoviridae virus family is comprised of at least three genera: Ebolavirus, which currently includes five species Zaire (EBOV), Sudan (SUDV), Bundibygo (BDBV), Tai Forest (TAFV) and Reston (RESTV), Marburgvirus, which currently includes two species Marburg (MARV) and Ravn (RAW), and Cuervavirus, which currently includes a single species LLovia virus (LLOV). RAW and LLOV are examples of filoviruses that have been identified only recently and a number of additional new species and genera may continue to emerge.

TABLE 2

Family Filoviridae: currently identified filovirus genera, species, and nomenclature

| Genus name | Species name | Virus name (Abbreviation) |
|---|---|---|
| *Cueva virus* | Lloviu cueva virus | Lioviu virus (LLOV) |
| *Ebolavirus* | Bundibugyo ebolavirus | Bundibugyo virus (BDBV) |
| | Reston ebolavirus | Reston virus (RESTV) |
| | Sudan ebolavirus | Sudan virus (SUDV) |
| | Taï Forest ebolavirus | Taï Forst virus (TAFV) |
| | Zaire ebolavirus | Ebola virus (EBOV) |
| *Marburgvirus* | Marburg marburgvirus | Marburg virus (MARV) |
| | | Ravn virus (RAVV) |

Glycoproteins from Filoviridae family members can be expressed in pseudotyped viruses (e.g. VSV pseudotype) to identify compounds that inhibit filovirus infection. Based on the structural similarities and/or differences between the viral glycoprotein target and/or host cell targets, the inhibitor compounds may act on only a single filovirus glycoprotein or on a broad spectrum of filoviruses. Furthermore, given the basic functional and structural similarities of glycoproteins among different families of enveloped viruses it is proable that a given compound class may act across a broad range of enveloped viruses.

Alignments of representative filovirus glycoprotein sequences were generated to illustrate the amino acid homology among different filovirus species.

TABLE 3

Homology of filovirus glycoproteins - created by Clustal2.1

| Species/Genbank ID | Zaire | Bundi | T Forest | Reston | Sudan | Marburg |
|---|---|---|---|---|---|---|
| Zaire/AAB81004 | 100 | 68.0 | 66.5 | 59.9 | 56.8 | 32.7 |
| Bundibugyo/AGL73453 | 68.0 | 100 | 73.6 | 60.4 | 57.7 | 33.0 |
| Tai Forest/YP_003815426 | 66.5 | 73.6 | 100 | 59.5 | 57.7 | 33.9 |
| Reston/BAB69006 | 59.9 | 60.4 | 59.5 | 100 | 61.4 | 32.7 |
| Sudan/AAB37096 | 56.8 | 57.7 | 57.7 | 61.4 | 100 | 33.0 |
| Marburg/AAC40460 | 32.7 | 33.0 | 33.9 | 32.7 | 33.0 | 100 |

A matrix comparison of the amino acid homology (homology is defined as the number of identities between any two sequences, divided by the length of the alignment, and represented as a percentage) as determined from the Clustal2.1 program (http://www.ebi.ac.uk/Tools/msa/clustalo/) among and between distinct filovirus genus and species is illustrated in Table 3. Glycoproteins among virus species within the same filovirus genus (e.g., Ebolavirus) are more homologous to each other than to those in another genus (Marburgvirus). However, currently available filovirus glycoproteins exhibit significant homology (>30% identity from any one member to another). Given this homology for some chemical series it is possible to identify compounds that exhibit activity against a broad-spectrum of filoviruses.

Similar alignments were subsequently carried out with a number of class I glycoproteins from other enveloped virus families. Each of the glycoproteins from the other enveloped viruses exhibit <20% identity with any of the filovirus glycoproteins. Although there are similarities in functional and structural characteristics among the class I glycoproteins, there are clear distinctions including dependence on low pH, receptor binding, location of the fusion peptide [White, J. M.; Delos, S. E.; Brecher, M.; Schornberg, K. *Structures and mechanisms of viral membrane fusion proteins: multiple variations on a common theme*. Crit. Rev. Biochem. Mol., Biol. (2008) 43:189-219] and given the low amino acid sequence homology across class I virus families it becomes unlikely that a given chemical series that inhibits filovirus cell entry/fusion would also exhibit similar inhibitory activities with other envelope class I glycoprotein virus families.

the racemic acid with amines [Hamill, H.; McKervey, M. A. *The resolution of 3-methyl-5-bromoadamantane carboxylic acid*. Chem. Comm. 1969, 864; Applequist, J.; Rivers, P., Applequist, D. E. *Theoretical and experimental studies of optically active bridgehead-substituted adamantanes and related compounds*. J. Am. Chem. Soc. 1969, 91, 5705-5711] and via derivatization of the racemic acid using a chiral auxiliary [Aoyama, M; Hara, S. *Synthesis of optically active fluoroadamantane derivatives having different substituents on the tert-carbons and its use as non-racemizable source for new optically active adamantane derivatives*. Tetrahedron 2013, 69, 10357-10360].

Complexes formed between a protein and two enantiomers are diastereomers, and as a result have different chemical properties. Therefore dissociation constants between the protein and the two enantiomers may differ and even involve different binding sites [Silverman, R. B., Holladay, M. W. *Drug receptor and chirality*. In: The organic chemistry of drug design and drug action, 3rd ed.; Academic Press, Amsterdam, Boston, 2014, p. 140-145, Academic Press. Amsterdam]. According to the nomenclature by Ariens, when there is isomeric stereoselectivity, the more potent isomer is termed the "eutomer", and the less potent isomer is called the "distomer" [Ariens, E. J. *Stereochemistry: a source of problems in medicinal chemistry*. Med. Res. Rev. 1986, 6, 451-466. *Stereochemistry in the analysis of drug action, part II*. Med. Chem Rev. 1987, 7, 367], The ratio of the potency of the more potent enantiomer to the less potent enantiomer is termed "eudistic ratio".

TABLE 4

Homology matrix between filoviruses and other class I glycoprotein viruses-created by Clustal2.1

| | | | | | | | | | | | |
|---|---|---|---|---|---|---|---|---|---|---|---|
| Z AAB81004 | 100 | 66.5 | 68.0 | 56.8 | 59.9 | 32.7 | 17.0 | 12.8 | 13.4 | 14.2 | 13.7 |
| T YP_003815426 | 66.5 | 100 | 73.6 | 57.7 | 59.5 | 33.9 | 17.7 | 12.0 | 12.0 | 13.8 | 14.2 |
| B AGL73453 | 68.0 | 73.6 | 100 | 57.7 | 60.4 | 33.0 | 17.9 | 12.3 | 12.3 | 13.4 | 14.7 |
| S AAB37096 | 56.8 | 57.7 | 57.7 | 100 | 61.4 | 33.0 | 16.4 | 12.9 | 13.0 | 14.8 | 12.8 |
| R BAB69006 | 59.9 | 59.5 | 60.4 | 61.4 | 100 | 32.7 | 19.8 | 12.9 | 11.8 | 14.6 | 13.5 |
| M AAC40460 | 32.7 | 33.9 | 33.0 | 33.0 | 32.7 | 100 | 15.7 | 10.7 | 8.7 | 12.2 | 14.1 |
| INF ACP41105 | 17.0 | 17.7 | 17.9 | 16.4 | 19.8 | 15.7 | 100 | 14.5 | 12.6 | 11.8 | 11.2 |
| LASV NP_694870 | 12.8 | 12.0 | 12.3 | 12.9 | 12.9 | 10.7 | 14.5 | 100 | 43.2 | 18.8 | 18.3 |
| JUNV AY619641 | 13.4 | 12.0 | 12.3 | 13.0 | 11.8 | 8.7 | 12.6 | 43.2 | 100 | 15.2 | 14.3 |
| Nipah AP238467 | 14.2 | 13.8 | 13.4 | 14.8 | 14.6 | 12.2 | 11.8 | 18.8 | 15.2 | 100 | 20.8 |
| Measles AF21882 | 13.7 | 14.2 | 14.7 | 12.8 | 11.2 | 14.1 | 13.5 | 18.3 | 14.3 | 20.8 | 100 |

Abbreviations:
M: Marburg,
Z: Zaire,
T: Tai Forest,
B: Bundibugyo,
S: Sudan,
R: Reston,
INF: Influenza,
LASV: Lassa virus,
JUNV: Junin virus;
Genbank ID in bold Optical Activity of Adamantane Derivatives The four bridgehead positions of adamantane are formally analogous to the four tetrahedral valances of carbon. Adamantanes with four different bridgehead substituents are therefore chiral. [[Bingham, R. C.; Schleyer, P. R. (1971) *Recent developments in the chemistry of adamantane and related polycyclic hydrocarbons*. In: Chemistry of Adamantanes. Fortschritte der Chemischen Forschung, vol. 18/1. Springer, Berlin, Heidelberg], Optically active adamantanecarboxylic acids have been prepared through resolution of We previously discovered that racemates of certain carboxamides of adamantane carboxylic acids are potent inhibitors of Ebolavirus and Marburgvirus infections (PCT/US2017/013560). We now have prepared single enantiomers of certain racematic mixtures and surprisingly discovered that one enantiomer was more potent compared to the opposite enantiomer and to the racemate for Ebolavirus. Unexpectedly, the eudistic ratio was reversed for Marburgvirus where the less potent enantiomer against Ebolavirus was more potent against Marburgvirus infection.

DESCRIPTION OF THE DRAWINGS

None

BRIEF DESCRIPTION OF THE INVENTION

The present invention relates to methods of inhibiting filoviruses (or any virus whose cell entry is mediated by filovirus glycoproteins) infection in humans, other mammals, or in cell culture, to treating filovirus infection, to methods of inhibiting the replication of filoviruses, to methods of reducing the amount of filoviruses, and to compositions that can be employed for such methods. These methods, applications, and compositions apply not only to Filoviridae viruses but also to any virus, whether naturally emerging or engineered, whose cell entry properties are determined by filovirus glycoproteins.

In one embodiment, the method comprises administering to humans, other mammals, cell culture, or biological sample a therapeutically effective amount of a compound represented by Structural Formulae I, Ia, and Ib for treatment of filovirus infection or a pharmaceutically acceptable salt, and a pharmaceutically acceptable carrier, diluent, or vehicle thereof, wherein:

X is selected from the group consisting of O and H;

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

$R^2$ is selected from ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_{5s}$ to $C_{10}$) cycloalkenyl is optionally substituted with at least one $R^8$ group;

$NR^{3a}R^{3b}$ is selected from the group consisting of

-continued

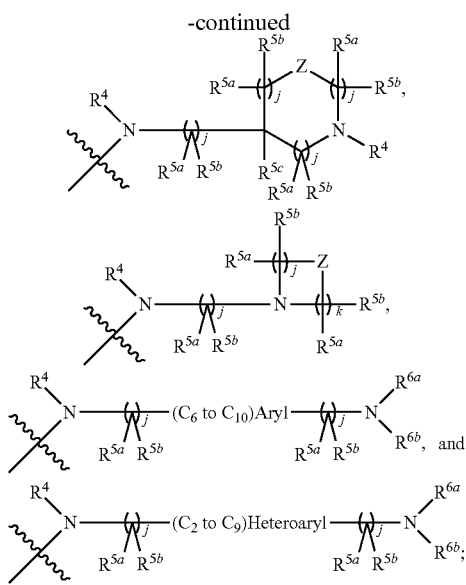

Z is selected from the group consisting of —O—, —S—, —S(O)—, and —S(O)$_2$—;

each $R^4$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^8$ group;

each of the $R^{5a}$, $R^{5b}$, and $R^{5c}$ is independently selected from hydrogen, halogen, OH, nitro, $CF_3$, —$NR^{6a}R^{6b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^7$, —C(O)$NR^{6a}R^{6b}$, —S(O)$_m R^7$, —S(O)$_m NR^{6a}R^{6b}$, —$NR^{6a}$S(O)$_m R^7$, —(CH$_2$)$_n$C(O)$R^7$, —(CH$_2$)$_n$C(O)N($R^{6a}R^{6b}$), —(CH$_2$)$_n$N($R^{6a}R^{6b}$), —OC(O)$R^7$, —$NR^{6a}$C(O)$R^7$, and —$NR^{6a}$C(O)N($R^{6a}R^{6b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^8$ group;

each of the $R^{6a}$ and $R^{6b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^8$ group, or $R^{6a}$ and $R^{6b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^8$ group;

each of the $R^7$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^8$ group;

each $R^8$ is independently selected from hydrogen, halogen, OH, nitro, $CF_3$, —$NR^{9a}R^{9b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{10}$, —C(O)$NR^{9a}R^{9b}$, —S(O)$_m R^{10}$, —S(O)$_m NR^{9a}R^{9b}$, —$NR^{9a}$S(O)$_m R^{10}$, —(CH$_2$)$_n$C(O)$OR^{10}$, —(CH$_2$)$_n$C(O)N($R^{9a}R^{9b}$), —(CH$_2$)$_n$N($R^{9a}R^{9b}$), —OC(O)$R^{15}$, —O(CH$_2$)$_n$O—, —$NR^{9a}$C(O)$R^{10}$, and —$NR^{9a}$C(O)N($R^{9a}R^{9b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{11}$ group;

each of the $R^{9a}$ and $R^{9b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{11}$ group, or $R^{9a}$ and $R^{9b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{11}$ group;

each $R^{10}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{11}$ group;

each $R^{11}$ is independently selected from hydrogen, halogen, OH, nitro, $CF_3$, —$NR^{12a}R^{12b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{18}$, —C(O)N$R^{12a}R^{12b}$, —S(O)$_m R^{13}$, —S(O)$_m$N$R^{12a}R^{12b}$, —N$R^{12a}$S(O)$_m R^{13}$, —(CH$_2$)$_n$C(O)O$R^{13}$, —(CH$_2$)$_n$C(O)N($R^{12a}R^{12b}$), —(CH$_2$)$_n$N($R^{12a}R^{12b}$), —OC(O)$R^{13}$, —N$R^{12a}$C(O)$R^{13}$, and —N$R^{12a}$C(O)N($R^{12a}R^{12b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{14}$ group;

each of the $R^{12a}$ and $R^{12b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{14}$ group, or $R^{12a}$ and $R^{12b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{14}$ group;

each $R^{13}$ is independently selected from hydrogen, halogen, OH, nitro, CF$_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{16}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{14}$ group;

each $R^{14}$ is independently selected from hydrogen, halogen, OH, nitro, CF$_3$, —N$R^{15a}R^{15b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{16}$, —C(O)N$R^{15a}R^{15b}$, —S(O)$_m R^{16}$, —S(O)$_m$N$R^{15a}R^{15b}$, —N$R^{15a}$S(O)$_m R^{16}$, —(CH$_2$)$_n$C(O)O$R^{16}$, —(CH$_2$)$_n$C(O)N($R^{15a}R^{15b}$), —(CH$_2$)$_n$N($R^{15a}R^{15b}$), —OC(O)$R^{16}$, —N$R^{15a}$C(O)$R^{16}$, and —N$R^{15a}$C(O)N($R^{15a}R^{15b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{15a}$ and $R^{15b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{15a}$ and $R^{15b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, CF$_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, CF$_3$, —N$R^{18a}R^{18b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{19}$, —C(O)N$R^{18a}R^{18b}$, —S(O)$_m R^{19}$, —S(O)$_m$N$R^{18a}R^{18b}$, —N$R^{18a}$S(O)$_m R^{19}$, —(CH$_2$)$_n$C(O)O$R^{19}$, —(CH$_2$)$_n$C(O)N($R^{18a}R^{18b}$), —(CH$_2$)$_n$N($R^{18a}R^{18b}$), —OC(O)$R^{19}$, —N$R^{18a}$C(O)$R^{19}$, and —N$R^{18a}$C(O)N($R^{18a}R^{18b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{19}$ is independently selected from hydrogen, halogen, OH, nitro, CF$_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, CF$_3$, —N$R^{21a}R^{21b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{22}$, —C(O)N$R^{21a}R^{21b}$, —S(O)$_m R^{22}$, —S(O)$_m$N$R^{21a}R^{21b}$, —N$R^{21a}$S(O)$_m R^{22}$, —(CH$_2$)$_n$C(O)O$R^{22}$, —(CH$_2$)$_n$C(O)N($R^{21a}R^{21b}$), —(CH$_2$)$_n$N($R^{21a}R^{21b}$), —OC(O)$R^{22}$, —N$R^{21a}$C(O)$R^{22}$, and —N$R^{21a}$C(O)N($R^{21a}R^{21b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{21a}$ and $R^{21b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

DETAILED DESCRIPTION OF THE INVENTION

The present invention relates to methods of inhibiting filoviruses (or any virus whose cell entry is mediated by filovirus glycoproteins) infection in humans, other mammals, or in cell culture, to treating filovirus infection, to methods of inhibiting the replication of filoviruses, to methods of reducing the amount of filoviruses, and to compositions that can be employed for such methods. These methods, applications, and compositions apply not only to Filoviridae viruses but also to any virus, whether naturally emerging or engineered, whose cell entry properties are determined by filovirus glycoproteins.

In one embodiment, the method comprises administering to humans, other mammals, cell culture, or biological sample a therapeutically effective amount of a compound represented by Structural Formulae I, Ia, and Ib for treatment of filovirus infection

I

Ia

Ib or a pharmaceutically acceptable salt, and a pharmaceutically acceptable carrier, diluent, or vehicle thereof, wherein:

X is selected from the group consisting of O and H;

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

$R^2$ is selected from ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl is optionally substituted with at least one $R^8$ group;

$NR^{3a}R^{3b}$ is selected from the group consisting of

-continued

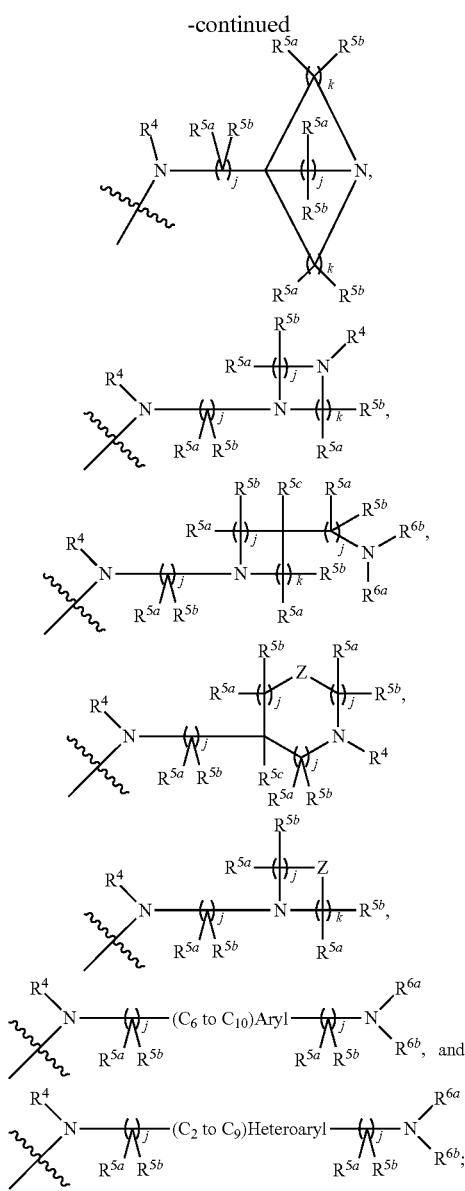

Z is selected from the group consisting of —O—, —S—, —S(O)—, and —S(O)$_2$—;

each R$^4$ is independently selected from hydrogen, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^8$ group;

each of the R$^{5a}$, R$^{5b}$, and R$^{5c}$ is independently selected from hydrogen, halogen, OH, nitro, CF$_3$, —NR$^{6a}$R$^{6b}$, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, —C(O)R$^7$, —C(O)NR$^{6a}$R$^{6b}$, —S(O)$_m$R$^7$, —S(O)$_m$NR$^{6a}$R$^{6b}$, —NR$^{6a}$S(O)$_m$R$^7$, —(CH$_2$)$_n$C(O)OR$^7$, —(CH$_2$)$_n$C(O)N(R$^{6a}$R$^{6b}$), —(CH$_2$)$_n$N(R$^{6a}$R$^{6b}$), —OC(O)R$^7$, —NR$^{6a}$C(O)R$^7$, and —NR$^{6a}$C(O)N(R$^{6a}$R$^{6b}$), wherein each of the said (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl is optionally substituted with at least one R$^8$ group;

each of the R$^{6a}$ and R$^{6b}$ is independently selected from hydrogen, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^8$ group, or R$^{6a}$ and R$^{6b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^8$ group;

each of the R$^7$ is independently selected from hydrogen, (C$_1$ to C$_{10}$) alkyl, (C$_1$ to C$_{10}$) alkenyl, (C$_1$ to C$_{10}$) alkynyl, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl, wherein each of the said (C$_1$ to C$_{10}$) alkyl, (C$_1$ to C$_{10}$) alkenyl, (C$_1$ to C$_{10}$) alkynyl, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl is optionally substituted with at least one R$^8$ group;

each R$^8$ is independently selected from hydrogen, halogen, OH, nitro, CF$_3$, —NR$^{9a}$R$^{9b}$, oxo, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)R$^{10}$, —C(O)NR$^{9a}$R$^{9b}$, —S(O)$_m$R$^{10}$, —S(O)$_m$NR$^{9a}$R$^{9b}$, —NR$^{9a}$S(O)$_m$R$^{10}$, —(CH$_2$)$_n$C(O)OR$^{10}$, —(CH$_2$)$_n$C(O)N(R$^{9a}$R$^{9b}$), —(CH$_2$)$_n$N(R$^{9a}$R$^{9b}$), —OC(O)R$^{15}$, —O(CH$_2$)$_n$O—, —NR$^{9a}$C(O)R$^{10}$, and —NR$^{9a}$C(O)N(R$^{9a}$R$^{9b}$), wherein each of the said (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one R$^{11}$ group;

each of the R$^{9a}$ and R$^{9b}$ is independently selected from hydrogen, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{11}$ group, or $R^{9a}$ and $R^{9b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{11}$ group;

each $R^{10}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{11}$ group;

each $R^{11}$ is independently selected from hydrogen, halogen, OH, nitro, $CF_3$, —$NR^{12a}R^{12b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{18}$, —C(O)$NR^{12a}R^{12b}$, —S(O)$_m R^{13}$, —S(O)$_m NR^{12a}R^{12b}$, —$NR^{12a}$S(O)$_m R^{13}$, —(CH$_2$)$_n$C(O)O$R^{13}$, —(CH$_2$)$_n$C(O)N($R^{12a}R^{12b}$), —(CH$_2$)$_n$N($R^{12a}R^{12b}$), —OC(O)$R^{13}$, —$NR^{12a}$C(O)$R^{13}$, and —$NR^{12a}$C(O)N($R^{12a}R^{12b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{14}$ group;

each of the $R^{12a}$ and $R^{12b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{14}$ group, or $R^{12a}$ and $R^{12b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{14}$ group;

each $R^{13}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{14}$ group;

each $R^{14}$ is independently selected from hydrogen, halogen, OH, nitro, $CF_3$, —$NR^{15a}R^{15b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{16}$, —C(O)$NR^{15a}R^{15b}$, —S(O)$_m R^{16}$, —S(O)$_m NR^{15a}R^{15b}$, —$NR^{15a}$S(O)$_m R^{16}$, —(CH$_2$)$_n$C(O)O$R^{16}$, —(CH$_2$)$_n$C(O)N($R^{15a}R^{15b}$), —(CH$_2$)$_n$N($R^{15a}R^{15b}$), —OC(O)$R^{16}$, —$NR^{15a}$C(O)$R^{16}$, and —$NR^{15a}$C(O)N($R^{15a}R^{15b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{15a}$ and $R^{15b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{15a}$ and $R^{15b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, $CF_3$, —$NR^{18a}R^{18b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{19}$, —C(O)$NR^{18a}R^{18b}$, —S(O)$_m R^{19}$, —S(O)$_m NR^{18a}R^{18b}$, —$NR^{18a}$S(O)$_m R^{19}$, —(CH$_2$)$_n$C(O)O$R^{19}$, —(CH$_2$)$_n$C(O)N($R^{18a}R^{18b}$), —(CH$_2$)$_n$N($R^{18a}R^{18b}$), —OC(O)$R^{19}$, —$NR^{18a}$C(O)$R^{19}$, and —$NR^{18a}$C(O)N($R^{18a}R^{18b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{19}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, $CF_3$, —$NR^{21a}R^{21b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{22}$, —$C(O)NR^{21a}R^{21b}$, —$S(O)_mR^{22}$, —$S(O)_mNR^{21a}R^{21b}$, —$NR^{21a}S(O)_mR^{22}$, —$(CH_2)_nC(O)OR^{22}$, —$(CH_2)_nC(O)N(R^{21a}R^{21b})$, —$(CH_2)_nN(R^{21a}R^{21b})$, —$OC(O)R^{22}$, —$NR^{21a}C(O)R^{22}$, and —$NR^{21a}C(O)N(R^{21a}R^{21b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, (CB to $C_{10}$) aryl, and ($C_2$ to $C_9$) heteroaryl, or $R^{21a}$ and $R^{21b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

In another embodiment, the method comprises administering to humans, other mammals, cell culture, or biological sample a therapeutically effective amount of an enantiomerically pure compound represented by Structural Formula Ia for treatment of filovirus infection Ia or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the method comprises administering to humans, other mammals, cell culture, or biological sample a therapeutically effective amount of an enantiomerically pure compound represented by Structural Formula Ib for treatment of filovirus infection Ib or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the method comprises administering to humans, other mammals, cell culture, or biological sample a therapeutically effective amount of a racemic compound represented by Structural Formula I for treatment of filovirus infection, or a pharmaceutically acceptable salt, and a pharmaceutically acceptable carrier, diluent, or vehicle thereof, wherein $R^1$ is phenyl, and $R^2$, X, and $NR^{3a}R^{3b}$ are defined as above.

In another embodiment, the method comprises administering to humans, other mammals, cell culture, or biological sample a therapeutically effective amount of an enantiomerically pure compound represented by Structural Formula Ia for treatment of filovirus infection, or a pharmaceutically acceptable salt, and a pharmaceutically acceptable carrier, diluent, or vehicle thereof, wherein $R^1$ is phenyl, and $R^2$, X, and $NR^{3a}R^{3b}$ are defined as above.

In another embodiment, the method comprises administering to humans, other mammals, cell culture, or biological sample a therapeutically effective amount of an enantiomerically pure compound represented by Structural Formula Ib for treatment of filovirus infection, or a pharmaceutically acceptable salt, and a pharmaceutically acceptable carrier, diluent, or vehicle thereof, wherein $R^1$ is phenyl, and $R^2$, X, and $NR^{3a}R^{3b}$ are defined as above.

In another embodiment, the method comprises administering to humans, other mammals, cell culture, or biological sample a therapeutically effective amount of a racemic compound represented by Structural Formula I for treatment of filovirus infection, or a pharmaceutically acceptable salt, and a pharmaceutically acceptable carrier, diluent, or vehicle thereof, wherein $R^1$ is phenyl, X and $NR^{3a}R^{3b}$ are defined as above, and $R^2$ is selected from the group consisting of methyl, ethyl, propyl, fluoromethyl, ethoxymethyl, chloroethyl, and fluoroethyl.

In another embodiment, the method comprises administering to humans, other mammals, cell culture, or biological sample a therapeutically effective amount of an enantiomerically pure compound represented by Structural Formula Ia for treatment of filovirus infection, or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the method comprises administering to humans, other mammals, cell culture, or biological sample a therapeutically effective amount of an enantiomerically pure compound represented by Structural Formula Ib for treatment of filovirus infection, or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the method comprises administering to humans, other mammals, cell culture, or biological sample a therapeutically effective amount of racemic compound represented by Structural Formula I for treatment of filovirus infection, or a pharmaceutically acceptable salt, and a pharmaceutically acceptable carrier, diluent, or vehicle thereof, wherein $R^1$ is phenyl and X is H or O, and $NR^{3a}R^{3b}$ is selected from the group consisting of:

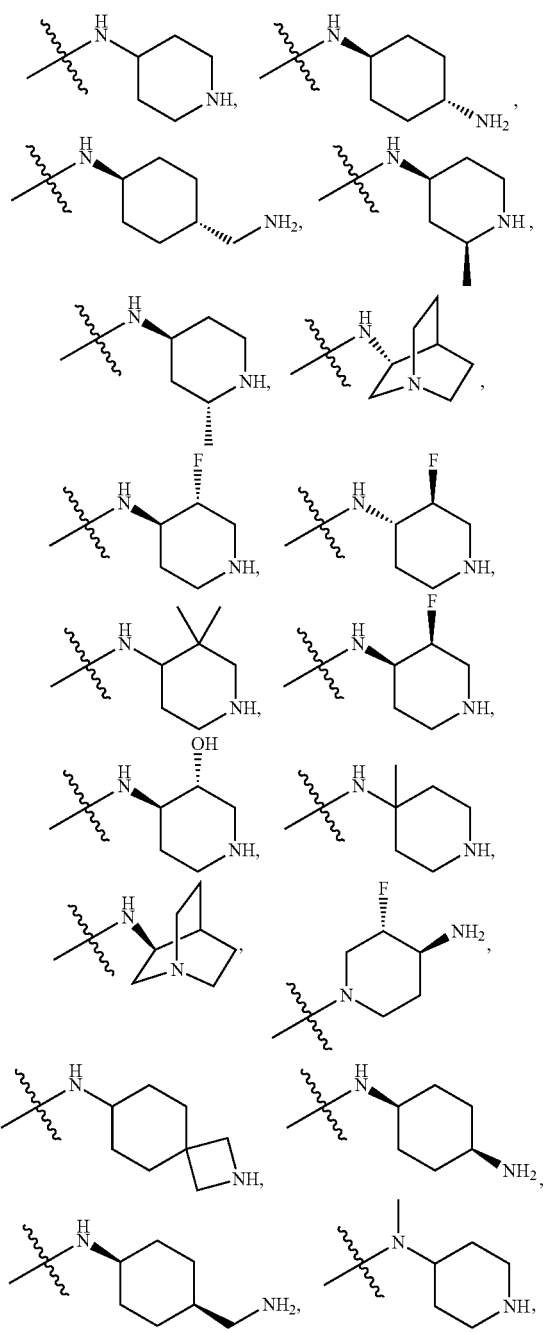

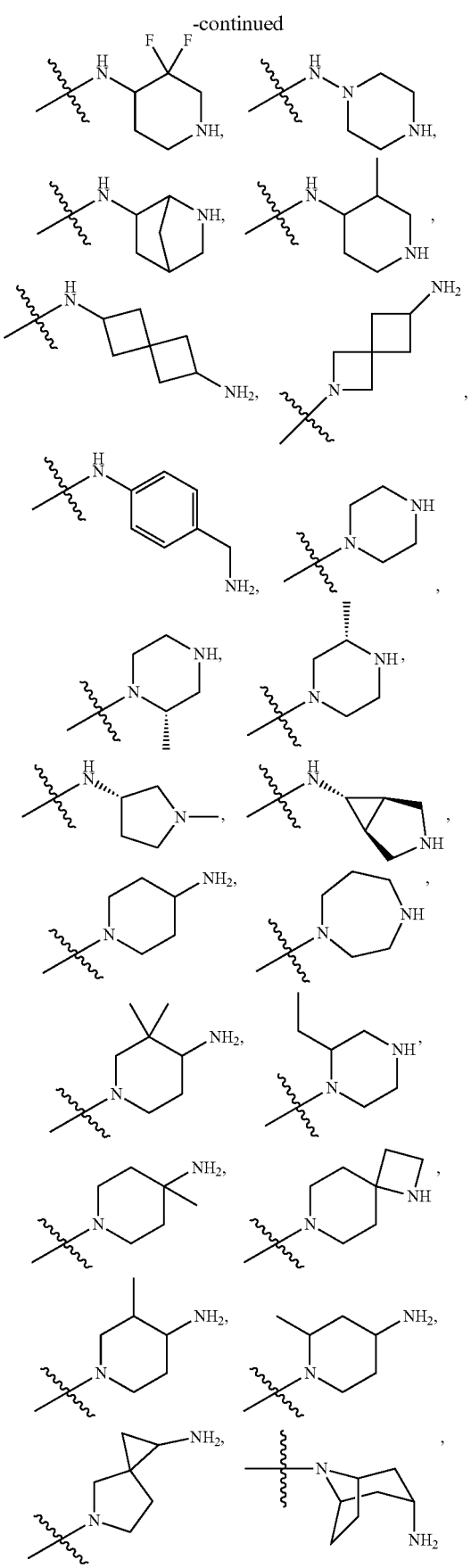

or a pharmaceutically acceptable salt, and a pharmaceutically acceptable carrier, diluent, or vehicle thereof, wherein $R^1$, X, and $NR^{3a}R^{3b}$ are defined as above.

In another embodiment, the method comprises administering to humans, other mammals, cell culture, or biological sample a therapeutically effective amount of an enantiomerically pure compound represented by Structural Formula Ib for treatment of filovirus infection, or a pharmaceutically acceptable salt, and a pharmaceutically acceptable carrier, diluent, or vehicle thereof, wherein $R^1$, X, and $NR^{3a}R^{3b}$ are defined as above.

In another embodiment, the method comprises administering to humans, other mammals, cell culture, or biological sample a therapeutically effective amount of an enantiomerically pure compound represented by Structural Formulae Ia and Ib for treatment of filovirus infection.

In another embodiment, the method comprises administering to humans, other mammals, cell culture, or biological sample a therapeutically effective amount of a compound represented by Structural Formulae I, Ia, and Ib for treatment of Ebolavirus infection.

In another embodiment, the method comprises administering to humans, other mammals, cell culture, or biological sample a therapeutically effective amount of a compound represented by Structural Formulae I, Ia, and Ib for treatment of Marburgvirus infection.

In another embodiment, the method comprises of inhibiting Ebolavirus.

In another embodiment, the method comprises of inhibiting Marburgvirus.

In another embodiment, the method comprises of including administering a therapeutic amount of a therapeutic agent selected from the group consisting of Ribavirin, viral RNA-dependent-RNA polymeras inhibitors including favipiravir, Triazavirin, Remdesivir (GS-5734), monoclonal antibody therapies including, ZMapp, REGN3470-3471-3479, mAb 114, vaccines including, cAd3-EBOZ, rVSV-ZEBOV, small interfering RNAs and microRNAs and immunomodulators.

In another embodiment, the method comprises the inhibiting of Ebolavirus glycoprotein.

In another embodiment, the method comprises the inhibiting of Marburgvirus glycoprotein.

In another embodiment, the method comprises administering to humans, other mammals, cell culture, or biological sample a therapeutically effective amount of compound selected from the group consisting of the compounds described as examples A1 to A69, B1 to B71, and $C_1$ to $C_{71}$ for treatment of filovirus infection, or a pharmaceutically acceptable salt, and a pharmaceutically acceptable carrier, diluent, or vehicle thereof, wherein $R^1$, $R^2$, X, and $NR^{3a}R^{3b}$ are defined as above.

In one embodiment, the invention relates to compounds represented by Structural Formulae I, Ia, and Ib -continued

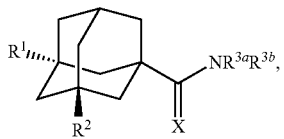

Ib or a pharmaceutically acceptable salt, and a pharmaceutically acceptable carrier, diluent, or vehicle thereof, wherein:

X is selected from the group consisting of O and H;

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

$R^2$ is selected from ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl is optionally substituted with at least one $R^8$ group;

$NR^{3a}R^{3b}$ is selected from the group consisting of

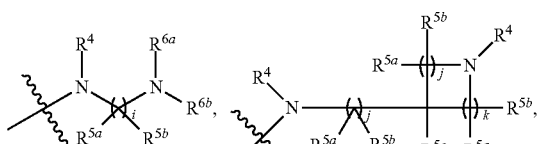

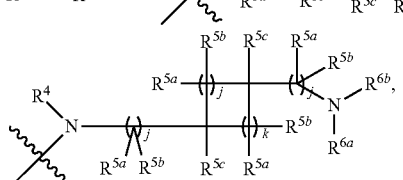

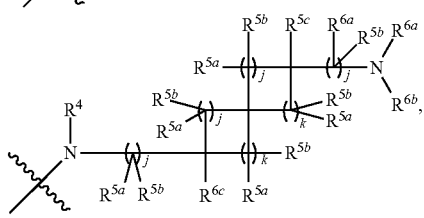

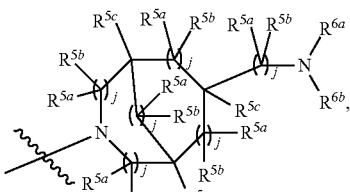

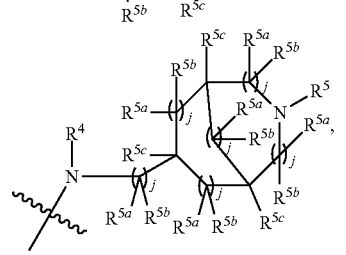

Z is selected from the group consisting of —O—, —S—, —S(O)—, and —S(O)$_2$—;

each $R^4$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$)

arylene, and ($C_2$ to $C_9$) heteroarylene is optionally substituted with at least one $R^8$ group;

each of the $R^{5a}$, $R^{5b}$, and $R^{5c}$ is independently selected from hydrogen, halogen, OH, nitro, $CF_3$, —$NR^{6a}R^{6b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —$C(O)R^7$, —$C(O)NR^{6a}R^{6b}$, —$S(O)_mR^7$, —$S(O)_mNR^{6a}R^{6b}$, —$NR^{6a}S(O)_mR^7$, —$(CH_2)_nC(O)OR^7$, —$(CH_2)_nC(O)N(R^{6a}R^{6b})$, —$(CH_2)_nN(R^{6a}R^{6b})$, —$OC(O)R^7$, —$NR^{6a}C(O)R^7$, and —$NR^{6a}C(O)N(R^{6a}R^{6b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^8$ group;

each of the $R^{6a}$ and $R^{6b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^8$ group, or $R^{6a}$ and $R^{6b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^8$ group;

each of the $R^7$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^8$ group;

each $R^8$ is independently selected from hydrogen, halogen, OH, nitro, $CF_3$, —$NR^{9a}R^{9b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{10}$, —$C(O)NR^{9a}R^{9b}$, —$S(O)_mR^{10}$, —$S(O)_mNR^{9a}R^{9b}$, —$NR^{9a}S(O)_mR^{10}$, —$(CH_2)_nC(O)OR^{10}$, —$(CH_2)_nC(O)N(R^{9a}R^{9b})$, —$(CH_2)_nN(R^{9a}R^{9b})$, —$OC(O)R^{15}$, —$O(CH_2)_nO$—, —$NR^{9a}C(O)R^{10}$, and —$NR^{9a}C(O)N(R^{9a}R^{9b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{11}$ group;

each of the $R^{9a}$ and $R^{9b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{11}$ group, or $R^{9a}$ and $R^{9b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{11}$ group;

each $R^{10}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{11}$ group;

each $R^{11}$ is independently selected from hydrogen, halogen, OH, nitro, $CF_3$, —$NR^{12a}R^{12b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{18}$, —$C(O)NR^{12a}R^{12b}$, —$S(O)_mR^{13}$, —$S(O)_mNR^{12a}R^{12b}$, —$NR^{12a}S(O)_mR^{13}$, —$(CH_2)_nC(O)OR^{13}$, —$(CH_2)_nC(O)N(R^{12a}R^{12b})$, —$(CH_2)_nN(R^{12a}R^{12b})$, —$OC(O)R^{13}$, —$NR^{12a}C(O)R^{13}$, and —$NR^{12a}C(O)N(R^{12a}R^{12b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{14}$ group;

each of the $R^{12a}$ and $R^{12b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{14}$ group, or $R^{12a}$ and $R^{12b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{14}$ group;

each $R^{13}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{14}$ group;

each $R^{14}$ is independently selected from hydrogen, halogen, OH, nitro, $CF_3$, —$NR^{15a}R^{15b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{16}$, —$C(O)NR^{15a}R^{15b}$, —$S(O)_mR^{16}$, —$S(O)_mNR^{15a}R^{15b}$, —$NR^{15a}S(O)_mR^{16}$, —$(CH_2)_kC(O)OR^{16}$, —$(CH_2)_nC(O)N(R^{15a}R^{15b})$, —$(CH_2)_nN(R^{15a}R^{15b})$, —$OC(O)R^{16}$, —$NR^{15a}C(O)R^{16}$, and —$NR^{15a}C(O)N(R^{15a}R^{15b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{15a}$ and $R^{15b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{15a}$ and $R^{15b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, $CF_3$, —$NR^{18a}R^{18b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{19}$, —$C(O)NR^{18a}R^{18b}$, —$S(O)_mR^{19}$, —$S(O)_mNR^{18a}R^{18b}$, —$NR^{18a}S(O)_mR^{19}$, —$(CH_2)_kC(O)OR^{19}$, —$(CH_2)_nC(O)N(R^{18a}R^{18b})$, —$(CH_2)_nN(R^{18a}R^{18b})$, —$OC(O)R^{19}$, —$NR^{18a}C(O)R^{19}$, and —$NR^{18a}C(O)N(R^{18a}R^{18b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{19}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, $CF_3$, —$NR^{21a}R^{21b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{22}$, —$C(O)NR^{21a}R^{21b}$, —$S(O)_mR^{22}$, —$S(O)_mNR^{21a}R^{21b}$, —$NR^{21a}S(O)_mR^{22}$, —$(CH_2)_kC(O)OR^{22}$, —$(CH_2)_nC(O)N(R^{21a}R^{21b})$, —$(CH_2)_nN(R^{21a}R^{21b})$, —$OC(O)R^{22}$, —$NR^{21a}C(O)R^{22}$, and —$NR^{21a}C(O)N(R^{21a}R^{21b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{21a}$ and $R^{21b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

In another embodiment, the invention relates to enantiomerically pure compounds represented by Structural Formula Ia

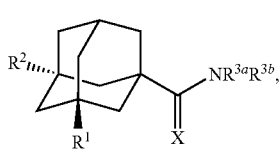

Ia or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the invention relates to enantiomerically pure compounds represented by Structural Formula Ib

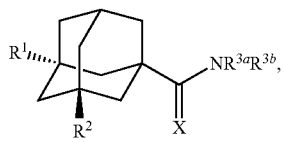

or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the invention relates to compounds represented by Structural Formula I, or a pharmaceutically acceptable salt, and a pharmaceutically acceptable carrier, diluent, or vehicle thereof, wherein $R^1$ is phenyl, and $R^2$, X, and $NR^{3a}R^{3b}$ are defined as above.

In another embodiment, the invention relates to enantiomerically pure compounds represented by Structural Formula Ia, or a pharmaceutically acceptable salt, and a pharmaceutically acceptable carrier, diluent, or vehicle thereof, wherein $R^1$ is phenyl, and $R^2$, X, and $NR^{3a}R^{3b}$ are defined as above.

In another embodiment, the invention relates to enantiomerically pure compounds represented by Structural Formula Ib, or a pharmaceutically acceptable salt, and a pharmaceutically acceptable carrier, diluent, or vehicle thereof, wherein $R^1$ is phenyl, and $R^2$, X, and $NR^{3a}R^{3b}$ are defined as above.

In another embodiment, the invention relates compounds represented by Structural Formula I, or a pharmaceutically acceptable salt, and a pharmaceutically acceptable carrier, diluent, or vehicle thereof, wherein $R^1$ is phenyl, X and $NR^{3a}R^{3b}$ are defined as above, and $R^2$ is selected from the group consisting of methyl, ethyl, propyl, fluoromethyl, ethoxymethyl, chloroethyl, and fluoroethyl.

In another embodiment, the invention relates to enantiomerically pure compound represented by Structural Formula Ia, or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the invention relates enantiomerically pure compounds represented by Structural Formula Ib, or a pharmaceutically acceptable salt, and a pharmaceutically acceptable carrier, diluent, or vehicle thereof, wherein $R^1$, $R^2$, X, and $NR^{3a}R^{3b}$ are defined as above.

In another embodiment, the invention relates to compounds represented by Structural Formula I for treatment of filovirus infection, or a pharmaceutically acceptable salt, and a pharmaceutically acceptable carrier, diluent, or vehicle thereof, wherein $R^1$ is phenyl, X is O or H, and $NR^{3a}R^{3b}$ is selected from the group consisting of

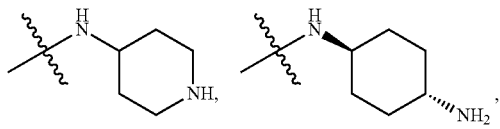

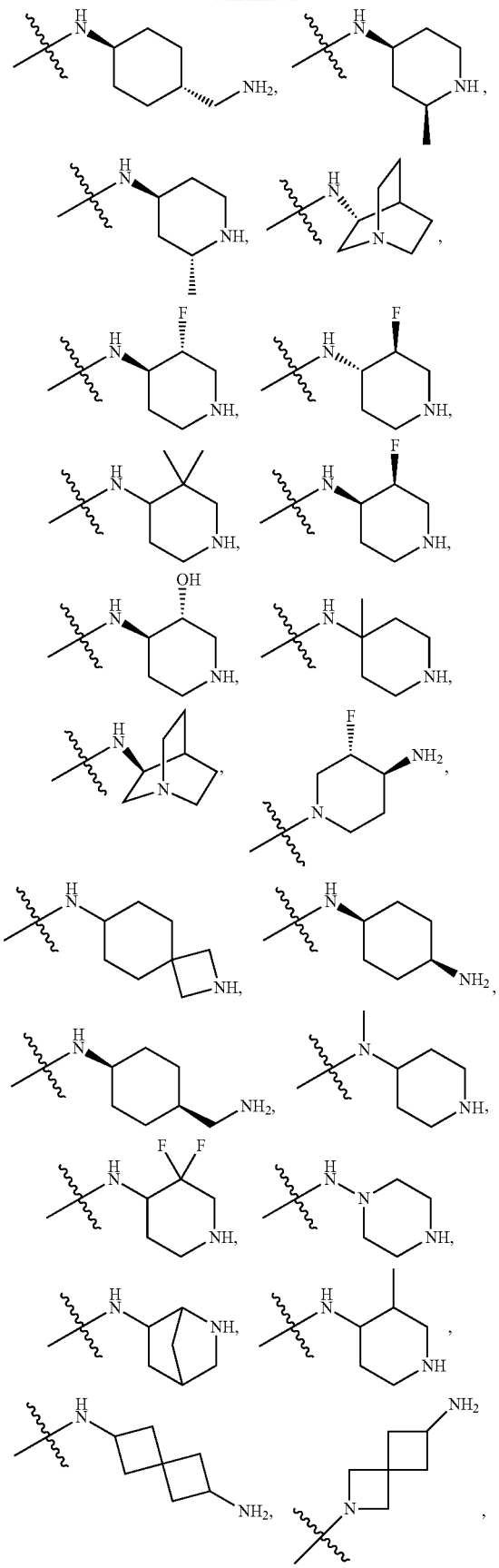

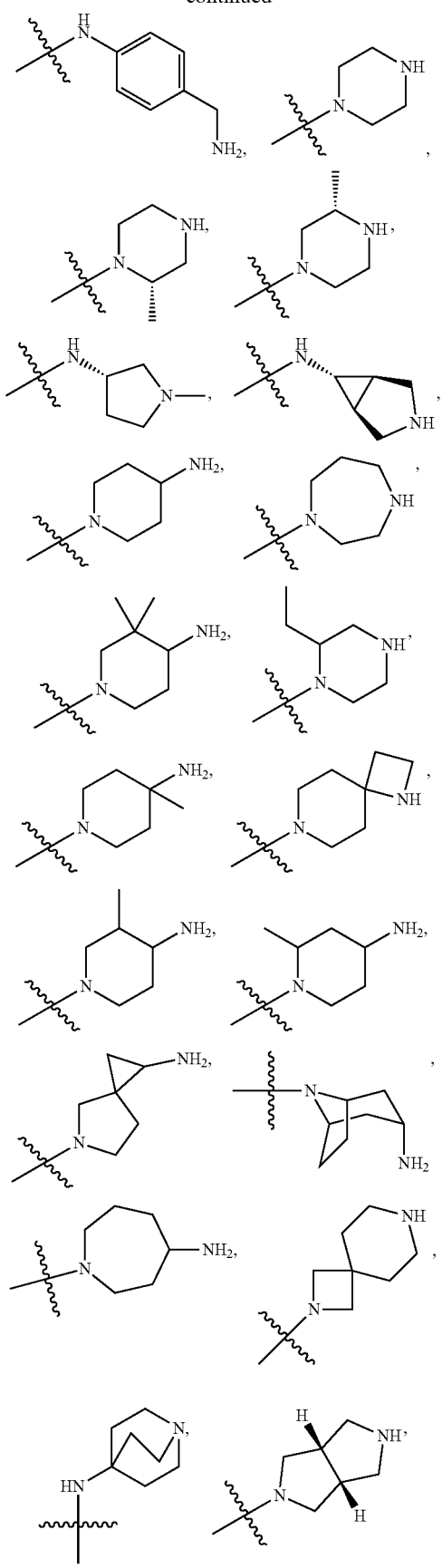
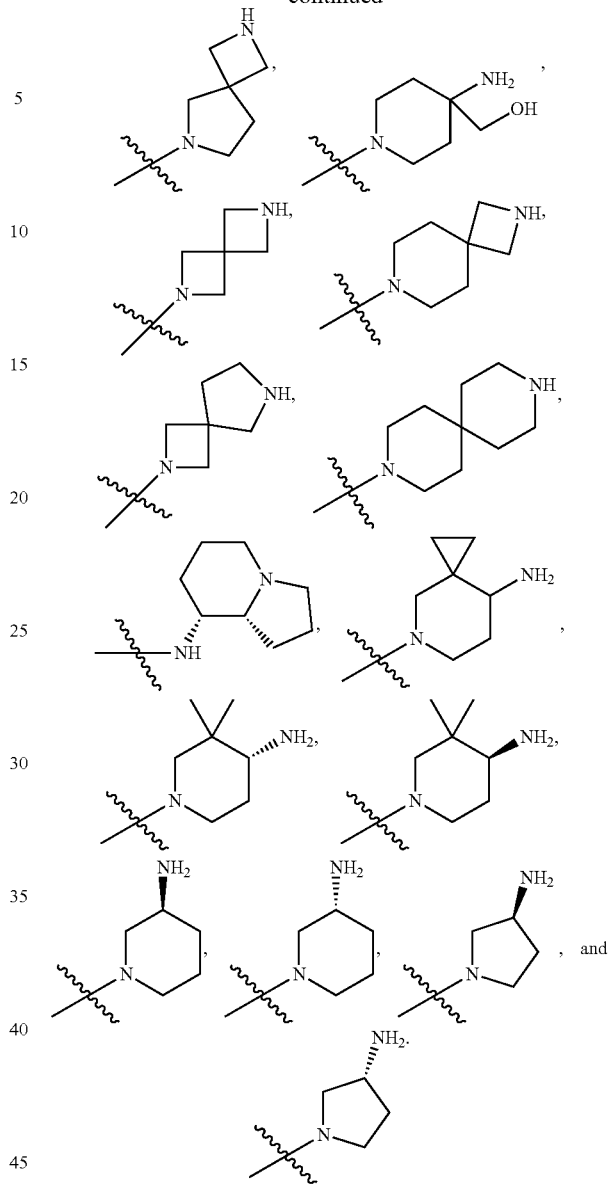

In another embodiment, the invention relates to enantiomerically pure compounds represented by Structural Formula Ia, or a pharmaceutically acceptable salt, and a pharmaceutically acceptable carrier, diluent, or vehicle thereof, wherein $R^1$ is phenyl, X and $NR^{3a}R^{3b}$ are defined as above.

In another embodiment, the invention relates to enantiomerically pure compounds represented by Structural Formula Ib, or a pharmaceutically acceptable salt, and a pharmaceutically acceptable carrier, diluent, or vehicle thereof, wherein $R^1$ is phenyl, X and $NR^{3a}R^{3b}$ are defined as above.

In another embodiment, the invention relates to compounds, or a pharmaceutically acceptable salt, and a pharmaceutically acceptable carrier, diluent, or vehicle thereof, selected from the group consisting of the compounds described as examples A1 to A69, B1 to B71, and C1 to C71.

In another embodiment, the invention relates to compounds, or a pharmaceutically acceptable salt, and a pharmaceutically acceptable carrier, diluent, or vehicle thereof, selected from the group consisting of:
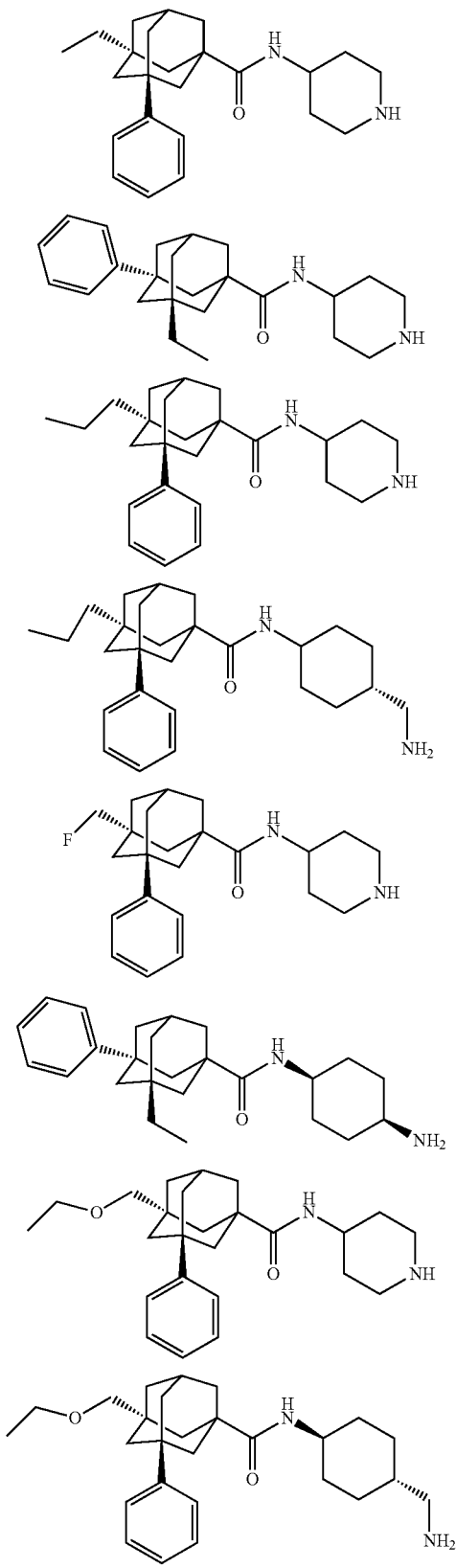
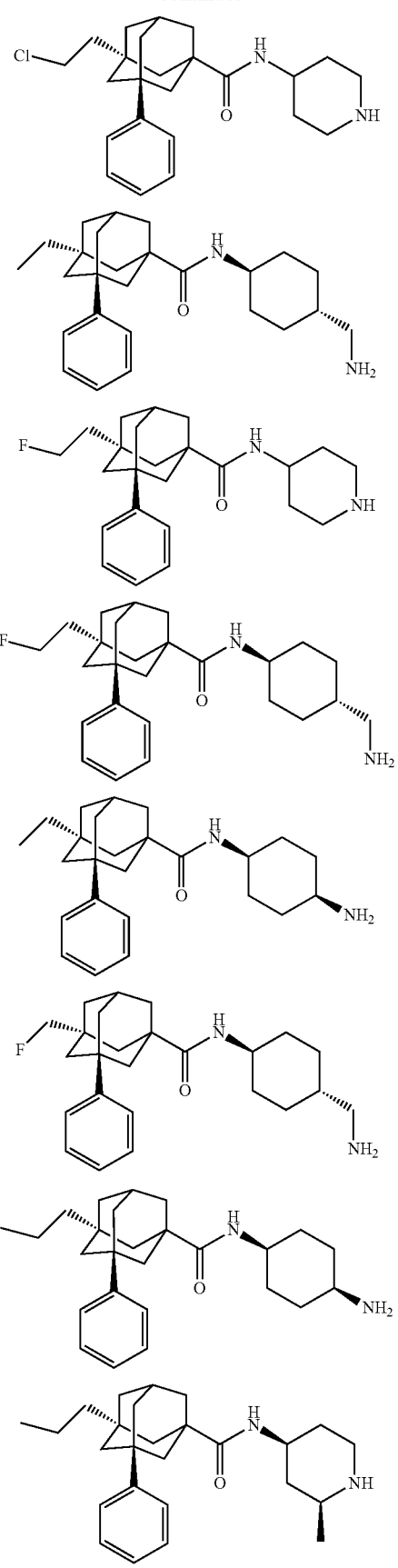

37
-continued
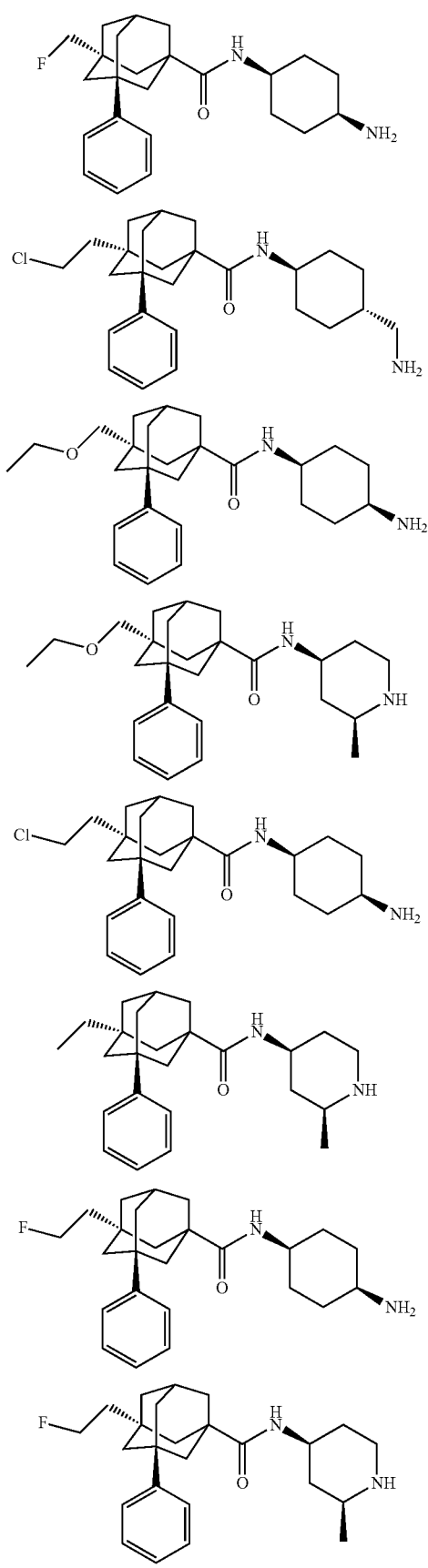
38
-continued
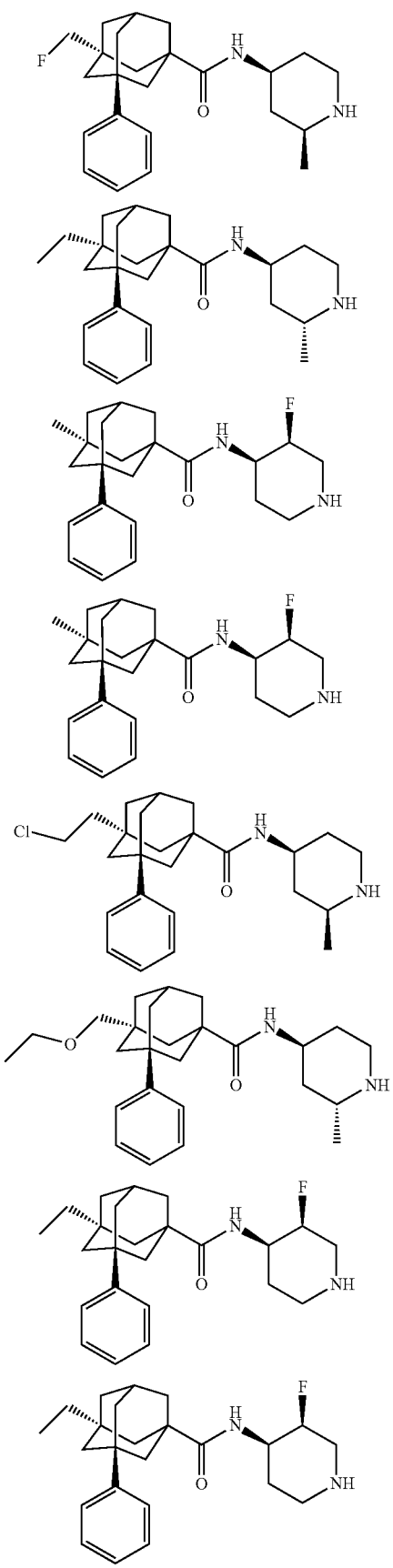

-continued
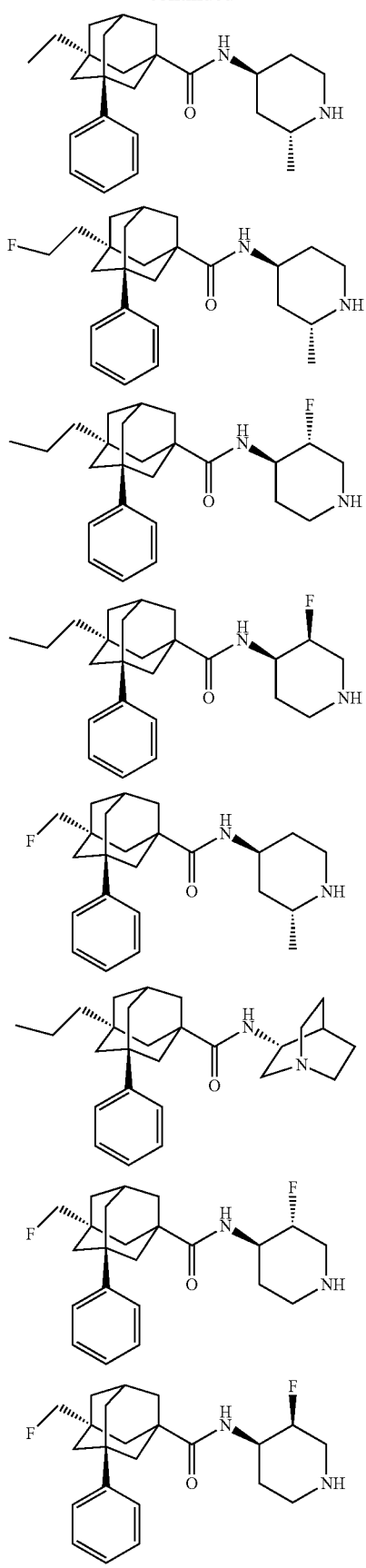
-continued
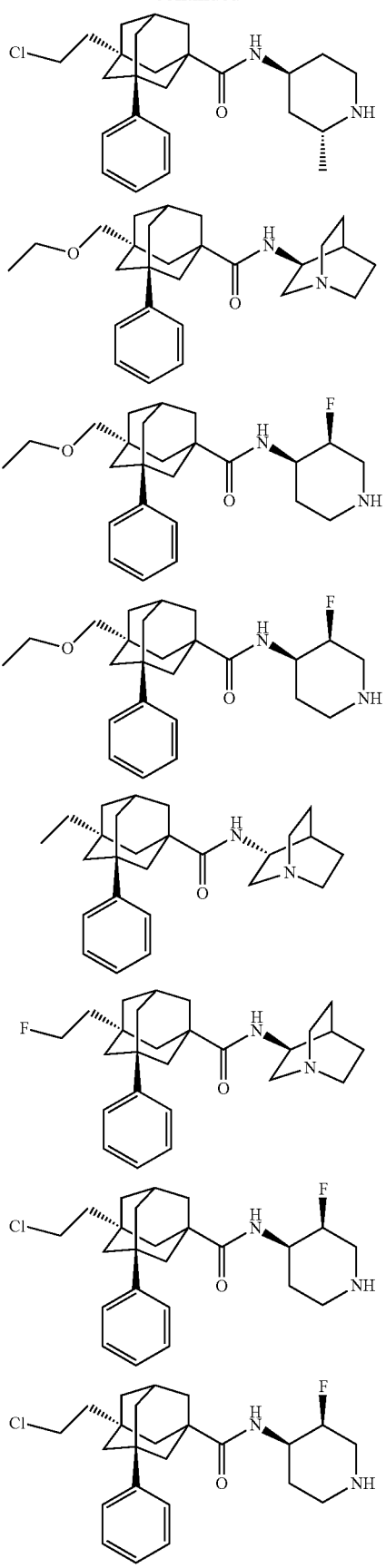

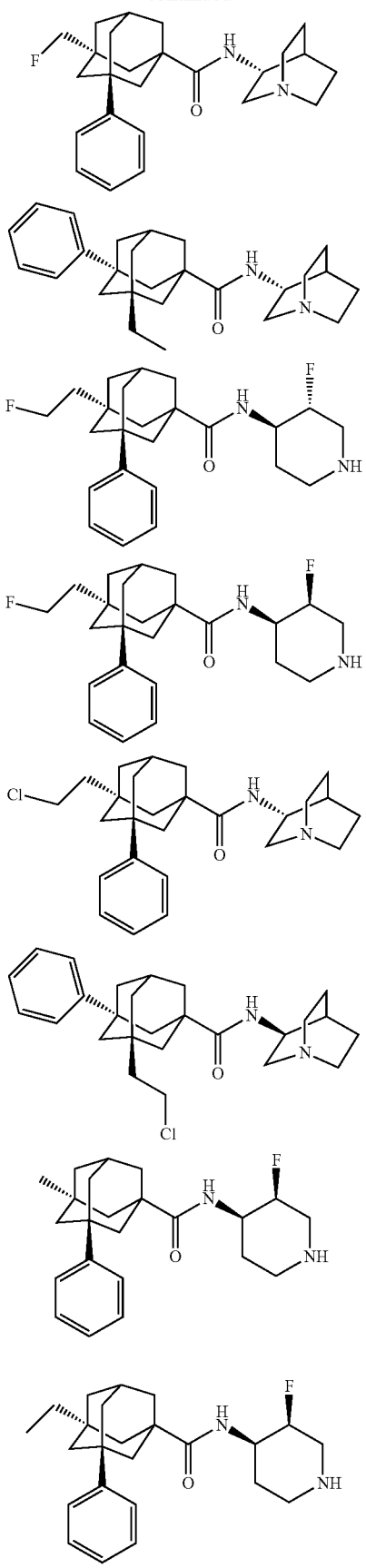
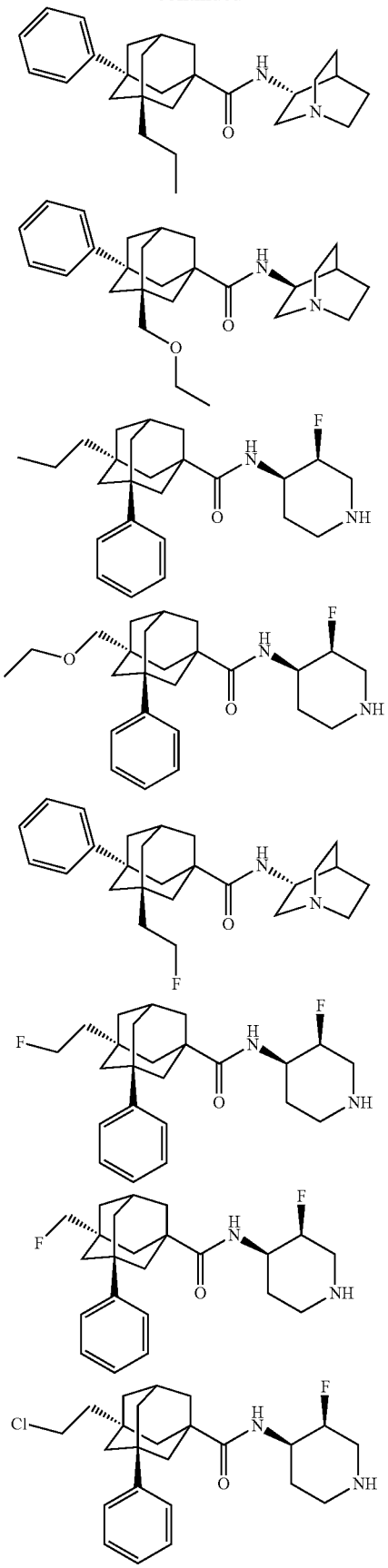

43
-continued
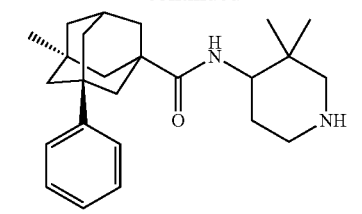
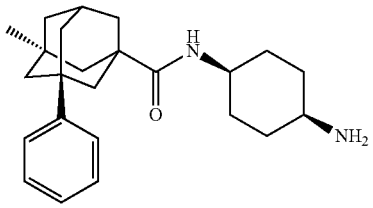
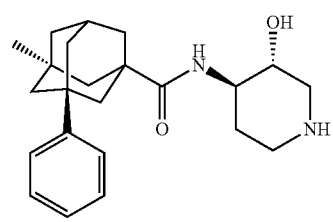
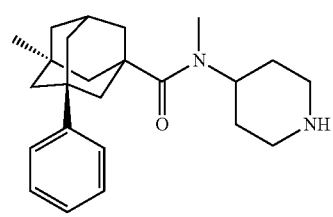
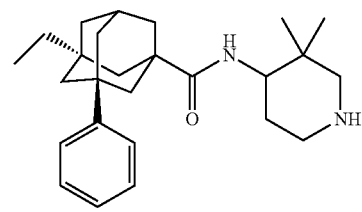
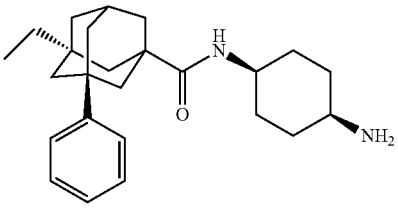
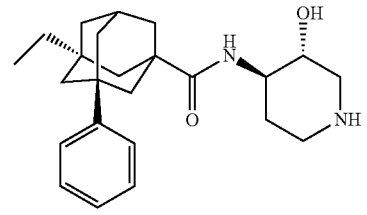
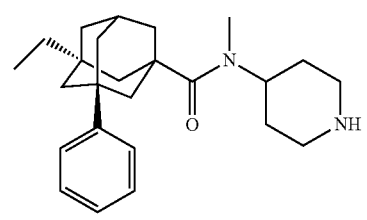
44
-continued
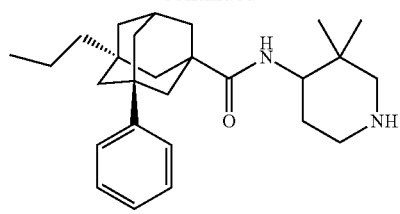
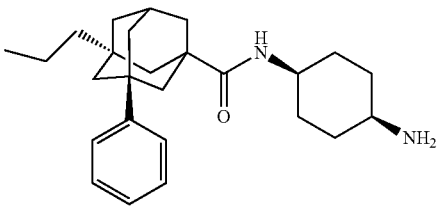
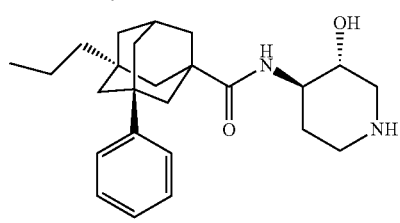
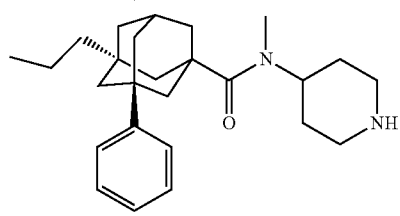
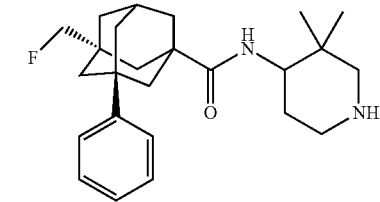
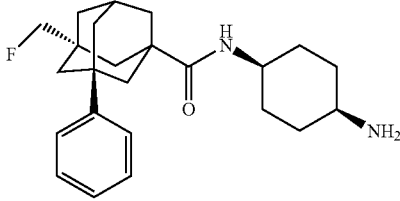
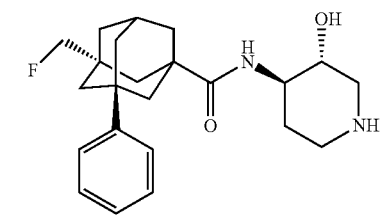
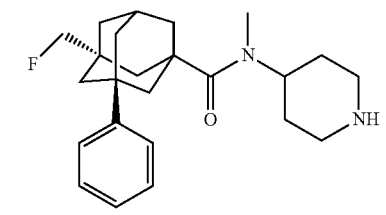

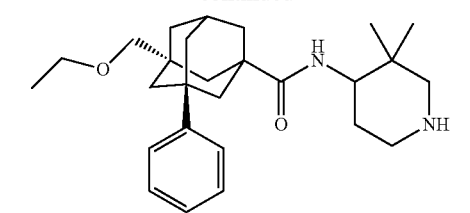
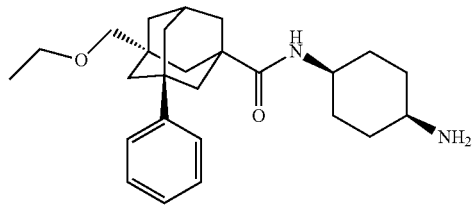
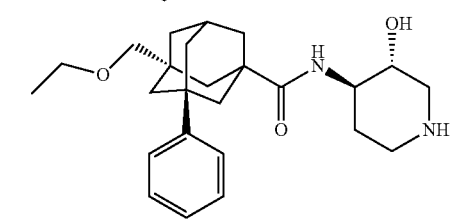
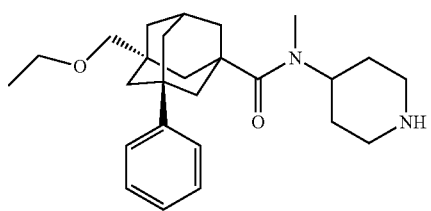
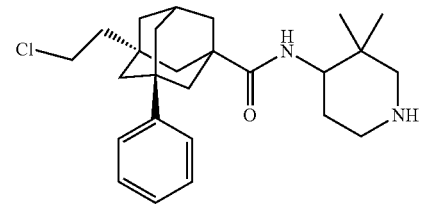
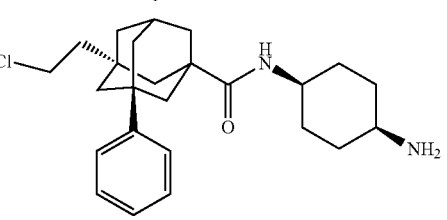
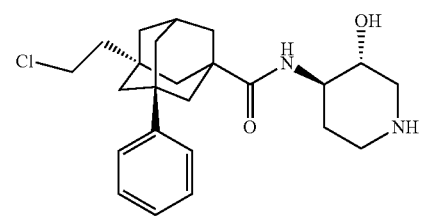
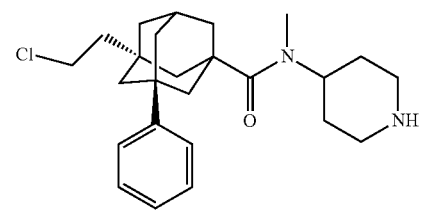
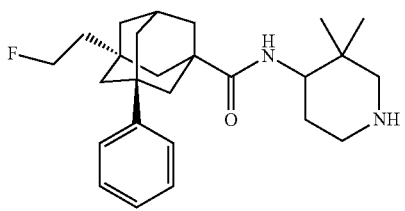
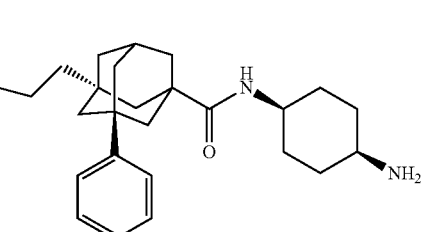
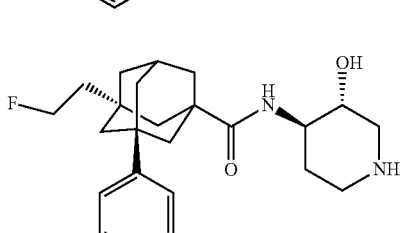
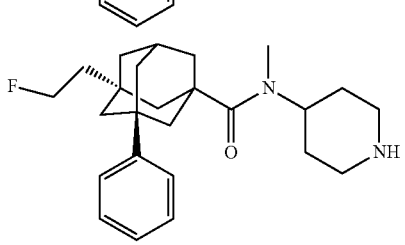
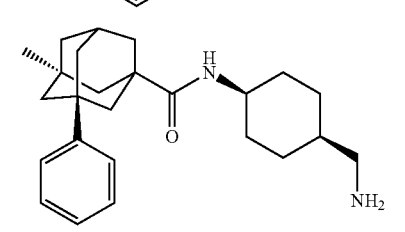
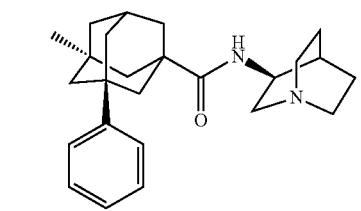
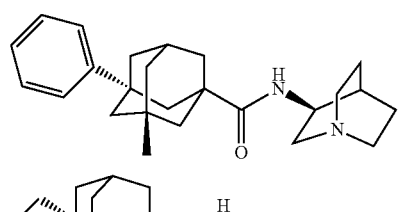
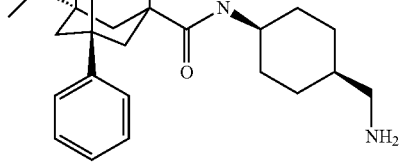

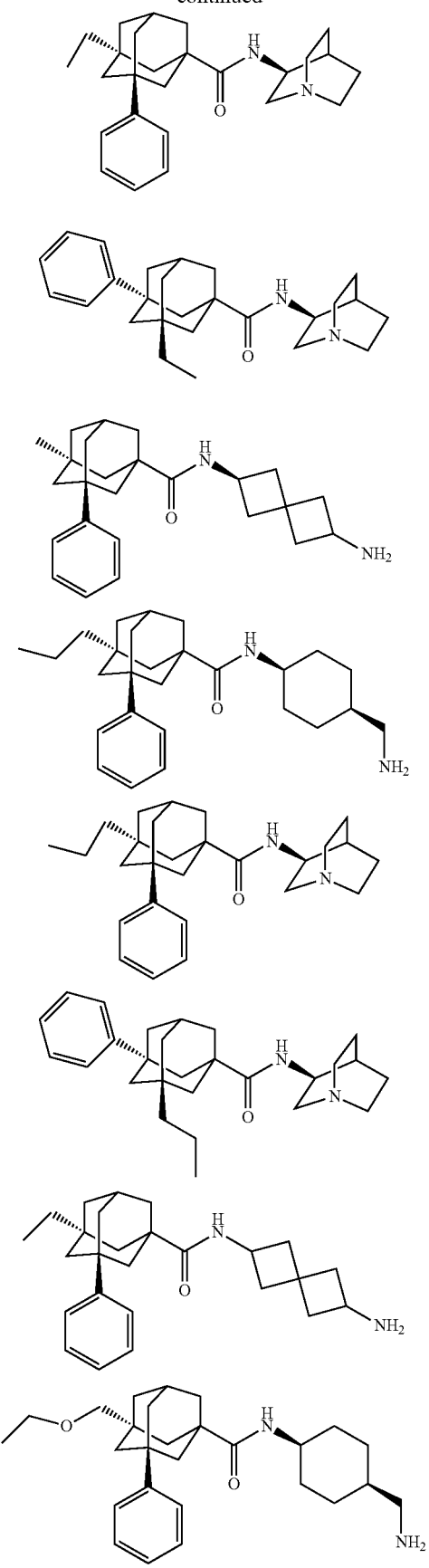
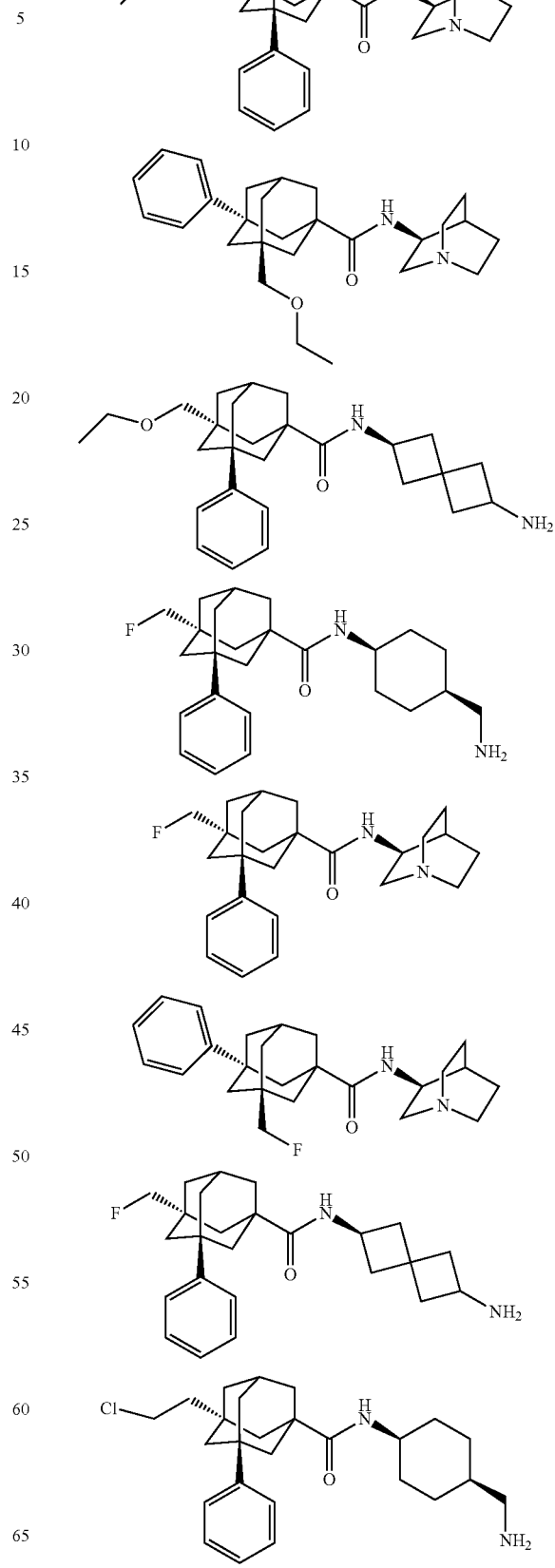

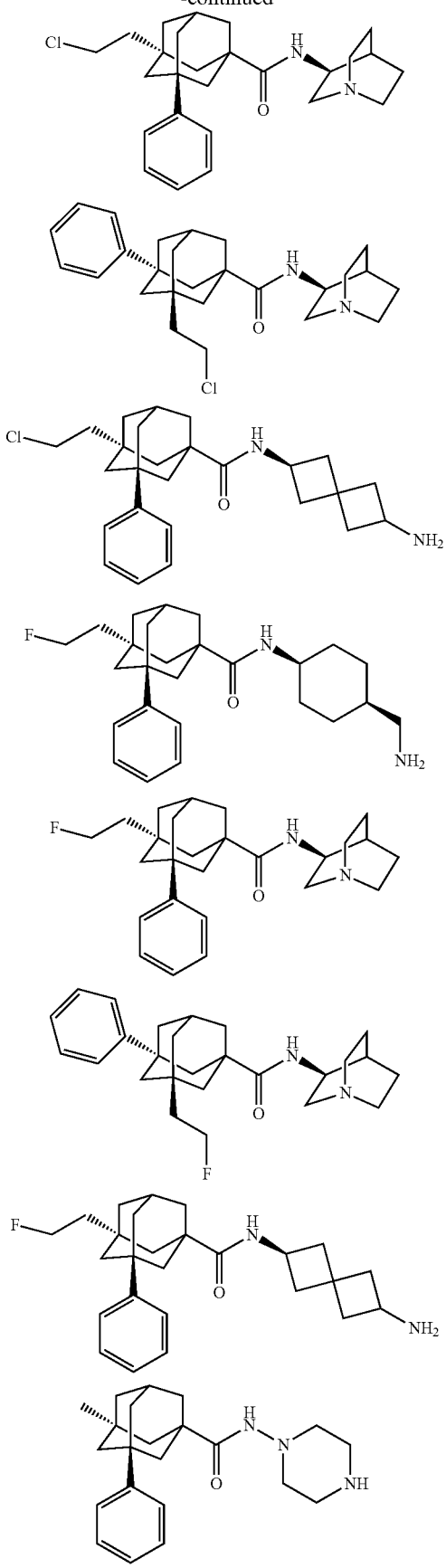
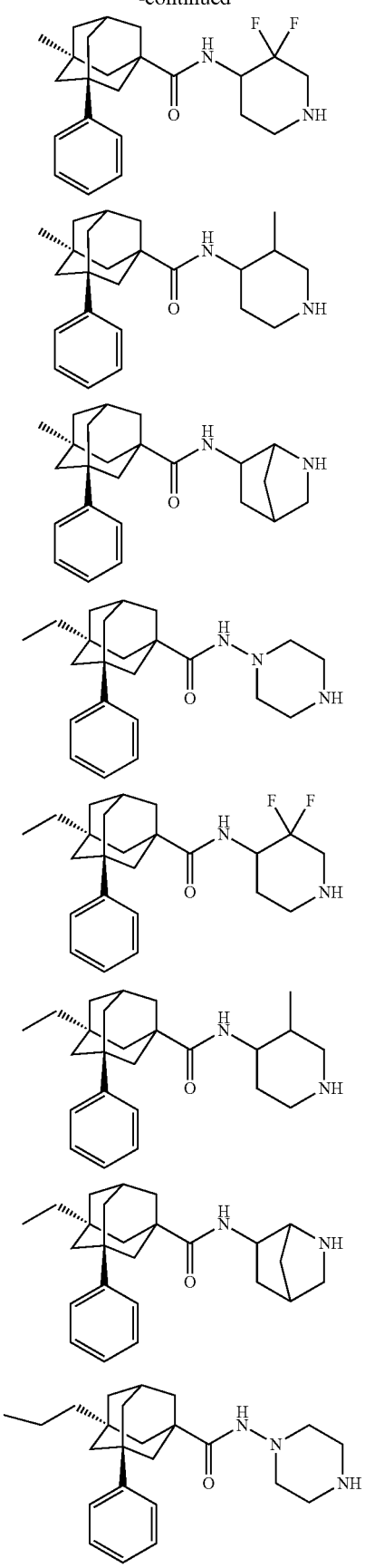

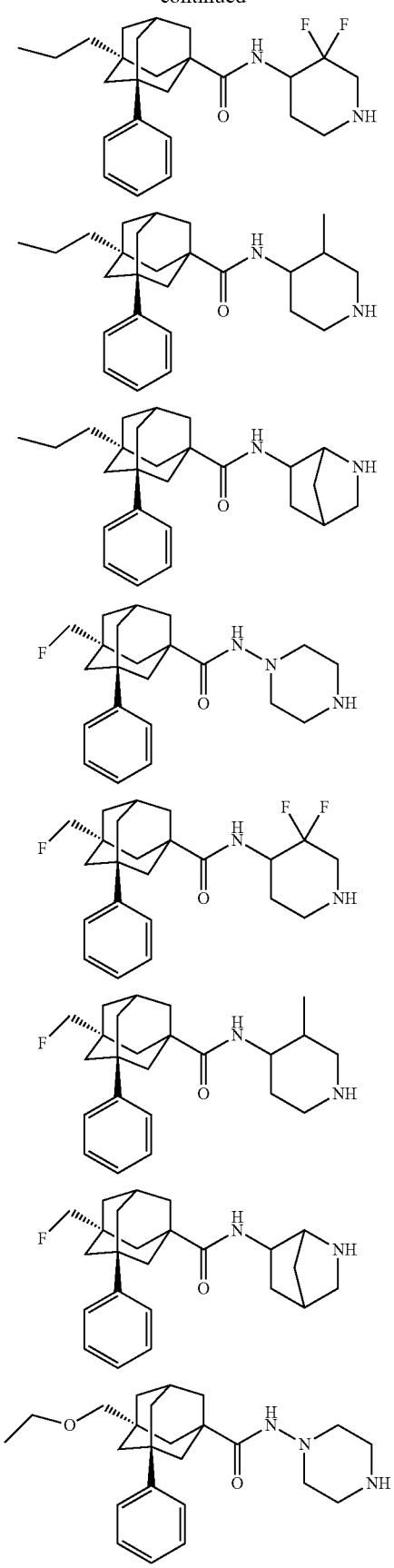
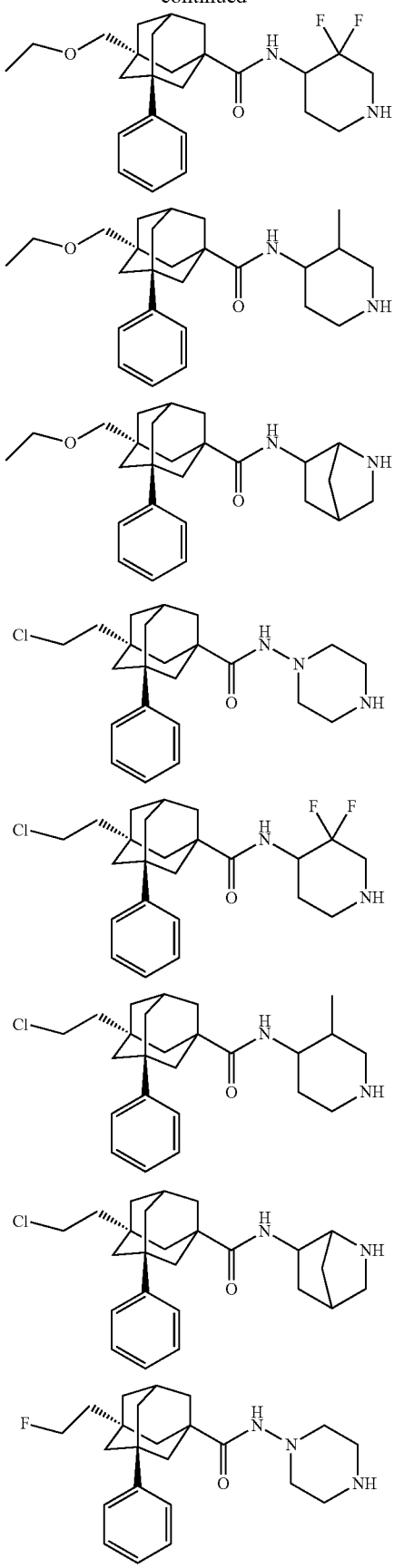

53
-continued
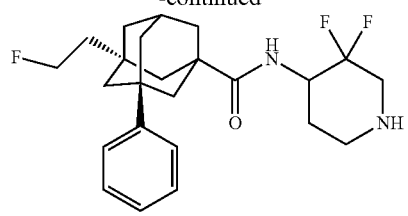
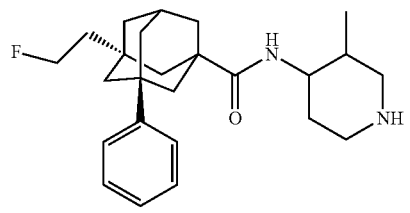
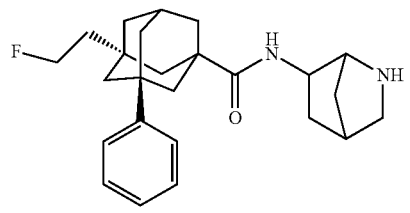
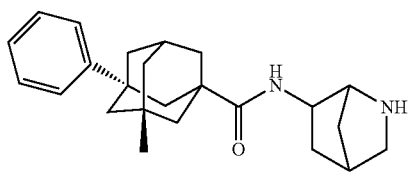
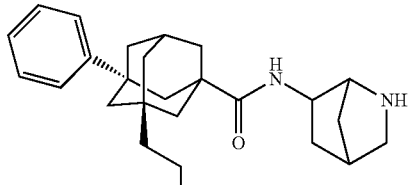
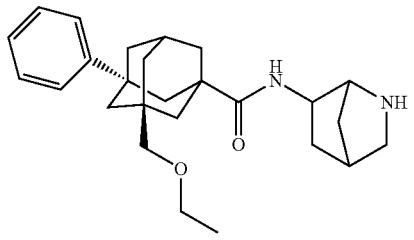
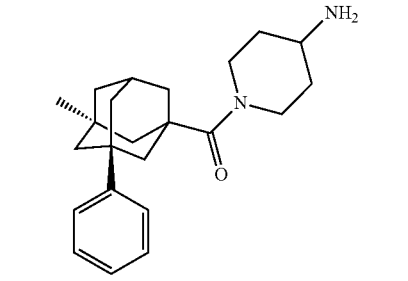
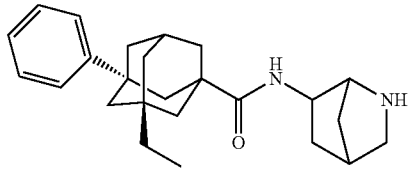
54
-continued
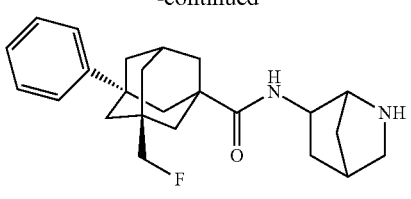
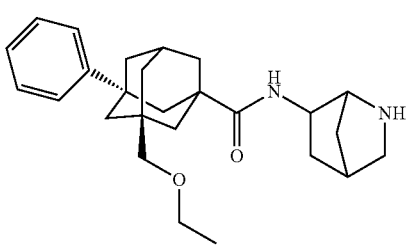
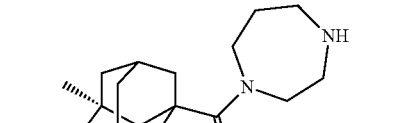
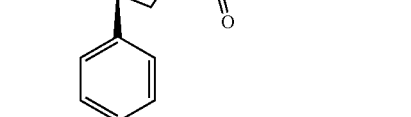
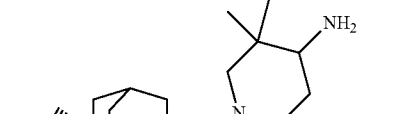
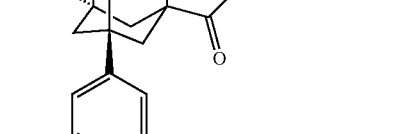
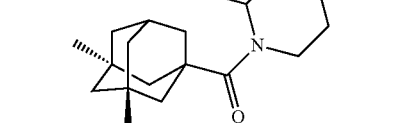
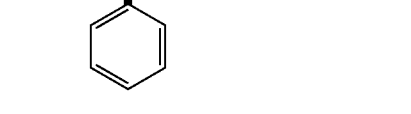
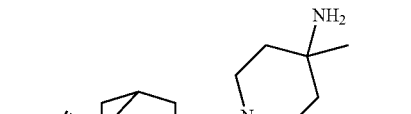
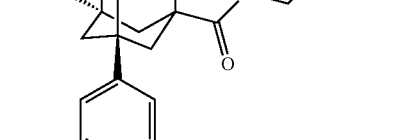

-continued
55
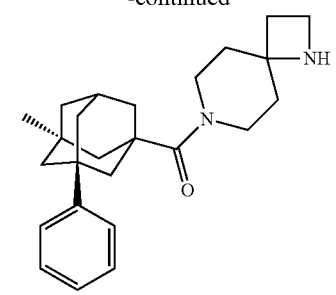
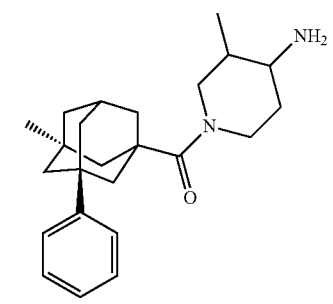
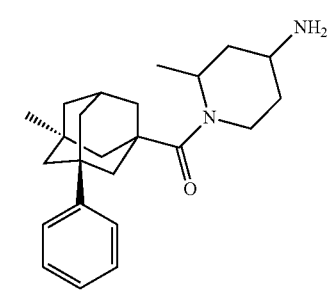
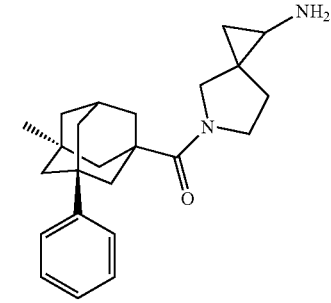
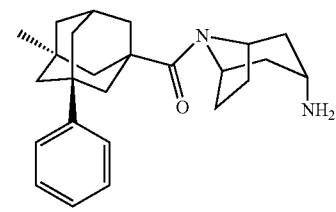
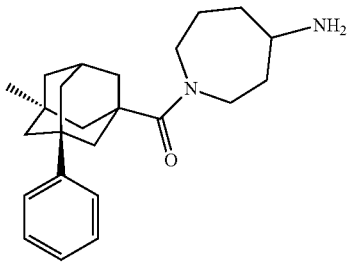
56
-continued
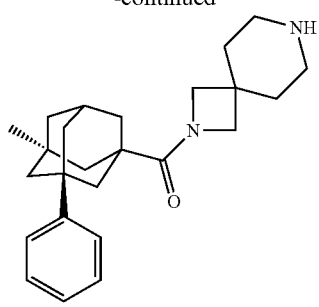
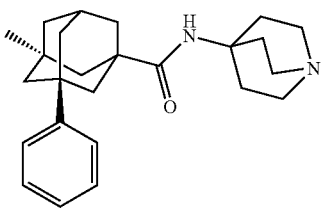
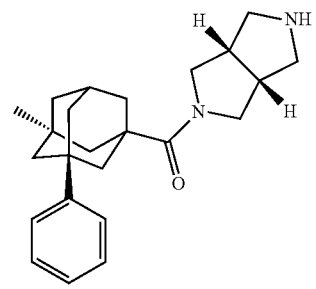
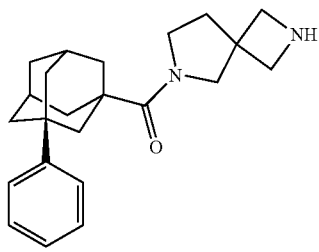
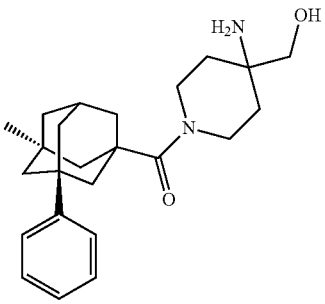
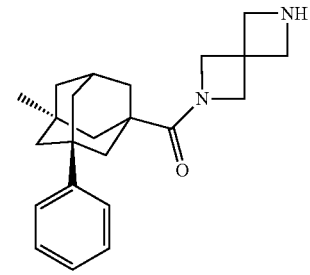

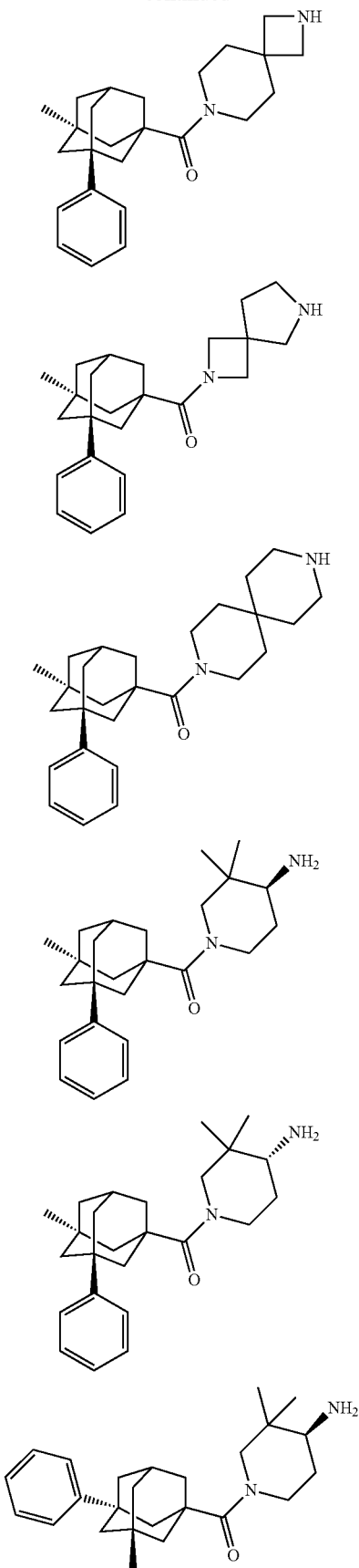

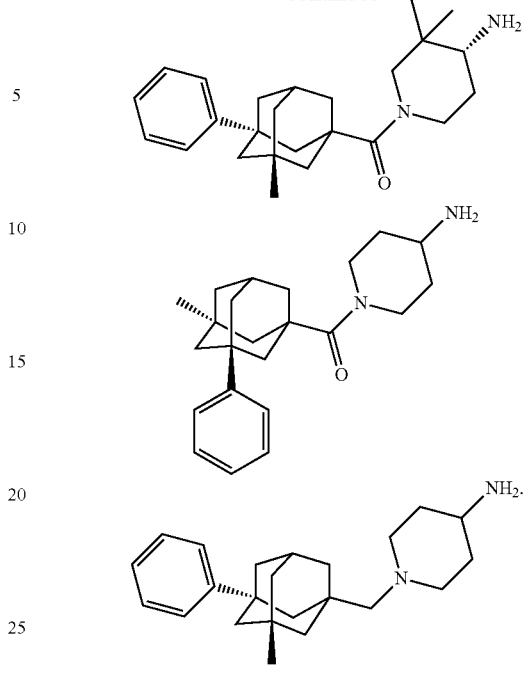

Definitions

As used herein, the terms "comprising" and "including" are used in their open, non-limiting sense.

The terms "halo" and/or "halogen" refer to fluorine, chlorine, bromine or iodine.

The term "($C_1$ to $C_{10}$) alkyl" refers to a saturated aliphatic hydrocarbon radical including straight chain and branched chain groups of 1 to 8 carbon atoms. Examples of ($C_1$ to $C_{10}$) alkyl groups include methyl, ethyl, propyl, 2-propyl, n-butyl, iso-butyl, tert-butyl, pentyl, and the like. The terms "Me" and "methyl," as used herein, mean a —$CH_3$ group. The terms "Et" and "ethyl," as used herein, mean a —$C_2H_5$ group.

The term "($C_2$ to $C_{10}$) alkenyl", as used herein, means an alkyl moiety comprising 2 to 10 carbons having at least one carbon-carbon double bond. The carbon-carbon double bond in such a group may be anywhere along the 2 to 10 carbon chain that will result in a stable compound. Such groups include both the E and Z isomers of said alkenyl moiety. Examples of such groups include, but are not limited to, ethene, propene, 1-butene, 2-butene, 1-pentene, 2-pentene, 1-hexene, 2-hexene, and 3-hexene. Examples of such groups include, but are not limited to, ethenyl, propenyl, butenyl, allyl, and pentenyl.

The term "allyl," as used herein, means a —$CH_2CH$=$CH_2$ group.

As used herein, the term "($C_2$ to $C_{10}$) alkynyl" means an alkyl moiety comprising from 2 to 8 carbon atoms and having at least one carbon-carbon triple bond. The carbon-carbon triple bond in such a group may be anywhere along the 2 to 10 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

The term "($C_1$ to $C_{10}$) alkoxy", as used herein, means an O-alkyl group wherein said alkyl group contains from 1 to 8 carbon atoms and is straight, branched, or cyclic.

Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The term "($C_6$ to $C_{10}$) aryl", as used herein, means a group derived from an aromatic hydrocarbon containing from 6 to 10 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

The term "($C_6$ to $C_{10}$) arylene" is art-recognized, and as used herein pertains to a bivalent moiety obtained by removing a hydrogen atom from a ($C_6$ to $C_{10}$) aryl ring, as defined above.

"($C_2$ to $C_9$) heteroaryl", as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The $C_2$ to $C_9$ heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "($C_2$ to $C_{10}$) heteroarylene" is art-recognized, and as used herein pertains to a bivalent moiety obtained by removing a hydrogen atom from a ($C_6$ to $C_{10}$) heteroaryl ring, as defined above.

The term "($C_2$ to $C_{10}$) cycloheteroalkyl", as used herein, means a non-aromatic, monocyclic, bicyclic, tricyclic, spirocyclic, or tetracyclic group having a total of from 4 to 13 atoms in its ring system, and containing from 5 to 10 carbon atoms and from 1 to 4 heteroatoms each independently selected from O, S and N, and with the proviso that the ring of said group does not contain two adjacent O atoms or two adjacent S atoms. Furthermore, such ($C_2$ to $C_{10}$) cycloheteroalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a ($C_2$ to $C_{10}$) cycloheteroalkyl group contains a sulfur atom, said sulfur atom may be oxidized with one or two oxygen atoms to afford either a sulfoxide or sulfone. An example of a 4 membered cycloheteroalkyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such ($C_2$ to $C_{10}$) cycloheteroalkyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8, diazaspiro[4.5]dec-8-yl. The ($C_2$ to $C_{10}$) heteroaryl groups may be C-attached or N-attached where such is possible. For instance, a group derived from piperazine may be piperazin-1-yl (N-attached) or piperazin-2-yl (C-attached).

The term "($C_2$ to $C_{10}$) cycloheteroalkylene" is art-recognized, and as used herein pertains to a bidentate moiety obtained by removing a hydrogen atom from a ($C_6$ to $C_{10}$) cycloheteroalkyl ring, as defined above.

The term "($C_3$ to $C_{10}$) cycloalkyl group" means a saturated, monocyclic, fused, spirocyclic, or polycyclic ring structure having a total of from 3 to 10 carbon 5 ring atoms. Examples of such groups include, but are not limited to, cyclopropyl, cyclobutyl, cyclopentyl, cyclopentenyl, cyclohexyl, cycloheptyl, and adamantyl.

The term "($C_3$ to $C_{10}$) cycloalkylene" is art-recognized, and as used herein pertains to a bidentate moiety obtained by removing a hydrogen atom from a ($C_3$ to $C_{10}$) cycloalkyl ring, as defined above.

The term "spirocyclic" as used herein has its conventional meaning, that is, any compound containing two or more rings wherein two of the rings have one ring carbon in common. The rings of a spirocyclic compound, as herein defined, independently have 3 to 20 ring atoms. Preferably, they have 3 to 10 ring atoms. Non-limiting examples of a spirocyclic compound include spiro[3.3]heptane, spiro[3.4]octane, and spiro[4.5]decane.

The term "($C_5$ to $C_8$) cycloalkenyl" means an unsaturated, monocyclic, fused, spirocyclic ring structures having a total of from 5 to 8 carbon ring atoms. Examples of such groups include, but not limited to, cyclopentenyl, cyclohexenyl.

The term cyano" refers to a —C≡N group.

An "aldehyde" group refers to a carbonyl group, —C(O)R, where R is hydrogen.

An "alkoxy" group refers to both an —O-alkyl and an —O-cycloalkyl group, as defined herein.

An "alkoxycarbonyl" refers to a —C(O)OR.

An "alkylaminoalkyl" group refers to an -alkyl-NR-alkyl group.

An "alkylsulfonyl" group refer to a —$SO_2$ alkyl.

An "amino" group refers to an —$NH_2$ or an —NRR' group.

An "aminoalkyl" group refers to an -alky-NRR' group.

An "aminocarbonyl" refers to a —C(O)NRR'.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)Oaryl.

An "arylsulfonyl" group refers to a —$SO_2$aryl.

A "C-amido" group refers to a —C(O)NRR' group.

A "carbonyl" group refers to a —C(O)R.

A "C-carboxyl" group refers to a —C(O)OR groups.

A "carboxylic acid" group refers to a C-carboxyl group in which R is hydrogen.

A "cyano" group refers to a —CN group.

A "dialkylamionalkyl" group refers to an -(alkyl)N(alkyl)$_2$ group.

A "halo" or "halogen" group refers to fluorine, chlorine, bromine or iodine.

A "haloalkyl" group refers to an alkylgroup substituted with one or more halogen atoms.

A "heteroalicycloxy" group refers to a heteroalicyclic-O group with heteroalicyclic as defined herein.

A "heteroaryloxyl" group refers to a heteroaryl-O group with heteroaryl as defined herein.

A "hydroxy" group refers to an —OH group.

An "N-amido" group refers to a —R'C(O)NR group.

An "N-carbamyl" group refers to a —ROC(O)NR— group.

A "nitro" group refers to a —NO$_2$ group.

An "N-Sulfonamido" group refers to a —NR—S(O)$_2$R group.

An "N-thiocarbamyl" group refers to a ROC(S)NR' group.

An "O-carbamyl" group refers to a —OC(O)NRR' group.

An "O-carboxyl" group refers to a RC(O)O— group.

An "O-thiocarbamyl" group refers to a —OC(S)NRR' group.

An "oxo" group refers to a carbonyl moiety such that alkyl substituted by oxo refers to a ketone group.

A "perfluoroalkyl group" refers to an alkyl group where all of the hydrogen atoms have been replaced with fluorine atoms.

A "phosphonyl" group refers to a —P(O)(OR)$_2$ group.

A "silyl" group refers to a —SiR$_3$ group.

An "S-sulfonamido" group refers to a —S(O)$_2$NR— group.

A "sulfinyl" group refers to a —S(O)R group.

A "sulfonyl" group refers to a —S(O)$_2$R group.

A "thiocarbonyl" group refers to a —C(=S)—R group.

A "trihalomethanecarbonyl" group refers to a Z$_3$CC(O)— group, where Z is halogen.

A "trihalomethanesulfonamido" group refers to a Z$_3$CS(O)$_2$NR— group, where Z is halogen.

A "trihalomethanesulfonyl" group refers to a Z$_3$CS(O)$_2$— group, where Z is halogen.

A "trihalomethyl" group refers to a —CZ$_3$ group.

A "C-carboxyl" group refers to a —C(O)OR groups.

The term "substituted," means that the specified group or moiety bears one or more substituents.

The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a C$_6$ aryl group, also called "phenyl" herein, is substituted with one additional substituent, one of ordinary skill in the art would understand that such a group has 4 open positions left on carbon atoms of the C$_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a C$_6$ aryl group in the present compounds is said to be "disubstituted," one of ordinary skill in the art would understand it to mean that the C$_6$ aryl has 3 carbon atoms remaining that are unsubstituted. Those three unsubstituted carbon atoms are each bound to one hydrogen atom to fill their valencies.

The term "solvate," is used to describe a molecular complex between compounds of the present invention and solvent molecules. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof.

The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate.

Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The term "pharmaceutically acceptable formulation", as used herein, means a combination of a compound of the invention, or a salt or solvate thereof, and a carrier, diluent, and/or excipient(s) that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention.

The term "virus inhibiting amount" as used herein, refers to the amount of a compound of the present invention, or a salt or solvate thereof, required to inhibit the cell entry of an enveloped virus in vivo, such as in a mammal, or in vitro. The amount of such compounds required to cause such inhibition can be determined without undue experimentation using methods described herein and those known to those of ordinary skill in the art.

The terms "treat", "treating", and "treatment" with reference to enveloped virus infection, in mammals, particularly a human, include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition.

The compositions are delivered in effective amounts. The term "effective amount" refers to the amount necessary or sufficient to realize a desired biologic effect and/or reduce the viral load. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. In addition, based on testing, toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular inhibitor and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug.

"Dose" and "dosage" are used interchangeably herein. For any compound described herein, the therapeutically effective amount can be initially determined from preliminary in vitro studies and/or animal models. A therapeutically effective dose can also be determined from human data for inhibitors that have been tested in humans and for compounds, which are known to exhibit similar pharmacological activities, such as other related active agents. The applied dose can be adjusted based on the relative bioavailability and potency of the administered compound. Adjusting the dose to achieve maximal efficacy based on the methods described above and other methods well-known in the art, is well within the capabilities of the ordinarily skilled artisan. In certain embodiments, the methods of the invention are useful for treating infection with enveloped viruses.

Unless indicated otherwise, all references herein to the inventive compounds include references to salts, solvates, and complexes thereof, including polymorphs, stereoisomers, tautomers, and isotopically labeled versions thereof. For example, compounds of the present invention can be pharmaceutically acceptable salts and/or pharmaceutically acceptable solvates.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. A pure enantiomer can be contaminated with up to 10% of the opposite enantiomer.

The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

In accordance with a convention used in the art, the symbol is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

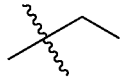 [SMILES: *CC]

represents an ethyl group,

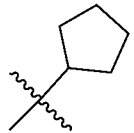 [SMILES: *C1CCCC1]

represents a cyclopentyl group, etc.

The compounds of the present invention may have asymmetric carbon atoms. The carbon-carbon bonds of the compounds of the present invention may be depicted herein using a solid line (———), a solid wedge (◥), or a dotted wedge (⋯⋯). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

("R") unless otherwise defined, a substituent "R" may reside on any atom of the ring system, assuming replacement of a depicted, implied, or expressly defined hydrogen from one of the ring atoms, so long as a stable structure is formed.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenyl ethyl amine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E L Eliel (Wiley, New York, 1994), the disclosure of which is incorporated herein by reference in its entirety.

Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. Examples of tautomerism include keto and enol tautomers. A single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof. Cis/trans isomers may be separated by conventional techniques well known to those skilled in the art, for example, chromatography and fractional crystallization.

The compounds of the present invention may be administered as prodrugs. Thus certain derivatives of compounds of Formula I which may have little or no pharmacological activity themselves can, when administered to a mammal, be converted into a compound of Formula I having the desired activity, for example, by hydrolytic cleavage. Such derivatives are referred to as "prodrugs". Prodrugs can, for example, be produced by replacing appropriate functionalities present in the compound of Formula I with certain moieties known to those skilled in the art. See, e.g. "Prodrugs as Novel Delivery Systems", Vol. 14, ACS Symposium Series (T Higuchi and W Stella) and "Bioreversible Carriers in Drug Design", Pergamon Press, 1987 (ed. E B Roche, American Pharmaceutical Association), the disclosures of which are incorporated herein by reference in their entireties. Some examples of such prodrugs include: an ester moiety in the place of a carboxylic acid functional group; an ether moiety or an amide moiety in place of an alcohol functional group; and an amide moiety in place of a primary or secondary amino functional group. Further examples of replacement groups are known to those of skill in the art. See, e.g. "Design of Prodrugs" by H Bundgaard (Elsevier, 1985), the disclosure of which is incorporated herein by reference in its entirety. It is also possible that certain compounds of Formulae I, Ia, or Ib may themselves act as prodrugs of other compounds of Formula I, Ia, or Ib.

Salts of the present invention can be prepared according to methods known to those of skill in the art. Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methanesulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phosphate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals or humans, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, $^2$H increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

To treat or prevent diseases or conditions mediated in part or whole by enveloped virus infection, a pharmaceutical composition of the invention is administered in a suitable formulation prepared by combining a therapeutically effective amount (i.e., an enveloped virus GP- or host cell partner-modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer.

For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrotidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures.

Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a cosolvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a cosolvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal, such as a human, suffering from a condition or disease mediated by an enveloped virus, either alone or as part of a pharmaceutically acceptable formulation, once a day, twice a day, three times a day, four times a day, or even more frequently.

The compounds of the present invention, or salts or solvates thereof, may be administered to humans or mammals suffering from a condition or disease mediated by a filovirus, arenavirus, or other enveloped virus in combination with at least one other agent used for treatment, alone or as part of a pharmaceutically acceptable formulation, once a day, twice a day, three times a day, four times a day, or even more frequently.

Those of ordinary skill in the art will understand that with respect to the compounds of the present invention, the particular pharmaceutical formulation, the dosage, and the number of doses given per day to humans or mammals requiring such treatment, are all choices within the knowledge of one of ordinary skill in the art and can be determined without undue experimentation.

Combination Therapy

Compounds of Structural Formula I of the invention may be combined with other therapeutic agents. The inhibitor and other therapeutic agent may be administered simultaneously or sequentially. When the other therapeutic agents are administered simultaneously they can be administered in the same or separate formulations, but are administered at the same time. The other therapeutic agents are administered sequentially with one another and with the inhibitors, when the administration of the other therapeutic agents and the inhibitors is temporally separated. The separation in time between the administration of these compounds may be a matter of minutes or it may be longer. Other therapeutic agents include but are not limited to anti-viral vaccines and anti-viral agents. In some instances the inhibitors are administered with multiple therapeutic agents, i.e., 2, 3, 4 or even more different anti-viral agents.

An anti-viral vaccine is a formulation composed of one or more viral antigens and one or more adjuvants. The viral antigens include proteins or fragments thereof as well as whole killed virus. Adjuvants are well known to those of skill in the art.

Antiviral agents are compounds, which prevent infection of cells by viruses or replication of the virus within the cell. There are many fewer antiviral drugs than antibacterial drugs because viruses are more dependent on host cell factors than bacteria. There are several stages within the process of viral infection, which can be blocked or inhibited by antiviral agents. These stages include, attachment of the virus to the host cell (immunoglobulin or binding peptides), membrane penetration inhibitors, e.g. T-20, uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, resimiquimod, favipiravir, BCX4430, and GS-5374 or their analogues.

The interferons are cytokines which are secreted by virus-infected cells as well as immune cells. The interferons function by binding to specific receptors on cells adjacent to the infected cells, causing the change in the cell which protects it from infection by the virus, α- and β-interferon also induce the expression of Class I and Class II MHC molecules on the surface of infected cells, resulting in increased antigen presentation for host immune cell recognition, α- and β-interferons are available as recombinant proteins and have been used for the treatment of chronic hepatitis B and C infection. At the dosages that are effective for anti-viral therapy, interferons may have severe side effects such as fever, malaise and weight loss.

Anti-viral agents, which may be useful in combination with Structural Formula I of the invention, include but are not limited to immunoglobulins, amantadine, interferons, nucleotide analogues, small interfering RNAs (siRNAs) and other protease inhibitors (other than the papain-like cysteine protease inhibitors—although combinations of papain-like cysteine protease inhibitors are also useful). Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; AVI-7537: Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Favipiravir; Fiacitabine; Fialuridine; Fosarilate; Fosfonet; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon, Stavudine; Tilorone Hydrochloride; TKM Ebola; Triazavirin; Trifluridine; Valacyclovir Hydrochloride; Vidarabine; Vidarabine Phosphate; Vidarabine Sodium Phosphate; Viroxime; Zalcitabine; Zidovudine; Zinviroxime; and ZMapp.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes an antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Another type of immunoglobulin therapy is active immunization. This involves the administration of antibodies or antibody fragments to viral surface proteins.

In the following Preparations and Examples, "Ac" means acetyl, "Me" means methyl, "Et" means ethyl, "Ph" means phenyl, "Py" means pyridine, "BOC", "Boc" or "boc" means N-tert-butoxycarbonyl, "Ns" means 2-Nitrophenylsulfonyl, "CMMP" means (cyanomethylene) trimethyl phosphorane", DCM" ($CH_2Cl_2$) means dichloromethane or methylene chloride, "DCE" means dichloroethane or ethylene chloride, "DIAD" means diisopropylazadicarboxylate, "DIPEA" or "DIEA" means diisopropyl ethyl amine, "DMA" means N,N-dimethylacetamide, "DMAP" means 4-dimethylaminopyridine, "DME" means 1,2-dimethoxyethane, "DMF" means N,N-dimethyl formamide, "DMSO" means dimethylsulfoxide, "DPPA" means diphenylphosphorylazide, "DPPP" means 1,3-bis(diphenylphosphino) propane, "EDCl" means 3-(ethyliminomethyleneamino)-N,N-dimethylpropan-1-amine, "EtOAc" means ethyl acetate, "HATU" means 1-[Bis(dimethylamino)methylene]-1H-1,2,3-triazolo[4,5-b]pyridinium 3-oxide hexafluorophosphate, "HOAt" means 1-hydroxy-7 azabenzotriazole, "HOAc" means acetic acid, "IPA" means isopropyl alcohol, "LDA" means lithium diisopropylamide, "NMP" means 1-methyl 2-pyrrolidinone, "TEA" means triethyl amine, "TFA" means trifluoroacetic acid, "TOSMIC" means toluenesulfonylmethyl isocyanide, "$MgSO_4$" means magnesium sulphate, "NaHMDS" or "NHMDS" means sodium hexamethyldisilazide, "$Na_2SO_4$" means sodium sulphate, "MeOH" means methanol, "$Et_2O$" means diethyl ether, "EtOH" means ethanol, "$H_2O$" means water, "HCl" means hydrochloric acid, "$POCb$" means phosphorus oxychloride, "SOCk" means thionylchloride, "$K_2CO_3$" means potassium carbonate, "THF" means tetrahydrofuran, "DBU" means 1,8-diazabicyclo[5.4.0]undec-7-ene, "LAH" means lithium aluminium hydride, "LiHMDS" or "LHMDS" means lithium hexamethyldisilazide, "TBABr" means tetra butyl ammonium bromide, "TBME" or "MTBE" means tert-butyl methyl ether, "TMS" means trimethylsilyl, "PMHS" means polymethylhydrosiloxane, "MCPBA" means 3-chloroperoxy benzoic acid, "N" means Normal, "M" means molar, "mL" means millilitre, "mmol" means millimoles, "µmol" means micromoles, "eq." means equivalent, "° C." means degrees Celsius, "Pa" means pascals, "Xanthphos" means 4,5-bis(diphenylphosphino)-9,9-dimethylxanthene, "r.t." means room temperature.

Methods of Preparation.

Compounds of the present invention may be prepared using the reaction routes and synthetic schemes described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

In one general synthetic process, compounds of the Structural Formula I can be prepared according to Scheme 1 by reacting carboxylic acid 1-1 with amine $NHR^{3a}R^{3b}$ in the presence of a coupling reagent such as EDCl or HATU and a base such as DIEA or triethylamine in a solvent such as DMF or dichloromethane to provide the desired product of Formula I. Alternatively, carboxylic acid 1-1 can react with $SOCl_2$ to form acid chloride 1-2 which can react with amine $NHR^{3a}R^{3b}$ in presence of a base such as DIEA or triethylamine in a solvent such as DMF or dichloroethane to form amide I in which X=O. This amide can be reduced by a strong reducing agent such as lithium aluminum hydride in a solvent such as tetrahydrofuran or diethyl ether to form amine I in which X=H.

Scheme 1

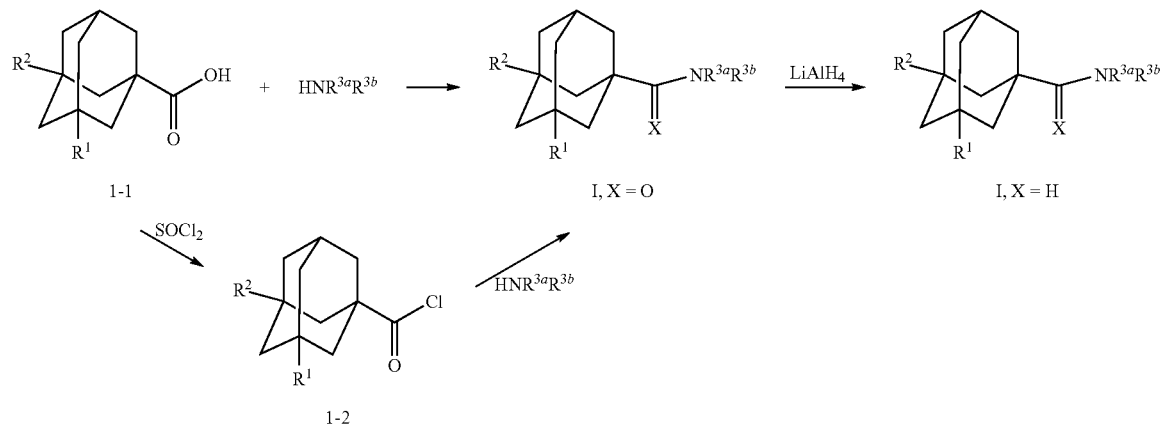

In another general synthetic process, compounds of the Structural Formula Ia can be prepared according to Scheme 2 by reacting enantiomerically pure carboxylic acid 2-1 with amine $NHR^{3a}R^{3b}$ in the presence of a coupling reagent such as EDCl or HATU and a base such as DIEA or triethylamine in a solvent such as DMF or dichloroethane to provide the desired product of Formula Ia. Alternatively, carboxylic acid 2-1 can react with $SOCl_2$ to form acid chloride 2-2 which can react with amine $NHR^{3a}R^{3b}$ in presence of a base such as DIEA or triethylamine in a solvent such as DMF or dichloroethane to form amide Ia in which X=O. This amide can be reduced by a strong reducing agent such as lithium aluminum hydride in a solvent such as tetrahydrofuran or diethyl ether to form amine Ia in which X=H.

Scheme 2

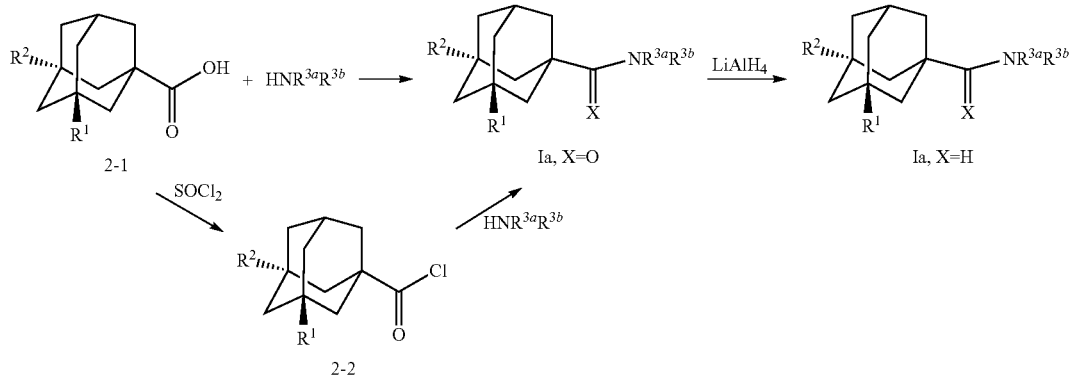

In another general synthetic process, compounds of the Structural Formula Ib can be prepared according to Scheme 3 by reacting enantiomerically pure carboxylic acid 3-1 with amine $NHR^{3a}R^{3b}$ in the presence of a coupling reagent such as EDCl or HATU and a base such as DIEA or triethylamine in a solvent such as DMF or dichloroethane to provide the desired product of Formula Ib. Alternatively, carboxylic acid 3-1 can react with $SOCl_2$ to form acid chloride 3-2 which can react with amine $NHR^{3a}R^{3b}$ in presence of a base such as DIEA or triethylamine in a solvent such as DMF or dichloroethane to form amide Ib in which X=O. This amide can be reduced by a strong reducing agent such as lithium aluminum hydride in a solvent such as tetrahydrofuran or diethyl ether to form amine Ib in which X=H.

Scheme 3

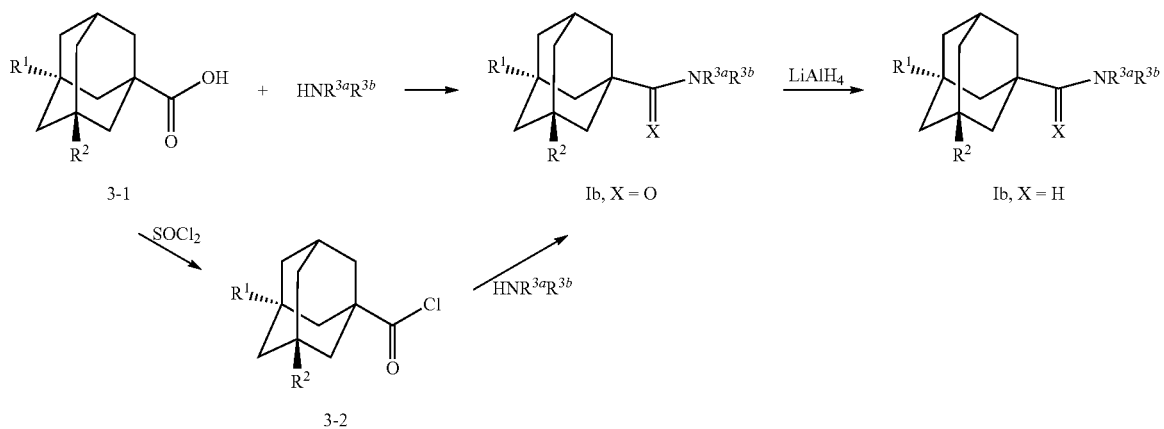

Preparation of Intermediates rac-3-ethyl-5-phenyladamantane-1-carboxylic Acid

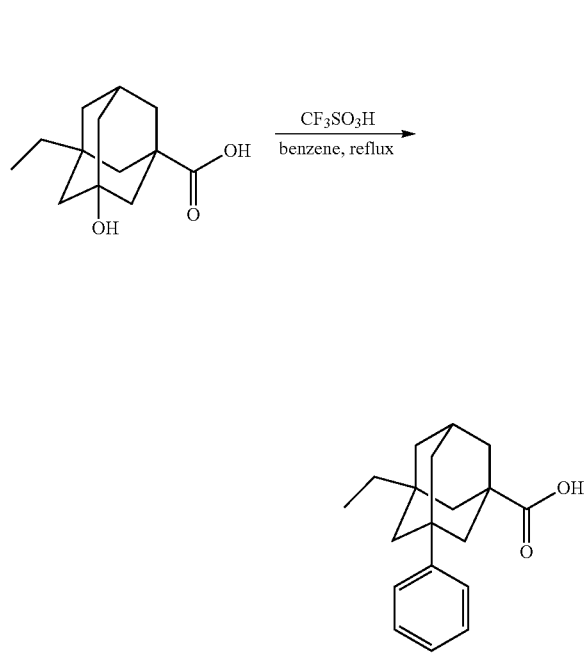

To a solution of 3-ethyl-5-hydroxyadamantane-1-carboxylic acid (1 g, 4.46 mmol) in benzene (14 mL) was added triflic acid (0.67 g, 4.46 mmol) dropwise at r.t. The reaction mixture was refluxed for 4 h. Then cooled in an ice-bath and several drops of saturated NaHCO₃ were added. The reaction mixture was partitioned between water and MTBE. The organic phase was washed with water, dried over Na₂SO₄, filtered, and concentrated in vacuo. The residue was purified by SiO₂ column chromatography (hexanes/EtOAc from 4:1 to 7:3) to give 0.84 g (66%) of the title compound as a white solid. $^1$H NMR (300 MHz, CDCl₃) δ 7.38-7.29 (m, 4H), 7.22-7.16 (m, 1H), 2.34-2.27 (m, 1H), 2.01 (br. s, 2H), 1.91-1.79 (m, 4H), 1.70-1.62 (m, 2H), 1.59 (br. s, 2H), 1.51-1.42 (m, 2H), 1.25 (q, 2H), 0.83 (t, 3H).

1,3-dimethyl 5-phenyladamantane-1,3-dicarboxylate

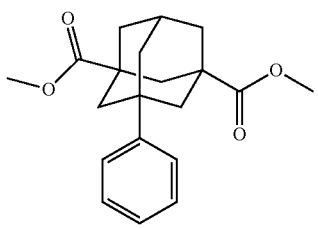

The title compound was prepared from 1,3-dimethyl 5-hydroxyadamantane-1,3-dicarboxylate and benzene in the same manner as described above for rac-3-ethyl-5-phenyladamantane-1-carboxylic acid. $^1$H NMR (500 MHz, CDCl₃) δ 7.37-7.30 (m, 4H), 7.20 (t, 1H), 3.67 (s, 6H), 2.38-2.35 (m, 1H), 2.07 (br. s, 2H), 2.05-1.99 (m, 4H), 1.92-1.85 (m, 6H).

rac-3-(methoxycarbonyl)-5-phenyladamantane-1-carboxylic Acid

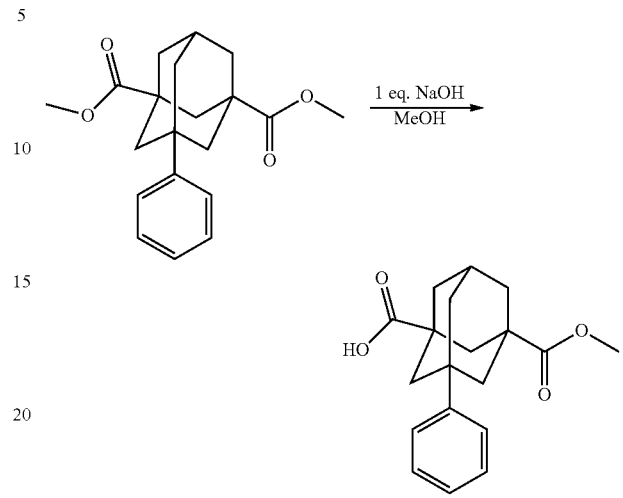

To a solution of 1,3-dimethyl 5-phenyladamantane-1,3-dicarboxylate (2 g, 6.1 mmol) in MeOH (16 mL) was added NaOH (0.24 g, 6.1 mmol). The reaction mixture was stirred at 50° C. overnight, then cooled to r.t. and concentrated in vacuo. The residue was dissolved in water, acidified with 1N HCl, and extracted with EtOAc. The organic layer was dried over Na₂SO₄, filtered, and concentrated in vacuo. The residue was purified by SiO₂ column chromatography (hexanes/EtOAc from 4:1 to 1:2) to give 0.6 g (31%) of the title compound as a white solid.

rac-methyl 3-(hydroxymethyl)-5-phenyladamantane-1-carboxylate

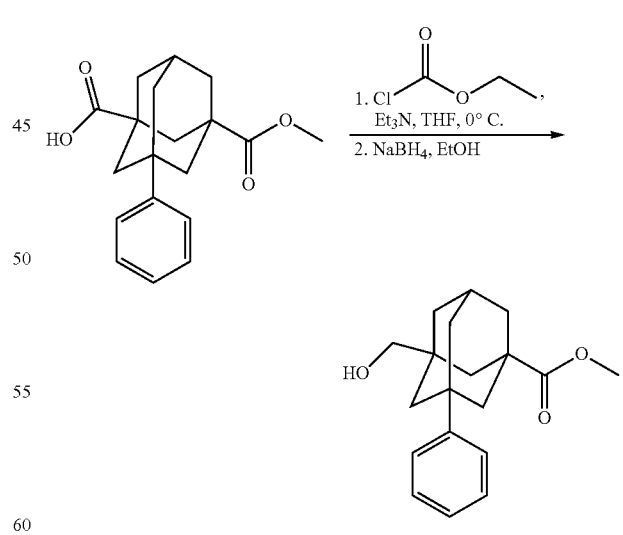

To a solution of rac-3-(methoxycarbonyl)-5-phenyladamantane-1-carboxylic acid (0.6 g, 1.9 mmol) in THF (12 mL) cooled to 0° C. was added triethylamine (0.96 g, 9.5 mmol), followed by ethyl chloroformate (0.31 g, 2.9 mmol) under N₂ atmosphere. The resulting mixture was stirred at this temperature for 30 min, then filtered and concentrated in vacuo. The residue was dissolved in a mixture of THF (2 mL) and EtOH (12 mL) and cooled to 0° C., then NaBH$_4$ (0.18 g, 4.8 mmol) was added to it in three portions. The reaction mixture was brought to r.t. and stirred for 2 h. Then 1N HCl was added, volatiles were removed in vacuo, and the aqueous layer was extracted with EtOAc. The organic layer was dried over Na$_2$SO$_4$, filtered, and concentrated in vacuo. The residue was purified by SiO$_2$ column chromatography (hexanes/EtOAc from 4:1 to 6:4) to give 0.23 g (40%) of the title compound as a colorless oil.

rac-methyl 3-phenyl-5-{[(trifluoromethane)sulfonyloxy]methyl}adamantane-1-carboxylate

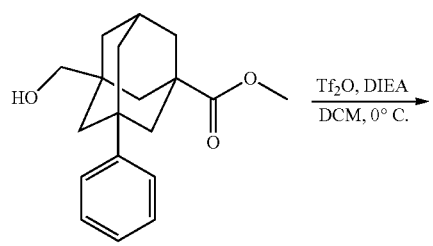

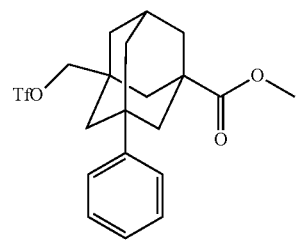

To a solution of rac-methyl 3-(hydroxymethyl)-5-phenyl-adamantane-1-carboxylate (96 mg, 0.32 mmol) in DCM (2 mL) cooled to 0° C. was added DIEA (54 mg, 0.42 mmol), followed by Tf$_2$O (0.1 g, 0.35 mmol) in DCM (0.6 mL). The reaction mixture was brought to r.t. gradually and stirred for 2 h. Then DCM (10 mL) was added, reaction mixture was washed quickly with water. The organic layer was dried over Na$_2$SO$_4$, filtered, and concentrated in vacuo. The residue was purified by flash chromatography on SiO$_2$ (hexanes/EtOAc 7:3) to give 125 mg (90%) of the title compound as a colorless oil.

rac-methyl 3-(fluoromethyl)-5-phenyladamantane-1-carboxylate

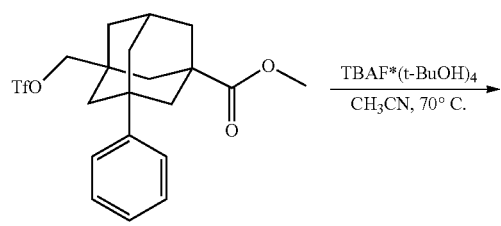

-continued

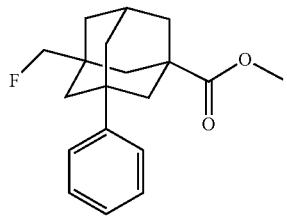

To a solution of rac-methyl 3-phenyl-5-{[(trifluoromethane)sulfonyloxy]methyl}adamantane-1-carboxylate (0.125 g, 0.29 mmol) in CH$_3$CN (1.5 mL) was added TBAF (f-BuOH)$_4$ (0.26 g, 0.46 mmol) (Kim, D. W.; Jeong, H.-J.; Lim, S. T.; Sohn, M.-H. Angew. Chem. Int. Ed. 2008, 47, 8404-8406). The reaction mixture was stirred at 70° C. for 2 h. Then, the solvent was removed in vacuo, the residue was partitioned between EtOAc and water; organic layer was dried over Na$_2$SO$_4$, filtered, and concentrated in vacuo. The residue was purified by flash chromatography on SiO$_2$ (hexanes/EtOAc 4:1) to give 50 mg (57%) of the title compound as a colorless oil. $^1$H NMR (500 MHz, CDCl$_3$) δ 7.37-7.30 (m, 4H), 7.20 (t, 1H), 4.08 (d, 2H), 3.67 (s, 3H), 2.36-2.34 (m, 1H), 2.06 (br. s, 0.3H), 2.04 (br. s, 0.7H), 1.99 (t, 0.7H), 1.97 (t, 0.3H), 1.94-1.82 (m, 4H), 1.75 (br. s, 2H), 1.71 (br. s, 2H), 1.57 (d, 2H).

rac-3-(fluoromethyl)-5-phenyladamantane-1-carboxylic Acid

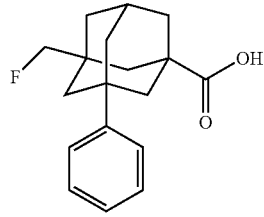 [SMILES: O=C(O)C12CC3CC(CF)(C1)CC(c1ccccc1)(C3)C2]

The title compound was prepared from rac-methyl 3-(fluoromethyl)-5-phenyladamantane-1-carboxylate using excess of NaOH in the same manner as described above for rac-3-(methoxycarbonyl)-5-phenyladamantane-1-carboxylic acid.

rac-3-(ethoxymethyl)-5-phenyladamantane-1-carboxylic Acid

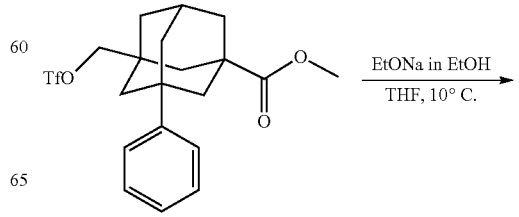

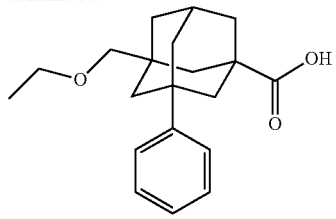

To a solution of EtONa in EtOH (21 wt. %, 0.03 mL, 0.076 mmol) in THF (0.5 mL) cooled to 10° C. was added a solution of rac-methyl 3-phenyl-5-{[(trifluoromethane)sulfonyloxy]methyl}adamantane-1-carboxylate (22 mg, 0.051 mmol) in THF (0.3 mL) dropwise under N₂ atmosphere. The resulting mixture was stirred at r.t. overnight. Then, the solvent was removed in vacuo, 1N HCl was added, and aqueous layer was extracted with EtOAc. The organic layer was dried over Na₂SO₄, filtered, and concentrated in vacuo to give 15 mg (94%) of the crude product as a colorless oil, which was used in the next step without further purification.

rac-methyl-3-carbamoyl-5-phenyladamantane-1-carboxylate

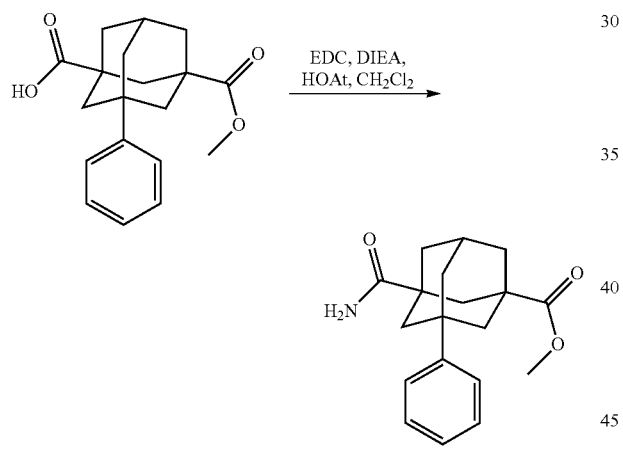

The title compound was prepared from rac-3-(methoxycarbonyl)-5-phenyladamantane-1-carboxylic acid and 2M ammonia in dioxane solution using general procedure 1. LC/MS m/z: 314.29 (M+H)⁺, 355.38 (M+H+CH₃CN)⁺ rac-methyl-3-cyano-5-phenyladamantane-1-carboxylate

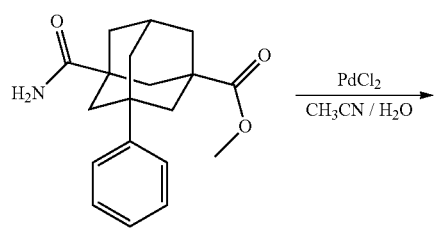

To a solution of rac-methyl-3-carbamoyl-5-phenyladamantane-1-carboxylate (170 mg, 0.54 mmol) in 2 mL of acetonitrile and 2 mL water is added PdCl₂ (9.5 mg, 0.054 mmol). The resulting mixture is stirred at room temperature overnight, then diluted with ethyl acetate, extracted three times with ethyl acetate, the pooled organic extracts dried over Na₂SO₄, and the solvent removed in vacuo to afford 133 mg of the title compound as a viscous oil pure enough for immediate use.

rac-3-cyano-5-phenyladamantane-1-carboxylic Acid

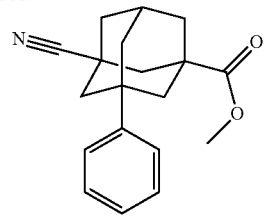

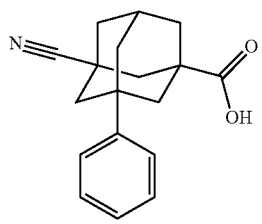 [SMILES: N#CC12CC3CC(C(=O)O)(C1)CC(c1ccccc1)(C3)C2]

The title compound was prepared from rac-methyl-3-cyano-5-phenyladamantane-1-carboxylate and excess sodium hydroxide in the same manner as described above for rac-3-(methoxycarbonyl)-5-phenyladamantane-1-carboxylic acid. LC/MS m/z 280.34 (M−H)⁻, 561.51 (2M−H)⁻

(1S,3R,5R,7S)-3-methyl-5-phenyladamantane-1-carboxylic acid and (1R,3S,5S,7R)-3-methyl-5-phenyladamantane-1-carboxylic Acid

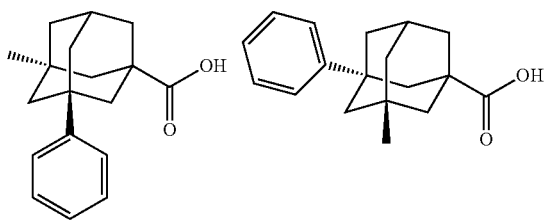

The title compounds were obtained by chiral separation of racemic 3-methyl-5-phenyladamantane-1-carboxylic acid (commercially available from Enamine, product number EN300-54568] on a prep. Agilent 1200 (Chiralpak AS 20×250 mm, 10 um; mobile phase: n-hexane-2-propanol-TFA, 97-3-0; flow rate: 13 mL/min, injection: 40 mg). Each enantiomer was separately converted to the corresponding methyl ester whose optical rotation was compared with published data [Aoyama, M; Hara, S. *Synthesis of optically active fluoroadamantane derivatives having different substituents on the tert-carbons and its use as non-racemizable* source for new optically active adamantane derivatives. Tetrahedron 2013, 69, 10357-10360].
In a similar way the following intermediates can be prepared by chiral separation of the corresponding racemic acid:
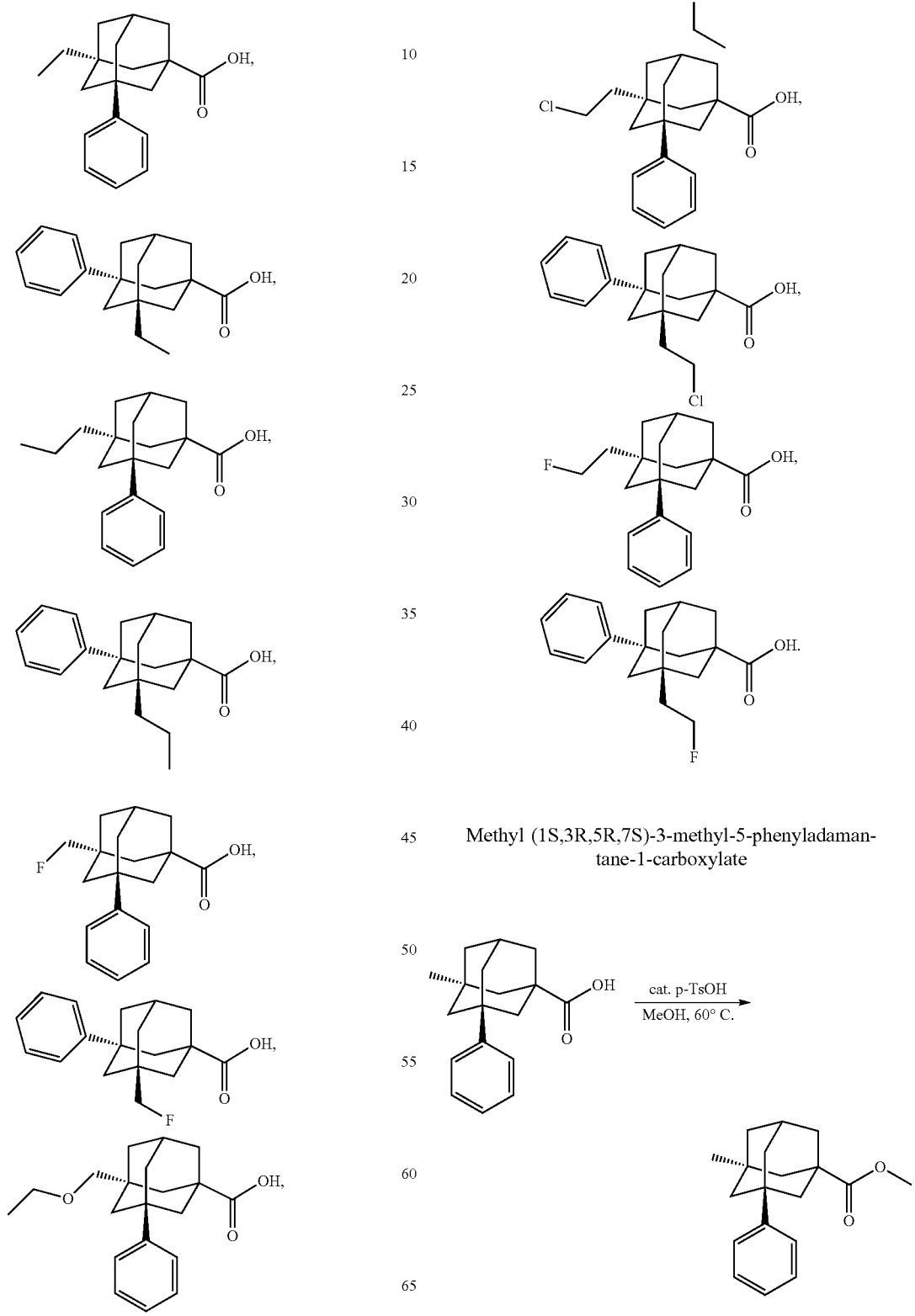
Methyl (1S,3R,5R,7S)-3-methyl-5-phenyladamantane-1-carboxylate To a solution of (1S,3R,5R,7S)-3-methyl-5-phenyladamantane-1-carboxylic acid (15 mg, 0.055 mmol) in MeOH (1 mL) was added cat. p-toluenesulfonic acid. The reaction mixture was stirred at 60° C. for 3 h. Then, the solvent was removed in vacuo, the residue was partitioned between EtOAc and water; organic layer was dried over Na$_2$SO$_4$, filtered, and concentrated in vacuo. The residue was purified by flash chromatography on SiO$_2$ (hexanes/EtOAc 4:1) to give 8 mg (50%) of the title compound as a colorless oil. [α]$_D^{23}$=−1.93 (c=0.124, CHCl$_3$); Lit. [α]$_D^{23}$=−1.50 (c=0.1, CHCl$_3$).

Methyl (1R,3S,5S,7R)-3-methyl-5-phenyladamantane-1-carboxylate

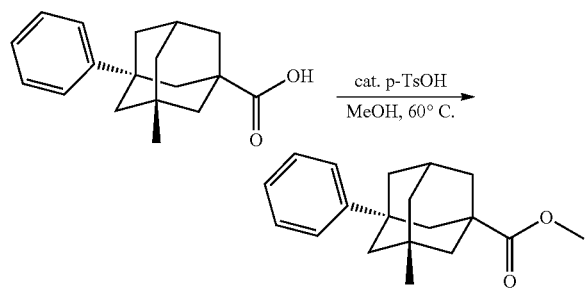

To a solution of (1R,3S,5S,7R)-3-methyl-5-phenyladamantane-1-carboxylic acid (15 mg, 0.055 mmol) in MeOH (1 mL) was added cat. p-toluenesulfonic acid. The reaction mixture was stirred at 60° C. for 3 h. Then, the solvent was removed in vacuo, the residue was partitioned between EtOAc and water; organic layer was dried over Na$_2$SO$_4$, filtered, and concentrated in vacuo. The residue was purified by flash chromatography on SiO$_2$ (hexanes/EtOAc 4:1) to give 9 mg (56%) of the title compound as a colorless oil. [α]$_D^{23}$=+4.48 (c=0.154, CHCl$_3$); Lit. [α]$_D^{23}$=+1.50 (c=0.1, CHCl$_3$). Examples.

General procedure 1 for preparation of examples A1 to A69.

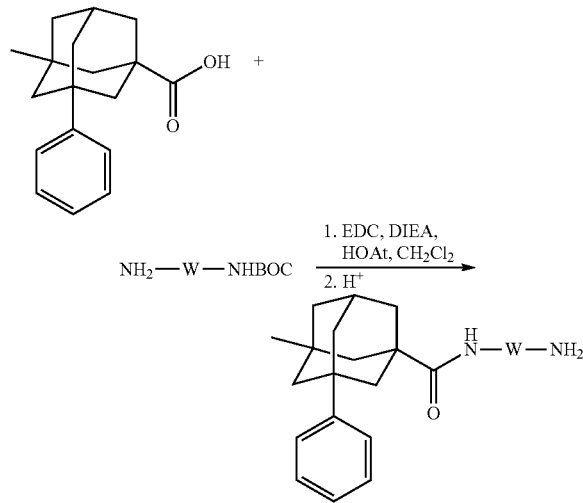

To a solution of 3-phenyl-5-methyl adamantane-1-carboxylic acid (11 mg, 0.041 mmol) in 1 mL of anhydrous CH$_2$Cl$_2$ was added N,N-diisopropylethylamine (9 uL, 0.049 mmol), EDC hydrochloride (10 mg, 0.049 mmol), and 1-hydroxy-7-azabenzotriazole (HOAt, 6.5 mg, 0.049 mmol) sequentially. The resulting reaction mixture was stirred at room temperature for 0.5 h, then mono Boc protected diamine NH$_2$—W—NHBOC (0.05 mmol) was added. The reaction mixture was stirred at room temperature for 12 h, diluted with CH$_2$Cl$_2$ and washed with saturated aq. NaHCO$_3$ solution. The organic phase was dried over Na$_2$SO$_4$, filtered, and concentrated in vacuo to give a residue. It was dissolved in 1 mL of CH$_2$Cl$_2$, and trifluoroacetic acid (0.1 mL) was added and stirred for 2 h at r.t. The solvent was evaporated, the residue was treated with saturated aq. NaHCO$_3$ solution and extracted with ethylacetate. The organic phase was dried over Na$_2$SO$_4$, filtered, and evaporation of solvent gave a residue which was purified either by flash SiO$_2$ column chromatography or preparative HPLC.

General procedure 2 for preparation of examples A61 to A69, B69 to B71, and C69 to C71.

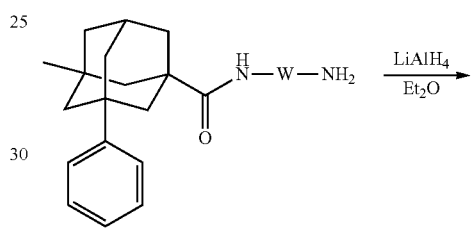

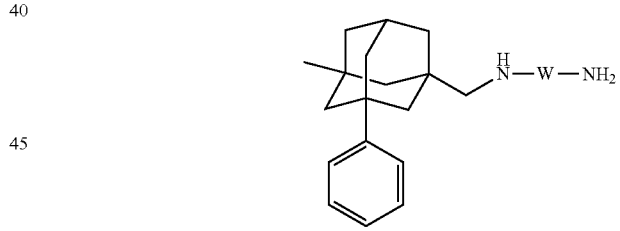

To a solution of starting amide prepared by following general procedure 1 above (35 mg, 0.1 mmol) in diethyl ether (2 mL) is added 0.1 mL of 1.6M lithium aluminum hydride solution in diethyl ether. The ethereal solution is brought to reflux, stirred for 12 hours, and then cooled to 0° C. 10 uL water is then added, followed by 10 uL 15% aqueous NaOH solution, and finally 30 uL of water. The resulting mixture is stirred until an easily filtered solid is formed, and then filtered. The filtrate is concentrated in vacuo and the residue purified by preparative HPLC.

Examples B1 to B16 and B58 were prepared from (1S, 3R,5R,7S)-3-methyl-5-phenyladamantane-1-carboxylic acid using general procedure 1.

Examples C1 to C16 and C58 were prepared from (1R, 3S,5S,7R)-3-methyl-5-phenyladamantane-1-carboxylic acid using general procedure 1.

| Ex. | Starting materials | Product/Name | Analytical Data |
|---|---|---|---|
| A1 | tert-butyl 4-amino piperidine-1-carboxylate rac-3-methyl-5-phenyladamantane-1-carboxylic acid | rac-3-methyl-5-phenyl-N-(piperidin-4-yl)adamantane-1-carboxamide | $^1$H NMR (300 MHz, CDCl$_3$) δ 7.37-7.29 (m, 4H), 7.21-7.16 (m, 1H), 5.73 (d, 0.6H), 5.50 (dd, 0.4H), 4.28 (d, 0.4H), 4.07-3.91 (m, 1H), 3.60 (d, 0.6H), 3.42 (d, 1H), 3.03-2.86 (m, 2H), 2.30 (br. s, 1H), 2.23-2.00 (m, 2H), 1.91-1.71 (m, 8H), 1.61 (br. s, 2H), 1.55 (br. s, 2H), 1.47 (br. s, 2H), 0.93 (s, 3H). LC/MS m/z: 353.39 (M + H)$^+$, 394.33 (M + H + CH$_3$CN)$^+$ |
| B1 | tert-butyl 4-amino piperidine-1-carboxylate (1S,3R,5R,7S)-3-methyl-5-phenyl adamantane-1-carboxylic acid | (1S,3R,5R,7S)-3-methyl-5-phenyl-N-(piperidin-4-yl) adamantane-1-carboxamide | LC/MS m/z: 353.38(M + H)$^+$ |
| C1 | tert-butyl 4-amino piperidine-1-carboxylate (1R,3S,5S,7R)-3-methyl-5-phenyl adamantane-1-carboxylic acid | (1S,3R,5S,7R)-3-methyl-5-phenyl-N-(piperidin-4-yl) adamantane-1-carboxamide | LC/MS m/z: 353.38(M + H)$^+$ |
| A2 | trans-tert-butyl N-(4-aminocyclohexyl) carbamate rac-3-methyl-5-phenyladamantane-1-carboxylic acid | rac-trans-N-(4-aminocyclohexyl)-3-methyl-5-phenyl adamantane-1-carboxamide hydrochloride | $^1$H NMR (500 MHz, DMSO-d$_6$) δ 8.00 (br. s, 3H), 7.36 (d, 2H), 7.30 (t, 2H), 7.20 (d, 1H), 7.16 (t, 1H), 3.54-3.47 (m, 1H), 2.91-2.86 (m, 1H), 2.20-2.15 (m, 1H), 1.97-1.90 (m, 2H), 1.81-1.64 (m, 8H), 1.54-1.44 (m, 4H), 1.40 (br. s, 2H), 1.37-1.22 (m, 4H), 0.87 (s, 3H). LC/MS m/z: 367.42(M + H)$^+$, 408.36 (M + H + CH$_3$CN)$^+$, 733.73 (2M + H)$^+$ |
| B2 | trans-tert-butyl N-(4-aminocyclohexyl) carbamate (1S,3R,5R,7S)-3-methyl-5-phenyl adamantane-1-carboxylic acid | (1S,3R,5R,7S)-trans-N-(4-aminocyclohexyl)-3-methyl-5-phenyladamantane-1-carboxamide hydrochloride | $^1$H NMR (500 MHz, DMSO-d$_6$) δ 7.82 (br. s, 3H), 7.36 (dd, 2H), 7.30 (t, 2H), 7.20-7.15 (m, 2H), 3.54-3.47 (m, 1H), 2.93-2.86 (m, 1H), 2.20-2.15 (m, 1H), 1.94-1.89 (m, 2H), 1.81-1.64 (m, 8H), 1.55-1.44 (m, 4H), 1.40 (br. s, 2H), 1.37-1.23 (m, 4H), 0.88 (s, 3H).LC/MS m/z: 367.40 (M + H)$^+$, 408.40 (M + H + CH$_3$CN)$^+$, 733.74 (2M + H)$^+$ |

| Ex. | Starting materials | Product/Name | Analytical Data |
|---|---|---|---|
| C2 | trans-tert-butyl N-(4-aminocyclohexyl) carbamate (1R,3S,5S,7R)-3-methyl-5-phenyl adamantane-1-carboxylic acid | (1R,3S,5S,7R)-trans-N-(4-aminocyclohexyl)-3-methyl-5-phenyladamantane-1-carboxamide | $^1$H NMR (500 MHz, DMSO-d$_6$) δ 7.38-7.27 (m, 4H), 7.16 (t, 1H), 7.08 (d, 1H), 3.54-3.43 (m, 1H), 2.46-2.41 (m, 1H), 2.20-2.14 (m, 1H), 1.82-1.59 (m, 10H), 1.54-1.44 (m, 4H), 1.39 (br. s, 2H), 1.30-1.16 (m, 2H), 1.09-0.96 (m, 2H), 0.87 (s, 3H). LC/MS m/z: 367.44 (M + H)$^+$, 408.45 (M + H + CH$_3$CN)$^+$ |
| A3 | trans-tert-butyl N-[(4-amino cyclo hexyl)methyl] carbamate rac-3-methyl-5-phenyladamantane-1-carboxylic acid | rac-trans-N-[4-(aminomethyl)cyclohexyl]-3-methyl-5-phenyladamantane-1-carboxamide | $^1$H NMR (300 MHz, CDCl$_3$) δ 8.17 (br. s, 2H), 7.37-7.27 (m, 4H), 7.21-7.15 (m, 1H), 5.72 (d, 0.7H), 5.45 (d, 0.3H), 3.78-3.61 (m, 1H), 3.00-2.91 (m, 2H), 2.90-2.80 (m, 1H), 2.33-2.24 (m, 1H), 2.01-1.69 (m, 10H), 1.61-1.51 (m, 4H), 1.49-1.41 (m, 2H), 1.24-1.07 (m, 4H), 0.93 (s, 0.9H), 0.91 (s, 2.1H).LC/MS m/z: 381.39 (M + H)$^+$, 422.34 (M + H + CH$_3$CN)$^+$ |
| B3 | trans-tert-butyl N-[(4-aminocyclohexyl)methyl]carbamate (1S,3R,5R,7S)-3-methyl-5-phenyl adamantane-1-carboxylic acid | (1S,3R,5R,7S)-trans-N-[4-(aminomethyl)cyclohexyl]-3-methyl-5-phenyl adamantane-1-carboxamide | LC/MS m/z: 381.41(M + H)$^+$ |
| C3 | trans-tert-butyl N-[(4-aminocyclohexyl)methyl]carbamate (1R,3S,5S,7R)-3-methyl-5-phenyl adamantane-1-carboxylic acid | (1R,3S,5S,7R)-trans-N-[4-(aminomethyl)cyclohexyl]-3-methyl-5-phenyl adamantane-1-carboxamide | LC/MS m/z: 381.39(M + H)$^+$ |

| Ex. | Starting materials | Product/Name | Analytical Data |
|---|---|---|---|
| A4 | cis-tert-butyl-4-amino-2-methyl piperidine-1-carboxylate rac-3-methyl-5-phenyladamantane-1-carboxylic acid | rac-3-methyl-N-[(2S*,4S*)-2-methylpiperidin-4-yl]-5-phenyladamantane-1-carboxamide | $^1$H NMR (300 MHz, CDCl$_3$) δ 7.37-7.29 (m, 4H), 7.21-7.16 (m, 1H), 5.50 (d, 0.8H), 5.38 (d, 0.2H), 4.09-3.85 (m, 1H), 3.32-2.96 (m, 3H), 2.92-2.84 (m, 1H), 2.78 (td, 1H), 2.34-2.25 (m, 1H), 2.03-1.76 (m, 8H), 1.61 (br. s, 2H), 1.55 (br. s, 2H), 1.50-1.44 (m, 2H), 1.34 (d, 0.6H), 1.22 (d, 2.4H), 0.93 (s, 3H). LC/MS m/z: 367.34 (M + H)$^+$ |
| B4 | cis-tert-butyl-4-amino-2-methyl piperidine-1-carboxylate (1S,3R,5R,7S)-3-methyl-5-phenyl adamantane-1-carboxylic acid | (1S,3R,5R,7S)-3-methyl-N-[(2S*,4S*)-2-methylpiperidin-4-yl]-5-phenyladamantane-1-carboxamide | LC/MS m/z: 367.41(M + H)$^+$ |
| C4 | cis-tert-butyl-4-amino-2-methyl piperidine-1-carboxylate (1R,3S,5S,7R)-3-methyl-5-phenyl adamantane-1-carboxylic acid | (1R,3S,5S,7R)-3-methyl-N-[(2S*,4S*)-2-methyl piperidin-4-yl]-5-phenyl adamantane-1-carboxamide | LC/MS m/z: 367.50 (M + H)$^+$ |
| A5 | trans-tert-butyl-4-amino-3-fluoro piperidine-1-carboxylate rac-3-methyl-5-phenyladamantane-1-carboxylic acid | rac-N-[(3R*,4R*)-3-fluoro piperidin-4-yl]-3-methyl-5-phenyladamantane-1-carboxamide | $^1$H NMR (300 MHz, CDCl$_3$) δ 7.26-7.39 (m, 4H) 7.13-7.22 (m, 1H) 5.62 (d, 1 H) 4.19-4.37 (m, 0.5H) 4.05-4.17 (m, 0.5H) 3.98-4.03 (m, 1H) 3.22-3.86 (m, 1H) 2.84-2.98 (m, 1H) 2.59-2.84 (m, 1H) 2.25-2.34 (m, 1H) 1.99-2.17 (m, 2H) 1.70-1.93 (m, 6H) 1.51-1.67 (m, 4H) 1.19-1.40 (m, 2H) 0.93 (s, 3H). LC/MS m/z: 371.40 (M + H)$^+$ |

-continued

| Ex. | Starting materials | Product/Name | Analytical Data |
|---|---|---|---|
| B5 | tert-butyl (3R,4R)-4-amino-3-fluoro piperidine-1-carboxylate (1S,3R,5R,7S)-3-methyl-5-phenyl adamantane-1-carboxylic acid | (1S,3R,5R,7S)-N-[(3R,4R)-3-fluoropiperidin-4-yl]-3-methyl-5-phenyladamantane-1-carboxamide | LC/MS m/z: 371.39 (M + H)+ |
| C5 | tert-butyl (3R,4R)-4-amino-3-fluoro piperidine-1-carboxylate (1R,3S,5S,7R)-3-methyl-5-phenyl adamantane-1-carboxylic acid | (1R,3S,5S,7R)-N-[(3R,4R)-3-fluoropiperidin-4-yl]-3-methyl-5-phenyl adamantane-1-carboxamide | LC/MS m/z: 371.38 (M + H)+ |
| B6 | tert-butyl (3S,4S)-4-amino-3-fluoro piperidine-1-carboxylate (1S,3R,5R,7S)-3-methyl-5-phenyl adamantane-1-carboxylic acid | (1S,3R,5R,7S)-N-[(3S,4S)-3-fluoropiperidin-4-yl]-3-methyl-5-phenyl adamantane-1-carboxamide | LC/MS m/z: 371.35 (M + H)+ |
| C6 | tert-butyl (3S,4S)-4-amino-3-fluoro piperidine-1-carboxylate (1R,3S,5S,7R)-3-methyl-5-phenyl adamantane-1-carboxylic acid | (1R,3S,5S,7R)-N-[(3S,4S)-3-fluoropiperidin-4-yl]-3-methyl-5-phenyl adamantane-1-carboxamide | LC/MS m/z: 371.35 (M + H)+ |

-continued

| Ex. | Starting materials | Product/Name | Analytical Data |
|---|---|---|---|
| B7 | tert-butyl piperidin-4-ylcarbamate (1S,3R,5R,7S)-3-methyl-5-phenyl adamantane-1-carboxylic acid | 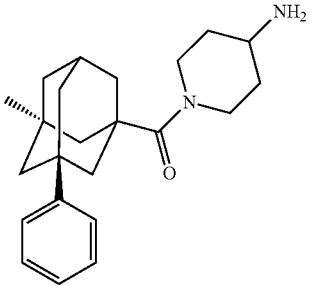<br>(4-aminopiperidin-1-yl)((1S,3R,5R,7S)-3-methyl-5-phenyladamantan-1-yl)methanone | LC/MS m/z: 353.38 (M + H)+ |
| C7 | tert-butyl piperidin-4-ylcarbamate (1R,3S,5S,7R)-3-methyl-5-phenyl adamantane-1-carboxylic acid | 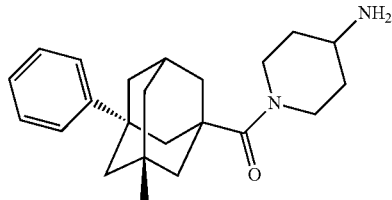<br>(4-aminopiperidin-1-yl)((1R,3S,5S,7R)-3-methyl-5-phenyladamantan-1-yl)methanone | LC/MS m/z: 353.38 (M + H)+ |
| B8 | tert-butyl (3,3-dimethylpiperidin-4-yl)carbamate (1S,3R,5R,7S)-3-methyl-5-phenyl adamantane-1-carboxylic acid | 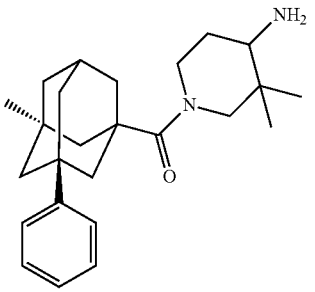<br>rac-(4-amino-3,3-dimethylpiperidin-1-yl)((1S,3R,5R,7S)-3-methyl-5-phenyladamantan-1-yl)methanone | LC/MS m/z: 381.41 (M + H)+ |
| C8 | tert-butyl (3,3-dimethylpiperidin-4-yl)carbamate (1R,3S,5S,7R)-3-methyl-5-phenyl adamantane-1-carboxylic acid | 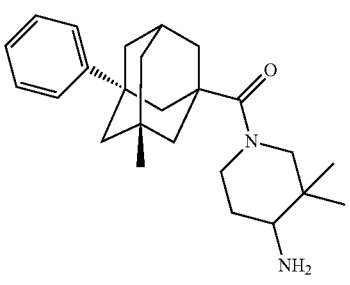<br>rac-(4-amino-3,3-dimethylpiperidin-1-yl)((1R,3S,5S,7R)-3-methyl-5-phenyladamantan-1-yl)methanone | LC/MS m/z: 381.41 (M + H)+ |

| Ex. | Starting materials | Product/Name | Analytical Data |
|---|---|---|---|
| B9 | tert-butyl (5-azaspiro[2.5]octan-8-yl)carbamate (1S,3R,5R,7S)-3-methyl-5-phenyl adamantane-1-carboxylic acid | 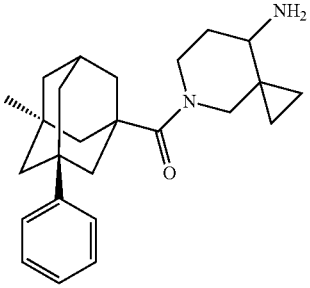<br>rac-(8-amino-5-azaspiro[2.5]octan-5-yl)((1S,3R,5R,7S)-3-methyl-5-phenyladamantan-1-yl)methanone | LC/MS m/z: 379.44 (M + H)⁺ |
| C9 | tert-butyl (5-azaspiro[2.5]octan-8-yl)carbamate (1R,3S,5S,7R)-3-methyl-5-phenyl adamantane-1-carboxylic acid | 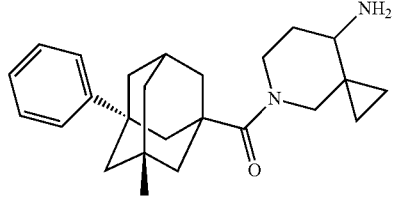<br>rac-(8-amino-5-azaspiro[2.5]octan-5-yl)((1R,3S,5S,7R)-3-methyl-5-phenyladamantan-1-yl)methanone | LC/MS m/z: 379.44 (M + H)⁺ |
| B10 | tert-butyl 1,8-diazaspiro[4.5]decane-1-carboxylate (1S,3R,5R,7S)-3-methyl-5-phenyl adamantane-1-carboxylic acid | 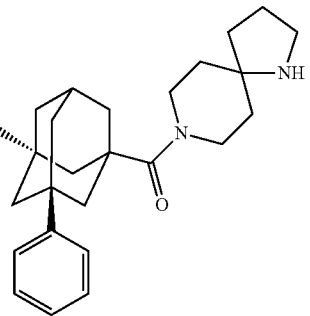<br>((1S,3R,5R,7S)-3-methyl-5-phenyladamantan-1-yl)(1,8-diazaspiro[4.5]decan-8-yl)methanone | LC/MS m/z: 393.41 (M + H)⁺ |
| C10 | tert-butyl 1,8-diazaspiro[4.5]decane-1-carboxylate (1R,3S,5S,7R)-3-methyl-5-phenyl adamantane-1-carboxylic acid | 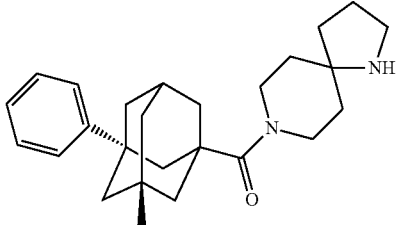<br>((1R,3S,5S,7R)-3-methyl-5-phenyladamantan-1-yl)(1,8-diazaspiro[4.5]decan-8-yl)methanone | LC/MS m/z: 393.41 (M + H)⁺ |

-continued

| Ex. | Starting materials | Product/Name | Analytical Data |
|---|---|---|---|
| B11 | tert-butyl (2-azaspiro[3.3]heptan-6-yl)-carbamate (1S,3R,5R,7S)-3-methyl-5-phenyl adamantane-1-carboxylic acid | 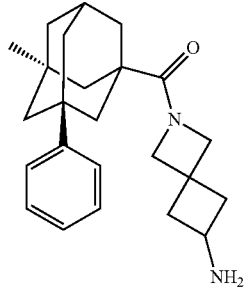<br>(6-amino-2-azaspiro[3.3]heptan-2-yl)((1S,3R,5R,7S)-3-methyl-5-phenyladamantan-1-yl)methanone | LC/MS m/z: 365.49 (M + H)$^+$ |
| C11 | tert-butyl (2-azaspiro[3.3]heptan-6-yl)-carbamate (1R,3S,5S,7R)-3-methyl-5-phenyl adamantane-1-carboxylic acid | 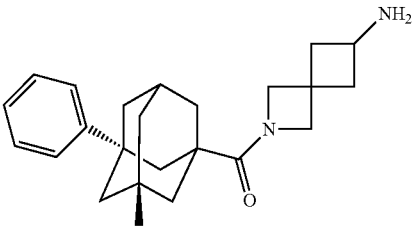<br>(6-amino-2-azaspiro[3.3]heptan-2-yl)((1R,3S,5S,7R)-3-methyl-5-phenyladamantan-1-yl)methanone | LC/MS m/z: 365.41 (M + H)$^+$ |
| B12 | tert-butyl (R)-(3,3-dimethylpiperidin-4-yl)carbamate (1S,3R,5R,7S)-3-methyl-5-phenyl adamantane-1-carboxylic acid | 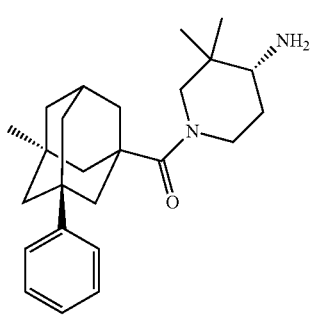<br>((R)-4-amino-3,3-dimethylpiperidin-1-yl)((1S,3R,5R,7S)-3-methyl-5-phenyladamantan-1-yl)methanone | LC/MS m/z: 381.42 (M + H)$^+$ |

-continued

| Ex. | Starting materials | Product/Name | Analytical Data |
|---|---|---|---|
| B13 | tert-butyl (S)-(3,3-dimethylpiperidin-4-yl)carbamate (1S,3R,5R,7S)-3-methyl-5-phenyl adamantane-1-carboxylic acid | 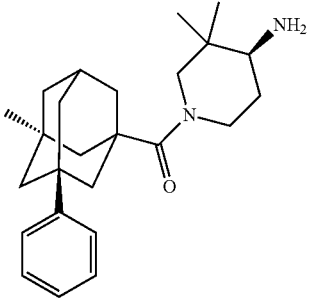<br>((S)-4-amino-3,3-dimethylpiperidin-1-yl)((1S,3R,5R,7S)-3-methyl-5-phenyladamantan-1-yl)methanone | LC/MS m/z: 381.47 (M + H)+ |
| B14 | tert-butyl (2R,4R)-4-amino-2-methylpiperidine-1-carboxylate (1S,3R,5R,7S)-3-methyl-5-phenyl adamantane-1-carboxylic acid | 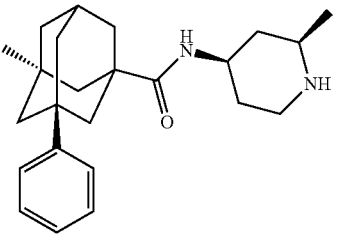<br>(1S,3R,5R,7S)-3-methyl-N-((2R,4R)-2-methylpiperidin-4-yl)-5-phenyladamantane-1-carboxamide | LC/MS m/z: 367.41 (M + H)+ |
| B15 | tert-butyl (2S,4S)-4-amino-2-methylpiperidine-1-carboxylate (1S,3R,5R,7S)-3-methyl-5-phenyl adamantane-1-carboxylic acid | 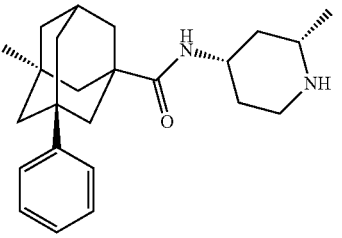<br>(1S,3R,5R,7S)-3-methyl-N-((2S,4S)-2-methylpiperidin-4-yl)-5-phenyladamantane-1-carboxamide | LC/MS m/z: 367.46 (M + H)+ |
| B16 | trans-tert-butyl N-(4-aminocyclohexyl)carbamate (1S,3R,5R,7S)-3-ethyl-5-phenyladamantane-1-carboxylic acid | 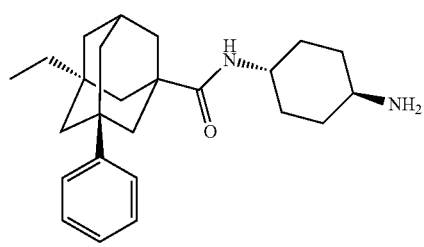<br>(1S,3R,5R,7S)-trans-N-(4-aminocyclohexyl)-3-ethyl-5-phenyladamantane-1-carboxamide | LC/MS m/z: 381.42 (M + H)+, 422.48 (M + H + CH3CN)+ |

-continued

| Ex. | Starting materials | Product/Name | Analytical Data |
|---|---|---|---|
| C16 | trans-tert-butyl N-(4-aminocyclohexyl) carbamate (1R,3S,5S,7R)-3-ethyl-5-phenyl adamantane-1-carboxylic acid | (1R,3S,5S,7R)-trans-N-(4-aminocyclohexyl)-3-ethyl-5-phenyladamantane-1-carboxamide | LC/MS m/z: 381.42 (M + H)+, 422.48 (M + H + CH3CN)+ |

Examples A17 to A57 were prepared from the appropriate starting material using General procedure 1.

| Ex. | Starting materials | Product/Name | Analytical Data |
|---|---|---|---|
| A17 | trans-tert-butyl-4-amino-3-fluoropiperidine-1-carboxylate rac-3-ethyl-5-phenyladamantane-1-carboxylic acid | rac-3-ethyl-N-[(3R*,4R*)-3-fluoropiperidin-4-yl]-5-phenyladamantane-1-carboxamide | LC/MS m/z: 385.41 (M + H)+ |
| A18 | tert-butyl (3R,4R)-4-amino-3-fluoro piperidine-1-carboxylate rac-3-ethyl-5-phenyladamantane-1-carboxylic acid | rac-3-ethyl-N-[(3R,4R)-3-fluoropiperidin-4-yl]-5-phenyladamantane-1-carboxamide | LC/MS m/z: 385.38 (M + H)+ |
| A19 | tert-butyl (3S,4S)-4-amino-3-fluoropiperidine-1-carboxylate rac-3-ethyl-5-phenyladamantane-1-carboxylic acid | rac-3-ethyl-N-[(3S,4S)-3-fluoropiperidin-4-yl]-5-phenyladamantane-1-carboxamide | LC/MS m/z: 385.38 (M + H)+ |

-continued

| Ex. | Starting materials | Product/Name | Analytical Data |
|---|---|---|---|
| A20 | tert-butyl 4-amino-3,3-dimethylpiperidine-1-carboxylate rac-3-ethyl-5-phenyl adamantane-1-carboxylic acid | 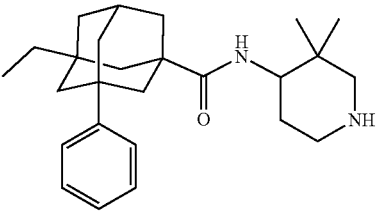 [SMILES: CCC12CC3CC(C(=O)NC4CCNCC4(C)C)(C1)CC(c1ccccc1)(C3)C2]<br>rac-N-(3,3-dimethylpiperidin-4-yl)-3-ethyl-5-phenyl adamantane-1-carboxamide | LC/MS m/z:395.37 (M + H)+ |
| A21 | cis-tert-butyl-4-amino-2-methylpiperidine-1-carboxylate rac-3-ethyl-5-phenyl adamantane-1-carboxylic acid | 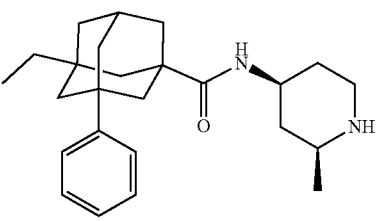 [SMILES: CCC12CC3CC(C(=O)N[C@H]4CCN[C@@H](C)C4)(C1)CC(c1ccccc1)(C3)C2]<br>rac-3-ethyl-N-[(2S*,4S*)-3-methylpiperidin-4-yl]-5-phenyl adamantane-1-carboxamide | LC/MS m/z: 381.42 (M + H)+ |
| A22 | trans-tert-butyl N-[(4-aminocyclohexyl)methyl]carbamate rac-3-ethyl-5-phenyladamantane-1-carboxylic acid | 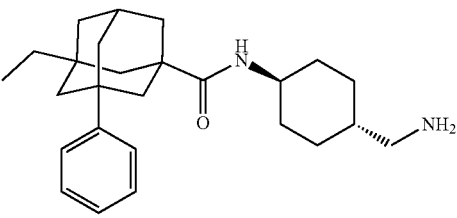<br>rac-trans-4-(aminometyl)-N-[(3-ethyl-5-phenyladamantan-1-yl)methyl]cyclohexan-1-amine | LC/MS m/z: 395.36 (M + H)+<br>436.40 (M + H + CH$_3$CN)+ |
| A23 | tert-butyl (3S*,4R*)-4-amino-3-fluoro piperidine-1-carboxylate rac-3-ethyl-5-phenyl adamantane-1-carboxylic acid | 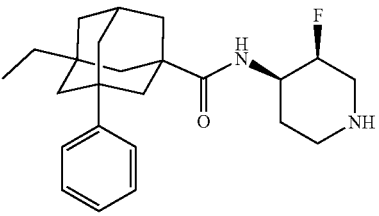<br>rac-3-ethyl-N-[(3S*,4R*)-3-fluoropiperidin-4-yl]-5-phenyl adamantane-1-carboxamide | LC/MS m/z: 385.35 (M + H)+ |
| A24 | tert-butyl N-[(3S*,4S*)-3-fluoropiperidin-4-yl]carbamate rac-3-ethyl-5-phenyl adamantane-1-carboxylic acid | 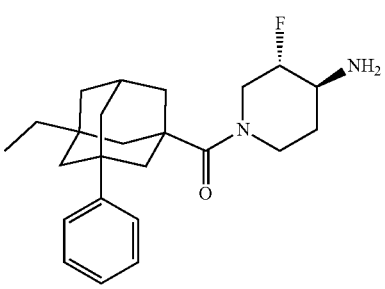<br>rac-(3S*,4S*)-1-[(3-ethyl-5-phenyladamantan-1-yl)carbonyl]-3-fluoropiperidin-4-amine | LC/MS m/z: 385.41 (M + H)+ |

-continued

| Ex. | Starting materials | Product/Name | Analytical Data |
|---|---|---|---|
| A25 | tert-butyl (3R*,4R*)-4-amino-3-hydroxy piperidine-1-carboxylate rac-3-ethyl-5-phenyl adamantane-1-carboxylic acid | rac-3-ethyl-N-(3R*,4R*)-3-hydroxypiperidin-4-yl]-5-phenyladamantan-1-carboxamide | LC/MS m/z: 383.42 (M + H)+ |
| A26 | tert-butyl 4-amino-4-methylpiperidine-1-carboxylate rac-3-ethyl-5-phenyladamantane-1-carboxylic acid | rac-3-ethyl-N-(4-methyl)piperidin-4-yl)-5-phenyl adamantane-1-carboxamide | LC/MS m/z: 381.36 (M + H)+ |
| A27 | tert-butyl 7-amino-2-azaspiro[3.5]nonane-2-carboxylate rac-3-ethyl-5-phenyladamantane-1-carboxylic acid | rac-N-{2-azaspiro[3.5]nonan-7-yl}-3-ethyl-5-phenyl adamantane-1-carboxamid | LC/MS m/z: 407.44 (M + H)+ |
| A28 | trans-tert-butyl N-(4-aminocyclohexyl)carbamate rac-3-(fluoromethyl)-5-phenyladamantane-1-carboxylic acid | rac-trans-N-(4-aminocyclohexyl)-3-(fluoromethyl)-5-phenyladamantane-1-carboxamide | LC/MS m/z: 385.42 (M + H)+ 769.70 (2M + H)+ |
| A29 | trans-tert-butyl N-(4-aminocyclohexyl) carbamate rac-3-(ethoxymethyl)-5-phenyladamantane-1-carboxylic acid | rac-trans-N-(4-aminocyclohexyl)-3-(ethoxymethyl)-5-phenyladamantane-1-carboxamide | LC/MS m/z: 411.45 (M + H)+ |

| Ex. | Starting materials | Product/Name | Analytical Data |
|---|---|---|---|
| A30 | tert-butyl 6-amino-2-azabicyclo[2.2.1]heptane-2-carboxylate rac-3-methyl-5-phenyladamantane-1-carboxylic acid | N-{2-azabicyclo[2.2.1]heptan-6-yl}-3-methyl-5-phenyl adamantane-1-carboxamide | LC/MS m/z: 365.34 (M + H)+ |
| A31 | tert-butyl 5-amino-2-azabicyclo[2.2.1]heptane-2-carboxylate rac-3-methyl-5-phenyladamantane-1-carboxylic acid | N-{2-azabicyclo[2.2.1]heptan-5-yl}-3-methyl-5-phenyl adamantane-1-carboxamide | LC/MS m/z: 365.35 (M + H)+ |
| A32 | tert-butyl (piperidin-4-yl) carbamate rac-3-ethyl-5-phenyl adamantane-1-carboxylic acid | (4-aminopiperidin-1-yl)(3-ethyl-5-phenyladamantan-1-yl)methanone | LC/MS m/z: 367.40 (M + H)+ |
| A33 | tert-butyl (piperidin-4-yl) carbamate rac-3-methyl-5-phenyl adamantane-1-carboxylic acid | (4-aminopiperidin-1-yl)(3-methyl-5-phenyladamantan-1-yl)methanone | LC/MS m/z: 353.39 (M + H)+ |
| A34 | tert-butyl 1,4-diazepane-1-carboxylate rac-3-methyl-5-phenyladamantane-1-carboxylic acid | (1,4-diazepan-1-yl) (3-methyl-5-phenyladamantan-1-yl) methanone | LC/MS m/z: 353.38 (M + H)+ |

| Ex. | Starting materials | Product/Name | Analytical Data |
|---|---|---|---|
| A35 | tert-butyl (3,3-dimethylpiperidin-4-yl)carbamate rac-3-methyl-5-phenyl adamantane-1-carboxylic acid | 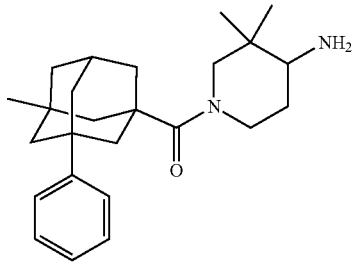 (4-amino-3,3-dimethylpiperidin-1-yl) (3-methyl-5-phenyladamantan-1-yl) methanone | LC/MS m/z: 381.42 (M + H)+ |
| A36 | tert-butyl 3-ethylpiperazine-1-carboxylate rac-3-methyl-5-phenyl adamantane-1-carboxylic acid | 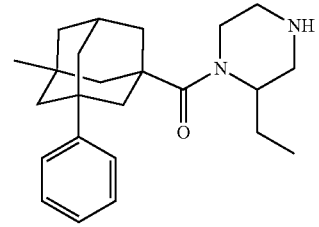 (2-ethylpiperazin-1-yl)(3-methyl-5-phenyladamantan-1-yl)methanone | LC/MS m/z: 367.37 (M + H)+ |
| A37 | tert-butyl (4-methylpiperidin-4-yl)carbamate rac-3-methyl-5-phenyladamantane-1-carboxylic acid | 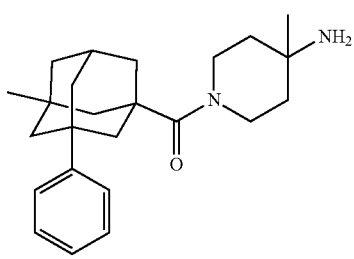 (4-amino-4-methylpiperidin-1-yl) (3-methyl-5-phenyladamantan-1-yl) methanone | LC/MS m/z: 367.24 (M + H)+ |
| A38 | tert-butyl 1,8-diazaspiro[4.5]decane-1-carboxylate rac-3-methyl-5-phenyl adamantane-1-carboxylic acid | 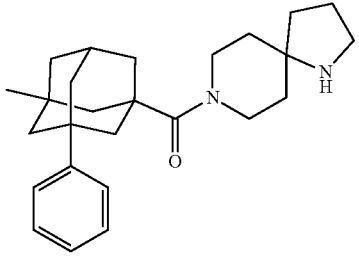 (3-methyl-5-phenyladamantan-1-yl) (1,8-diazaspiro[4.5]decan-8-yl) methanone | LC/MS m/z: 393.45 (M + H)+ |

-continued

| Ex. | Starting materials | Product/Name | Analytical Data |
|---|---|---|---|
| A39 | tert-butyl (3-methylpiperidin-4-yl) carbamate rac-3-methyl-5-phenyl adamantane-1-carboxylic acid | 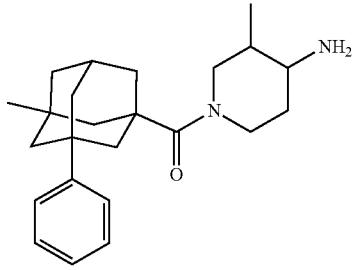<br>(4-amino-3-methylpiperidin 1-yl) (3-methyl-5-phenyladamantan-1-yl) methanone | LC/MS m/z: 367.46 (M + H)+ |
| A40 | tert-butyl (3-methylpiperidin-4-yl) carbamate rac-3-methyl-5-phenyladamantane-1-carboxylic acid | 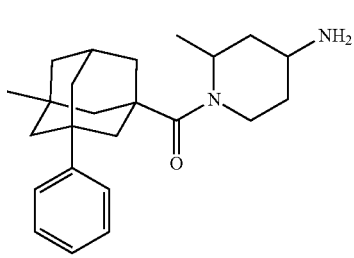<br>(4-amino-2-methylpiperidin 1-yl) (3-methyl-5-phenyladamantan-1-yl) methanone | LC/MS m/z: 367.35 (M + H)+ |
| A41 | tert-butyl (5-azaspiro[2.4]heptan-1-yl)carbamate rac-3-methyl-5-phenyladamantane-1-carboxylic acid | 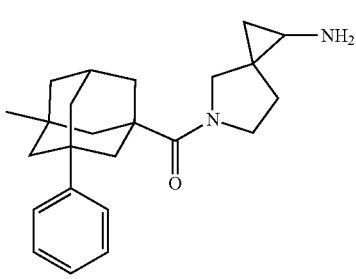<br>(1-amino-5-azaspiro[2.4]hepatan-5-yl) (3-methyl-5-phenyladamantan-1-yl) methanone | LC/MS m/z: 365.37 (M + H)+ |
| A42 | tert-butyl (8-azabicyclo[3.2.1]octan-3-yl)carbamate rac-3-methyl-5-phenyladamantane-1-carboxylic acid | 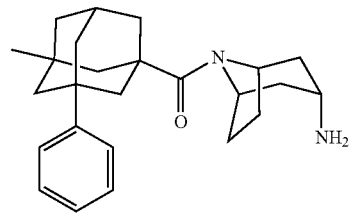<br>3-amino-8-azabicyclo[3.2.1]octan-8-yl) (3-methyl-5-phenyladamantan-1-yl) methanone | LC/MS m/z: 379.45 (M + H)+ |

| Ex. | Starting materials | Product/Name | Analytical Data |
|---|---|---|---|
| A43 | tert-butyl azepan-4-ylcarbamate rac-3-methyl-5-phenyl adamantane-1-carboxylic acid | (4-aminoazepan-1-yl) (3-methyl-5-phenyladamantan-1-yl) methanone | LC/MS m/z: 367.45 (M + H)+ |
| A44 | tert-butyl 2,7-diazaspiro[3.5]nonane-7-carboxylate rac-3-methyl-5-phenyladamantane-1-carboxylic acid | (3-methyl-5-phenyladamantan-1-yl) (2,7-diazaspiro[3.5]nonan-2-yl) methanone | LC/MS m/z: 379.45 (M + H)+ |
| A45 | tert-butyl-hexahydropyrrolo[3,4-c]pyrrole-2(1H)-carboxylate rac-3-methyl-5-phenyladamantane-1-carboxylic acid | (hexahydropyrrolo[3,4-c]pyrrol-2(1H)-yl) (3-methyl-5-phenyladamantan-1-yl) methanone | LC/MS m/z: 365.32 (M + H)+ |
| A46 | tert-butyl (4-(hydroxymethyl)piperidin-4-yl)carbamate rac-3-methyl-5-phenyl adamantane-1-carboxylic acid | ((4-amino-4-(hydroxymethyl)piperidin-1-yl (3-methyl-5-phenyladamantan-1-yl) methanone | LC/MS m/z: 383.37 (M + H)+ |

| Ex. | Starting materials | Product/Name | Analytical Data |
|---|---|---|---|
| A47 | tert-butyl 2,6-diazaspiro[3.3]heptane-2-carboxylate rac-3-methyl-5-phenyladamantane-1-carboxylic acid | 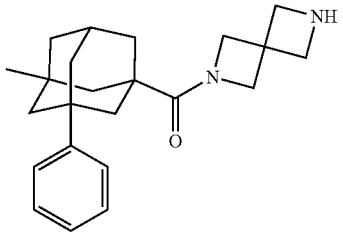<br>(3-methyl-5-phenyladamantan-1-yl) (2,6-diazaspiro[3.3]heptan-2-yl) methanone | LC/MS m/z: 351.37 (M + H)+ |
| A48 | tert-butyl 2,7-diazaspiro[3.5]nonane-2-carboxylate rac-3-methyl-5-phenyladamantane-1-carboxylic acid | 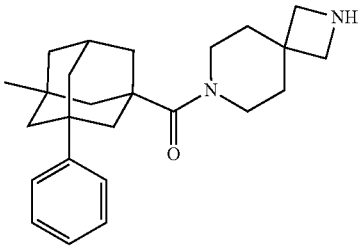<br>(3-methyl-5-phenyladamantan-1-yl) (2,7-diazaspiro[3.3]nonan-7-yl) methanone | LC/MS m/z: 379.43 (M + H)+ |
| A49 | tert-butyl 2,6-diazaspiro[3.4]octane-6-carboxylate rac-3-methyl-5-phenyladamantane-1-carboxylic acid | 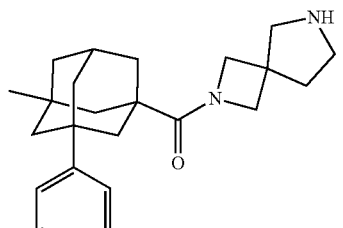<br>(3-methyl-5-phenyladamantan-1-yl) (2,6-diazaspiro[3.4]octan-2-yl) methanone | LC/MS m/z: 365.43 (M + H)+ |
| A50 | tert-butyl 3,9-diazaspiro[5.5]undecane-3-carboxylate rac-3-methyl-5-phenyladamantane-1-carboxylic acid | 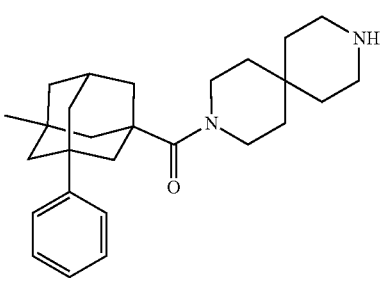<br>(3-methyl-5-phenyladamantan-1-yl) (3,9-diazaspiro[5.5]undecan-3-yl) methanone | LC/MS m/z: 407.45 (M + H)+ |

| Ex. | Starting materials | Product/Name | Analytical Data |
|---|---|---|---|
| A51 | tert-butyl 1,7-diazaspiro[3.5]nonane-1-carboxylate<br>rac-3-methyl-5-phenyladamantane-1-carboxylic acid | 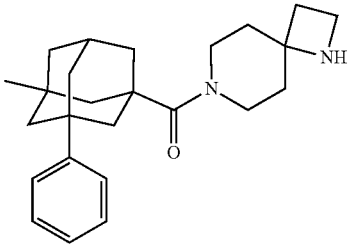<br>(3-methyl-5-phenyladamantan-1-yl) (1,7-diazaspiro[3.5]nonan-7-yl) methanone | LC/MS m/z: 379.44 (M + H)+ |
| A52 | tert-butyl 4-amino-3,3-dimethylpiperidine-1-carboxylate<br>rac-3-ethyl-5-phenyl adamantane-1-carboxylic acid | 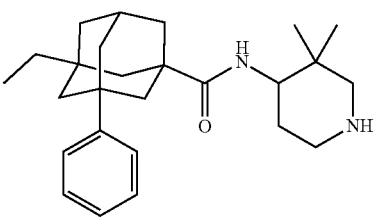<br>rac-N-(3,3-dimethylpiperidin-4-yl)-3-ethyl-5-phenyl adamantane-1-carboxamide | LC/MS m/z: 395.37 (M + H)+ |
| A53 | trans-tert-butyl N-(4-aminocyclohexyl) carbamate<br>rac-3-cyano-5-phenyladamantane-1-carboxylic acid | 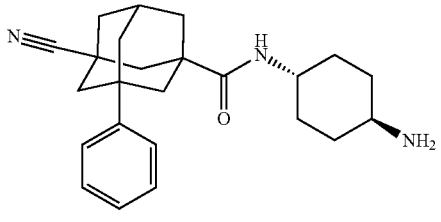<br>N-(4-aminocyclohexyl)-3-cyano-5-phenyladamantane-1-carboxamide | LC/MS m/z: 378.48 (M + H)+<br>419.38 (M + H + CH$_3$CN)+ |
| A54 | tert-butyl (S)-pyrrolidin-3-ylcarbamate<br>rac-3-methyl-5-phenyladamantane-1-carboxylic acid | 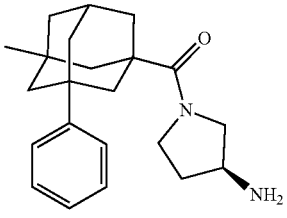<br>((S)-3-aminopyrrolidin-1-yl)(3-methyl-5-phenyladamantan-1-yl)methanone | LC/MS m/z: 339.36 (M + H)+ |
| A55 | tert-butyl (R)-pyrrolidin-3-ylcarbamate<br>rac-3-methyl-5-phenyladamantane-1-carboxylic acid | 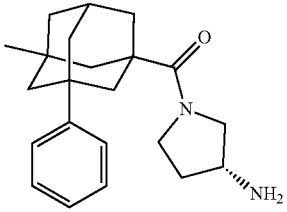<br>((R)-3-aminopyrrolidin-1-yl)(3-methyl-5-phenyladamantan-1-yl)methanone | LC/MS m/z: 339.31 (M + H)+ |

-continued

| Ex. | Starting materials | Product/Name | Analytical Data |
|---|---|---|---|
| A56 | tert-butyl (S)-piperidin-3-ylcarbamate<br>rac-3-methyl-5-phenyladamantane-1-carboxylic acid | ((S)-3-aminopiperidin-1-yl)(3-methyl-5-phenyladamantan-1-yl)methanone | LC/MS m/z: 353.35 (M + H)+ |
| A57 | tert-butyl (R)-piperidin-3-ylcarbamate<br>rac-3-methyl-5-phenyladamantane-1-carboxylic acid | ((R)-3-aminopiperidin-1-yl)(3-methyl-5-phenyladamantan-1-yl)methanone | LC/MS m/z: 353.35 (M + H)+ |

Examples A58 through A60, B58, and C58 were prepared using general procedure 1 omitting cleavage of the Boc-group under acidic conditions.

| Ex. | Starting materials | Product/Name | Analytical Data |
|---|---|---|---|
| A58 | (3R)-1-azabicyclo[2.2.2]octan-3-amine<br>rac-3-methyl-5-phenyladamantane-1-carboxylic acid | rac-N-[(3R)-1-azabicyclo[2.2.2]octan-3-yl]-3-methyl-5-phenyl adamantane-1-carboxamide | $^1$H NMR (300 MHz, CDCl$_3$) δ 7.41 (d, 2H), 7.33 (t, 2H), 7.20 (t, 1H), 4.33 (br:s. 1H), 3.85-3.66 (m, 2H), 3.36 (t, 1H), 3.26-2.88 (m, 4H), 2.31 (br:s, 2H), 2.09-1.40 (m,15H), 0.95 (s, 3H). LC/MS m/z: 379.33 (M + H)+, 420.35 (M + H + CH$_3$CN) |
| B58 | (3R)-1-azabicyclo[2.2.2]octan-3-amine<br>(1S,3R,5R,7S)-3-methyl-5-phenyl adamantane-1-carboxylic acid | (1S,3R,5R,7S)-N-[(3R)-1-azabicyclo[2.2.2]octan-3-yl]-3-methyl-5-phenyl adamantane-1-carboxamide | LC/MS m/z: 379.40 (M + H)+ |

| Ex. | Starting materials | Product/Name | Analytical Data |
|---|---|---|---|
| C58 | (3R)-1-azabicyclo[2.2.2]octan-3-amine (1R,3S,5S,7R)-3-methyl-5-phenyl adamantane-1-carboxylic acid | (1R,3S,5S,7R)-N-[(3R)-1-azabicyclo[2.2.2]octan-3-yl]-3-methyl-5-phenyl adamantane-1-carboxamide | LC/MS m/z: 379.40 (M + H)+ |
| A59 | cis-octahydroindolizin-8-amine rac-3-methyl-5-phenyladamantane-1-carboxylic acid | 3-methyl-N-(cis-octahydroinolizin-8-yl)-5-phenyladamantane-1-carboxamide | LC/MS m/z: 393.42 (M + H)+ |
| A60 | quinuclidin-4-amine rac-3-methyl-5-phenyladamantane-1-carboxylic acid | 3-methyl-5-phenyl-N-(quinuclidin-4-yl)adamantane-1-carboxamide | LC/MS m/z: 379.43 (M + H)+ |

Examples A61 to A69, B69 to B71, and C69 to C71 were prepared from the appropriate starting materials using general procedure 2.

| Ex. | Starting materials | Product/Name | Analytical Data |
|---|---|---|---|
| A61 | | N-((3-ethyl-5-phenyladamantan-1-yl)methyl)-3,3-dimethylpiperidin-4-amine | LC/MS m/z: 381.50 (M + H)+ |

| Ex. | Starting materials | Product/Name | Analytical Data |
|---|---|---|---|
| A62 | | N-((3-ethyl-5-phenyladamantan-1-yl)methyl)piperidin-4-amine | LC/MS m/z: 353.45 (M + H)+ |
| A63 | | N-((3-ethyl-5-phenyladamantan-1-yl)methyl)-2-methylpiperidin-4-amine | LC/MS m/z: 367.37 (M + H)+ |
| A64 | | 4-(aminomethyl)-N-((3-ethyl-5-phenyladamantan-1-yl)methyl)-cyclohexan-1-amine | LC/MS m/z: 381.33 (M + H)+ |
| A65 | | $N^1$-(3-methyl-5-phenyladamantan-1-yl)methyl)-cyclohexan-1,4-diamine | LC/MS m/z: 353.44 (M + H)+ |
| A66 | | $N^1$-(3-ethyl-5-phenyladamantan-1-yl)methyl)cyclohexane-1,4-diamine | LC/MS m/z: 367.42 (M + H)+ |

| Ex. | Starting materials | Product/Name | Analytical Data |
|---|---|---|---|
| A67 | | 1-(3-phenyladamantan-1-yl)methyl)piperazine | LC/MS m/z: 311.30 (M + H)+ |
| A68 | | 1-(3-phenyladamantan-1-yl)methyl)piperazine-4-amine | LC/MS m/z: 325.35 (M + H)+ |
| A69 | | 1-(3-methyl-5-phenyladamantan-1-yl)methyl)piperazine-4-amine | LC/MS m/z: 339.34 (M + H)+ |
| B69 | | 1-(((1S,3R,5R,7S)-3-methyl-5-phenyladamantan-1-yl)methyl)piperidin-4-amine | LC/MS m/z: 339.39 (M + H)+ |
| C69 | | 1-(((1R,3S,5S,7R)-3-methyl-5-phenyladamantan-1-yl)methyl)piperidin-4-amine | LC/MS m/z: 339.41 (M + H)+ |

-continued

| Ex. | Starting materials | Product/Name | Analytical Data |
|---|---|---|---|
| B70 | | (S)-3,3-dimethyl-1-(((1S,3R,5R,7S)-3-methyl-5-phenyladamantan-1-yl)methyl)piperidin-4-amine | LC/MS m/z: 367.43 (M + H)+ |
| B71 | | (R)-3,3-dimethyl-1-(((1S,3R,5R,7S)-3-methyl-5-phenyladamantan-1-yl)methyl)piperidin-4-amine | LC/MS m/z: 367.43 (M + H)+ |
| C70 | | (S)-3,3-dimethyl-1-(((1R,3S,5S,7R)-3-methyl-5-phenyladamantan-1-yl)methyl)piperidin-4-amine | LC/MS m/z: 367.43 (M + H)+ |
| C71 | | (R)-3,3-dimethyl-1-(((1R,3S,5S,7R)-3-methyl-5-phenyladamantan-1-yl)methyl)piperidin-4-amine | LC/MS m/z: 367.43 (M + H)+ |

Following the general procedures above using the appropriate starting materials, the following examples can be made.
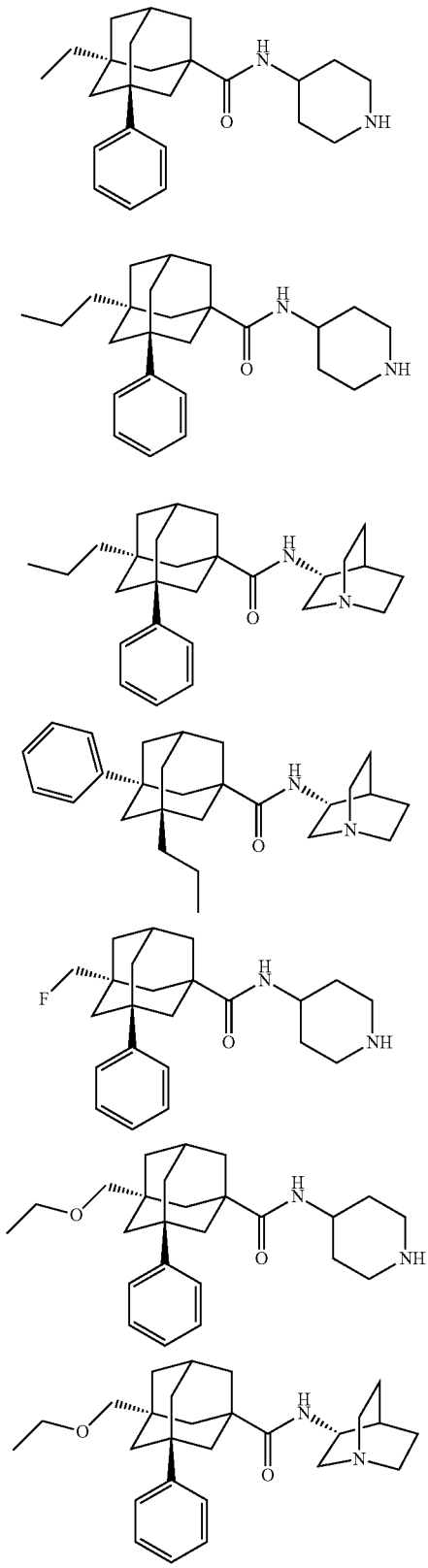
-continued
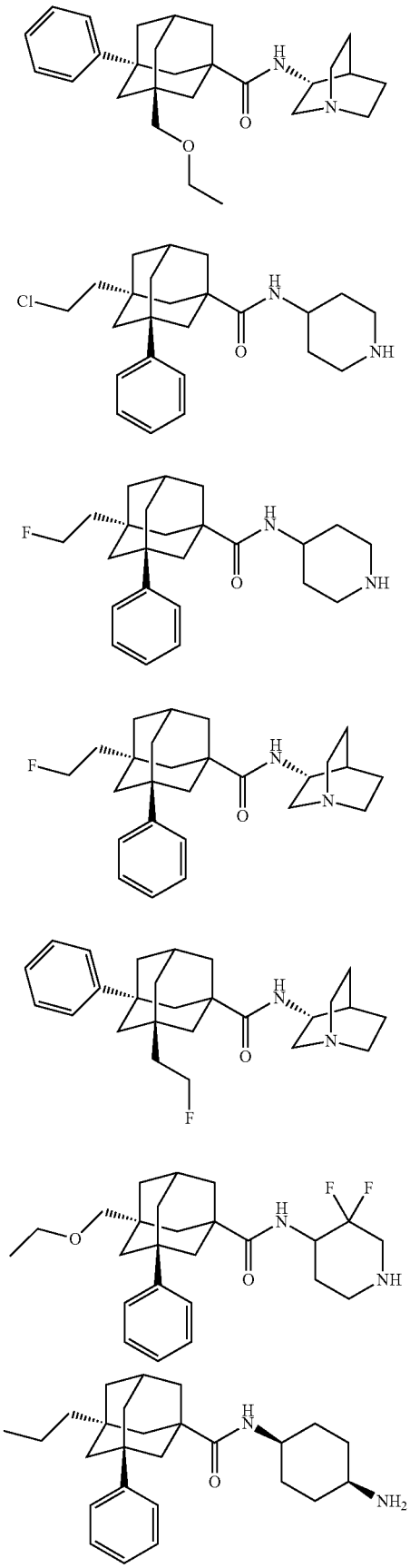

133
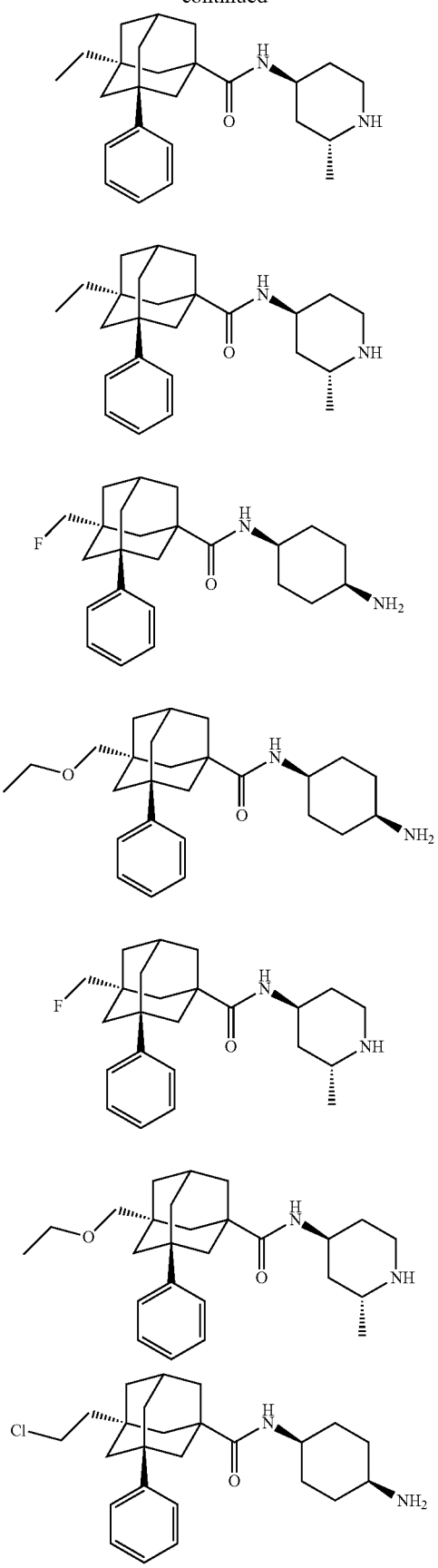
134
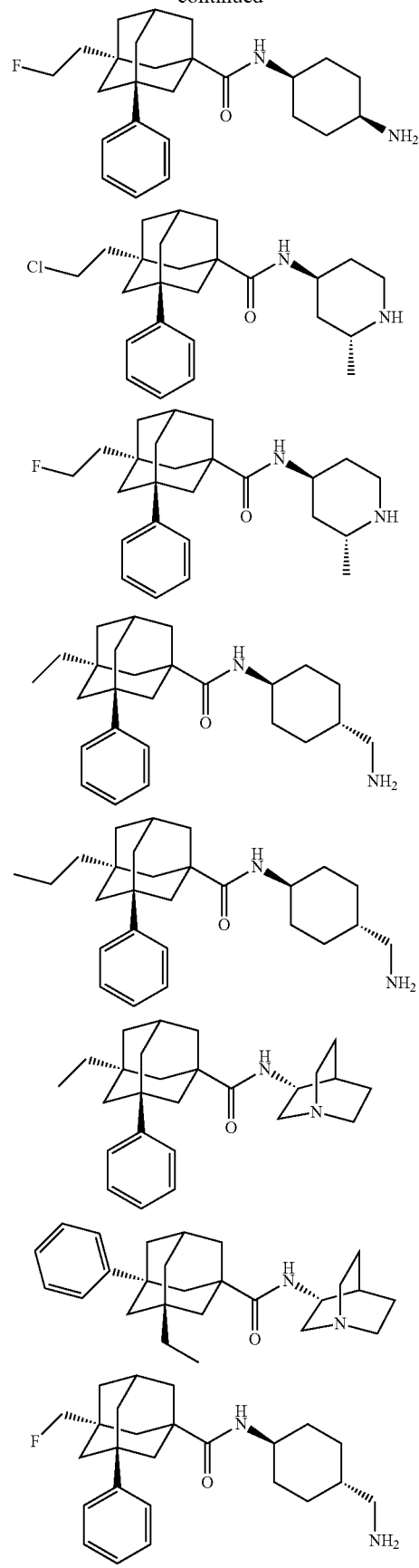

135
-continued
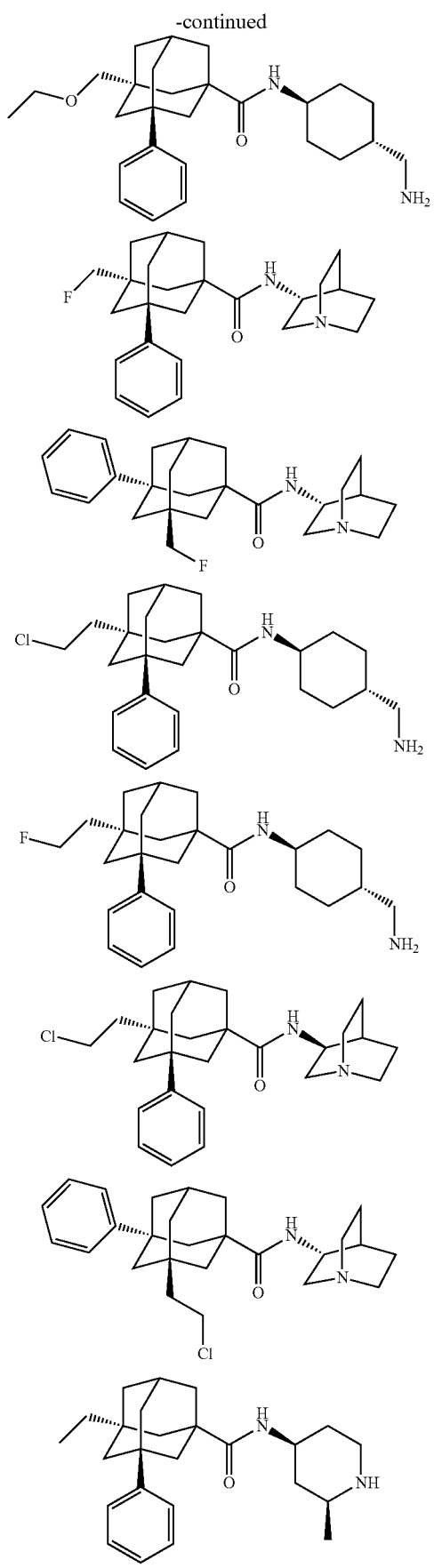
136
-continued
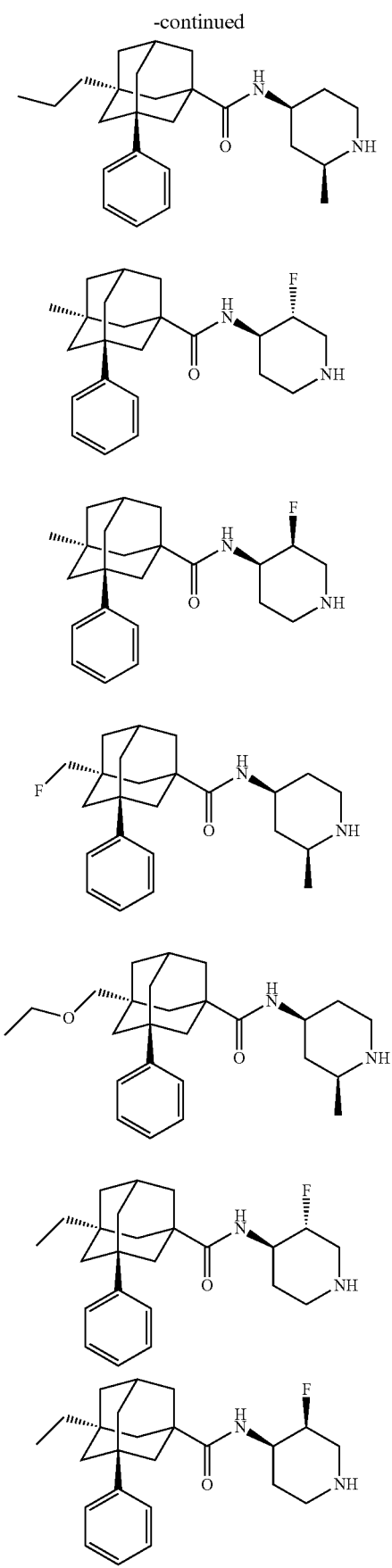

137
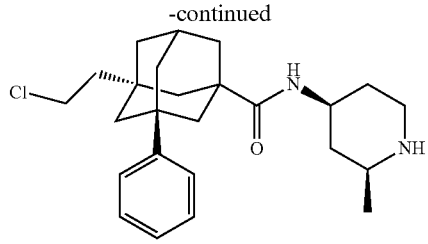
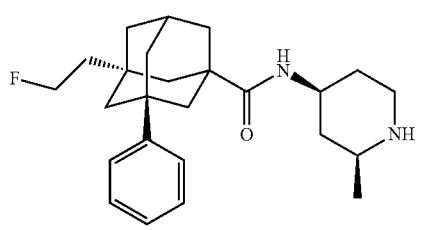
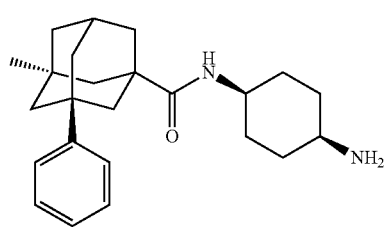
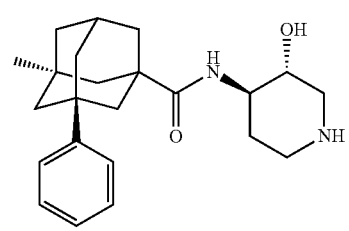
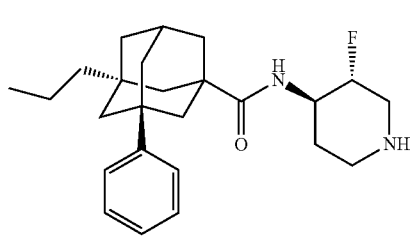
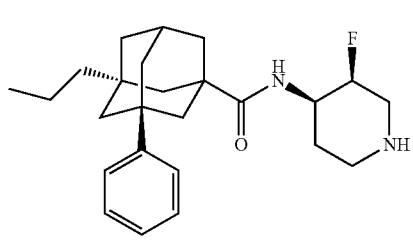
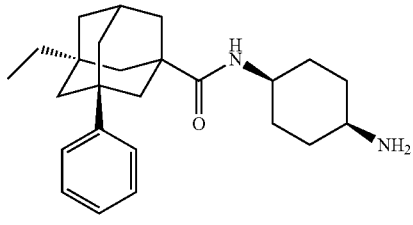
138
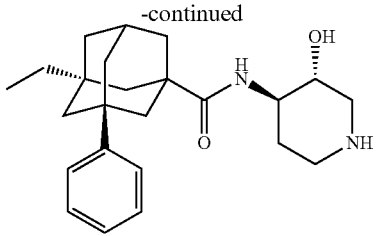
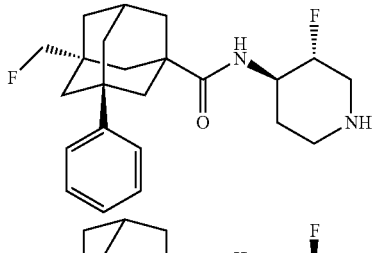
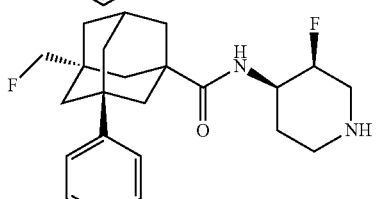
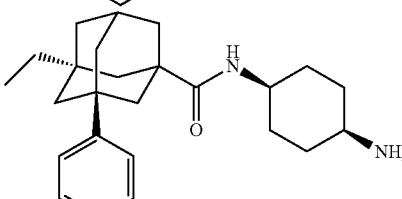
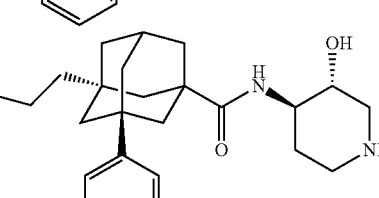
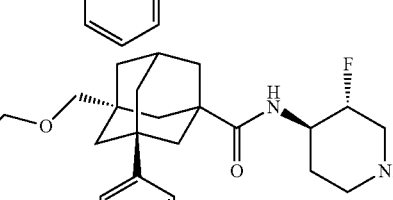
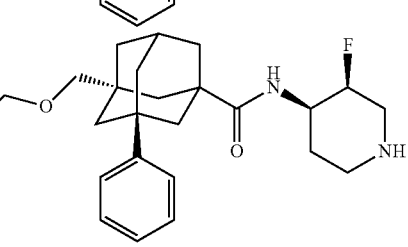
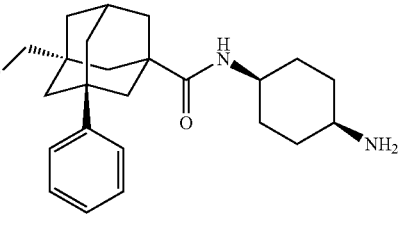

139
-continued
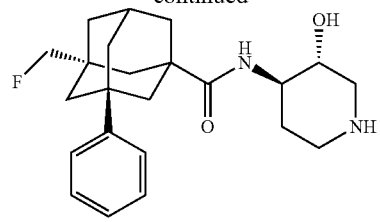
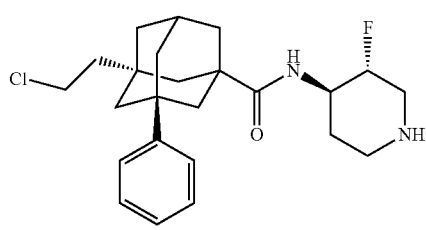
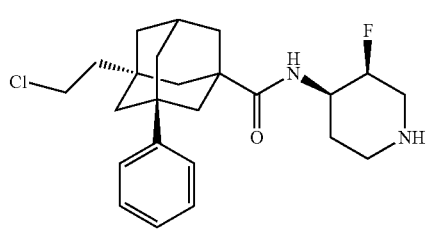
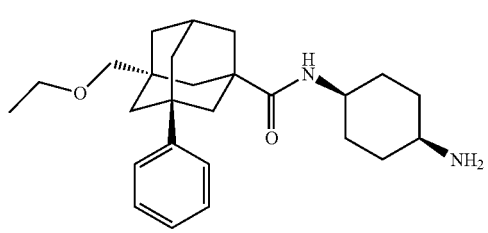
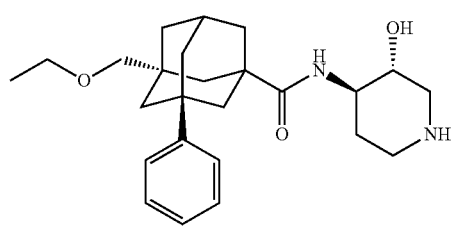
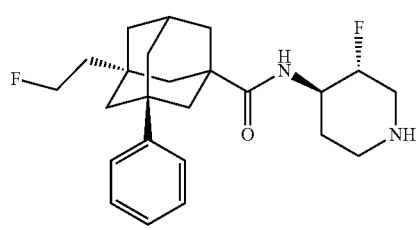
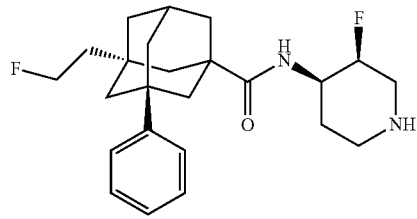
140
-continued
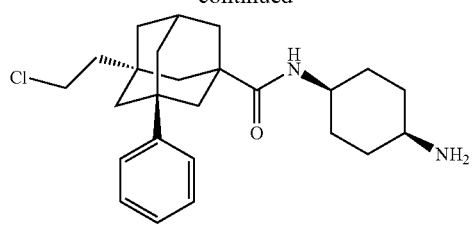
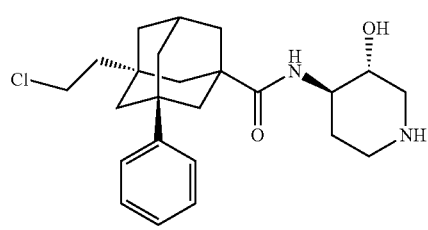
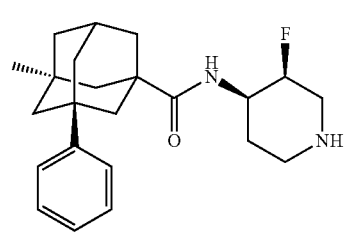
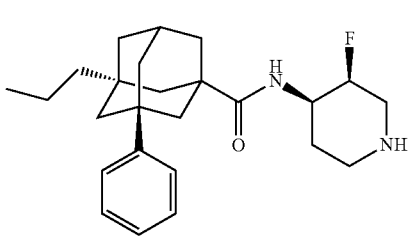
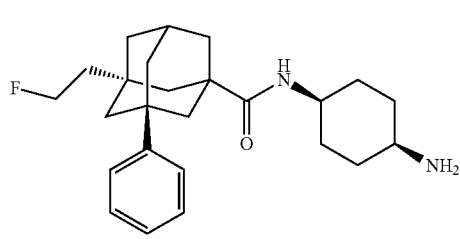
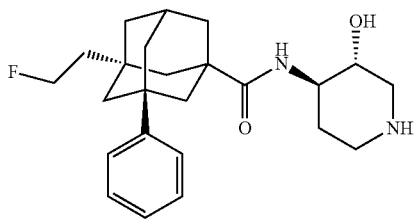
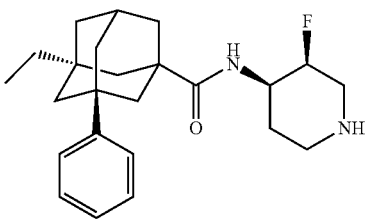

141
-continued
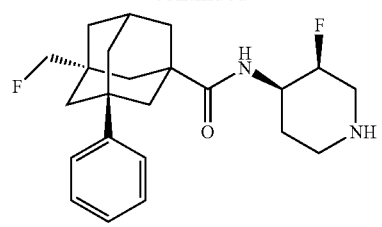
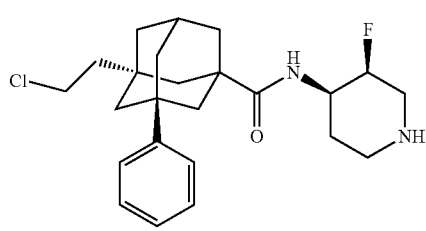
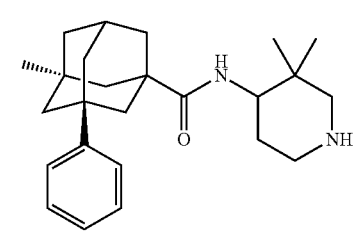
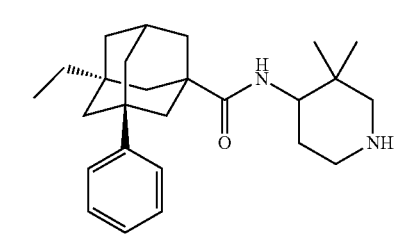
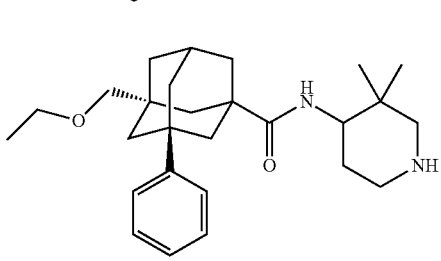
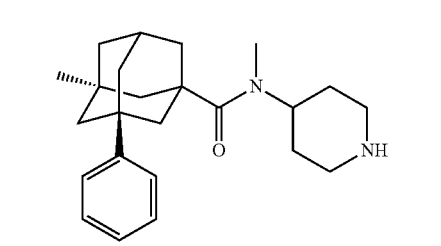
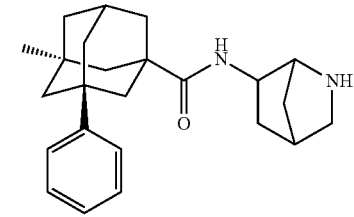
142
-continued
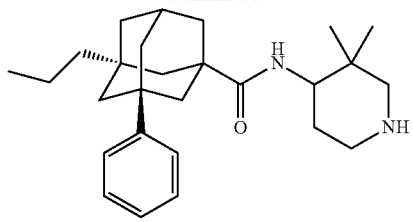
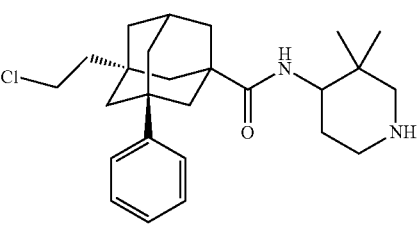
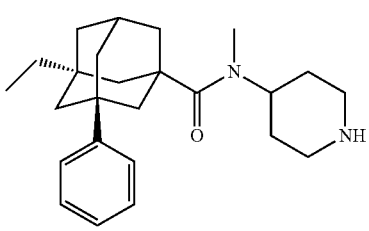
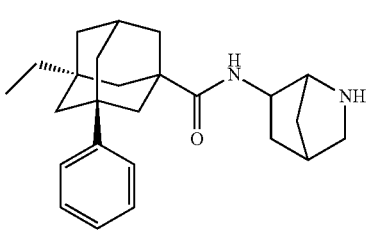
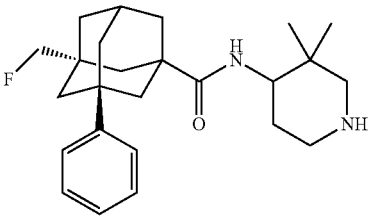
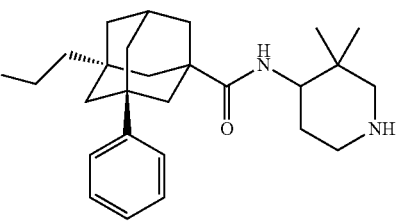
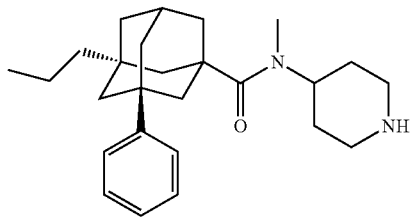

143
-continued
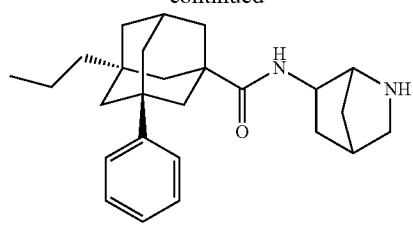
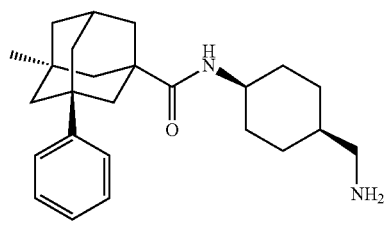
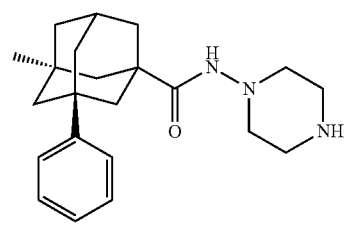
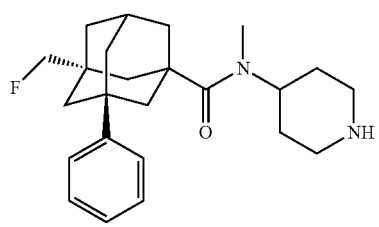
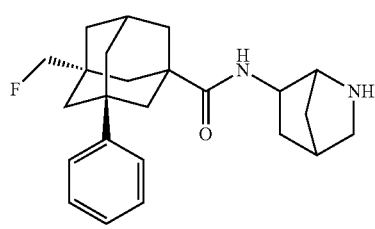
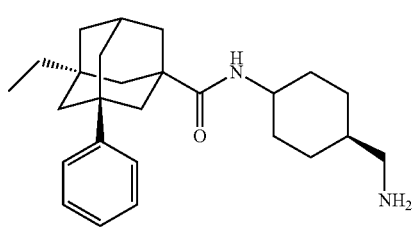
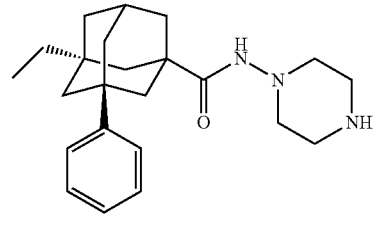
144
-continued
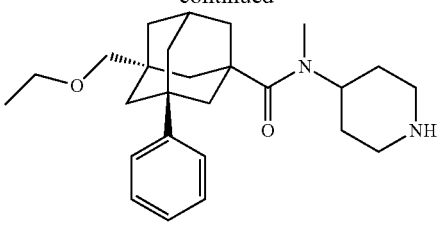
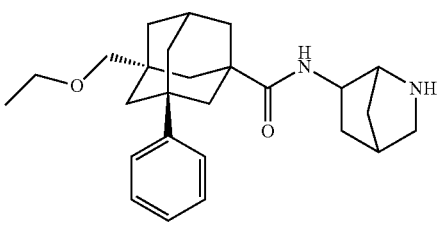
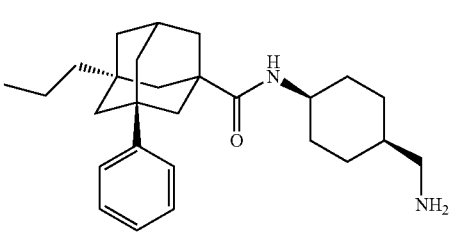
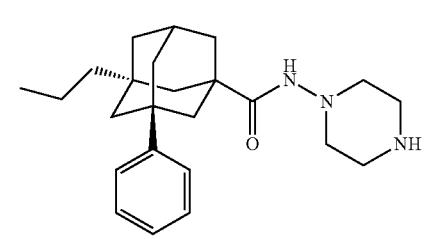
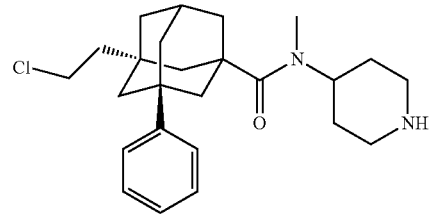
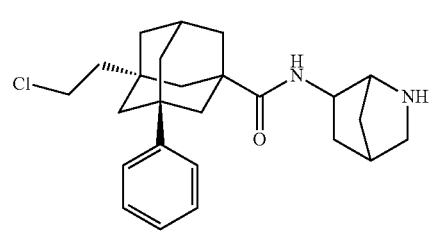
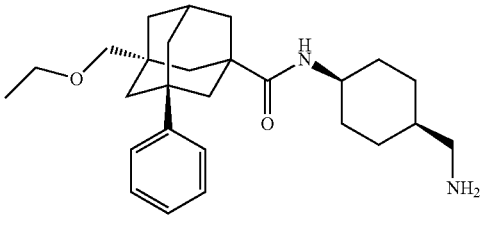

145
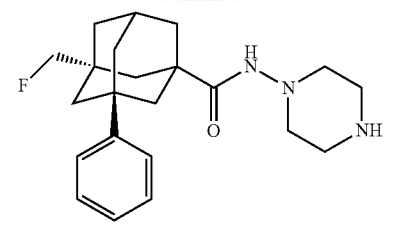
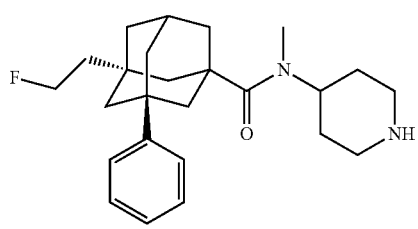
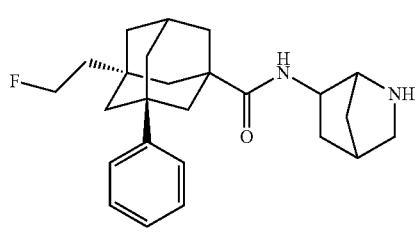
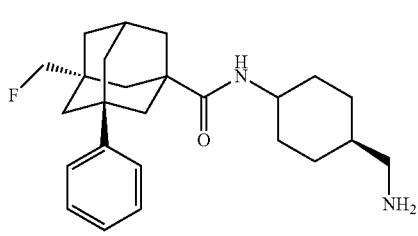
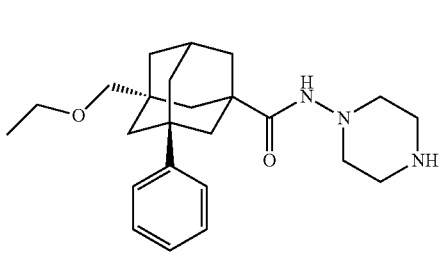
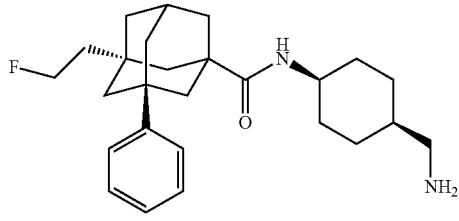
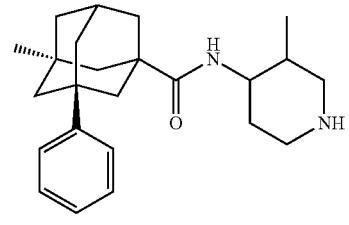
146
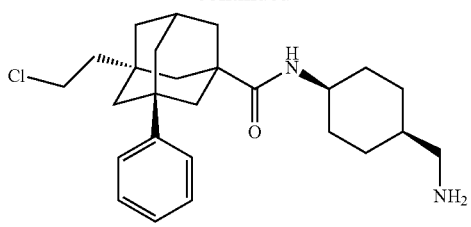
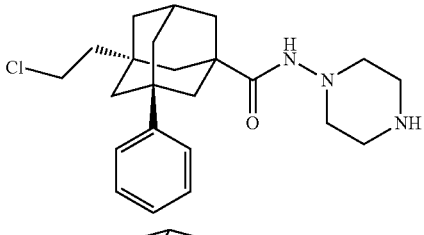
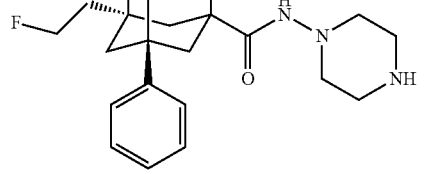
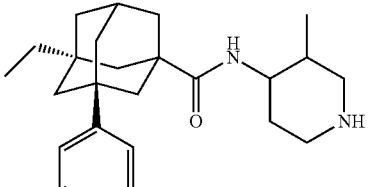
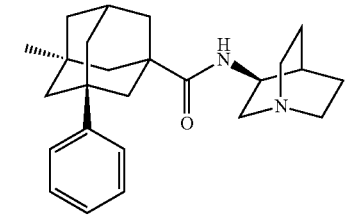
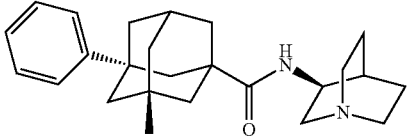
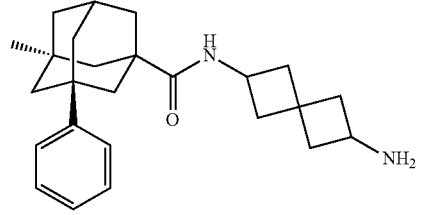

147
-continued
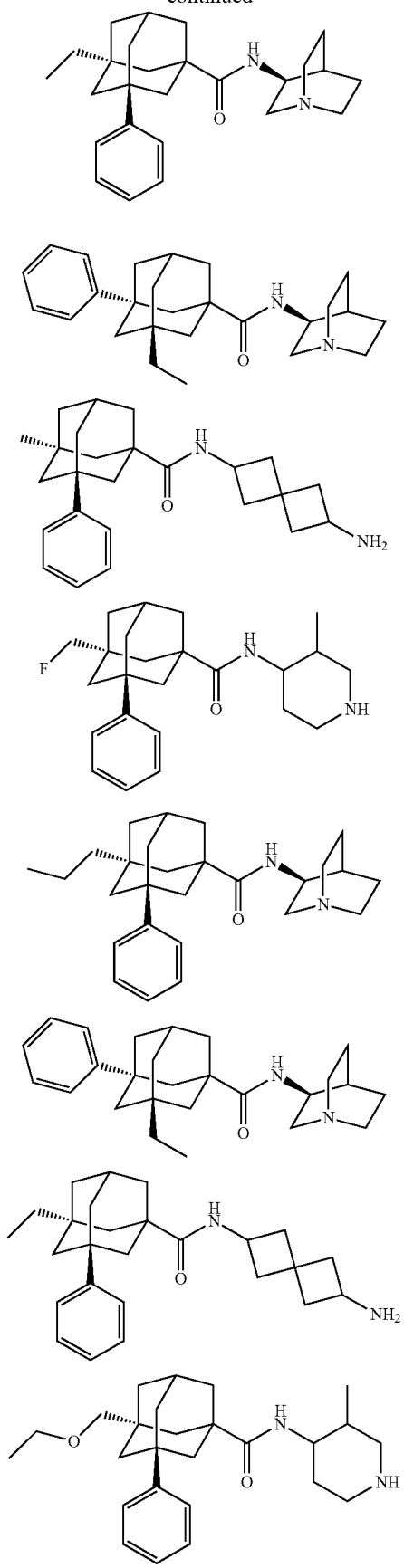
148
-continued
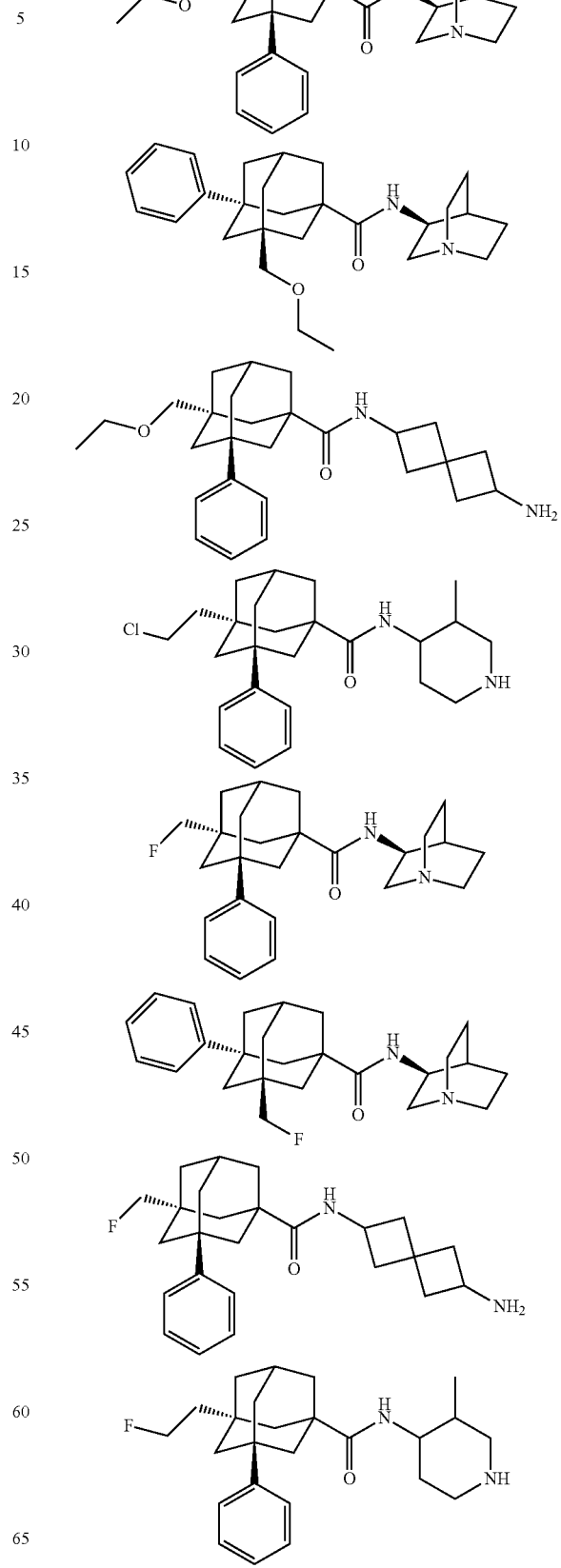

In some embodiments, the invention provides for methods of treating infection by members of the Fitoviridae family, which includes without limitation Ebolavirus, Marburgvirus, Cuevavirus, or any newly emerging filovirus genera. Five species of Ebolavirus have been identified: Zaire (EBOV), Bundibugyo (BDBV), Tai Forest (TAFV), Sudan (SUDV), and Reston (RESTV). Two species of Marburgvirus have been identified: (MARV) and Ravn (RAW). One species of Cuervavirus has currently been identified: Lloviu virus (LLOV).

In some embodiments, the compounds of the invention can selectively inhibit Ebolavirus infection. Infection by Ebolavirus in humans leads to Ebola Hemorrhagic Fever (EHF), the clinical manifestations of which are severe and/or fatal. The incubation period varies between four and sixteen days. The initial symptoms are generally a severe frontal and temporal headache, generalized aches and pains, malaise, and by the second day the victim will often have a fever. Later symptoms include watery diarrhea, abdominal pain, nausea, vomiting, a dry sore throat, and anorexia. By day seven of the symptoms, the patient will often have a maculopapular (small slightly raised spots) rash. At the same time the person may develop thrombocytopenia and hemorrhagic manifestations, particularly in the gastrointestinal tract, and the lungs, but it can occur from any orifice, mucous membrane or skin site. Ebolavirus infections may cause lesions in almost every organ, although the liver and spleen are the most noticeably affected. Both are darkened and enlarged with signs of necrosis. The cause of death (>75% in most outbreaks) is normally shock, associated with fluid and blood loss into the tissues. The hemorrhagic and connective tissue complications of the disease are not well understood, but may be related to onset of disseminated intra-vascular coagulation. Infectious virus may linger in some tissues of some infected individuals for weeks and months after the initial infection.

In some embodiments, the compounds of the invention may inhibit Marburgvirus infection. Marburg hemorrhagic fever (MHF) is a severe type of hemorrhagic fever associated with Marburgvirus infection, which affects both humans and non-human primates. The case-fatality rate for MHF was approximately 70% in a recent Angola outbreak. After an incubation period of 5-10 days, the onset of the disease is sudden and is marked by fever, chills, headache, and myalgia. Around the fifth day after the onset of symptoms, a maculopapular rash, most prominent on the trunk (chest, back, stomach), may occur. Nausea, vomiting, chest pain, a sore throat, abdominal pain, and diarrhea then may appear. Symptoms become increasingly severe and may include jaundice, inflammation of the pancreas, severe weight loss, delirium, shock, liver failure, massive hemorrhaging, and multi-organ dysfunction.

In some embodiments, the compounds of the invention may inhibit Cuervavirus infection or infections with any newly emerging filovirus.

In some embodiments, the compounds of the invention may inhibit infection by any virus, whether native or engineered, whose cell entry process is mediated by filovirus or hybrid filovirus glycoproteins.

Exemplary Kits

The invention also includes kits. The kit has a container housing an inhibitor of the invention and optionally additional containers with other therapeutics such as antiviral agents or viral vaccines. The kit also includes instructions for administering the component(s) to a subject who has or is at risk of having an enveloped viral infection.

In some aspects of the invention, the kit can include a pharmaceutical preparation vial, a pharmaceutical preparation diluent vial, and inhibitor. The vial containing the diluent for the pharmaceutical preparation is optional. The diluent vial contains a diluent such as physiological saline for diluting what could be a concentrated solution or lyophilized powder of inhibitor. The instructions can include instructions for mixing a particular amount of the diluent with a particular amount of the concentrated pharmaceutical preparation, whereby a final formulation for injection or infusion is prepared. The instructions may include instructions for use in an oral formulation, inhaler, intravenous injection or any other device useful according to the invention. The instructions can include instructions for treating a patient with an effective amount of inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Protocol A for Pseudotype Inhibitory Testing of Compounds.

Utilizing a VSV pseudotype system we screened a library collection of small molecule compounds [Cote, M.; Misasi, J.; Ren, T.; Bruchez, A.; Lee, K.; Filone, C. M.; Hensley, L.; Li, Q.; Ory, D.; Chandran, Cunningham, J. *Small molecule inhibitors reveal Niemann-Pick C1 is essential for Ebola virus infection*, Nature (2011) 477: 344-348; Chandran, K.; Sullivan, N. J.; Felbor, U.; Whelan, S. P.; Cunningham, J. M. *Endosomal proteolysis of the Ebola virus glycoprotein is necessary for infection*, Science 2005 308:1643-1645] to discover adamantane carboxamides (PCT/US2017/013560) that selectively inhibit viruses expressing filovirus glycoproteins and not viruses expressing glycoproteins from other viral families. Compounds of the current invention were discovered through the use of similar pseudotyped viruses. VSV viruses expressing the full-length VSV glycoprotein, as well as all pseudotyped VSV viruses expressing the other viral glycoproteins, were generated in cultured HEK-293T cells (ATCC CRL-3216), which were grown in 10 cm dishes in DMEM supplemented with 10% FBS, 1× Pen-Strep, non-essential amino acids and L-glutamine. When cells reached approximately 80% confluency, they were transfected with a mixture of 15 µg of the pCAGGS plasmid encoding one or more of the desired glycoproteins including native VSV or mucin-deleted EBOV [Genbank: AAB81004] or mucin-deleted BDBV [Genbank: AGL73453], or a full length EBOV [Genbank: AAB81004], SUDV [Genbank: YP_138523.1] or MARV [Genbank: AAC40460] glycoprotein construct and 45 µl of PEI (polyethylenimine) transfection reagent. The cells were incubated with the solution for 5 hours at 37° C. at 5% $CO_2$. The cells were then washed and the mixture replaced with supplemented DMEM and incubated at 37° C. at 5% $CO_2$ for approximately 16-18 hours. Subsequently cells were infected with approximately 50 µl of VSV parent pseudotype virus lacking VSV glycoprotein and containing the gene for luciferase. The cells were infected for 1 hour, then washed 1× with PBS and incubated in supplemented media. 24 hours post-infection, supernatant was collected, aliquoted and stored at −80° C. For VSV-Luciferase pseudotypes, one aliquot was thawed and tested in a serial dilution for luminescence activity in Vero cells as described in the Luciferase assay protocol (below). Each of the viral supernatants generated was diluted (from 1:100 to 1:2000) to give similar luminescence signal/background values of ≥200 and stored at −80° C. as aliquots for later use. Vero cells (ATCC: CCL-81) were grown in clear 384 well plates (3000 cells/well) in DMEM media with 10% FBS, 1× Pen-Strep, non-essential amino acids and L-glutamine. After incubating overnight at 37° C. and 5% $CO_2$, cells were treated with compounds at desired concentrations and pseudotyped virus in assay media. Assay media consisted of 50% Opti-MEM, 50% DMEM, with 1% FBS, Pen-Strep, non-essential amino acids and L-glutamine. Final DMSO concentration in the compound testing wells was kept ≤1% and control wells were treated with assay media and 1% DMSO. Cells were incubated for 24 hours at 37° C. and 5% $CO_2$. The compound-virus mixture was aspirated off the cells 24 hours post-infection and washed 1× with PBS. Cells were lysed using 20 µl of lysis buffer from a Luciferase kit diluted according to manufacturer's (Thermo Scientific) instructions. After incubating for approximately 20 minutes, 5 µl of cell lysate was transferred to an opaque white plate and mixed with 12.5 µl of Coelenterazine diluted in buffer. This mixture was incubated at room temperature for 10 minutes on a plate shaker, and then the luminescence was read using a plate reader (Beckman Coulter DTX 880 multimode detector with an emission of 535 nm) Luminescence signals were obtained for compound containing and control wells to determine % activity (inhibition of luciferase signal) for each compound.

Although we previously determined (PCT/US2017/013560) that adamantayl carboxamides do not inhibit native VSV (expressing the native glycoprotein) a number of compounds were also tested against native VSV in order to distinguish between inhibitory activities of the compounds on filovirus cell entry from those potentially acting against parent VSV virus that expresses the native VSV glycoprotein (rather than a filovirus glycoprotein). Compounds were tested in the pseduotyped assays in dose-response experiments to determine $EC_{50}$ values (concentration at half-maximal inhibition) and those exhibiting an $EC_{50} \geq 10$-fold below the concentration of half-maximal cell death ($CC_{50}$), as determined in parallel cytotoxicity assays, were thereby identified as filovirus cell entry inhibitors. Compounds exhibiting activity against one or more pseudotyped filoviruses without comparable cytotoxicity (or VSV activity), indicates they are of potential therapeutic interest to treat filovirus infection. For the cytotoxicity assays compounds were serially diluted and added to Vero cells (4000 cells/well) with final DMSO concentration maintained at 1% in growth media consisting of minimal essential media (MEM) with 2% FBS. The plates were incubated at 37° C. for 7 days, and then dead cells were removed by washing with Phosphate buffered saline (PBS). Cells were stained with neutral red vital dye for 1 hour and then de-stained with a solution of 50% ethanol/1% acetic acid solution. Absorbance was read at 540 nm and 690 nm on a Spectramax Plus 384 spectrophotometer. Data were analyzed as (540 nm-690 nm) and then compared to untreated controls to obtain % cell viability.

As shown in Table 5, compounds of the invention exhibited inhibition of pseudotyped viruses expressing filovirus glycoproteins well below that of cytotoxicity ($EC_{50}$ more than 10-fold below the $CC_{50}$) as well as the parental VSV (data are an average +/−sd, n=3 or 4). Surprisingly, amides prepared from enantiomerically pure (1S,3R,5R,7S)-3-methyl-5-phenyl adamantane-1-carboxylic acid (examples B1 to B58) were significantly more potent than the opposite enantiomer prepared from (1R,3S,5S,7R)-3-methyl-5-phenyl adamantane-1-carboxylic acid (examples C1 to C58) or the racemate with eudistic ratios ranging from 5 to 21 for Ebolavirus (EBOV). Unexpectedly, for Marburgvirus the enantioselectivity was reversed whereby the less potent enantiomer against Ebolavirus infection (example C58, prepared from (1R,3S,5S,7R)-3-methyl-5-phenyl adamantane-1-carboxylic acid) was 16-fold more potent against Marburgvirus infection compared to the opposite enantiomer (B58, prepared from (1S,3R,5R,7S)-3-methyl-5-phenyl adamantane-1-carboxylic acid). These unexpected results provide strong support for the development of enantiomerically pure adamantane carboxamides for the treatment of Filovirus infection.

TABLE 5

| Ex. | $EC_{50}$ (uM) Pseudotype Assays | | | | | | Cytotox (uM) $CC_{50}$ |
|---|---|---|---|---|---|---|---|
| | EBOV | *EBOV_FL | BDBV | SUDV | *MARV | *VSV | |
| A1 | 0.042 | 0.04 | 0.160 | 0.380 | 2.8 | >10 | 16.1 |
| B1 | 0.034 | 0.010 | 0.238 | 0.250 | >3 | ND | 12.3 |
| C1 | 0.238 | nd | 0.186 | 0.685 | ND | ND | 16.3 |
| A2 | 0.020 | 0.024 | 0.09 | 0.27 | 3.1 | >10 | 10.1 |
| B2 | 0.015 | 0.010 | 0.067 | 0.277 | 6.45 | ND | 19.1 |
| C2 | 0.135 | 0.209 | 0.252 | 0.767 | 8.72 | ND | 25.5 |
| A3 | 0.026 | 0.04 | 0.095 | 0.030 | 7.0 | >10 | 8.0 |
| B3 | 0.009 | 0.010 | 0.114 | 0.230 | 3.6 | ND | 6.11 |
| C3 | 0.073 | 0.030 | 0.190 | 0.855 | 3.17 | ND | 5.2 |
| A4 | 0.022 | 0.025 | 0.198 | 0.730 | 7.1 | >10 | 11.7 |
| B4 | 0.013 | ND | 0.104 | 0.166 | >3 | ND | 22.5 |
| C4 | 0.078 | 0.030 | 0.1777 | 1.02 | >3 | ND | 14.0 |
| A5 | 0.050 | 0.030 | 0.190 | 0.410 | 4.88 | >10 | 11.3 |
| B5 | 0.019 | 0.020 | 0.174 | 0.240 | >3 | nd | 11.9 |
| C5 | 0.169 | ND | 0.109 | 0.775 | >3 | nd | 11.6 |
| B6 | 0.036 | 0.020 | 0.193 | 0.320 | >3 | nd | 12.2 |
| C6 | 0.320 | ND | 0.250 | 0.480 | 2.98 | nd | 12.7 |
| B7 | 0.045 | 0.04 | 0.072 | 0.116 | 8 | nd | 31 |
| C7 | 0.124 | 0.17 | 0.198 | 0.335 | 8.2 | nd | 13 |
| B8 | 0.012 | 0.05 | 0.084 | 0.058 | nd | nd | 12.4 |
| C8 | 0.097 | nd | 0.123 | 0.55 | nd | nd | 12.37 |
| B9 | 0.025 | 0.06 | 0.085 | 0.075 | nd | nd | 8.9 |
| C9 | 0.269 | nd | 0.15 | 0.62 | nd | nd | nd |
| B10 | 0.045 | 0.05 | 0.071 | 0.11 | nd | nd | 12.3 |
| C10 | 0.1 | 0.18 | 0.085 | 0.155 | nd | nd | 12.71 |
| B11 | 0.064 | nd | 0.104 | 0.26 | nd | nd | 23.6 |
| C11 | 0.576 | nd | 0.315 | 0.96 | nd | nd | nd |
| B12 | 0.095 | nd | 0.105 | 0.2 | nd | nd | 13.3 |
| B13 | 0.014 | nd | 0.071 | 0.04 | nd | nd | 11.33 |
| B14 | 0.025 | nd | 0.25 | 0.73 | nd | nd | 14.43 |
| B15 | 0.035 | nd | 0.21 | 0.61 | nd | nd | 14.8 |
| B16 | 0.016 | nd | 0.057 | 0.18 | 3.02 | nd | nd |
| C16 | 0.353 | nd | 0.388 | 0.94 | 2.97 | nd | nd |
| A17 | 0.039 | 0.025 | 0.125 | 0.255 | 5.91 | nd | 6.0 |
| A18 | 0.20 | 0.030 | 0.203 | 0.303 | 3.5 | nd | 9.8 |
| A19 | 0.023 | 0.040 | 0.261 | 0.465 | 3.44 | nd | 7.3 |
| A20 | 0.042 | 0.030 | 0.135 | 0.330 | 1.57 | nd | 5.7 |
| A21 | 0.022 | 0.020 | 0.208 | 0.415 | 6.91 | nd | 3.9 |
| A22 | 0.019 | 0.010 | 0.185 | 0.416 | 2.8 | nd | 3.7 |
| A23 | 0.041 | 0.020 | 0.306 | 0.500 | 3.51 | nd | 7.8 |
| A24 | 0.203 | nd | 0.253 | 0.310 | nd | nd | 11.2 |
| A25 | 0.041 | 0.060 | 0.198 | 0.795 | 8.46 | nd | 11.8 |
| A26 | 0.13 | 0.200 | 0.333 | 0.605 | 2.57 | nd | 6.7 |

TABLE 5-continued

| | EC$_{50}$ (uM) Pseudotype Assays | | | | | | Cytotox (uM) |
|---|---|---|---|---|---|---|---|
| Ex. | EBOV | *EBOV_FL | BDBV | SUDV | *MARV | *VSV | CC$_{50}$ |
| A27 | 0.134 | nd | 0.567 | 1.75 | nd | nd | 7.9 |
| A28 | 0.062 | 0.140 | 0.596 | 1.54 | >10 | nd | 32.3 |
| A29 | 0.062 | nd | 0.790 | >1 | nd | nd | 16.3 |
| A30 | 0.250 | nd | 0.7 | 0.8 | 5.0 | nd | 30 |
| A31 | >1 | nd | >1 | >1 | >1 | nd | 26 |
| A32 | 0.042 | 0.065 | 0.09 | 0.215 | 7.6 | nd | 6 |
| A33 | 0.05 | 0.2 | 0.069 | 0.3 | nd | nd | 13.65 |
| A34 | 0.09 | nd | 0.12 | 0.18 | nd | nd | 23.65 |
| A35 | 0.01 | 0.02 | 0.071 | 0.08 | nd | nd | 10.2 |
| A36 | 0.171 | nd | 0.229 | 0.13 | nd | nd | 8.31 |
| A37 | 0.058 | nd | 0.0587 | 0.22 | nd | nd | 10.92 |
| A38 | 0.04 | 0.07 | 0.104 | 0.13 | nd | nd | 6.91 |
| A39 | 0.046 | nd | 0.091 | 0.21 | nd | nd | 13.24 |
| A40 | 0.069 | nd | 0.165 | 0.45 | nd | nd | 24.61 |
| A41 | 0.153 | nd | 0.209 | 0.68 | nd | nd | 27.68 |
| A42 | 0.033 | nd | 0.19 | 0.46 | nd | nd | 11.82 |
| A43 | 0.147 | nd | 0.126 | 0.37 | nd | nd | 12.95 |
| A44 | 0.045 | nd | 0.075 | 0.245 | nd | nd | 27.16 |
| A45 | 0.205 | nd | 0.301 | 0.33 | nd | nd | 30.6 |
| A46 | 0.041 | nd | 0.048 | 0.09 | nd | nd | 12.2 |
| A47 | 0.065 | nd | 0.238 | 0.335 | nd | nd | 42.27 |
| A48 | 0.014 | 0.14 | 0.035 | 0.035 | nd | nd | 13.7 |
| A49 | 0.023 | 0.19 | 0.109 | 0.2 | nd | nd | 21.9 |
| A50 | 0.061 | nd | 0.09 | 0.16 | nd | nd | 8.78 |
| A51 | 0.157 | nd | 0.228 | 0.52 | nd | nd | nd |
| A52 | 0.038 | 0.03 | 0.168 | 0.4 | 1.2 | nd | 5.7 |
| A53 | 0.67 | nd | >1 | >1 | nd | nd | nd |
| A54 | 0.12 | nd | 0.2 | 0.35 | nd | nd | 11.32 |
| A55 | 0.14 | nd | 0.16 | 0.37 | nd | nd | 12.63 |
| A56 | 0.107 | nd | 0.075 | 0.06 | nd | nd | 9.09 |
| A57 | 0.055 | nd | 0.17 | 0.22 | nd | nd | 7.88 |
| A58 | 0.074 | 0.070 | 0.198 | 0.383 | 0.282 | >10 | 7.2 |
| B58 | 0.036 | nd | 0.230 | 0.220 | 1.68 | nd | 8.0 |
| C58 | 0.785 | nd | 0.188 | 1.01 | 0.100 | nd | 10.1 |
| A59 | 0.026 | nd | 0.257 | 0.4 | nd | nd | 12.68 |
| A60 | 0.035 | nd | 0.12 | 0.33 | nd | nd | 23.1 |
| A61 | 0.8 | nd | 0.75 | 0.66 | nd | nd | 1.24 |
| A62 | 0.9 | nd | 0.5 | 0.54 | nd | nd | 1.62 |
| A63 | 0.725 | nd | 0.435 | 0.74 | nd | nd | 1.47 |
| A64 | 0.61 | nd | 0.3 | 0.53 | nd | nd | 1.24 |
| A65 | 0.28 | nd | 0.175 | 0.18 | 0.89 | nd | 1.62 |
| A66 | 0.22 | nd | 0.199 | 0.49 | 0.97 | nd | 4.06 |
| A67 | >1 | nd | >1 | >1 | nd | nd | nd |
| A68 | 0.6 | nd | 0.28 | 0.4 | >3 | nd | 7.47 |
| A69 | 0.321 | nd | 0.163 | 0.29 | 0.95 | nd | 2.2 |
| B69 | 0.429 | nd | 0.279 | 0.71 | 0.93 | nd | 4.67 |
| C69 | 0.313 | nd | 0.208 | 0.31 | 1.14 | nd | 3.8 |
| B70 | 0.628 | nd | 0.93 | 1.02 | nd | nd | nd |
| C70 | >1 | nd | 1.025 | 1.28 | nd | nd | nd |
| B71 | 1.184 | nd | 1.032 | >1 | nd | nd | nd |
| C71 | >1 | nd | >1 | >1 | nd | nd | nd |

*EBOV_FL: full-length Ebola Zaire GP, MARV, and VSV are also full-length glycoproteins CC$_{50}$ in Vero cells (120 h)

Protocol B—Native Ebola Plague and Viral Yield Reduction Assays.

Biosafety Safety Level 2 (BSL2) pseudotyped viruses expressing filovirus GPs were used (above) as surrogates to facilitate the identification of inhibitors of wild-type Biosafety safety level 4 (BSL4) filoviruses, which may only be studied in highly specialized containment facilities. To confirm activity against native BSL4 Ebola virus example compounds were tested against EBOV (Mayinga) in plaque forming assay format (Table 6) under stringent BSL4 testing requirements. In the plaque assay format confluent or near confluent (Vero) cell culture monolayers in 12-well disposable cell culture plates are prepared. Cells are maintained in MEM or DMEM supplemented with 10% FBS. For antiviral assays the same medium is used but with FBS reduced to 2% or less and supplemented with 1% penicillin/streptomycin. The test compound is prepared at four log$_{10}$ final concentrations in 2×MEM or 2×DMEM. The virus only and cytotoxicity (compound only) controls are run in parallel with each tested compound. Further, a known active drug (favipiravir) is tested as a positive control drug with each test run. Test compounds and positive controls are tested in biological triplicates. The assay is initiated by first removing growth media from the 12-well plates of cells, and infecting cells with 0.01 MOI of virus or about 50 to 100 plaque forming units (pfu). Cells are incubated for 60 min: 100 μl inoculum/well, at 37° C., 5% CO$_2$ with constant gentle rocking. Virus inoculum is removed, cells washed and overlaid with either 1% agarose or 1% methylcellulose diluted 1:1 with 2×MEM and supplemented with 2% FBS and 1% penicillin/streptomycin and supplemented with the corresponding drug concentration. Cells are incubated at 37° C. with 5% CO$_2$ for 10 days. The overlay is removed and plates stained with 0.05% crystal violet in 10% buffered formalin for approximately twenty minutes at room temperature. The plates are washed, dried and the number of plaques counted. The number of plaques in each set of compound dilution is converted to a percentage relative to the untreated virus control. The 50% effective ($EC_{50}$ virus-inhibitory) concentration is calculated by linear regression analysis. The cytotoxicity assay (In vitro Toxicology Assay Kit, Neutral red based; Sigma) is being performed in parallel in 96-well plates following the manufacturer's instructions. Briefly, growth medium is removed from confluent cell monolayers and replaced with fresh medium (total of 100 µL) containing the test compound with the concentrations as indicated for the primary assay. Control wells contain medium with the positive control or medium devoid of compound. A total of up to five replicates are performed for each condition. Plates are incubated for 3, 5, or 10 days at 37° C. with 5% $CO_2$. The plates are stained with 0.033% neutral red for approximately two hours at 37° C. in a 5% $CO_2$ incubator. The neutral red medium is removed by complete aspiration, and the cells rinsed 1× with phosphate buffered solution (PBS) to remove residual dye. The PBS is completely removed and the incorporated neutral red eluted with 1% acetic acid/50% ethanol for at least 30 minutes. Neutral red dye penetrates into living cells: the more intense the red color, the larger the number of viable cells present in the wells. The dye content in each well is quantified using a 96-well spectrophotometer at 540 nm wavelength and 690 nm wavelength (background reading). The 50% cytotoxic ($CC_{50}$, cell-inhibitory) concentrations are then calculated by linear regression analysis. The quotient of $CC_{50}$ divided by $EC_{50}$ gives the selectivity index ($SI_{50}$) value.

A set of compounds including a racemate (A2) and two enantiomers (B2 and C2) were tested in the plaque assay to determine if the stereoselective inhibition observed in the pseudotype assays translated directly to inhibition of the live virus (Table 6). An approximate difference and translation factor of 15-fold lower compound potency was observed in the BSL4 native virus plaque assay in comparison to the EBOV pseudotyped virus assay, which may reflect increased viral pathogenicity and differences in assay protocols. However, in both assay systems the B2 enantiomer is roughly twice the potency of the racemate A2 while the $EC_{50}$ of the other enantiomer (C2) is significantly lower than the racemate. The $SI_{50}$ selectivity index ($=CC_{50}/EC_{50}$) is typically used to determine whether a compound is exhibiting true antiviral inhibitory and $SI_{50}$ values >10 are accepted as confirmation of inhibitory activity against the virus, rather than artifactual activity reflecting cellular cytotoxicity. Compound B2 ($EC_{50}$=0.24, $SI_{50}$=282) represents a robust EBOV inhibitor and the data confirm the surprising enantioselective properties of adamantane carboxamides that determine filovirus inhibitory activities. One other enantiomer was tested in the plaque assay and it also exhibited potent inhibition of native EBOV with $EC_{50}$ and $SI_{50}$ values of 0.4 uM and 64, respectively. By comparison the positive control drug compound favipiravir exhibited $EC_{50}$ and $SI_{60}$ values of 17 uM and 59, respectively. Taken altogether, the data further validate the utilization of pseudotyped virus assays to identify and prioritize bona fide filovirus inhibitors that may be compatible with administration in mammals in vivo as a method of treatment for filovirus infection.

TABLE 6

| Example | $EC_{50}$ (uM) | $CC_{50}$ (uM) | $SI_{50}$ ($CC_{50}/EC_{50}$) |
|---|---|---|---|
| A2 | 0.43 | 66 | 153 |
| B2 | 0.24 | 67.6 | 282 |
| C2 | 2.67 | 21.4 | 8 |
| B58 | 0.40 | 25.7 | 64 |
| favipiravir | 17 | >1000 | >59 |

A further set of Ebola entry inhibitors identified from pseudotype virus cell assays were tested for efficacy against wild-type Ebola and Sudan species (Table 7). Some compounds were tested at different BSL-4 sites either by plaque, immunohistochemical staining for glycoprotein or virus yield reduction (VYR). For plaque and VYR assays, Vera cells were inoculated with virus at 1000 pfus along with different doses of compound. For immunohistochemical staining of virus glycoprotein, HeLa cells were inoculated with 1000 pfus of virus and quantitated for virus content using a high-throughput confocal imaging system. For determination of cytotoxicity, separate plates of cells were dosed only with compound but no virus to determine $CC_{50}$ values.

TABLE 7

| Example | Assay Format | Ebola Zaire | | | | Sudan Gulu | |
|---|---|---|---|---|---|---|---|
| | | $EC_{50}$ uM | SI ($CC_{50}/EC_{50}$) | $EC_{90}$ uM | SI ($CC_{50}/EC_{90}$) | $EC_{50}$ uM | SI ($CC_{50}/EC_{50}$) |
| B2 | Plaque | 0.24 | 282 | | | 1.1 | 14 |
| | Immuno | 0.44 | 76 | | | 0.18 | 64 |
| | VYR | | | 0.8 | 72.5 | | |
| B1 | Plaque | >3.2 | na | | | | |
| | Immuno | 0.64 | 51 | | | 0.12 | 285 |
| | VYR | | | 2.1 | >48 | | |
| B3 | Plaque | 0.43 | 7 | | | | |
| | Immuno | 0.57 | 58 | | | 0.12 | 119 |
| | VYR | | | 0.6 | 23 | | |
| B58 | Plaque | 0.40 | 64 | | | | |
| | Immuno | 0.90 | 37 | | | 0.15 | 157 |
| | VYR | | | 4.4 | 6.5 | | |
| B4 | Immuno | 0.62 | 54 | | | 0.15 | 155 |
| | VYR | | | 2.9 | >35 | | |
| B7 | Plaque | 0.88 | 99 | | | | |
| | Immuno | 1.90 | 17.4 | | | 0.17 | 198 |
| | CPE | | | | | 0.36 | 242 |
| A32 | Plaque | 1.33 | 64 | | | | |
| A69 | Immuno | 0.44 | 16 | | | 0.07 | 58 |
| A35 | Immuno | 1.14 | 29 | | | 0.14 | 136 |
| B8 | Plaque | | | | | 0.13 | 128 |

Tables 8 to 10. In addition to the ability of compounds to inhibit live filoviruses in vitro, compounds must also have certain drug-like properties for them to be used to inhibit filoviruses and provide methods of treatment for filovirus infection in mammals in vivo. Such compounds may exhibit drug-like properties including but not limited to chemical stability against degradation by and lack of inhibition of liver microsomal CYP p450 enzymes, cell permeability and oral bioavailability (if the drug is to delivered orally) and lack of inhibition of the hERG ion channel, which is associated with cardiac safety [Kerns, E. H. Li, D. *Drug-like Properties; Concepts, Structure Design and Methods from ADME to Toxicity Optimization*, (2008) Academic Press, Burlington Mass.], To characterize drug-like properties of the chemical series example compounds were evaluated for metabolic stability in human, mouse, monkey, and guinea pig liver microsome assays (Table 8). Compounds exhibiting half-lives ($T_{1/2}$)>60 minutes, or greater than 50% remaining at 60 minutes, indicate attractive chemical stability. The demonstration of good microsomal stability in human and nonhuman species facilitates the ability to test and optimize compounds in preclinical animal studies. To reduce or prevent serious/life-threatening conditions caused by exposure to lethal or permanently disabling toxic agents where human efficacy trials are not feasible or ethical (such as filovirus infection) the FDA has provided an approach to test and approve drugs using the Animal Efficacy Rule; whereby the FDA can rely on evidence from animal studies to provide substantial evidence of product effectiveness. In the absence of an epidemic filovirus outbreak in humans with a sufficiently large patient population efficacy data for new methods of treatment for filovirus infection may only be obtained from relevant animal models (e.g., mouse and monkey efficacy studies). Thus the translation of drug like-properties from one species to another significantly facilitates the testing and development of filovirus inhibitor compounds.

TABLE 8

| Liver Microsome Stability % Remaining after 60 Minutes | | | | |
|---|---|---|---|---|
| Example | Human | Mouse | Monkey | Guinea Pig |
| B2 | 100 | 71 | 85 | 100 |
| B1 | 81 | 87 | 83 | ND |
| B3 | 83 | 27 | 61 | ND |
| B4 | 82 | 92 | 54 | ND |
| B7 | 86 | 77 | 53 | 72 |
| A69 | 98 | 100 | 68 | 65 |
| A35 | 97 | 42 | 22 | 45 |
| B8 | 76 | 47 | 30 | 56 |
| A48 | 46 | 76 | 22 | 87 |
| B13 | 85 | 51 | 32 | 50 |

To further characterize compounds of the invention for the inhibition of filoviruses in mammals in vivo additional drug-like properties of an example compound (compounds A2 and B2) were determined including solubility, Caco-2 cell permeability, protein binding, Cyp-p450 inhibition and hERG ion channel inhibition (Table 9). The example compounds were not inhibitors of human Cyp-p450 enzymes 1A2, 2B6, 2C9, 2C19, 2D6 while for 3A4 it exhibited an $IC_{50}$ of ~28 uM for one substrate and >100 uM for another. The data indicate little if any metabolic liabilities related to Cyp-p450 inhibition (formation of metabolites was measured by LC/MS). In addition, the $IC_{50}$ for compound A2 against the hERG ion channel was >10 uM (the highest concentration tested), which indicates attractive cardiac safety properties. Compounds A2 and B2 exhibited high protein binding (5 uM test concentration) in PBS, which will factor in for in vivo efficacy studies and therapeutic dosing while its solubility at neutral pH is >500 uM, which will facilitate formulation and dissolution in vivo. To help determine the potential for oral administration we evaluated the permeability of compounds A2 and B2 (5 uM test concentration in PBS in absence or presence of P-gp inhibitor Verapamil) in the Caco-2 in vitro model where it demonstrated permeability but was found to be effluxed (ratio of B>A/A>B was 4.32 for A2 and 2.71 for B2) by P-gP; the addition of verapamil, a known P-gP pump inhibitor, inhibited the efflux to a ratio approx. 1.

TABLE 9

| | | A2 | B2 |
|---|---|---|---|
| Turbidimetric solubility (uM) | | >500 | >500 |
| Caco-2 Permeability $P_{aap}$ ($10^{-6}$ cm $s^{-1}$) | Mean A > B | 3.61 | 3.07 |
| | Mean B > A | 15.6 | 7.86 |
| | Efflux ratio | 4.32 | 2.71 |
| P-gp substrate ID Caco-2 Permeability (+Verapamil) $P_{aap}$ ($10^{-6}$ cm $s^{-1}$) | Mean A > B | 8.47 | 6.19 |
| | Mean B > A | 7.45 | 6.83 |
| | Efflux ratio | 0.88 | 1.11 |
| PPB fraction bound | Human | 97.5% | 96.1 |
| | Mouse | 98.6% | 98.9 |
| CYP Inhibition (uM) | 1A2 | >100 | >100 |
| | 2B6 | >100 | >100 |
| | 2C8 | nd | >100 |
| | 2C9 | >100 | >100 |
| | 2C19 | >100 | 51 |
| | 2D6 | >100 | >100 |
| | 3A4 (Testosterone) | 28 | 88 |
| | 3A4 (Midazolam) | >100 | >100 |
| hERG $IC_{50}$ (uM) | | >10 | nd |

These in vitro ADMET assay data indicate that the potent enantiomers are likely to have in vivo drug-like properties that are similar to the racemate. While the P-gP efflux of compound A2 and B2 was not ideal, there remained sufficient absorption to explore an IV/PO PK (intravenous/oral pharmacokinetic) study in mice. Compound A2, when administered (Table 10) as either 1 mg/kg IV or 10 mg/kg PO and analysis of blood plasma samples obtained over a 24 hr period, was found to demonstrate excellent oral bioavailability (72%), clearance was less than hepatic blood flow and the compound exhibited a half-life of 7.1 h and volume of distribution of 14 L/kg. These values are consistent with single or twice daily oral dosing.

TABLE 10

Table 10. Pharmacokinetic parameters of example A2 in male CD-1 mice

| Dose (mg/kg) | $t_{1/2}$ (h) | $T_{max}$ (h) | Cmax (ng/mL) | $AUC_{last}$ (h · ng/mL) | $AUC_{inf}$ (h · ng/mL) | Cl (mL/h · kg) | Vz (mL/kg) | F (%) |
|---|---|---|---|---|---|---|---|---|
| 1 (IV) | 5.4 | 0.083 | 129 ± 40 | 539 ± 23 | 561 | 1783 | 13900 | NA[a] |
| 10 (PO) | 7.1 | 6 | 239 ± 46 | 3590 ± 576 | 4040 | NC[b] | NC[b] | 72 |

[a]NA, not applicable;
[b]NC, not calculated.

In summary, example compounds of the invention exhibit enantioselective potencies of i) low nanomolar $EC_{50}$ activity against pseudotyped viruses expressing a range of filovirus glycoproteins and ii) sub uM $EC_{50}$ activities against native BSL4 filovirus with selectivity indices that confirm them as bona fide filovirus inhibitors. In addition, drug-like property characterization of example compounds indicate: iii) attractive microsome stability in human, mouse, monkey, and guinea pig (potential efficacy models for application of the Animal Efficacy Rule), and other drug-like properties and; iv) mouse PK properties for an example compound were characterized by a long half-life, low clearance and excellent oral bioavailability. These data indicate that the compounds of the invention have sufficient potency and drug-like properties to inhibit filoviruses in mammals in vivo as a method of treatment for filovirus infection.

This is further supported by comparisons between favipiravir and compounds of the invention. Favipiravir is a drug that has been evaluated in human clinical trials during the 2014-16 Ebola outbreak with 111 patients in Guinea as a method of treatment for Ebola virus infection. Although this study was not powered to define efficacy and tolerability the results indicated that patients with moderate levels of viremia (below $10^8$ genome copies/mL) responded to the drug (3-4 log drop in viral load) while those with higher levels (>$10^8$ genome copies/mL) of viremia did not [Sissoko, D. *Experimental Treatment with Favipiravir for Ebola Virus Disease (the JIKI Trial): A Historically Controlled, Single-Arm Proof-of-Concept Trial in Guinea*. (2016) PLoS Med. 2016 Mar. 1; 13(3):e1001967]. While efficacy was limited to those in early stages of infection it was likely limited by certain specific properties including potency and chemical stability, i.e., favipiravir's weak potency against EBOV and short half-life in humans (1-4 hr). In this context it is useful to compare the potency and dosing characteristics of favipiravir with compounds of the current invention to gauge the potential for their efficacy in inhibiting EBOV infection in mammals including humans. The published $EC_{50}$ for favipiravir against native EBOV virus has been reported as 67 uM [Oestereich, L. et al. *Successful treatment of advanced Ebola virus infection with T-705 (favipiravir) in a small animal model*. Antiviral Res. (2014) 105:17-21]. In our experiments, example compounds of the invention exhibit $EC_{50}$ values for BSL4 EBOV as low as 0.24 uM and 17 uM for favipiravir thus compounds of the invention may be more than 70 times more potent than favipiravir. Furthermore, while we have not tested our compounds in humans and cannot yet compare the bioavailability and pharmacokinetic properties of the two compounds in humans to date comparisons of the half-life of favipiravir (1.8 h with 150 mg/kg twice daily oral dosing) [Mentre, F., et al. *Dose regimen of favipiravir for Ebola virus disease*. Lancet Infect. Dis. (2015) 15(2):150-1] versus example compounds of the invention (7 hr half-life with 10 mg/kg single dosing, for compound A2) indicate that compounds of the current invention are significantly more potent than favipiravir and have greater potential to reach higher plasma concentrations in mammals. These comparisons provide compelling support for the utilization of compounds of the invention to inhibit filoviruses including in vitro in mammals and as methods of treatment for filovirus infection in humans.

What is claimed is:

1. A method of treating infections associated with viruses of the Filoviridae enveloped virus, or any virus expressing filovirus glycoproteins to mediate cell entry comprising administration of a therapeutically effective amount of a compound of Structural Formula I

I or a pharmaceutically acceptable salt, and a pharmaceutically acceptable carrier, diluent, or vehicle thereof, wherein:

$R^1$ is phenyl;

$R^2$ is selected from the group consisting of ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl is optionally substituted with at least one $R^8$ group;

$NR^{3a}R^{3b}$ is selected from the group consisting of each $R^8$ is independently selected from hydrogen, halogen, OH, nitro, $CF_3$, —$NR^{9a}R^{9b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{10}$, —C(O)$NR^{9a}R^{9b}$, —S(O)$_m R^{10}$, —S(O)$_m NR^{9a}R^{9b}$, —$NR^{9a}$S(O)$_m R^{10}$, —(CH$_2$)$_n$C(O)O$R^{10}$, —(CH$_2$)$_n$C(O)N($R^{9a}R^{9b}$), —(CH$_2$)$_n$N($R^{9a}R^{9b}$), —OC(O)$R^{15}$, —O(CH$_2$)$_n$O—, —$NR^{9a}$C(O)$R^{10}$, and —$NR^{9a}$C(O)N($R^{9a}R^{9b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$)

cycloalkylene, and ($C_2$ to $C_{10}$) cycloheteroalkylene is optionally substituted with at least one $R^{11}$ group;

each of the $R^{9a}$ and $R^{9b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_5$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{11}$ group, or $R^{9a}$ and $R^{9b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{11}$ group;

each $R^{10}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{11}$ group;

each $R^4$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{14}$ group;

each of the $R^{12a}$ and $R^{12b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{14}$ group, or $R^{12a}$ and $R^{12b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{14}$ group;

each $R^{13}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_5$ to $C_{10}$) aryl is optionally substituted with at least one $R^{14}$ group; each $R^4$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{16a}$ and $R^{16b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{16a}$ and $R^{16b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl; each $R^4$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_5$ to $C_{10}$) aryl;

each $R^{19}$ is independently selected from hydrogen, halogen, OH, nitro, $CF_3$, ($C_1$ to $C_{10}$) alkyl, ($C_2$ to $C_{10}$)

alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, $CF_3$, —$NR^{21a}R^{21b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{22}$, —$C(O)NR^{21a}R^{21b}$, —$S(O)_mR^{22}$, —$S(O)_mNR^{21a}R^{21b}$, —$NR^{21a}S(O)_mR^{22}$, —$(CH_2)_nC(O)OR^{22}$, —$(CH_2)_nC(O)N(R^{21a}R^{21b})$, —$(CH_2)_nN(R^{21a}R^{21b})$, —$OC(O)R^{22}$, —$NR^{21a}C(O)R^{22}$, and —$NR^{21a}C(O)N(R^{21a}R^{21b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{21a}$ and $R^{21b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

2. The method of claim 1, wherein $R^2$ is selected from the group consisting of methyl, ethyl, propyl, fluoromethyl, ethoxymethyl, chloroethyl, and fluoroethyl.

3. The method of claim 1, wherein the infection is associated with filovirus selected from the group consisting of Ebolavirus and Marburgvirus.

4. The method of claim 3, wherein the filovirus is Ebolavirus.

5. The method of claim 3, wherein the filovirus is Marburgvirus.

6. The method of claim 3, including administering a therapeutic amount of a therapeutic agent selected from the group consisting of Ribavirin, viral RNA-dependent-RNA polymerase inhibitors including favipiravir, Triazavirin, and Remdesivir (GS-5734), monoclonal antibody therapies including ZMapp, REGN3470-3471-3479, and mAb 114, vaccines including cAd3-EBOZ, and rVSV-ZEBOV, small interfering RNAs and microRNAs and immunomodulators.

7. The method of claim 4, including the inhibition of Ebolavirus glycoprotein.

8. The method of claim 5, including the inhibition of Marburgvirus glycoprotein.

9. A method of treating infections associated with viruses of the Filoviridae enveloped virus, or any virus expressing filovirus glycoproteins to mediate cell entry comprising administration of a therapeutically effective amount of an enantiomerically pure compound of Structural Formula Ia Ia or a pharmaceutically acceptable salt, and a pharmaceutically acceptable carrier, diluent, or vehicle thereof, wherein:

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

$R^2$ is selected from ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl is optionally substituted with at least one $R^8$ group;

$NR^{3a}R^{3b}$ is selected from the group consisting of

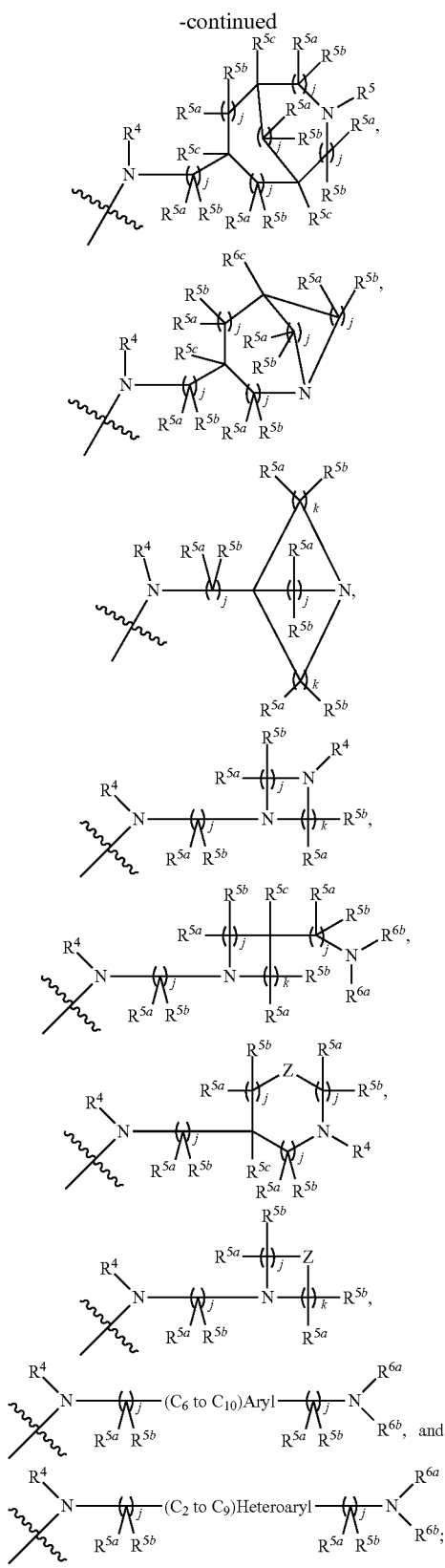

Z is selected from the group consisting of —O—, —S—, —S(O)—, and —S(O)$_2$—;

each R$^4$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteoaryl, (C$_6$ to C$_{10}$) arylene, and (C$_2$ to C$_9$) heteroarylene is optionally substituted with at least one R$^8$ group;

each of the R$^{5a}$, R$^{5b}$, and R$^{5c}$ is independently selected from hydrogen, halogen, OH, nitro, CF$_3$, —NR$^{6a}$R$^{6b}$, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, —C(O)R$^7$, —C(O)NR$^{6a}$R$^{6b}$, —S(O)$_m$R$^7$, —S(O)$_m$NR$^{6a}$R$^{6b}$, —NR$^{6a}$S(O)$_m$R$^7$, —(CH$_2$)$_n$C(O)OR$^7$, —(CH$_2$)$_n$C(O)N(R$^{6a}$R$^{6b}$), —(CH$_2$)$_n$N(R$^{6a}$R$^{6b}$), —OC(O)R$^7$, —NR$^{6a}$C(O)R$^7$, and —NR$^{6a}$C(O)N(R$^{6a}$R$^{6b}$), wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl is optionally substituted with at least one R$^8$ group;

each of the R$^{6a}$ and R$^{6b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^8$ group, or R$^{6a}$ and R$^{6b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^8$ group;

each of the R$^7$ is independently selected from hydrogen, (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl, wherein each of the said (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl is optionally substituted with at least one R$^8$ group;

each R$^8$ is independently selected from hydrogen, halogen, OH, nitro, CF$_3$, —NR$^{9a}$R$^{9b}$, oxo, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)R$^{10}$, —C(O)NR$^{9a}$R$^{9b}$, —S(O)$_m$R$^{10}$, —S(O)$_m$NR$^{9a}$R$^{9b}$, —NR$^{9a}$S(O)$_m$R$^{10}$, —(CH$_2$)$_n$C(O)OR$^{10}$, —(CH$_2$)$_n$C(O)N ($R^{9a}R^{9b}$), —(CH$_2$)$_n$N($R^{9a}R^{9b}$), —OC(O)R$^{15}$, —O(CH$_2$)$_n$O—, —NR$^{9a}$C(O)R$^{10}$, and —NR$^{9a}$C(O)N($R^{9a}R^{9b}$), wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one R$^{11}$ group;

each of the R$^{9a}$ and R$^{9b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^{11}$ group, or R$^{9a}$ and R$^{9b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^{11}$ group;

each R$^{10}$ is independently selected from hydrogen, (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl, wherein each of the said (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl is optionally substituted with at least one R$^{11}$ group;

each R$^{11}$ is independently selected from hydrogen, halogen, OH, nitro, CF$_3$, —NR$^{12a}$R$^{12b}$, oxo, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)R$^{10}$, —C(O)NR$^{9a}$R$^{9b}$, —S(O)$_m$R$^{10}$, —S(O)$_m$NR$^{9a}$R$^{9b}$, —NR$^{9a}$S(O)$_m$R$^{10}$, —(CH$_2$)$_n$C(O)OR$^{10}$, —(CH$_2$)$_n$C(O)N($R^{9a}R^{9b}$), —(CH$_2$)$_n$N($R^{9a}R^{9b}$), —OC(O)R$^{15}$, —O(CH$_2$)$_n$O—, —NR$^{9a}$C(O)R$^{10}$, and —NR$^{9a}$C(O)N($R^{9a}R^{9b}$), wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_2$ to C$_9$) heteroaryl, (C$_6$ to C$_{10}$) aryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one R$^{14}$ group;

each of the R$^{12a}$ and R$^{12b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^{14}$ group, or R$^{12a}$ and R$^{12b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^{14}$ group;

each R$^{13}$ is independently selected from hydrogen, halogen, OH, nitro, CF$_3$, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl, wherein each of the said (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_{10}$) cycloheteroalkyl, (C$_2$ to C$_9$) heteroaryl, and (C$_6$ to C$_{10}$) aryl is optionally substituted with at least one R$^{14}$ group;

each R$^{14}$ is independently selected from hydrogen, halogen, OH, nitro, CF$_3$, —NR$^{15a}$R$^{15b}$, oxo, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)R$^{16}$, —C(O)NR$^{15a}$R$^{15b}$, —S(O)$_m$R$^{16}$, —S(O)$_m$NR$^{15a}$R$^{15b}$, —NR$^{15a}$S(O)$_m$R$^{16}$, —(CH$_2$)$_n$C(O)OR$^{16}$, —(CH$_2$)$_n$C(O)N($R^{15a}R^{15b}$), —(CH$_2$)$_n$N($R^{15a}R^{15b}$), —OC(O)R$^{16}$, —NR$^{15a}$C(O)R$^{16}$, and —NR$^{15a}$C(O)N($R^{15a}R^{15b}$), wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one R$^{17}$ group;

each of the R$^{15a}$ and R$^{15b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl is optionally substituted with at least one R$^{17}$ group, or R$^{15a}$ and R$^{15b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^{17}$ group;

each R$^{16}$ is independently selected from hydrogen, halogen, OH, nitro, CF$_3$, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, $CF_3$, —$NR^{18a}R^{18b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{19}$, —$C(O)NR^{18a}R^{18b}$, —$S(O)_mR^{19}$, —$S(O)_mNR^{18a}R^{18b}$, —$NR^{18a}S(O)_mR^{19}$, —$(CH_2)_nC(O)OR^{19}$, —$(CH_2)_nC(O)N(R^{18a}R^{18b})$, —$(CH_2)_nN(R^{18a}R^{18b})$, —$OC(O)R^{19}$, —$NR^{18a}C(O)R^{19}$, and —$NR^{18a}C(O)N(R^{18a}R^{18b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{19}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, $CF_3$, —$NR^{21a}R^{21b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{22}$, —$C(O)NR^{21a}R^{21b}$, —$S(O)_mR^{22}$, —$S(O)_mNR^{21a}R^{21b}$, —$NR^{21a}S(O)_mR^{22}$, —$(CH_2)_nC(O)OR^{22}$, —$(CH_2)_nC(O)N(R^{21a}R^{21b})$, —$(CH_2)_nN(R^{21a}R^{21b})$, —$OC(O)R^{22}$, —$NR^{21a}C(O)R^{22}$, and —$NR^{21a}C(O)N(R^{21a}R^{21b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{21a}$ and $R^{21b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

i is 2, 3, 4, 5, or 6;

j is 0, 1, 2, 3, 4, or 5;

k is 1, 2, 3, 4, or 5;

m is 0, 1 or 2;

n is 0, 1, 2, 3, or 4.

10. The method of claim 9, wherein $R^1$ is phenyl.

11. The method of claim 10, wherein $R^2$ is selected from the group consisting of methyl, ethyl, propyl, fluoromethyl, ethoxymethyl, chloroethyl, and fluoroethyl.

12. The method of claim 10, wherein $NR^{3a}R^{3b}$ is selected from the group consisting of

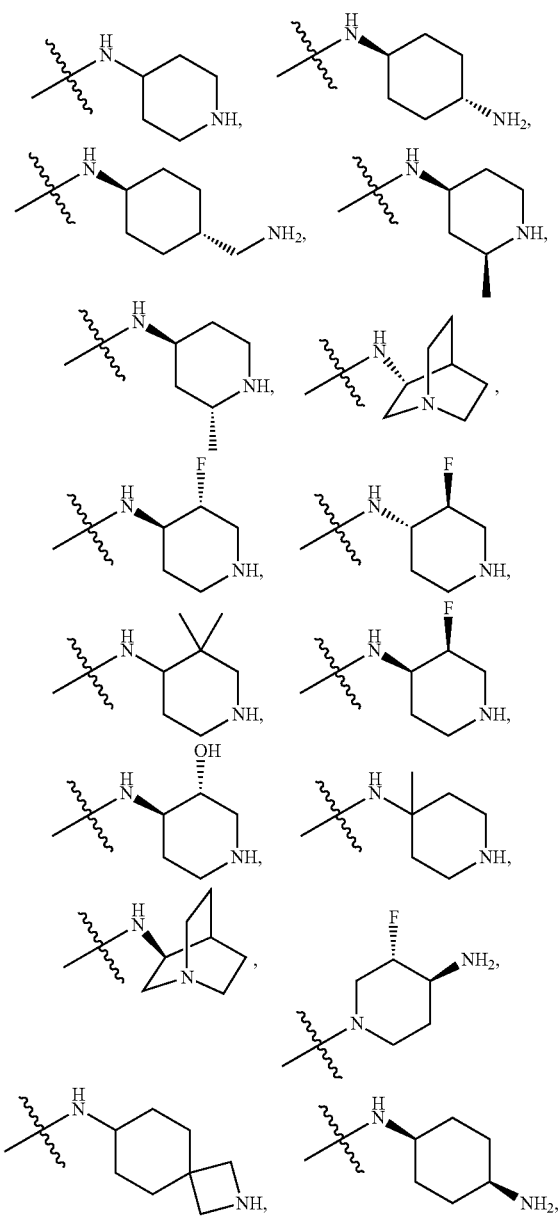

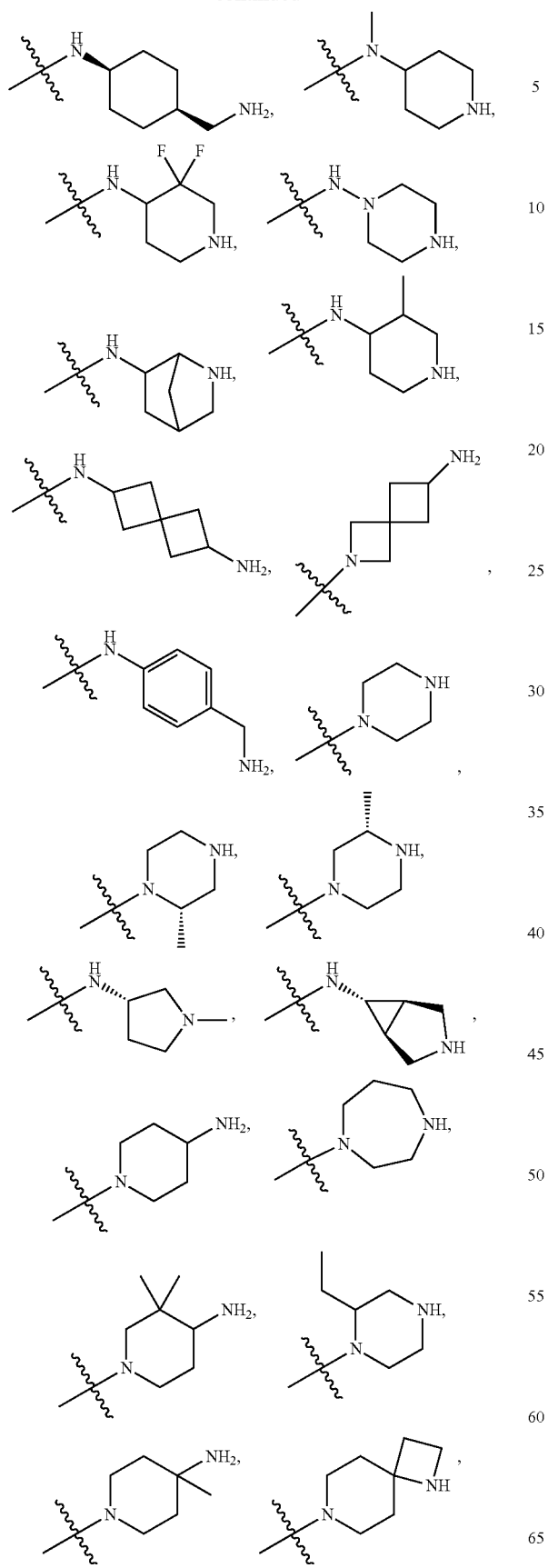
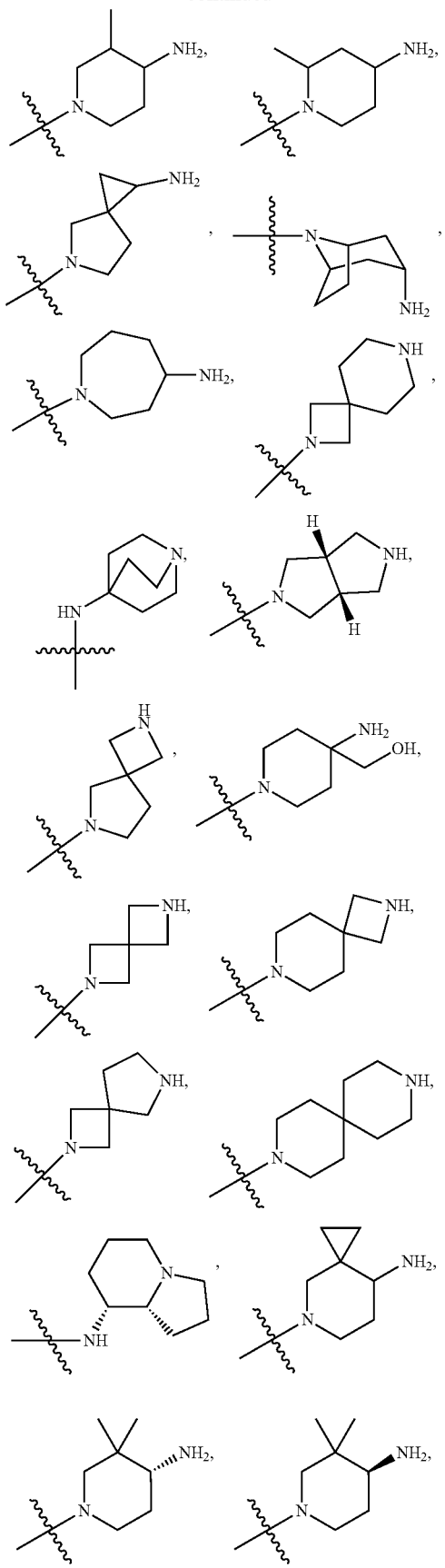

13. The method of claim 9, wherein the infection is associated with filovirus selected from the group consisting of Ebolavirus and Marburgvirus.

14. The method of claim 13, wherein the filovirus is Ebolavirus.

15. The method of claim 13, wherein the filovirus is Marburgvirus.

16. The method of claim 13, including administering a therapeutic amount of a therapeutic agent selected from the group consisting of Ribavirin, viral RNA-dependent-RNA polymerase inhibitors including favipiravir, Triazavirin, and Remdesivir (GS-5734), monoclonal antibody therapies including ZMapp, REGN3470-3471-3479, and mAb 114, vaccines including cAd3-EBOZ, and rVSV-ZEBOV, small interfering RNAs and microRNAs and immunomodulators.

17. The method of claim 14, including the inhibition of Ebolavirus glycoprotein.

18. The method of claim 15, including the inhibition of Marburgvirus glycoprotein.

19. A method of treating infections associated with viruses of the Filoviridae enveloped virus, or any virus expressing filovirus glycoproteins to mediate cell entry comprising administration of a therapeutically effective amount of a compound of Structural Formula Ib Ib or a pharmaceutically acceptable salt, and a pharmaceutically acceptable carrier, diluent, or vehicle thereof, wherein:

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

$R^2$ is selected from ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl is optionally substituted with at least one $R^8$ group;

$NR^{3a}R^{3b}$ is selected from the group consisting of

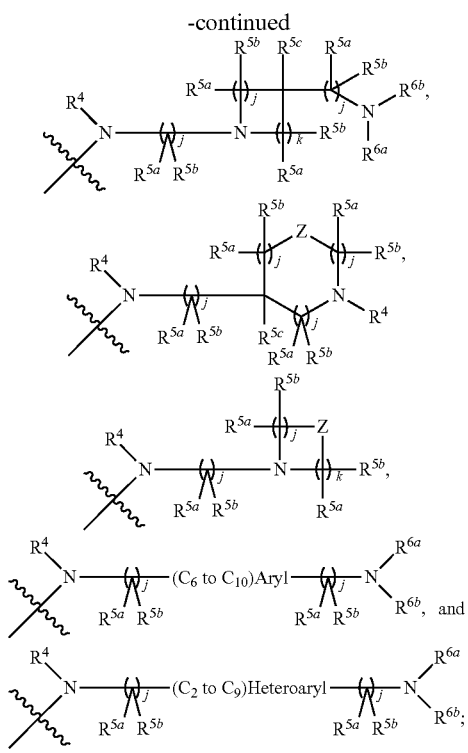

Z is selected from the group consisting of —O—, —S—, —S(O)—, and —S(O)$_2$—;

each $R^4$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteoaryl, ($C_6$ to $C_{10}$) arylene, and ($C_2$ to $C_9$) heteroarylene is optionally substituted with at least one $R^8$ group;

each of the $R^{5a}$, $R^{5b}$, and $R^{5c}$ is independently selected from hydrogen, halogen, OH, nitro, $CF_3$, —$NR^{6a}R^{6b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^7$, —C(O)$NR^{6a}R^{6b}$, —S(O)$_m R^7$, —S(O)$_m NR^{6a}R^{6b}$, —$NR^{6a}$S(O)$_m R^7$, —(CH$_2$)$_n$C(O)$OR^7$, —(CH$_2$)$_n$C(O)N($R^{6a}R^{6b}$), —(CH$_2$)$_n$N($R^{6a}R^{6b}$), —OC(O)$R^7$, —$NR^{6a}$C(O)$R^7$, and —$NR^{6a}$C(O)N($R^{6a}R^{6b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^8$ group;

each of the $R^{6a}$ and $R^{6b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^8$ group, or $R^{6a}$ and $R^{6b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^8$ group;

each of the $R^7$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^8$ group;

each $R^8$ is independently selected from hydrogen, halogen, OH, nitro, $CF_3$, —$NR^{9a}R^{9b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, cycloheteroalkylene, —C(O)$R^{10}$, —C(O)$NR^{9a}R^{9b}$, —S(O)$_m R^{10}$, —S(O)$_m NR^{9a}R^{9b}$, —$NR^{9a}$S(O)$_m R^{10}$, —(CH$_2$)$_n$C(O)$OR^{10}$, —(CH$_2$)$_n$C(O)N($R^{9a}R^{9b}$), —(CH$_2$)$_n$N($R^{9a}R^{9b}$), —OC(O)$R^{15}$, —O(CH$_2$)$_n$O—, —$NR^{9a}$C(O)$R^{10}$, and —$NR^{9a}$C(O)N($R^{9a}R^{9b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{11}$ group;

each of the $R^{9a}$ and $R^{9b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{11}$ group, or $R^{9a}$ and $R^{9b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{11}$ group;

each $R^{10}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{11}$ group;

each $R^{11}$ is independently selected from hydrogen, halogen, OH, nitro, $CF_3$, —$NR^{12a}R^{12b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{18}$, —$C(O)NR^{12a}R^{12b}$, —$S(O)_mR^{13}$, —$S(O)_mNR^{12a}R^{12b}$, —$NR^{12a}S(O)_mR^{13}$, —$(CH_2)_nC(O)OR^{13}$, —$(CH_2)_nC(O)N(R^{12a}R^{12b})$, —$(CH_2)_nN(R^{12a}R^{12b})$, —$OC(O)R^{13}$, —$NR^{12a}C(O)R^{13}$, and —$NR^{12a}C(O)N(R^{12a}R^{12b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{14}$ group;

each of the $R^{12a}$ and $R^{12b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{14}$ group, or $R^{12a}$ and $R^{12b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{14}$ group;

each $R^{13}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{14}$ group;

each $R^{14}$ is independently selected from hydrogen, halogen, OH, nitro, $CF_3$, —$NR^{15a}R^{15b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{16}$, —$C(O)NR^{15a}R^{15b}$, —$S(O)_mR^{16}$, —$S(O)_mNR^{15a}R^{15b}$, —$NR^{15a}S(O)_mR^{16}$, —$(CH_2)_nC(O)OR^{16}$, —$(CH_2)_nC(O)N(R^{15a}R^{15b})$, —$(CH_2)_nN(R^{15a}R^{15b})$, —$OC(O)R^{16}$, —$NR^{15a}C(O)R^{16}$, and —$NR^{15a}C(O)N(R^{15a}R^{15b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{15a}$ and $R^{15b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{15a}$ and $R^{15b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, $CF_3$, —$NR^{18a}R^{18b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{19}$, —$C(O)NR^{18a}R^{18b}$, —$S(O)_mR^{19}$, —$S(O)_mNR^{18a}R^{18b}$, —$NR^{18a}S(O)_mR^{19}$, —$(CH_2)_nC(O)OR^{19}$, —$(CH_2)_nC(O)N(R^{18a}R^{18b})$, —$(CH_2)_nN(R^{18a}R^{18b})$, —$OC(O)R^{19}$, —$NR^{18a}C(O)R^{19}$, and —$NR^{18a}C(O)N(R^{18a}R^{18b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{19}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, $CF_3$, —$NR^{21a}R^{21b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{22}$, —$C(O)NR^{21a}R^{21b}$, —$S(O)_mR^{22}$, —$S(O)_mNR^{21a}R^{21b}$, —$NR^{21a}S(O)_mR^{22}$, —$(CH_2)_nC(O)OR^{22}$, —$(CH_2)_nC(O)N(R^{21a}R^{21b})$, —$(CH_2)_nN(R^{21a}R^{21b})$, —$OC(O)R^{22}$, —$NR^{21a}C(O)R^{22}$, and —$NR^{21a}C(O)N(R^{21a}R^{21b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{21a}$ and $R^{21b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

20. The method of claim 19, wherein $R^1$ is phenyl.
21. The method of claim 20, wherein
$R^2$ is selected from the group consisting of methyl, ethyl, propyl, fluoromethyl, ethoxymethyl, chloroethyl, and fluoroethyl.
22. The method of claim 20, wherein $NR^{3a}R^{3b}$ is selected from the group consisting of

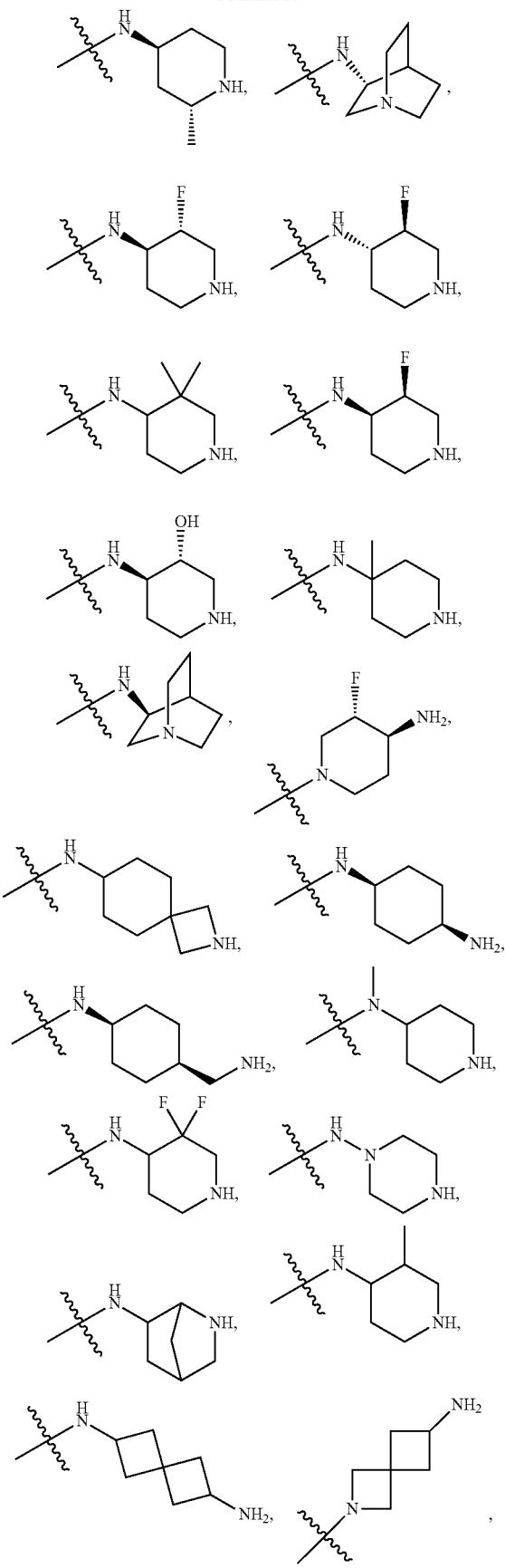

23. The method of claim 21, wherein the infection is associated with filovirus selected from the group consisting of Ebolavirus and Marburgvirus.

24. The method of claim 23, wherein the filovirus is Ebolavirus.

25. The method of claim 23, wherein the filovirus is Marburgvirus.

26. The method of claim 23, including administering a therapeutic amount of a therapeutic agent selected from the group consisting of Ribavirin, viral RNA-dependent-RNA polymerase inhibitors including favipiravir, Triazavirin, and Remdesivir (GS-5734), monoclonal antibody therapies including ZMapp, REGN3470-3471-3479, and mAb 114, vaccines including cAd3-EBOZ, and rVSV-ZEBOV, small interfering RNAs and microRNAs and immunomodulators.

27. The method of claim 24, including the inhibition of Ebolavirus glycoprotein.

28. The method of claim 25, including the inhibition of Marburgvirus glycoprotein.

29. A method of treating infections associated with viruses of the Filoviridae enveloped virus, or any virus expressing filovirus glycoproteins to mediate cell entry comprising administration of a therapeutically effective amount of a compound or a pharmaceutically acceptable salt, and a pharmaceutically acceptable carrier, diluent, or vehicle thereof, selected from the group consisting of:

187
-continued
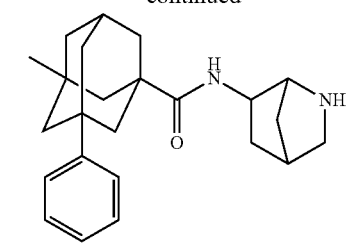
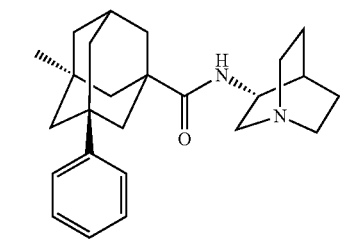
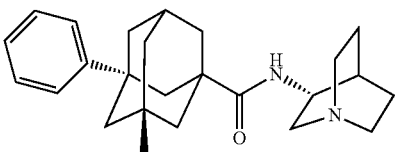
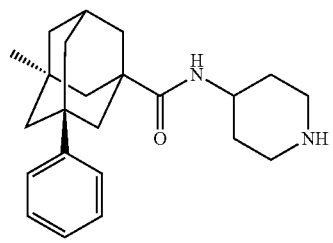
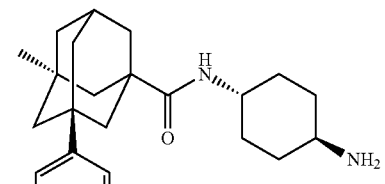
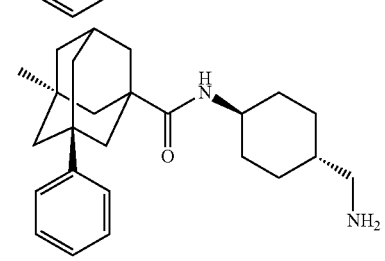
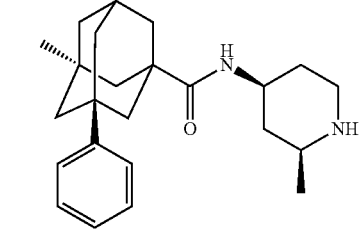
188
-continued
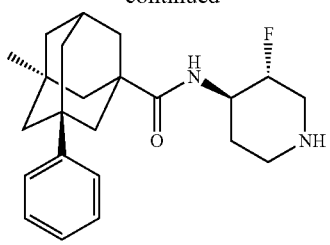
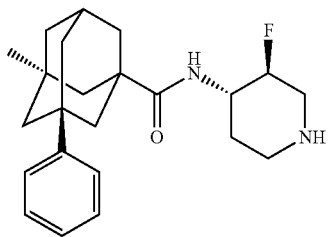
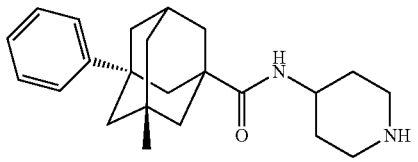
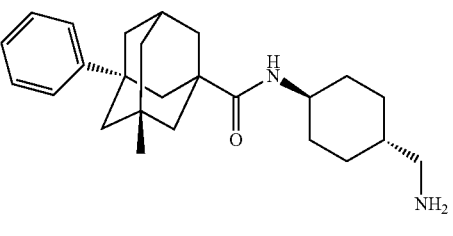
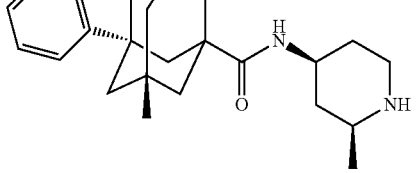
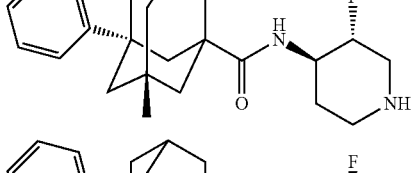
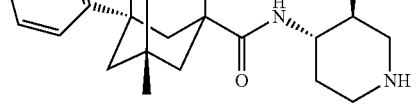

189
-continued
190
-continued
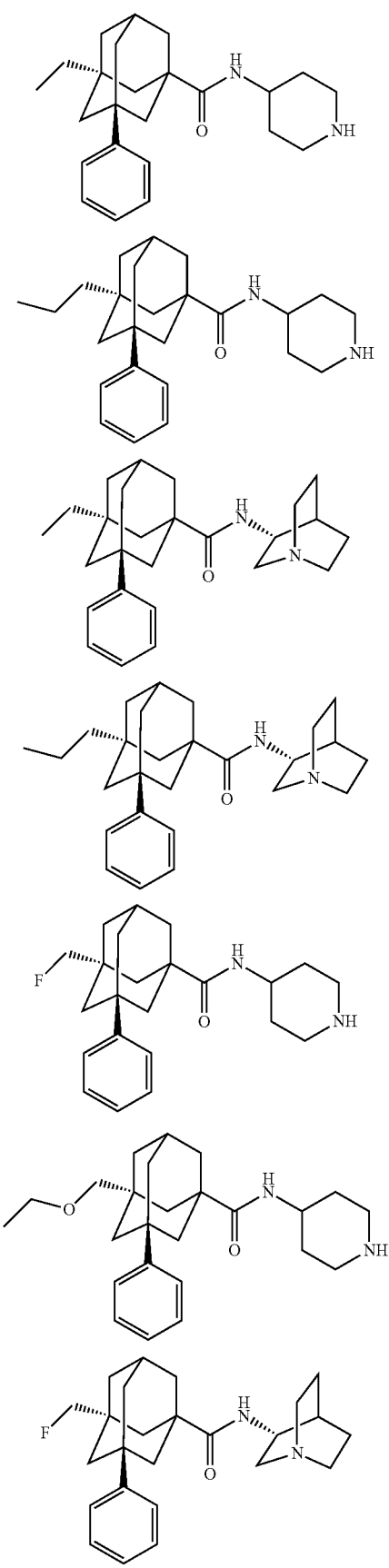
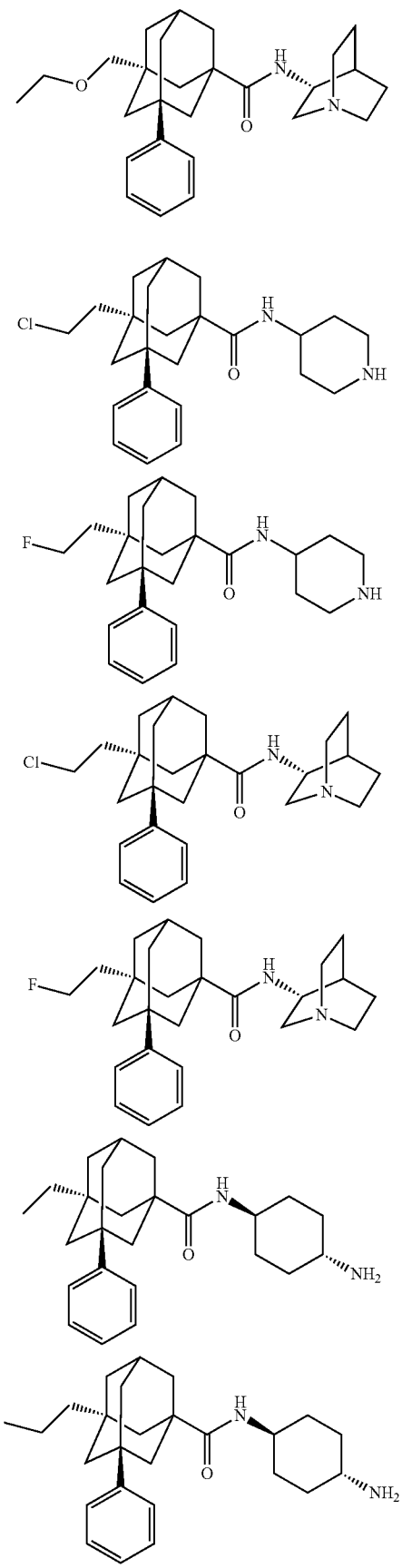

191
-continued
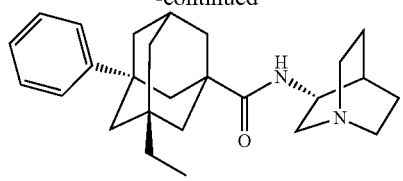
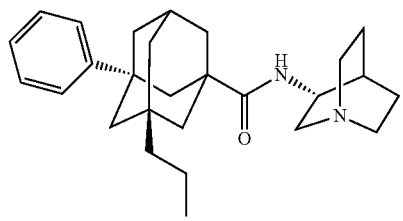
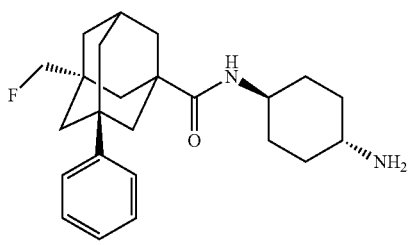
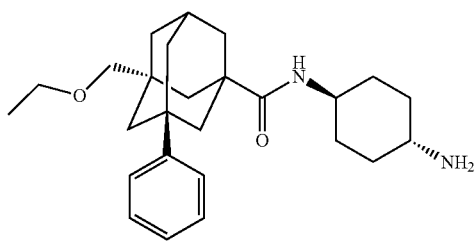
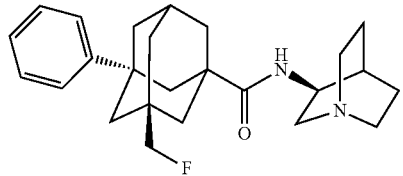
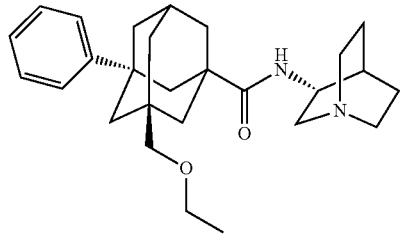
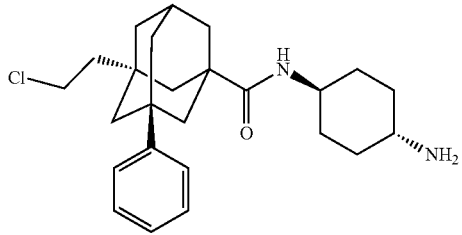
192
-continued
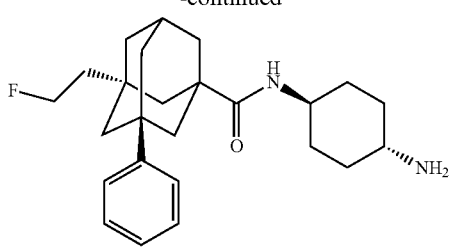
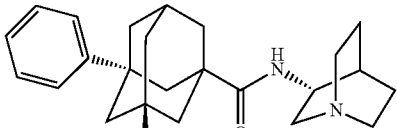
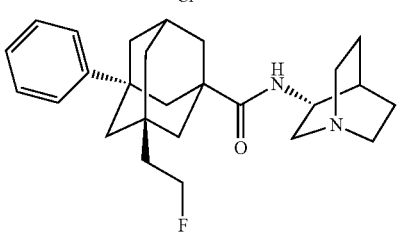
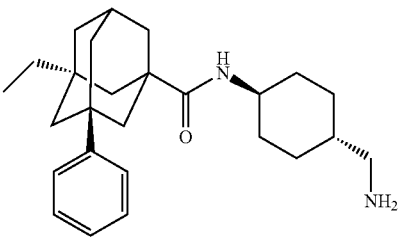
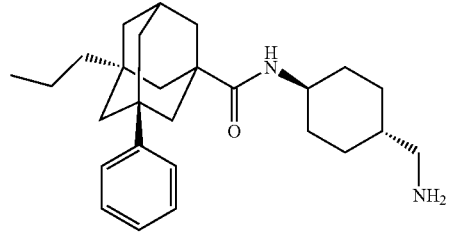
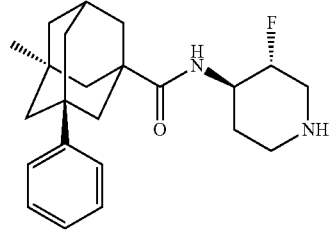
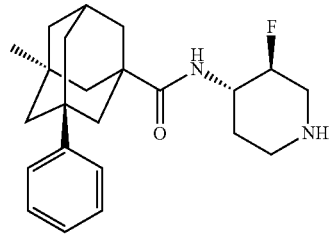

193
-continued
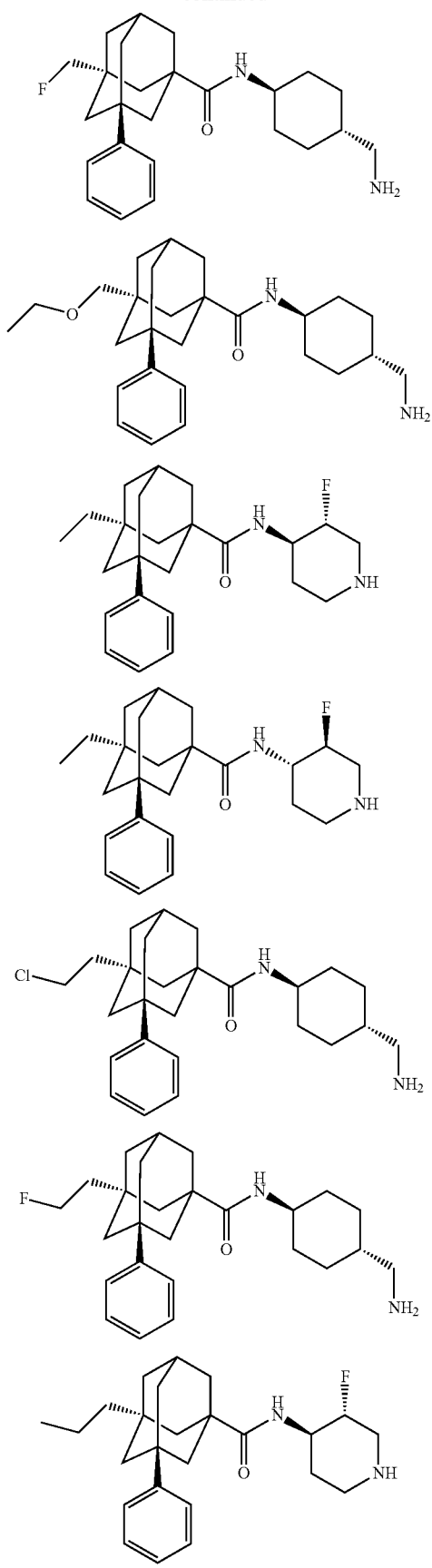
194
-continued
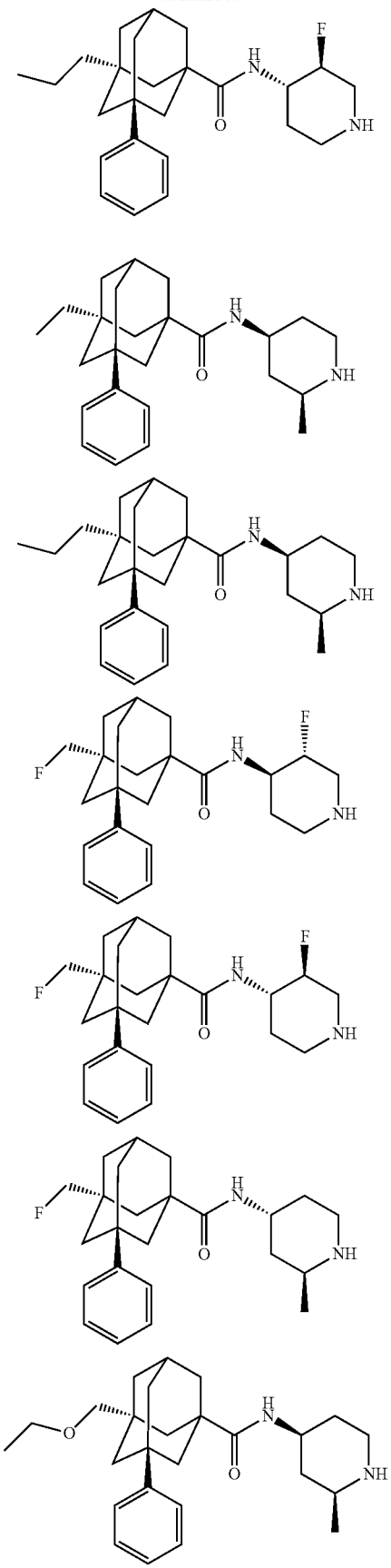

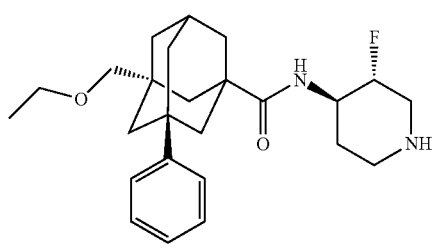
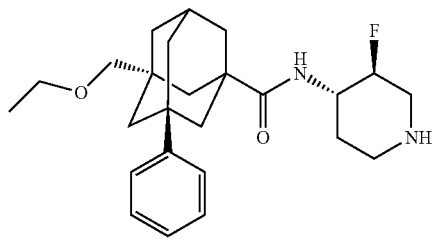
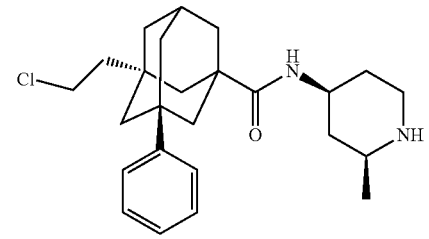
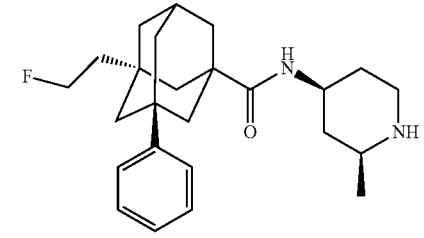
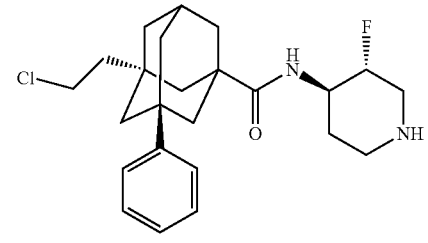
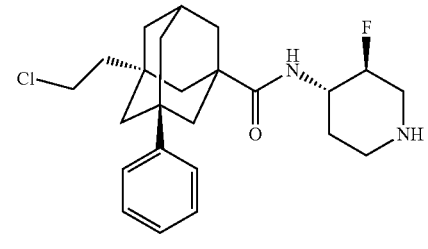
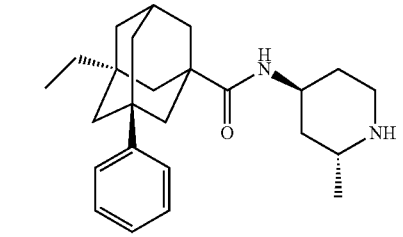
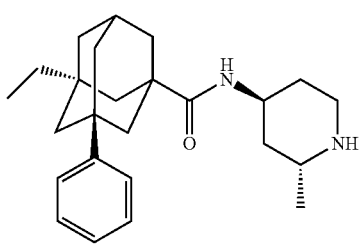
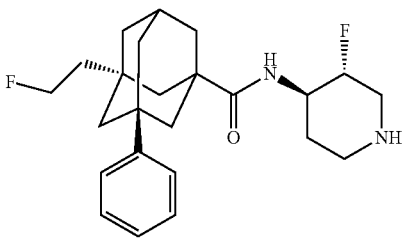
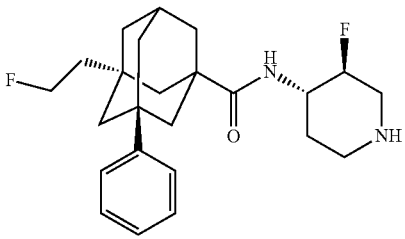
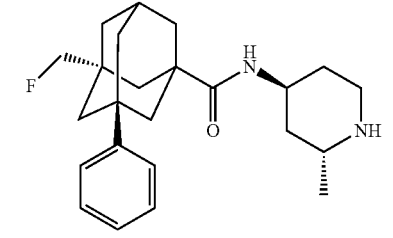
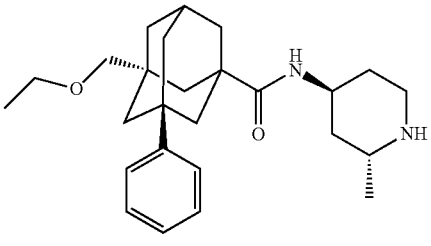
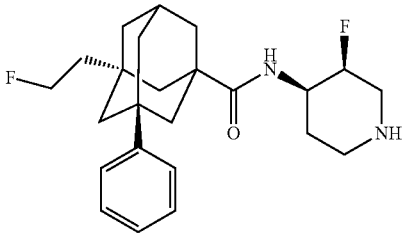
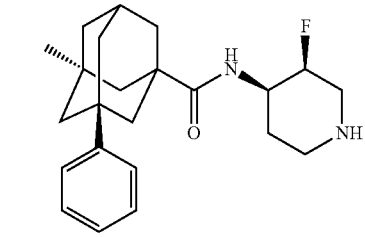

197
-continued
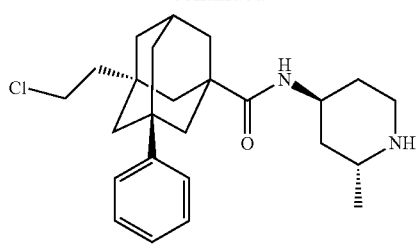
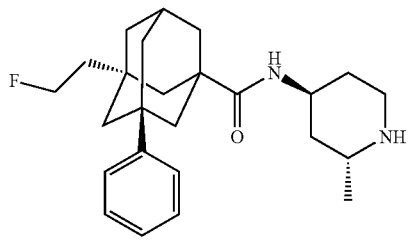
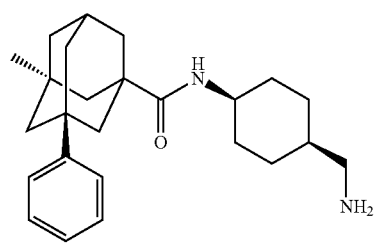
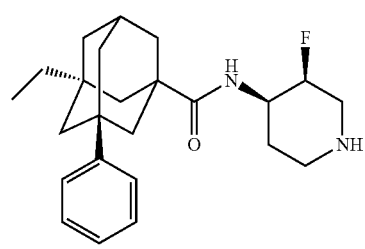
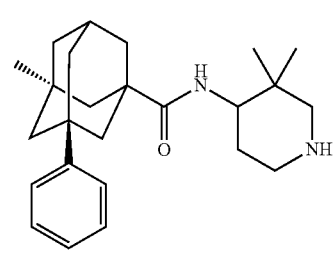
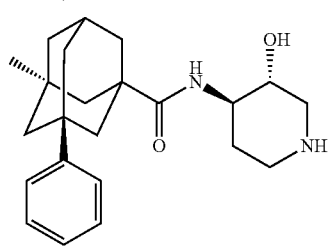
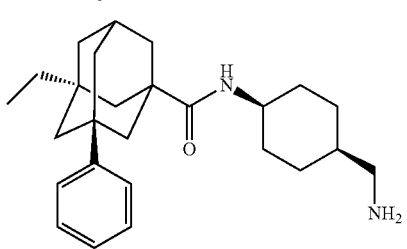
198
-continued
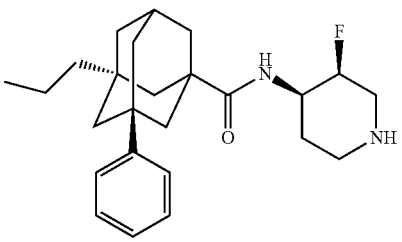
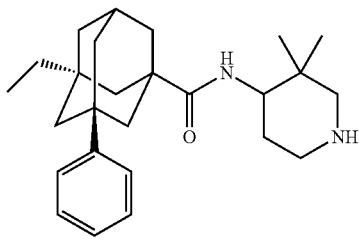
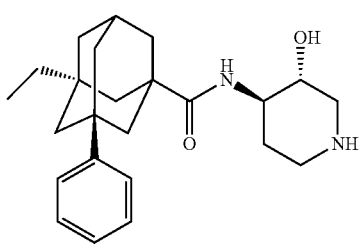
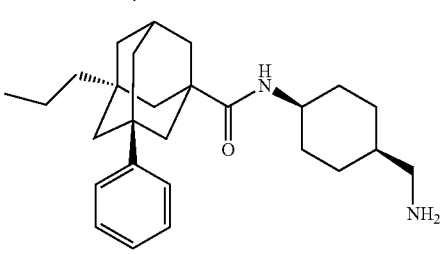
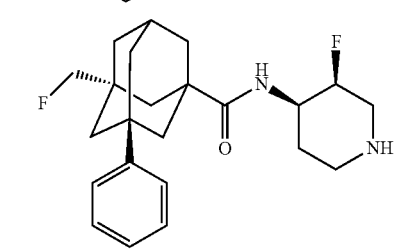
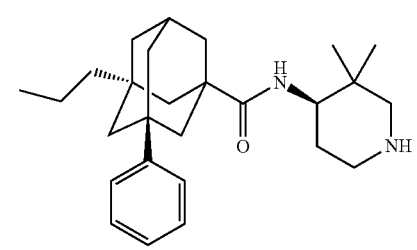
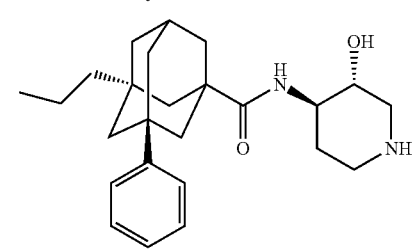

199
-continued
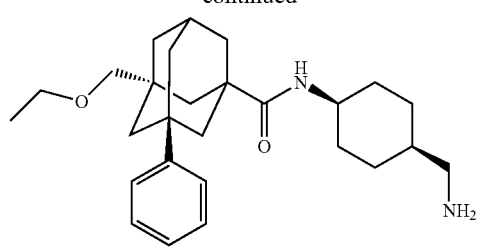
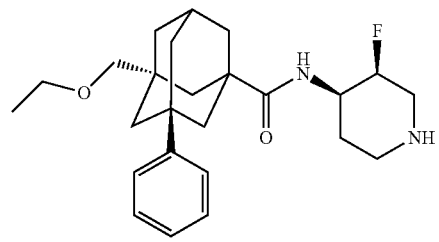
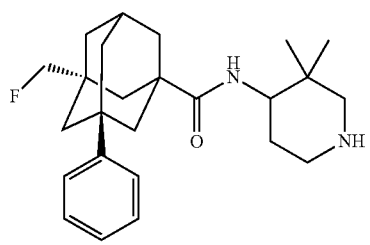
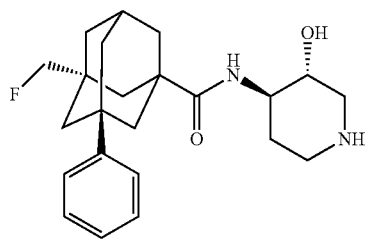
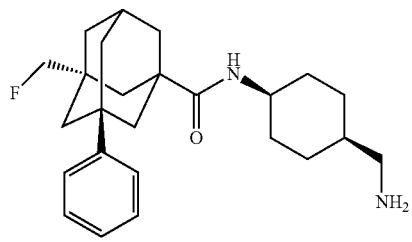
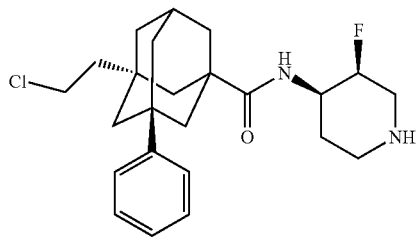
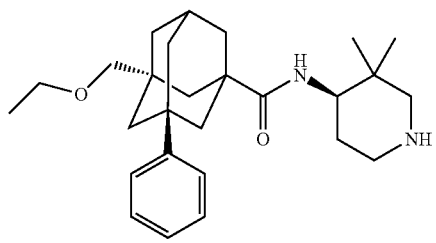
200
-continued
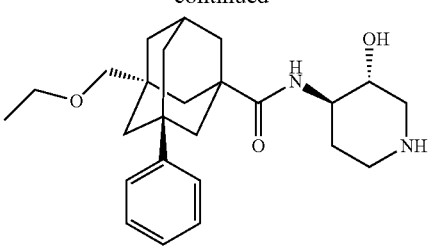
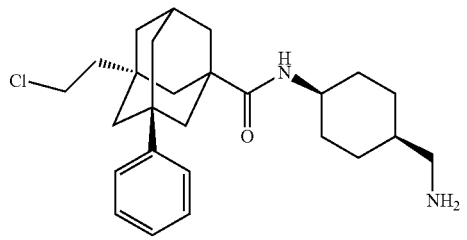
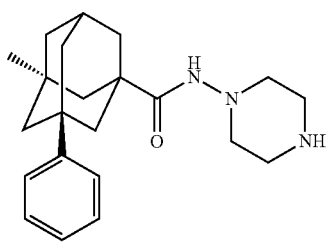
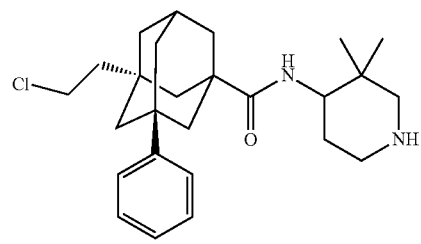
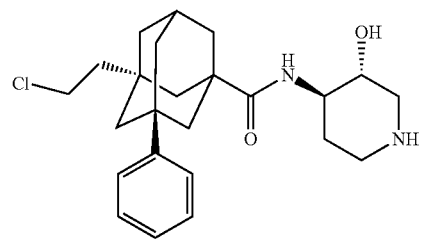
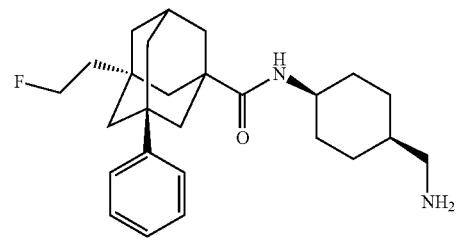
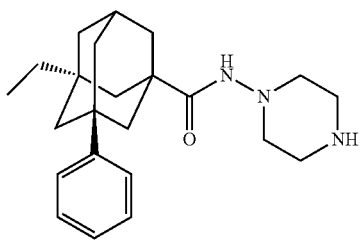

201
-continued
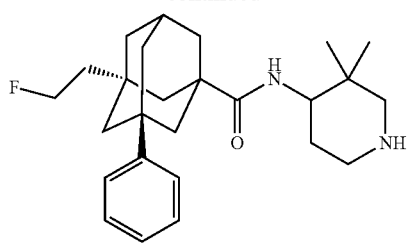
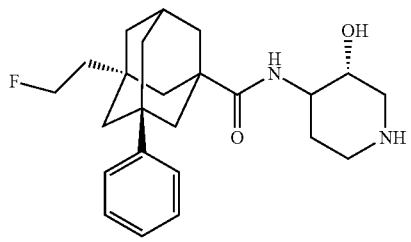
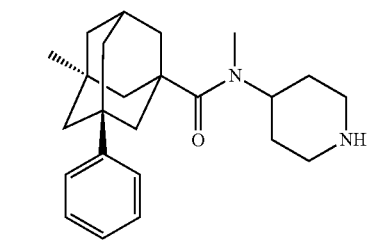
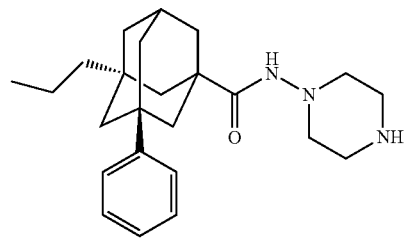
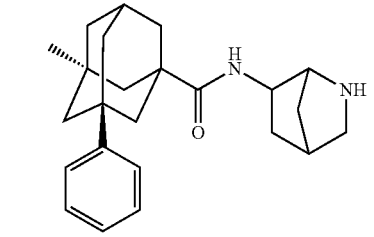
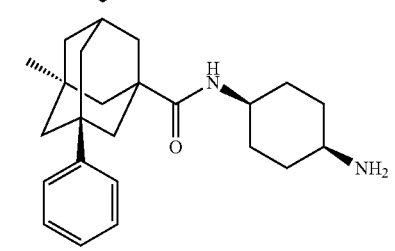
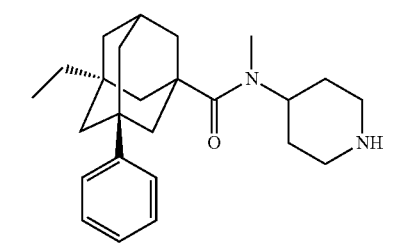
202
-continued
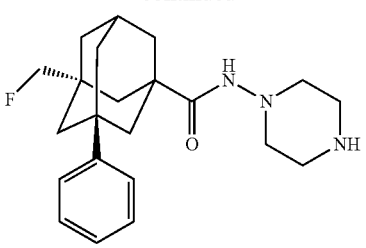
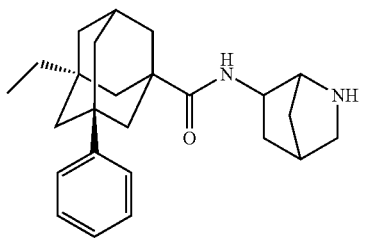
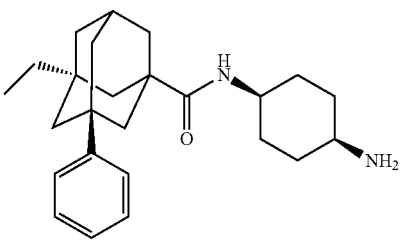
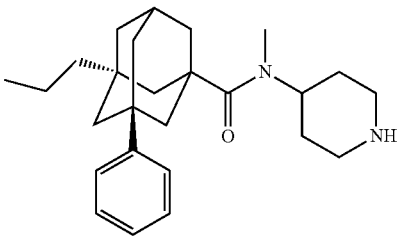
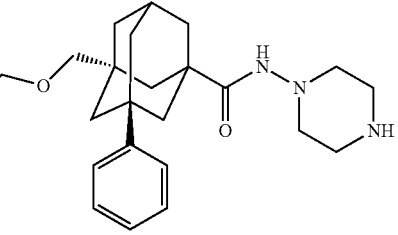
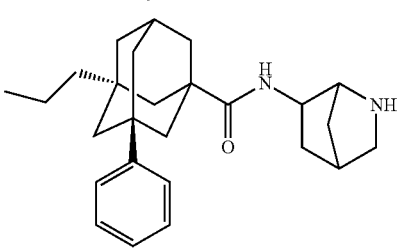
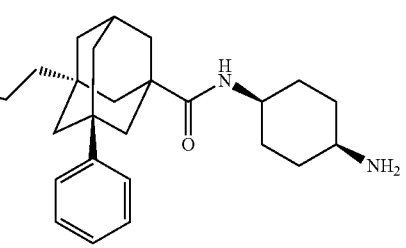

203
-continued
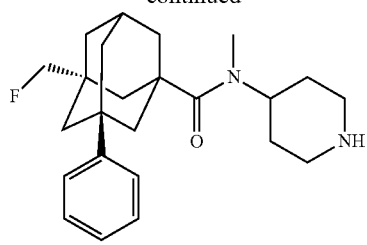
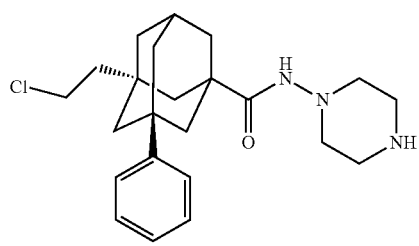
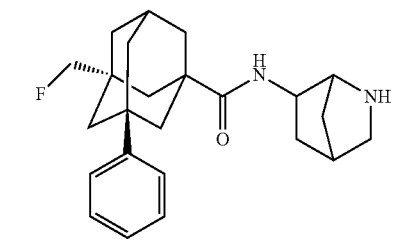
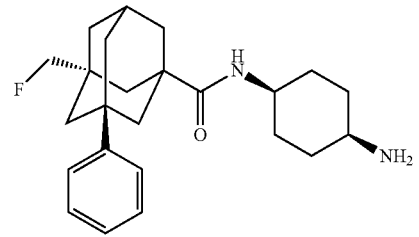
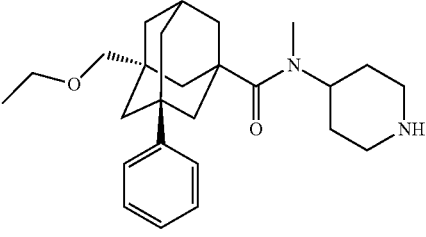
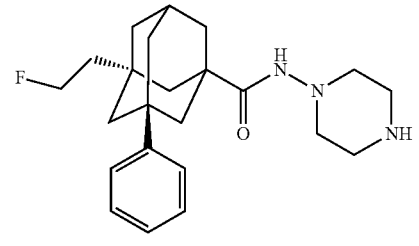
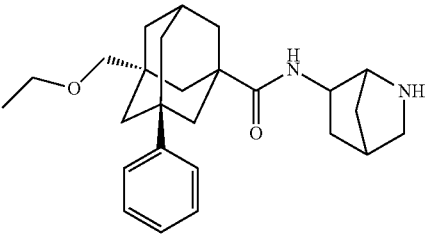
204
-continued
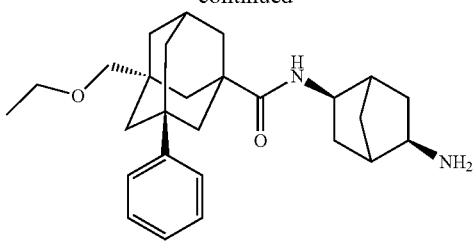
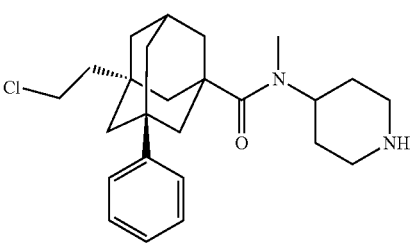
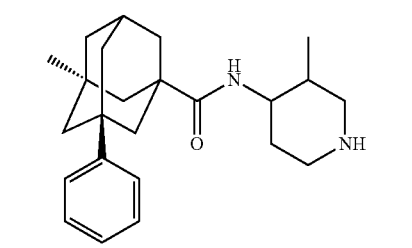
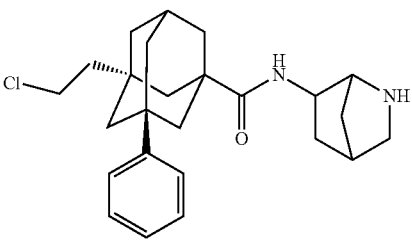
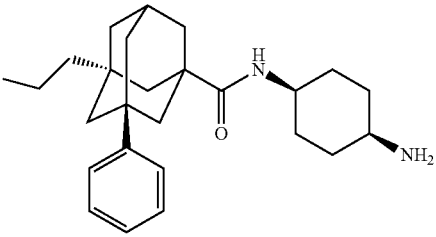
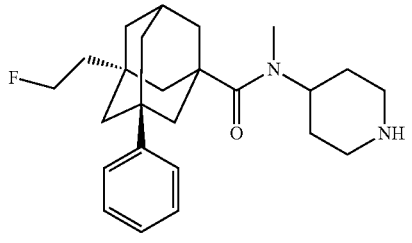
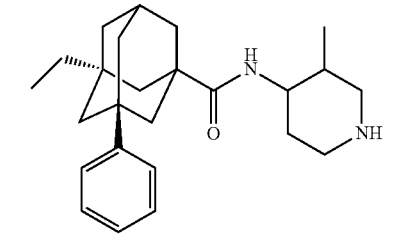

205
-continued
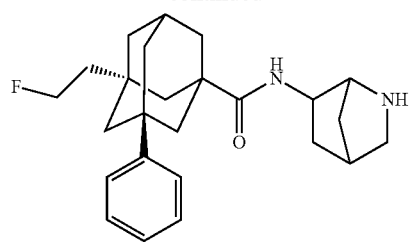
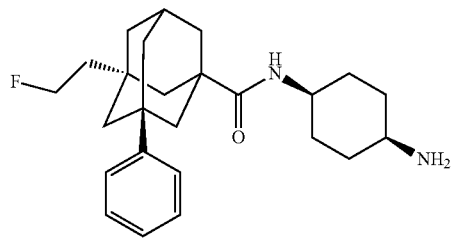
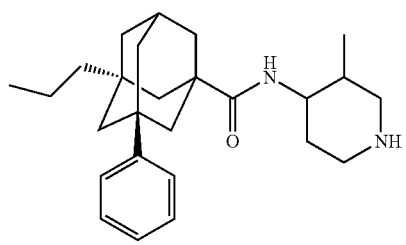
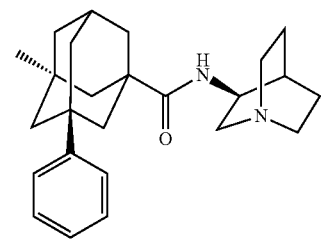
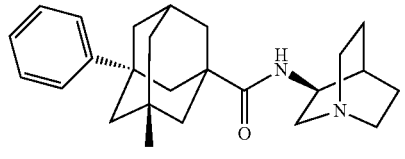
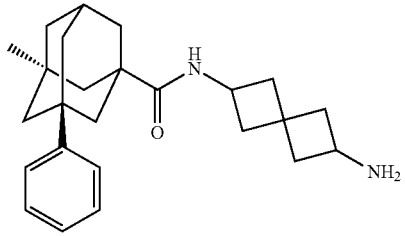
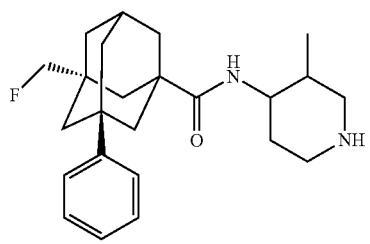
206
-continued
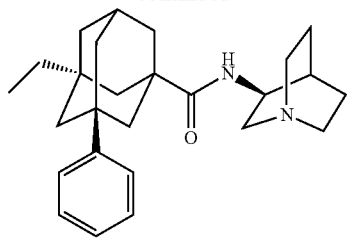
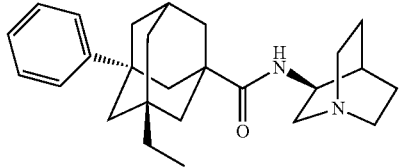
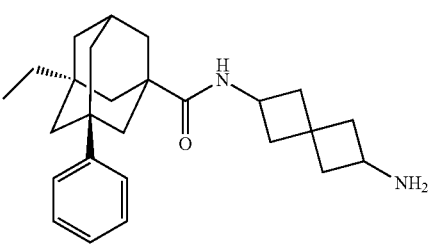
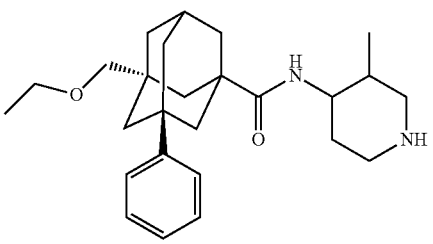
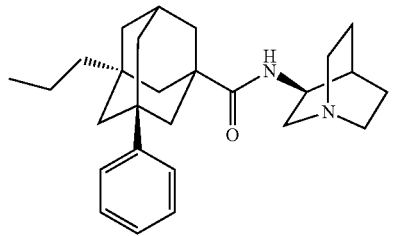
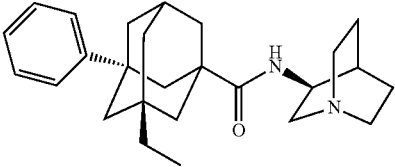
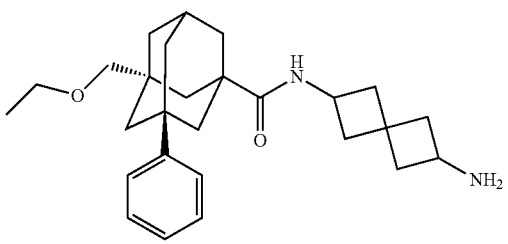

207
-continued
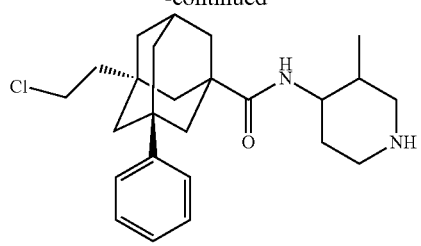
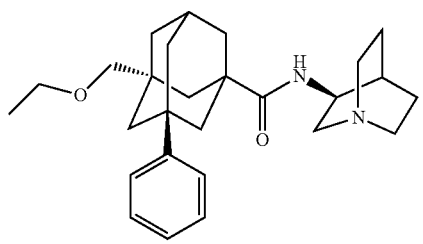
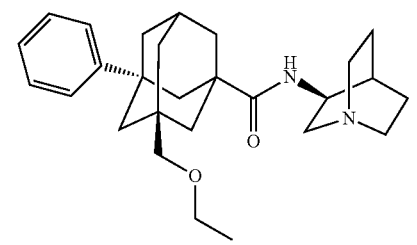
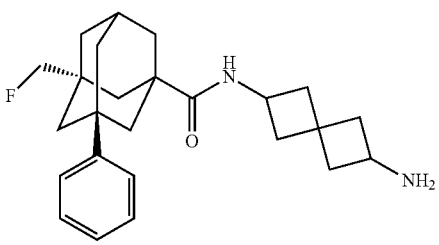
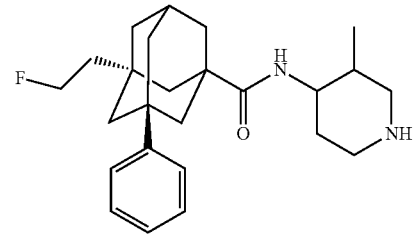
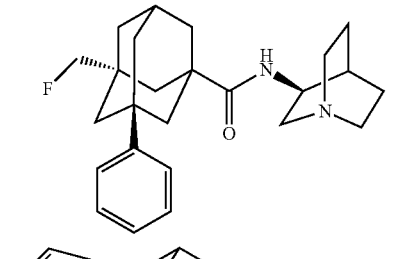
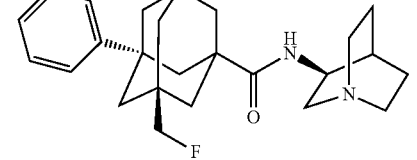
208
-continued
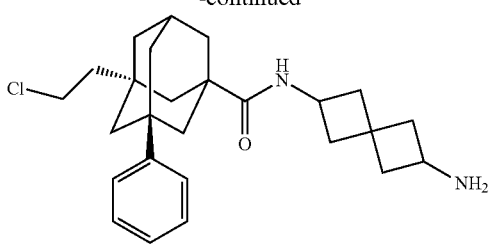
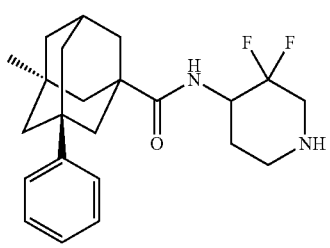
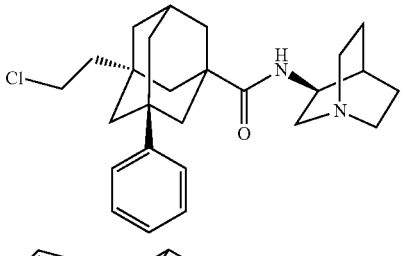
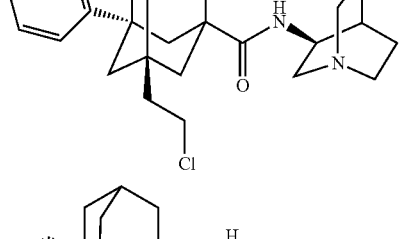
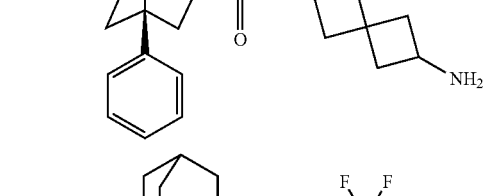
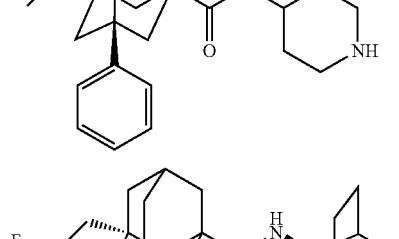
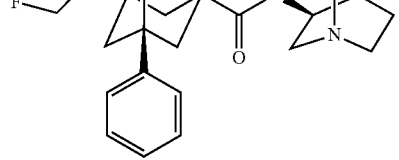

209
-continued
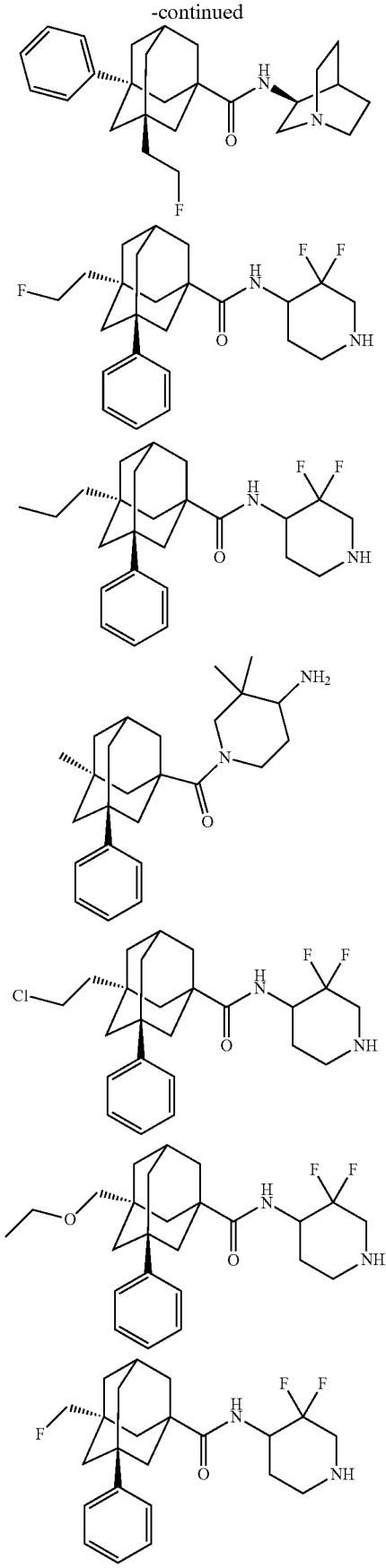
210
-continued
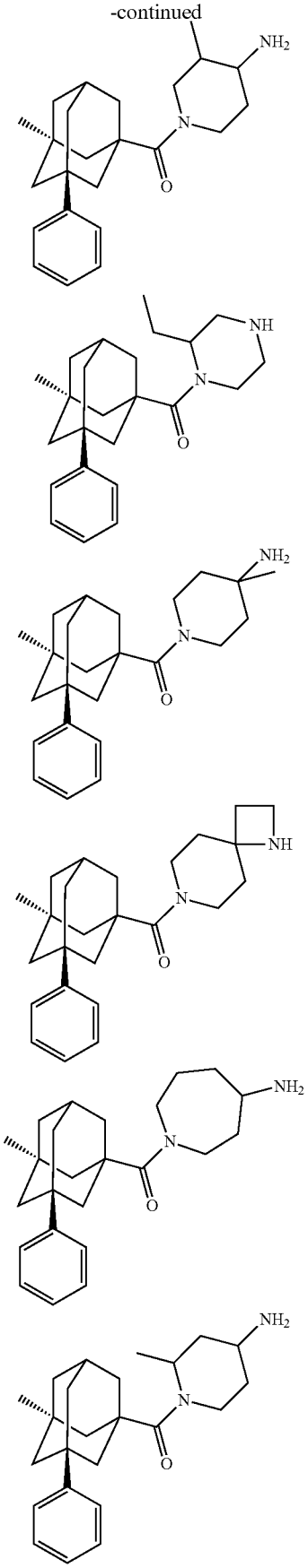

211
-continued
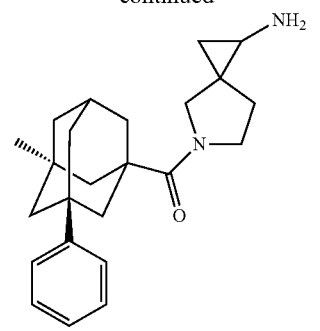
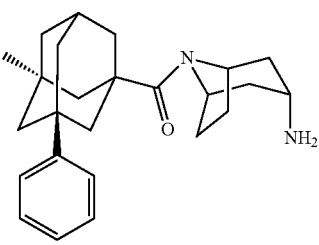
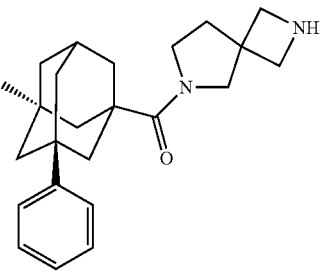
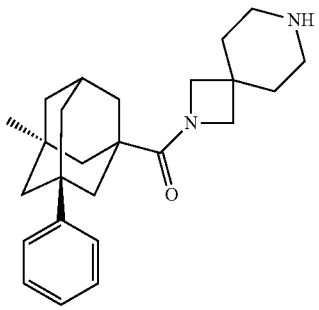
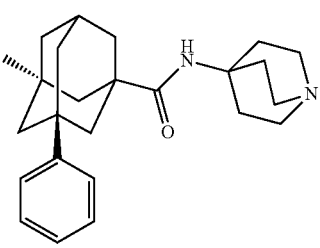
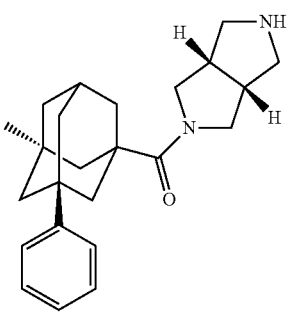
212
-continued
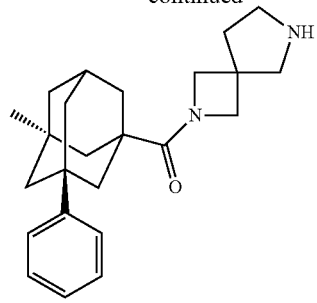
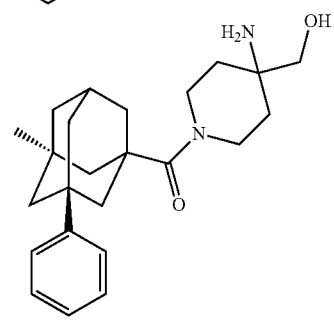
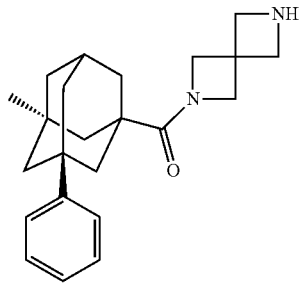
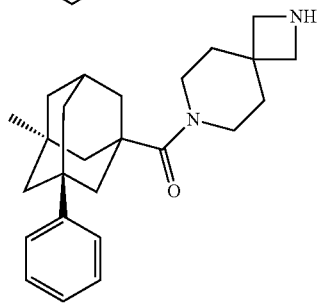
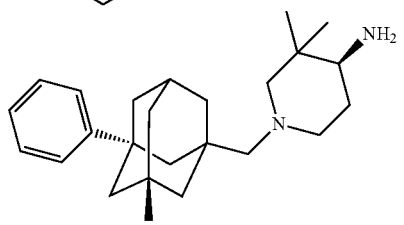
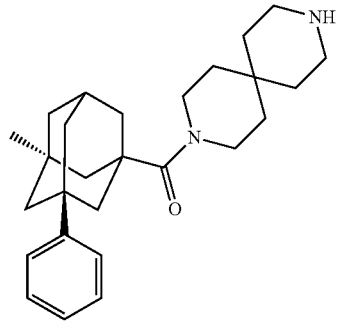

213
-continued
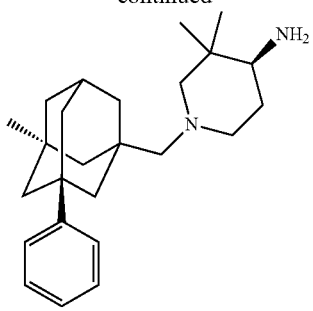
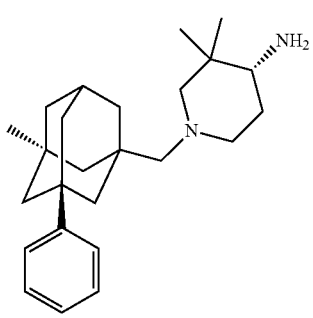
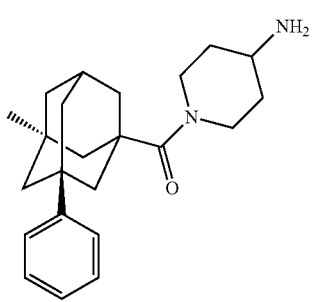
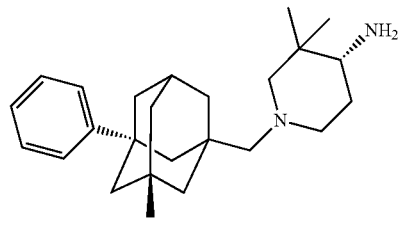
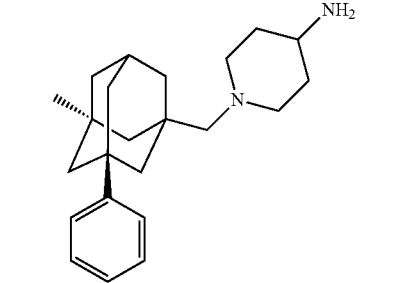
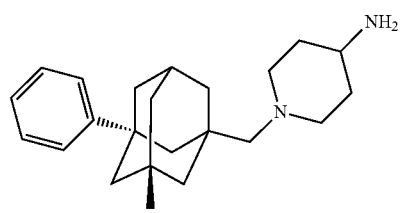
214
-continued
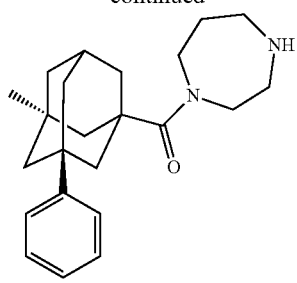
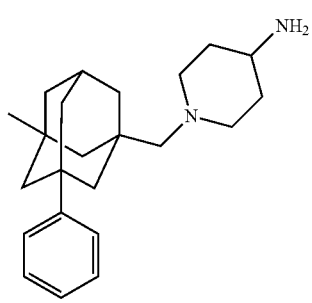
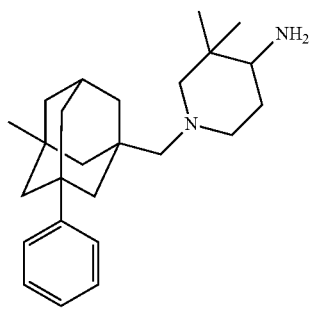
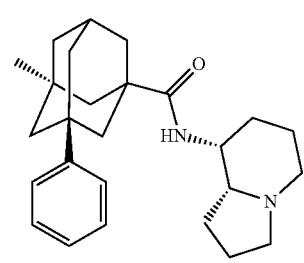
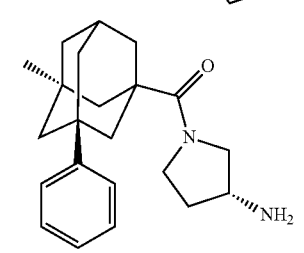
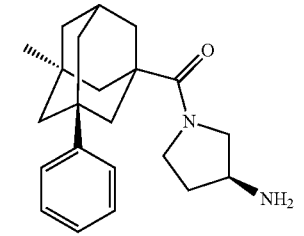

30. The method of claim 29, wherein the compound is selected from the group consisting of:

31. The method of claim 29, wherein the infection is associated with filovirus selected from the group consisting of Ebolavirus and Marburgvirus.

32. The method of claim 31, wherein the filovirus is Ebolavirus.

33. The method of claim 29, including administering a therapeutic amount of a therapeutic agent selected from the group consisting of Ribavirin, viral RNA-dependent-RNA polymerase inhibitors including favipiravir, Triazavirin, and Remdesivir (GS-5734), monoclonal antibody therapies including ZMapp, REGN3470-3471-3479, and mAb 114, vaccines including cAd3-EBOZ, and rVSV-ZEBOV, small interfering RNAs and microRNAs and immunomodulators.

34. The method of claim 30, wherein the infection is associated with filovirus selected from the group consisting of Ebolavirus and Marburgvirus.

35. The method of claim 34, wherein the filovirus is Ebolavirus.

36. The method of claim 35, including administering a therapeutic amount of a therapeutic agent selected from the group consisting of Ribavirin, viral RNA-dependent-RNA polymerase inhibitors including favipiravir, Triazavirin, and Remdesivir (GS-5734), monoclonal antibody therapies including ZMapp, REGN3470-3471-3479, and mAb 114, vaccines including cAd3-EBOZ, and rVSV-ZEBOV, small interfering RNAs and microRNAs and immunomodulators.

37. The method of claim 29, wherein the compound is:

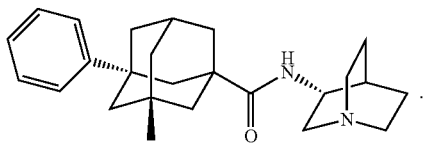 [SMILES: C[C@@]12CC3CC(C(=O)N[C@H]4CN5CCC4CC5)(C1)C[C@](c1ccccc1)(C3)C2]

38. The method of claim 37, wherein the filovirus is Marburgvirus.

39. The method of claim 38, including administering a therapeutic amount of a therapeutic agent selected from the group consisting of Ribavirin, viral RNA-dependent-RNA polymerase inhibitors including favipiravir, Triazavirin, and Remdesivir (GS-5734), monoclonal antibody therapies including ZMapp, REGN3470-3471-3479, and mAb 114, vaccines including cAd3-EBOZ, and rVSV-ZEBOV, small interfering RNAs and microRNAs and immunomodulators.

40. A compound represented by Structural Formula I

I 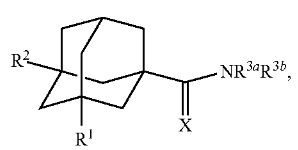 or a pharmaceutically acceptable salt, and a pharmaceutically acceptable carrier, diluent, or vehicle thereof, wherein:

$R^1$ is phenyl;

$R^2$ is selected from ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl is optionally substituted with at least one $R^8$ group;

$NR^{3a}R^{3b}$ is selected from the group consisting of

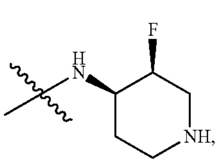

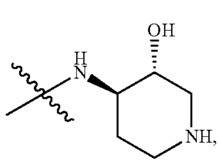

-continued

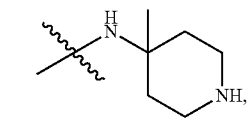

,

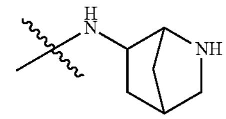

, and 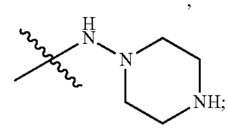 each $R^8$ is independently selected from hydrogen, halogen, OH, nitro, $CF_3$, $—NR^{9a}R^{9b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, $—C(O)R^{10}$, $—C(O)NR^{9a}R^{9b}$, $—S(O)_mR^{10}$, $—S(O)_mNR^{9a}R^{9b}$, $—NR^{9a}S(O)_mR^{10}$, $—(CH_2)_nC(O)OR^{10}$, $—(CH_2)_nC(O)N(R^{9a}R^{9b})$, $—(CH_2)_nN(R^{9a}R^{9b})$, $—OC(O)R^{15}$, $—O(CH_2)_nO—$, $—NR^{9a}C(O)R^{10}$, and $—NR^{9a}C(O)N(R^{9a}R^{9b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{11}$ group;

each of the $R^{9a}$ and $R^{9b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_5$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{11}$ group, or $R^{9a}$ and $R^{9b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{11}$ group;

each $R^{10}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$)

aryl, and ($C_2$ to $C_9$) heteroaryl is optionally substituted with at least one $R^{11}$ group;

each $R^{11}$ is independently selected from hydrogen, halogen, OH, nitro, $CF_3$, —$NR^{12a}R^{12b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{18}$, —$C(O)NR^{12a}R^{12b}$, —$S(O)_mR^{13}$, —$S(O)_mNR^{12a}R^{12b}$, —$NR^{12a}S(O)_mR^{13}$, —$(CH_2)_nC(O)OR^{13}$, —$(CH_2)_nC(O)N(R^{12a}R^{12b})$, —$(CH_2)_nN(R^{12a}R^{12b})$, —$OC(O)R^{13}$, —$NR^{12a}C(O)R^{13}$, and —$NR^{12a}C(O)N(R^{12a}R^{12b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{14}$ group;

each of the $R^{12a}$ and $R^{12b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{14}$ group, or $R^{12a}$ and $R^{12b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{14}$ group;

each $R^{13}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{14}$ group;

each $R^{14}$ is independently selected from hydrogen, halogen, OH, nitro, $CF_3$, —$NR^{15a}R^{15b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{16}$, —$C(O)NR^{15a}R^{15b}$, —$S(O)_mR^{16}$, —$S(O)_mNR^{15a}R^{15b}$, —$NR^{15a}S(O)_mR^{16}$, —$(CH_2)_nC(O)OR^{16}$, —$(CH_2)_nC(O)N(R^{15a}R^{15b})$, —$(CH_2)_nN(R^{15a}R^{15b})$, —$OC(O)R^{16}$, —$NR^{15a}C(O)R^{16}$, and —$NR^{15a}C(O)N(R^{15a}R^{15b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{15a}$ and $R^{15b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{15a}$ and $R^{15b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, $CF_3$, —$NR^{18a}R^{18b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{19}$, —$C(O)NR^{18a}R^{18b}$, —$S(O)_mR^{19}$, —$S(O)_mNR^{18a}R^{18b}$, —$NR^{18a}S(O)_mR^{19}$, —$(CH_2)_nC(O)OR^{19}$, —$(CH_2)_nC(O)N(R^{18a}R^{18b})$, —$(CH_2)_nN(R^{18a}R^{18b})$, —$OC(O)R^{19}$, —$NR^{18a}C(O)R^{19}$, and —$NR^{18a}C(O)N(R^{18a}R^{18b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{19}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, $CF_3$, —$NR^{21a}R^{21b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)R$^{22}$, —C(O)NR$^{21a}$R$^{21b}$, —S(O)$_m$R$^{22}$, —S(O)$_m$NR$^{21a}$R$^{21b}$, —NR$^{21a}$S(O)$_m$R$^{22}$, —(CH$_2$)$_n$C(O)OR$^{22}$, —(CH$_2$)$_n$C(O)N(R$^{21a}$R$^{21b}$), —(CH$_2$)$_n$N(R$^{21a}$R$^{21b}$), —OC(O)R$^{22}$, —NR$^{21a}$C(O)R$^{22}$, and —NR$^{21a}$C(O)N(R$^{21a}$R$^{21b}$), wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one R$^{22}$ group;

each of the R$^{21a}$ and R$^{21b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl, or R$^{21a}$ and R$^{21b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S;

each R$^{22}$ is independently selected from hydrogen, halogen, OH, nitro, CF$_3$, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

41. The compound of claim 40, wherein R$^2$ is selected from the group consisting of methyl, ethyl, propyl, fluoromethyl, ethoxymethyl, chloroethyl, and fluoroethyl.

42. An enantiomerically pure compound represented by Structural Formula Ia

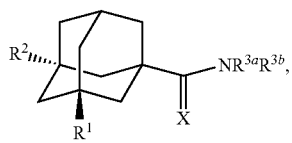

or a pharmaceutically acceptable salt, and a pharmaceutically acceptable carrier, diluent, or vehicle thereof, wherein:

R$^1$ is selected from (C$_6$ to C$_{10}$) aryl and (C$_2$ to C$_9$) heteroaryl, wherein each of the said (C$_6$ to C$_{10}$) aryl and (C$_2$ to C$_9$) heteroaryl is optionally substituted with at least one R$^4$ group;

R$^2$ is selected from (C$_1$ to C$_{10}$) alkyl, (C$_2$ to C$_{10}$) alkenyl, (C$_2$ to C$_{10}$) alkynyl, (C$_3$ to C$_{10}$) cycloalkyl, and (C$_5$ to C$_{10}$) cycloalkenyl, wherein each of the said (C$_1$ to C$_{10}$) alkyl, (C$_2$ to C$_{10}$) alkenyl, (C$_2$ to C$_{10}$) alkynyl, (C$_3$ to C$_{10}$) cycloalkyl, and (C$_5$ to C$_{10}$) cycloalkenyl is optionally substituted with at least one R$^8$ group;

NR$^{3a}$R$^{3b}$ is selected from the group consisting of

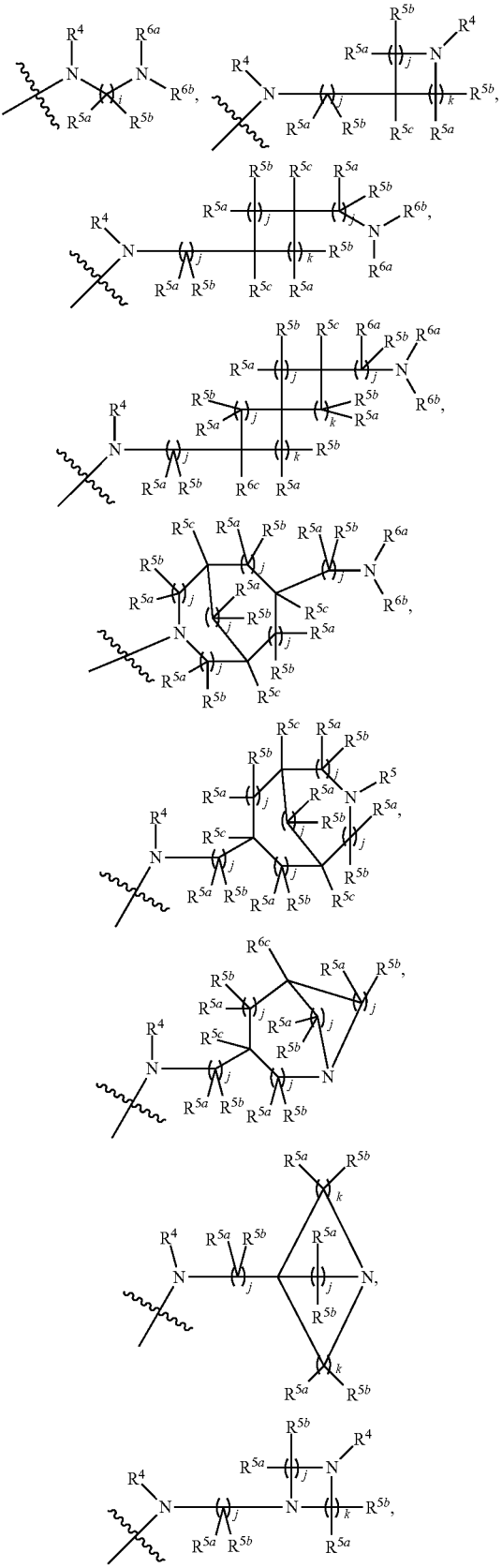

-continued

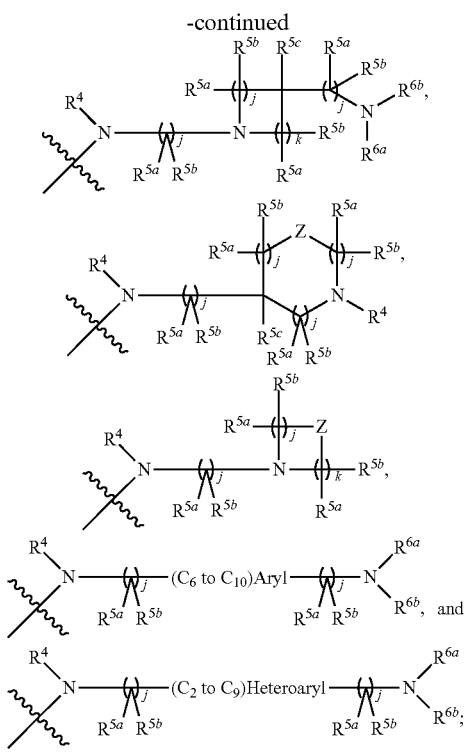

Z is selected from the group consisting of —O—, —S—, —S(O)—, and —S(O)$_2$—;

each R$^4$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteoaryl, ($C_6$ to $C_{10}$) arylene, and ($C_2$ to $C_9$) heteroarylene is optionally substituted with at least one R$^8$ group;

each of the R$^{5a}$, R$^{5b}$, and R$^{5c}$ is independently selected from hydrogen, halogen, OH, nitro, CF$_3$, —NR$^{6a}$R$^{6b}$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)R$^7$, —C(O)NR$^{6a}$R$^{6b}$, —S(O)$_m$R$^7$, —S(O)$_m$NR$^{6a}$R$^{6b}$, —NR$^{6a}$S(O)$_m$R$^7$, —(CH$_2$)$_n$C(O)OR$^7$, —(CH$_2$)$_n$C(O)N(R$^{6a}$R$^{6b}$), —(CH$_2$)$_n$N(R$^{6a}$R$^{6b}$), —OC(O)R$^7$, —NR$^{6a}$C(O)R$^7$, and —NR$^{6a}$C(O)N(R$^{6a}$R$^{6b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one R$^8$ group;

each of the R$^{6a}$ and R$^{6b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_5$) cycloheteroalkyl, ($C_6$ to $C_{10}$) aryl, ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one R$^8$ group, or R$^{6a}$ and R$^{6b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one R$^8$ group;

each of the R$^7$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one R$^8$ group;

each R$^8$ is independently selected from hydrogen, halogen, OH, nitro, CF$_3$, —NR$^{9a}$R$^{9b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)R$^{10}$, —C(O)NR$^{9a}$R$^{9b}$, —S(O)$_m$R$^{10}$, —S(O)$_m$NR$^{9a}$R$^{9b}$, —NR$^{9a}$S(O)$_m$R$^{10}$, —(CH$_2$)$_n$C(O)OR$^{10}$, —(CH$_2$)$_n$C(O)N(R$^{9a}$R$^{9b}$), —(CH$_2$)$_n$N(R$^{9a}$R$^{9b}$), —OC(O)R$^{15}$, —O(CH$_2$)$_n$O—, —NR$^{9a}$C(O)R$^{10}$, and —NR$^{9a}$C(O)N(R$^{9a}$R$^{9b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one R$^{11}$ group;

each of the R$^{9a}$ and R$^{9b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_5$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one R$^{11}$ group, or R$^{9a}$ and R$^{9b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one R$^{11}$ group;

each R$^{10}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{11}$ group;

each $R^{11}$ is independently selected from hydrogen, halogen, OH, nitro, $CF_3$, $-NR^{12a}R^{12b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, $-C(O)R^{13}$, $-C(O)NR^{12a}R^{12b}$, $-S(O)_mR^{13}$, $-S(O)_mNR^{12a}R^{12b}$, $-NR^{12a}S(O)_mR^{13}$, $-(CH_2)_nC(O)OR^{13}$, $-(CH_2)_nC(O)N(R^{12a}R^{12b})$, $-(CH_2)_nN(R^{12a}R^{12b})$, $-OC(O)R^{13}$, $-NR^{12a}C(O)R^{13}$, and $-NR^{12a}C(O)N(R^{12a}R^{12b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{14}$ group;

each of the $R^{12a}$ and $R^{12b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$)cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{14}$ group, or $R^{12a}$ and $R^{12b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{14}$ group;

each $R^{13}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{14}$ group;

each $R^{14}$ is independently selected from hydrogen, halogen, OH, nitro, $CF_3$, $-NR^{15a}R^{15b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, $-C(O)R^{16}$, $-C(O)NR^{15a}R^{15b}$, $-S(O)_mR^{16}$, $-S(O)_mNR^{15a}R^{15b}$, $-NR^{15a}S(O)_mR^{16}$, $-(CH_2)_nC(O)OR^{16}$, $-(CH_2)_nC(O)N(R^{15a}R^{15b})$, $-(CH_2)_nN(R^{15a}R^{15b})$, $-OC(O)R^{16}$, $-NR^{15a}C(O)R^{16}$, and $-NR^{15a}C(O)N(R^{15a}R^{15b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{15a}$ and $R^{15b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{15a}$ and $R^{15b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, $CF_3$, $-NR^{18a}R^{18b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, $-C(O)R^{19}$, $-C(O)NR^{18a}R^{18b}$, $-S(O)_mR^{19}$, $-S(O)_mNR^{18a}R^{18b}$, $-NR^{18a}S(O)_mR^{19}$, $-(CH_2)_nC(O)OR^{19}$, $-(CH_2)_nC(O)N(R^{18a}R^{18b})$, $-(CH_2)_nN(R^{18a}R^{18b})$, $-OC(O)R^{19}$, $-NR^{18a}C(O)R^{19}$, and $-NR^{18a}C(O)N(R^{18a}R^{18b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{19}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, $CF_3$, —$NR^{21a}R^{21b}$, oxo, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{22}$, —$C(O)NR^{21a}R^{21b}$, —$S(O)_mR^{22}$, —$S(O)_mNR^{21a}R^{21b}$, —$NR^{21a}S(O)_mR^{22}$, —$(CH_2)_nC(O)OR^{22}$, —$(CH_2)_nC(O)N(R^{21a}R^{21b})$, —$(CH_2)_nN(R^{21a}R^{21b})$, —$OC(O)R^{22}$, —$NR^{21a}C(O)R^{22}$, and —$NR^{21a}C(O)N(R^{21a}R^{21b})$, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{21a}$ and $R^{21b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, $CF_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

43. The compound of claim 42, wherein $R^1$ is phenyl.
44. The compound of claim 43, wherein $R^2$ is selected from the group consisting of methyl, ethyl, propyl, fluoromethyl, ethoxymethyl, chloroethyl, and fluoroethyl.
45. The compound of claim 43, wherein $NR^{3a}R^{3b}$ is selected from the group consisting of

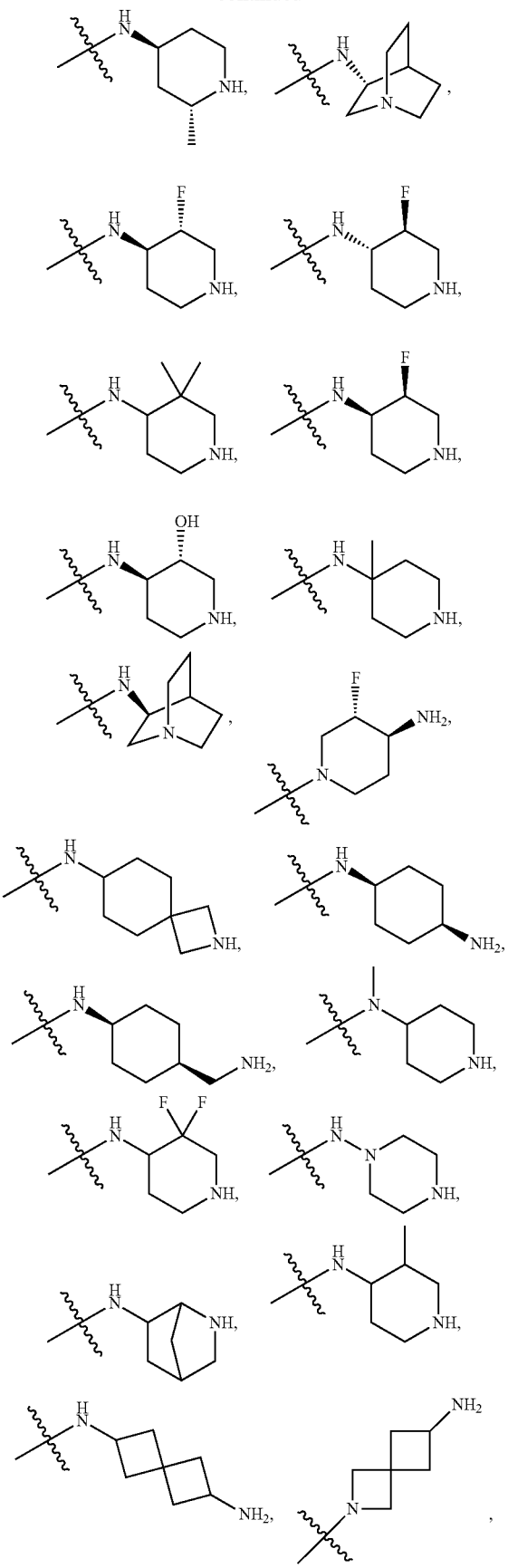

-continued

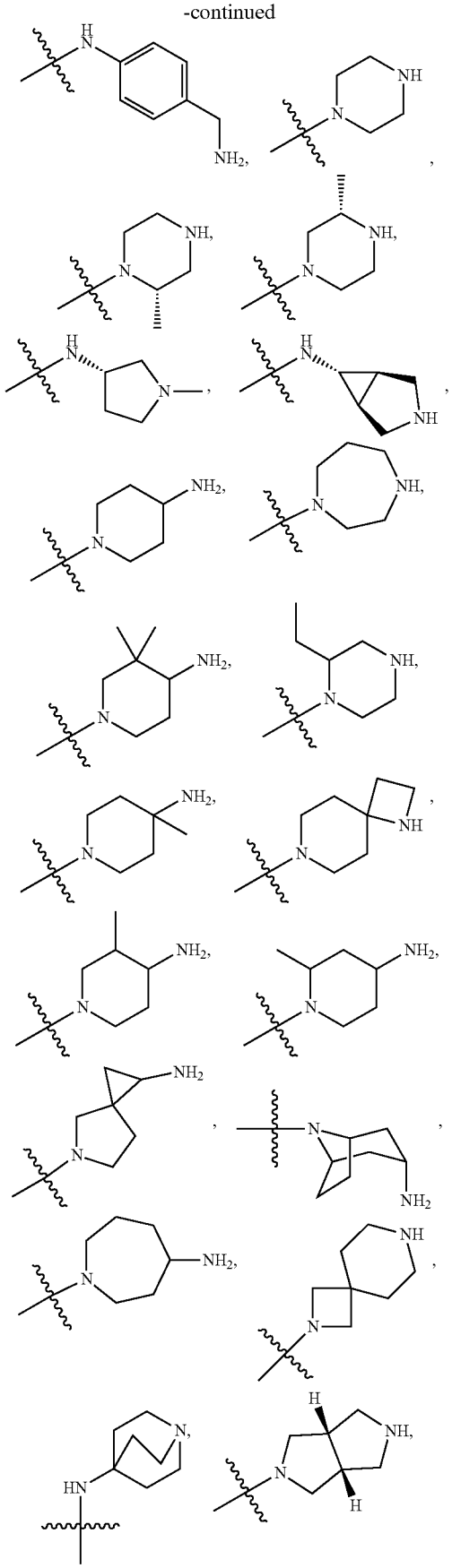

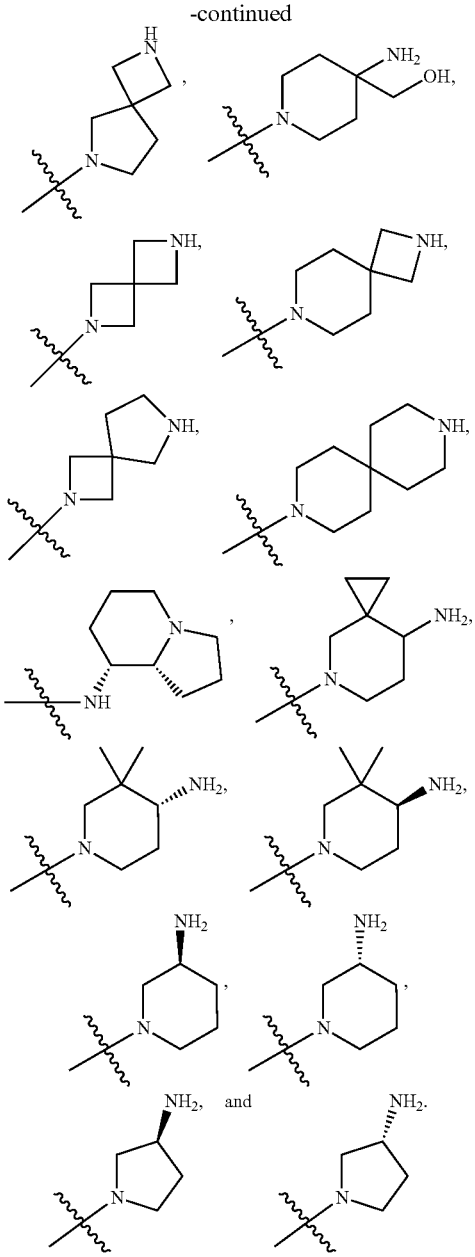

46. An enantiomerically pure compound of Structural Formula Ib

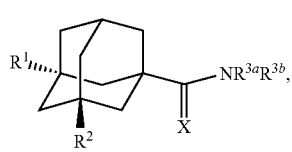

Ib or a pharmaceutically acceptable salt, and a pharmaceutically acceptable carrier, diluent, or vehicle thereof, wherein:

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

R² is selected from (C₁ to C₁₀) alkyl, (C₂ to C₁₀) alkenyl, (C₂ to C₁₀) alkynyl, (C₃ to C₁₀) cycloalkyl, and (C₅ to C₁₀) cycloalkenyl, wherein each of the said ($C_1$ to $C_{10}$) alkyl, ($C_2$ to $C_{10}$) alkenyl, ($C_2$ to $C_{10}$) alkynyl, ($C_3$ to $C_{10}$) cycloalkyl, and ($C_5$ to $C_{10}$) cycloalkenyl is optionally substituted with at least one $R^8$ group;

$NR^{3a}R^{3b}$ is selected from the group consisting of

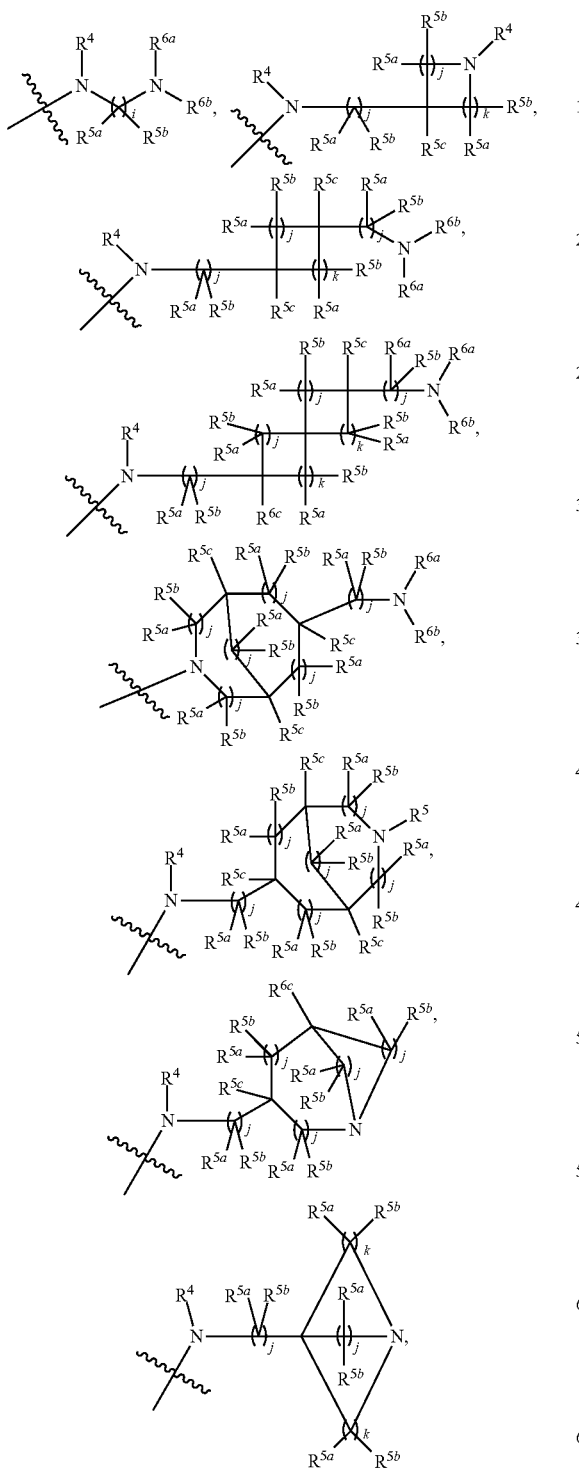

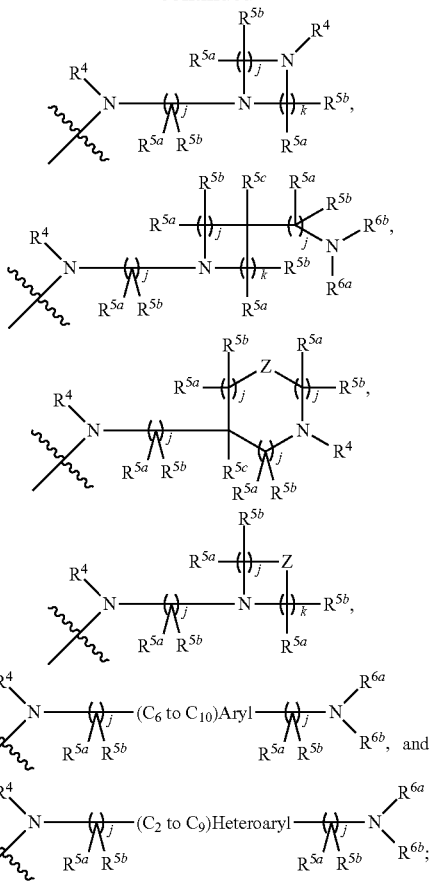

Z is selected from the group consisting of —O—, —S—, —S(O)—, and —S(O)₂—;

each $R^4$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteoaryl, ($C_6$ to $C_{10}$) arylene, and ($C_2$ to $C_9$) heteroarylene is optionally substituted with at least one $R^8$ group;

each of the $R^{5a}$, $R^{5b}$, and $R^{5c}$ is independently selected from hydrogen, halogen, OH, nitro, $CF_3$, —$NR^{6a}R^{6b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^7$, —C(O)$NR^{6a}R^{6b}$, —S(O)$_m R^7$, —S(O)$_m NR^{6a}R^{6b}$, —$NR^{6a}$S(O)$_m R^7$, —(CH$_2$)$_n$C(O)O$R^7$, —(CH$_2$)$_n$C(O)N($R^{6a}R^{6b}$), —(CH$_2$)$_n$N($R^{6a}R^{6b}$), —OC(O)$R^7$, —$NR^{6a}$C(O)$R^7$, and —$NR^{6a}$C(O)N($R^{6a}R^{6b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^8$ group;

each of the R$^{6a}$ and R$^{6b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^8$ group, or R$^{6a}$ and R$^{6b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^8$ group;

each of the R$^7$ is independently selected from hydrogen, (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl, wherein each of the said (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, and (C$_2$ to C$_9$) heteroaryl is optionally substituted with at least one R$^8$ group;

each R$^8$ is independently selected from hydrogen, halogen, OH, nitro, CF$_3$, —NR$^{9a}$R$^{9b}$, oxo, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_9$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)R$^{10}$, —C(O)NR$^{9a}$R$^{9b}$, —S(O)$_m$R$^{10}$, —S(O)$_m$NR$^{9a}$R$^{9b}$, —NR$^{9a}$S(O)$_m$R$^{10}$, —(CH$_2$)$_n$C(O)OR$^{10}$, —(CH$_2$)$_n$C(O)N(R$^{9a}$R$^{9b}$), —OC(O)R$^{15}$, —O(CH$_2$)$_n$O—, —NR$^{9a}$C(O)R$^{10}$, and —NR$^{9a}$C(O)N(R$^{9a}$R$^{9b}$), wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one R$^{11}$ group;

each of the R$^{9a}$ and R$^{9b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_5$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^{11}$ group, or R$^{9a}$ and R$^{9b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^{11}$ group;

each R$^{10}$ is independently selected from hydrogen, (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl, wherein each of the said (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl is optionally substituted with at least one R$^{11}$ group;

each R$^{11}$ is independently selected from hydrogen, halogen, OH, nitro, CF$_3$, —NR$^{12a}$R$^{12b}$, oxo, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)R$^{18}$, —C(O)NR$^{12a}$R$^{12b}$, —S(O)$_m$R$^{13}$, —S(O)$_m$NR$^{12a}$R$^{12b}$, —NR$^{12a}$S(O)$_m$R$^{13}$, —(CH$_2$)$_n$C(O)OR$^{13}$, —(CH$_2$)$_n$C(O)N(R$^{12a}$R$^{12b}$), —(CH$_2$)$_n$N(R$^{12a}$R$^{12b}$), —OC(O)R$^{13}$, —NR$^{12a}$C(O)R$^{13}$, and —NR$^{12a}$C(O)N(R$^{12a}$R$^{12b}$), wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_2$ to C$_9$) heteroaryl, (C$_6$ to C$_{10}$) aryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one R$^{14}$ group;

each of the R$^{12a}$ and R$^{12b}$ is independently selected from hydrogen, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene, wherein each of the said (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, and (C$_2$ to C$_9$) heteroarylene is optionally substituted with at least one R$^{14}$ group, or R$^{12a}$ and R$^{12b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S, and wherein the said (C$_2$ to C$_{10}$) cycloheteroalkyl ring is optionally substituted with at least one R$^{14}$ group;

each R$^{13}$ is independently selected from hydrogen, halogen, OH, nitro, CF$_3$, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl, wherein each of the said (C$_1$ to C$_{10}$) alkyl, (C$_2$ to C$_{10}$) alkenyl, (C$_2$ to C$_{10}$) alkynyl, (C$_3$ to C$_{10}$) cycloalkyl, (C$_5$ to C$_{10}$) cycloalkenyl, (C$_2$ to C$_{10}$) cycloheteroalkyl, (C$_2$ to C$_9$) heteroaryl, and (C$_5$ to C$_{10}$) aryl is optionally substituted with at least one R$^{14}$ group;

each R$^{14}$ is independently selected from hydrogen, halogen, OH, nitro, CF$_3$, —NR$^{15a}$R$^{15b}$, oxo, (C$_1$ to C$_{10}$) alkyl, (C$_2$ to C$_{10}$) alkenyl, (C$_2$ to C$_{10}$) alkynyl, (C$_1$ to C$_{10}$) alkoxy, aryloxy, cyano, (C$_3$ to C$_{10}$) cycloalkyl, (C$_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{16}$, —C(O)N$R^{15a}R^{15b}$, —S(O)$_m R^{16}$, —S(O)$_m$N$R^{15a}R^{15b}$, —N$R^{15a}$S(O)$_m R^{16}$, —(CH$_2$)$_n$C(O)O$R^{16}$, —(CH$_2$)$_n$C(O)N($R^{15a}R^{15b}$), —(CH$_2$)$_n$N($R^{15a}R^{15b}$), —OC(O)$R^{16}$, —N$R^{15a}$C(O)$R^{16}$, and —N$R^{15a}$C(O)N($R^{15a}R^{15b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{17}$ group;

each of the $R^{15a}$ and $R^{15b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{17}$ group, or $R^{15a}$ and $R^{15b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{17}$ group;

each $R^{16}$ is independently selected from hydrogen, halogen, OH, nitro, CF$_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{17}$ is independently selected from hydrogen, halogen, OH, nitro, CF$_3$, —N$R^{18a}R^{18b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{19}$, —C(O)N$R^{18a}R^{18b}$, —S(O)$_m R^{19}$, —S(O)$_m$N$R^{18a}R^{18b}$, —N$R^{18a}$S(O)$_m R^{19}$, —(CH$_2$)$_n$C(O)O$R^{19}$, —(CH$_2$)$_n$C(O)N($R^{18a}R^{18b}$), —(CH$_2$)$_n$N($R^{18a}R^{18b}$), —OC(O)$R^{19}$, —N$R^{18a}$C(O)$R^{19}$, and —N$R^{18a}$C(O)N($R^{18a}R^{18b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{20}$ group;

each of the $R^{18a}$ and $R^{18b}$ is independently selected from hydrogen, ($C_1$ to $C_{10}$) alkyl, ($C_2$ to $C_{10}$) alkenyl, ($C_2$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_5$ to $C_{10}$) aryl;

each $R^{19}$ is independently selected from hydrogen, halogen, OH, nitro, CF$_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{20}$ is independently selected from hydrogen, halogen, OH, nitro, CF$_3$, —N$R^{21a}R^{21b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{22}$, —C(O)N$R^{21a}R^{21b}$, —S(O)$_m R^{22}$, —S(O)$_m$N$R^{21a}R^{21b}$, —N$R^{21a}$S(O)$_m R^{22}$, —(CH$_2$)$_n$C(O)O$R^{22}$, —(CH$_2$)$_n$C(O)N($R^{21a}R^{21b}$), —(CH$_2$)$_n$N($R^{21a}R^{21b}$), —OC(O)$R^{22}$, —N$R^{21a}$C(O)$R^{22}$, and —N$R^{21a}$C(O)N($R^{21a}R^{21b}$), wherein each of the said ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{21a}$ and $R^{21b}$ is independently selected from hydrogen, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{21a}$ and $R^{2b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{22}$ is independently selected from hydrogen, halogen, OH, nitro, CF$_3$, ($C_1$ to $C_{10}$) alkyl, ($C_2$ to $C_{10}$) alkenyl, ($C_2$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4.

47. The compound of claim 46, wherein $R^1$ is phenyl.

48. The compound of claim 47, wherein
$R^2$ is selected from the group consisting of methyl, ethyl, propyl, fluoromethyl, ethoxymethyl, chloroethyl, and fluoroethyl.

49. The compound of claim 47, wherein N$R^{3a}R^{3b}$ is selected from the group consisting of

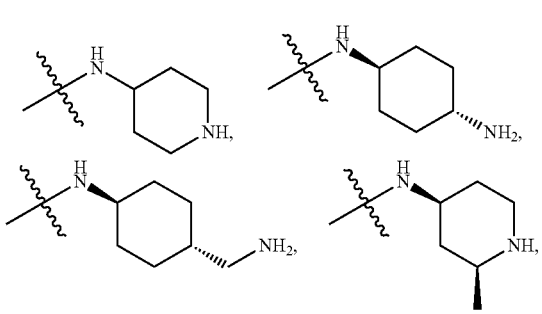

237
-continued
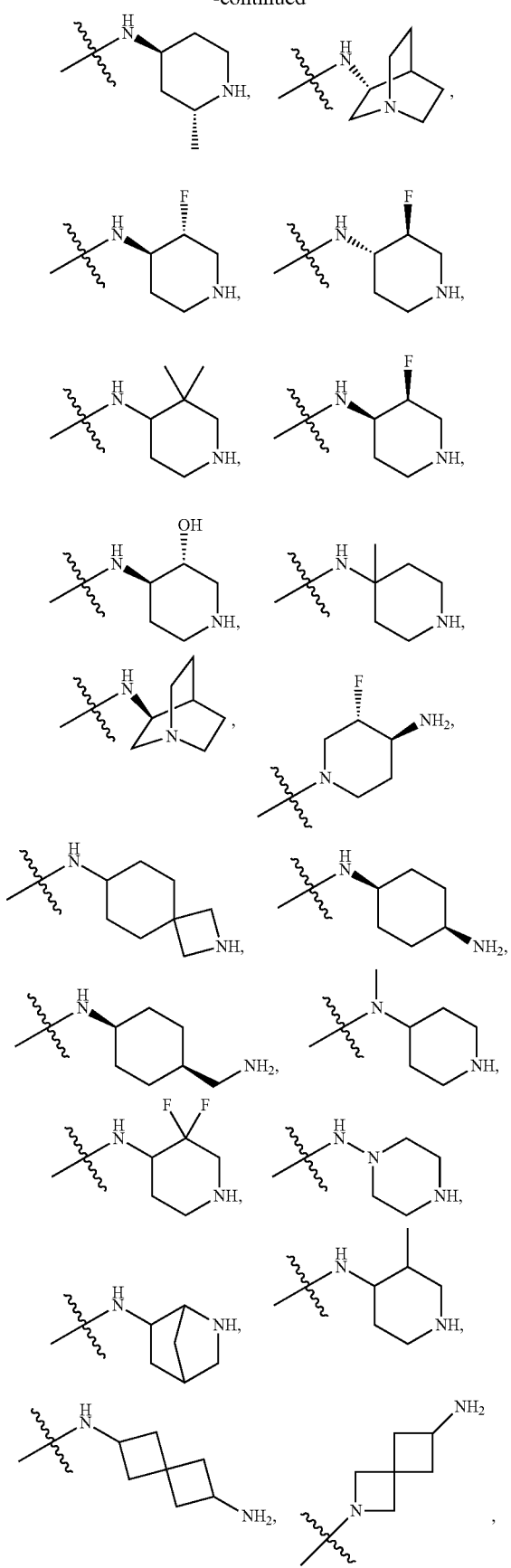
238
-continued
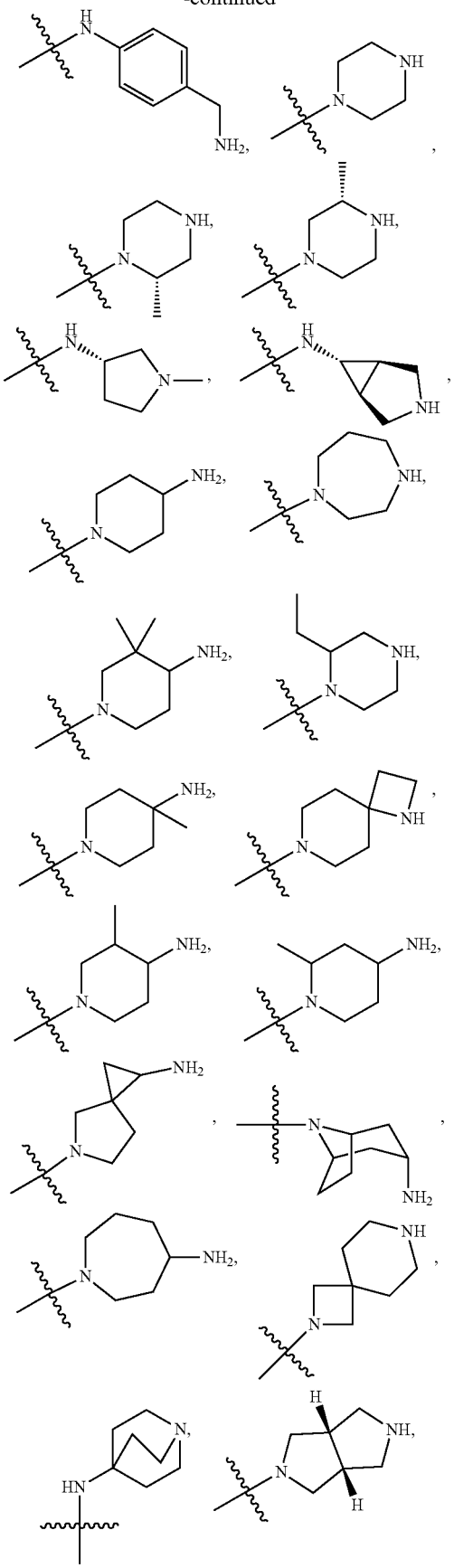

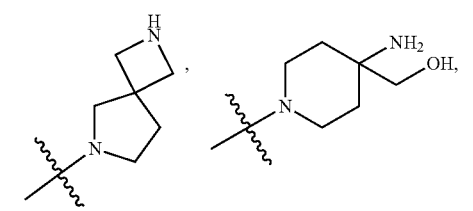
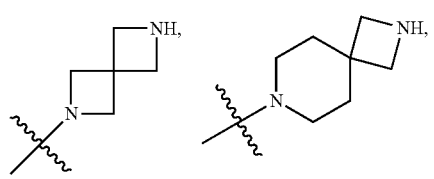
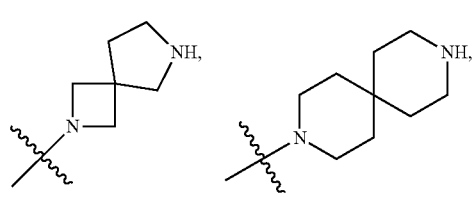
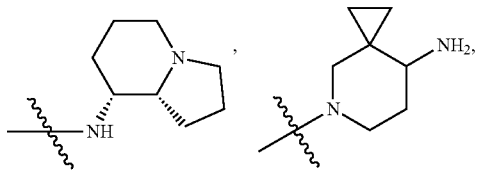
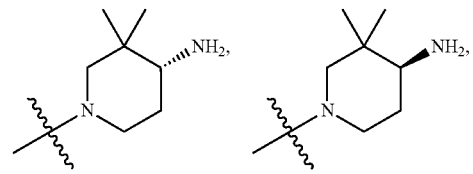
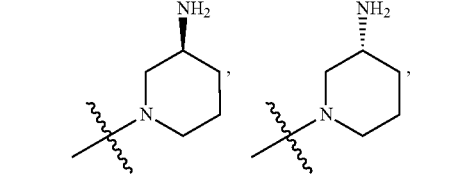
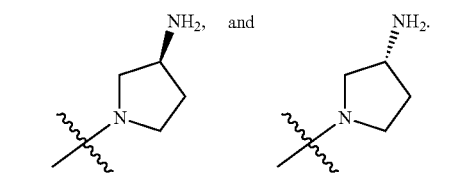
50. A compound selected from the group consisting of:
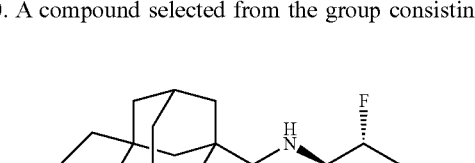
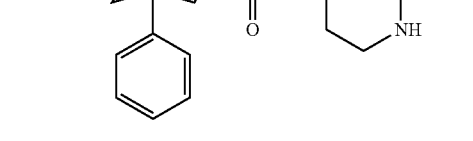
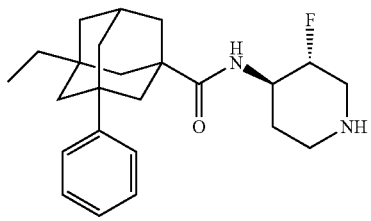
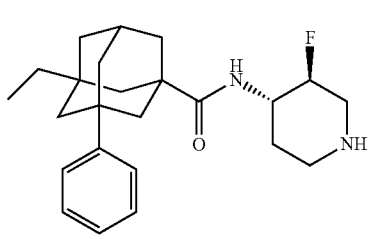
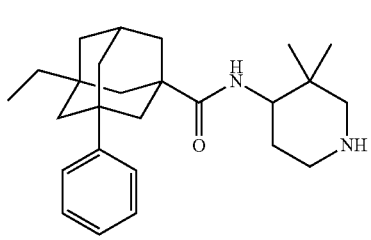
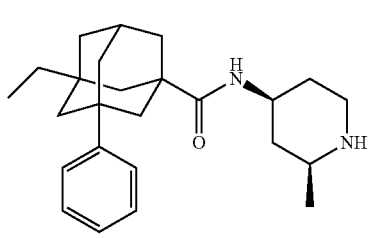
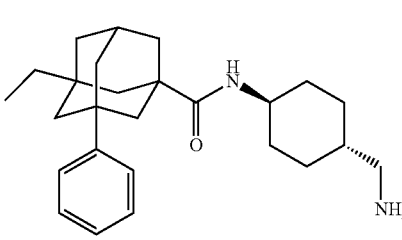
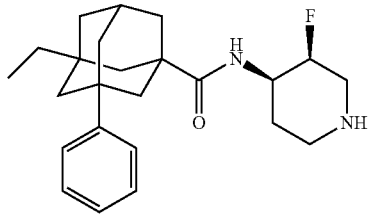
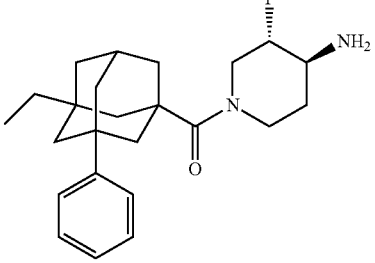

-continued
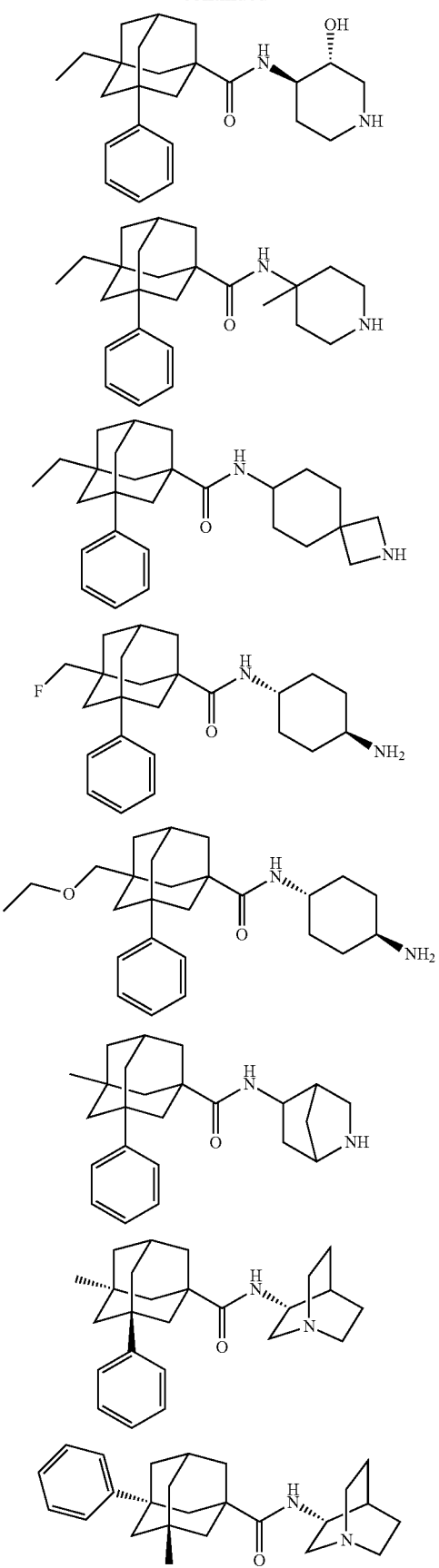
-continued
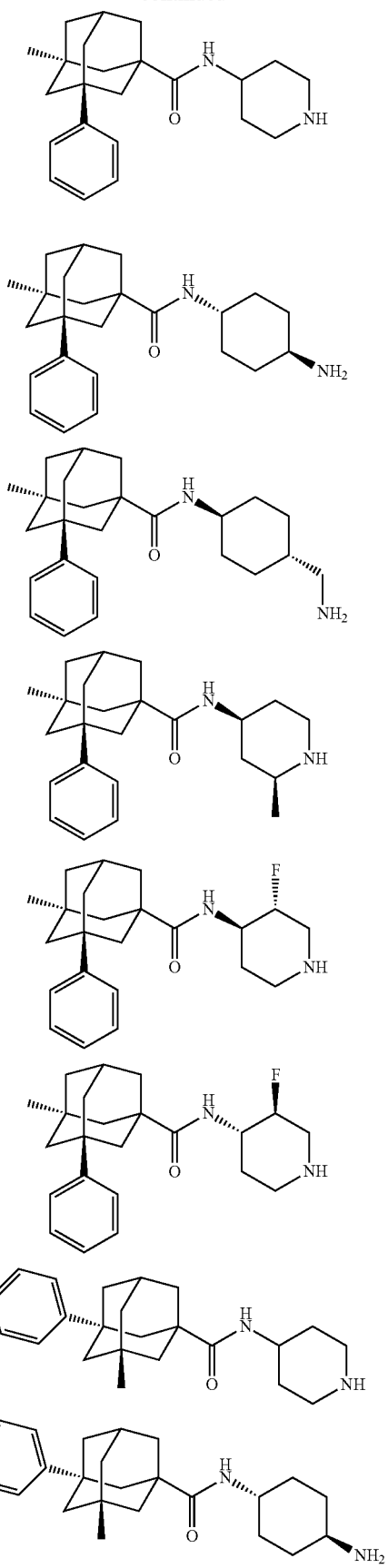

243
-continued
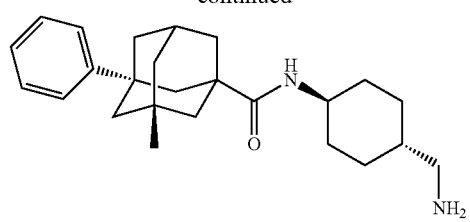
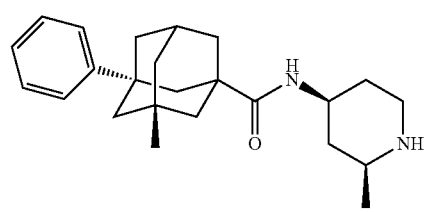
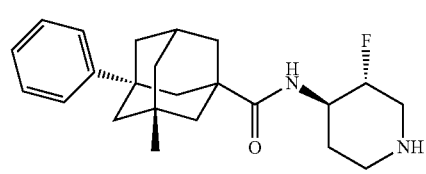
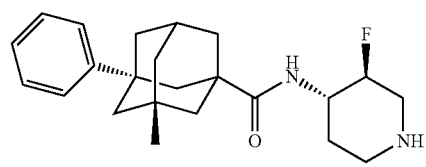
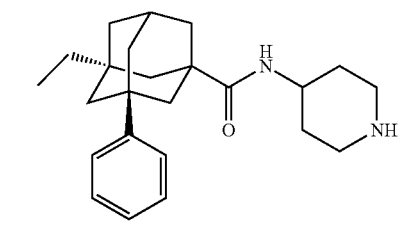
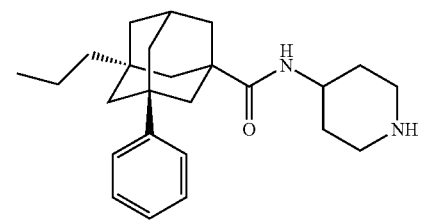
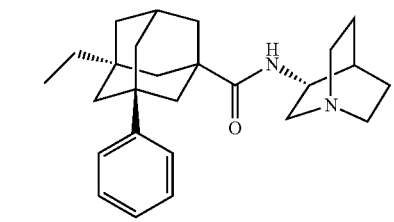
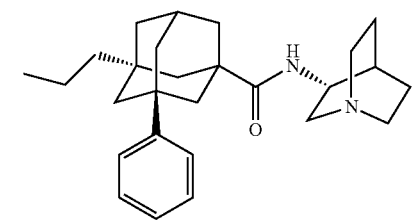
244
-continued
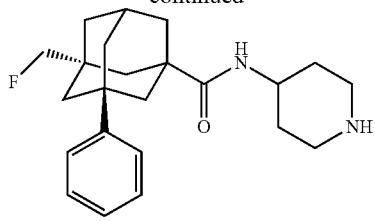
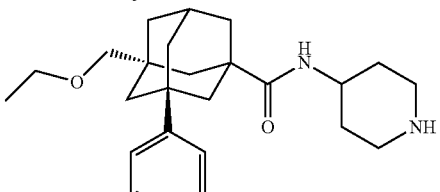
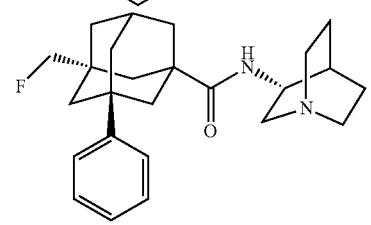
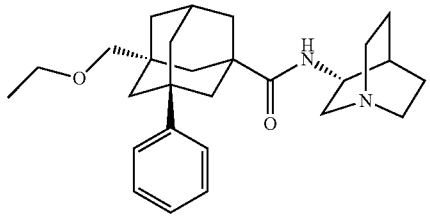
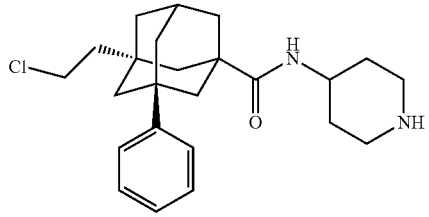
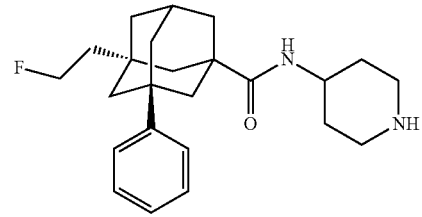
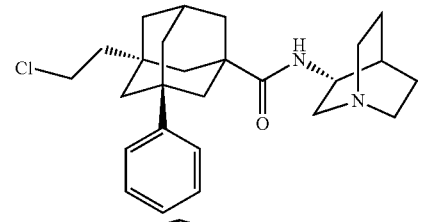
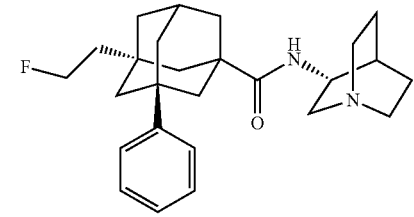

245
-continued
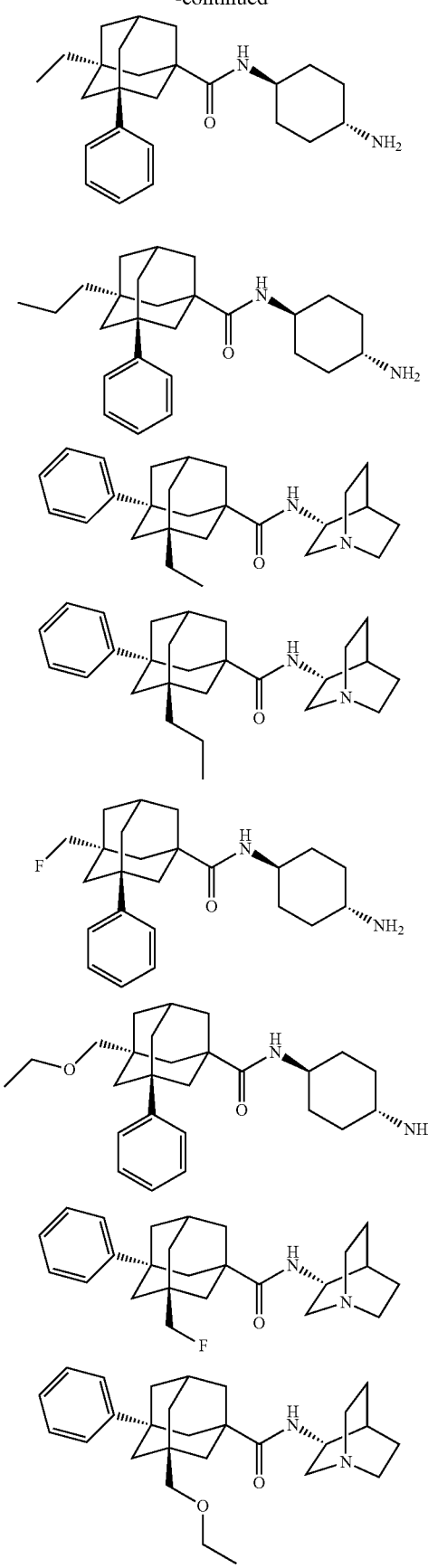
246
-continued
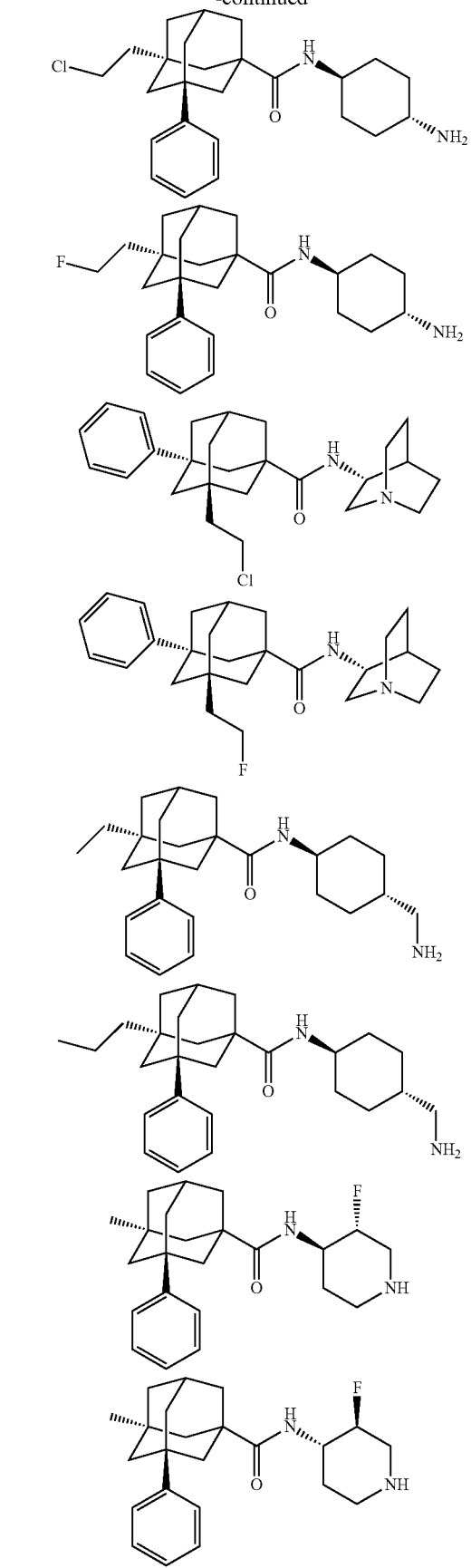

247
-continued
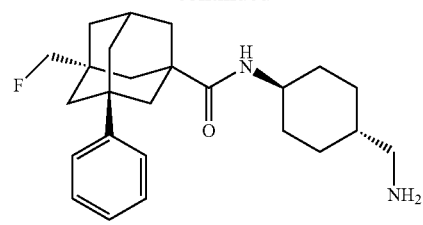
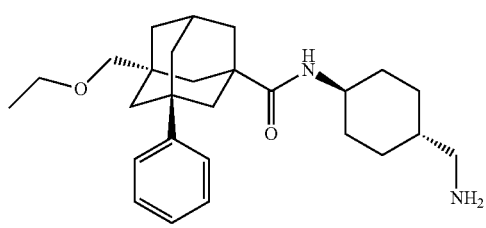
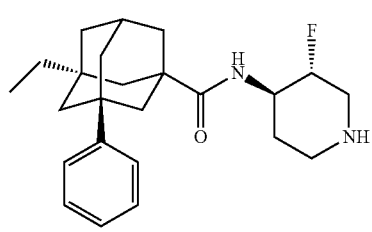
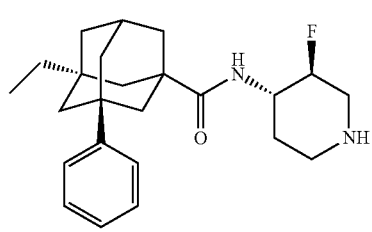
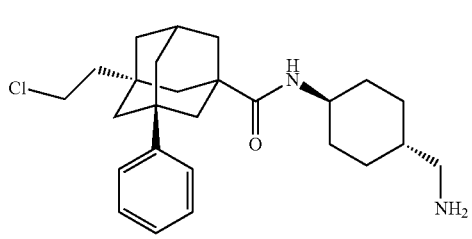
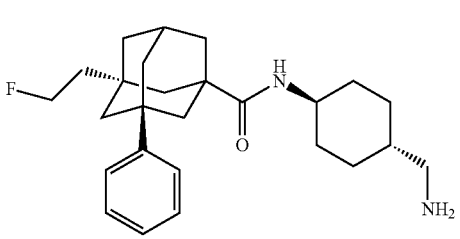
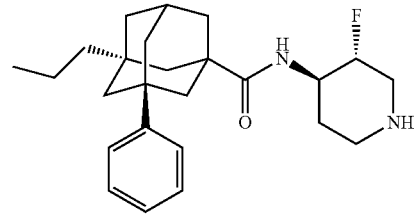
248
-continued
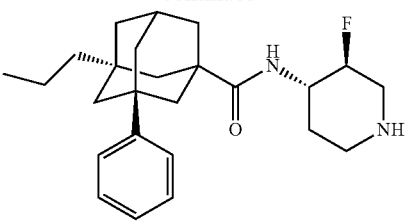
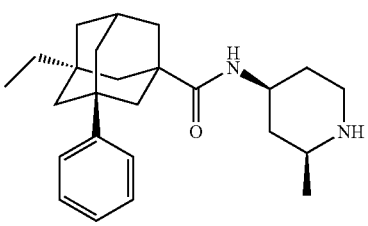
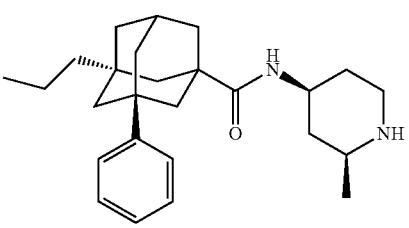
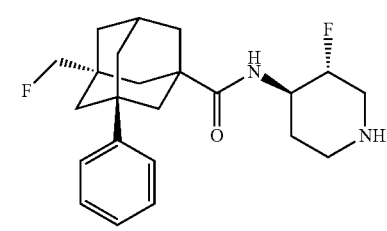
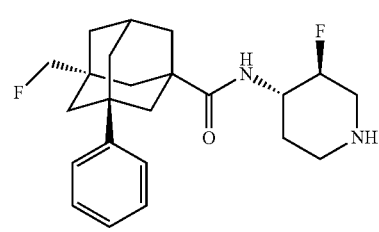
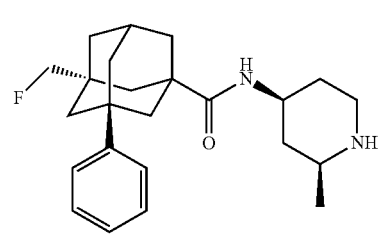
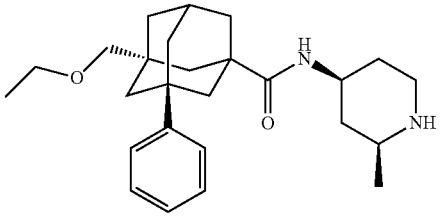

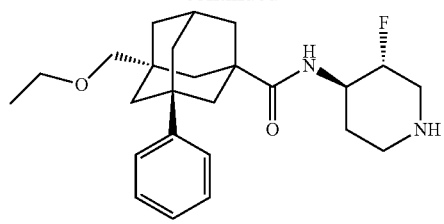
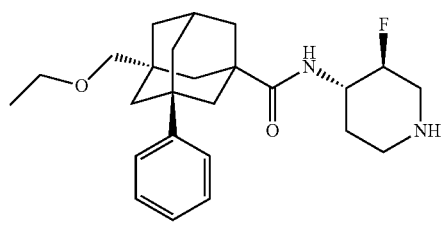
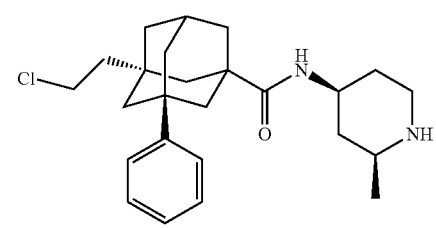
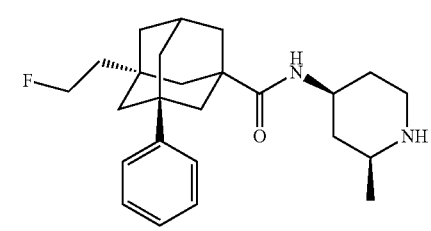
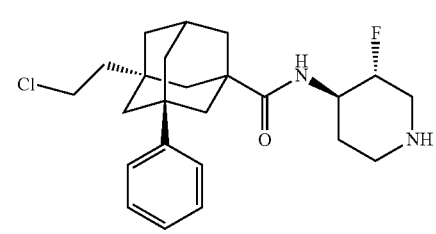
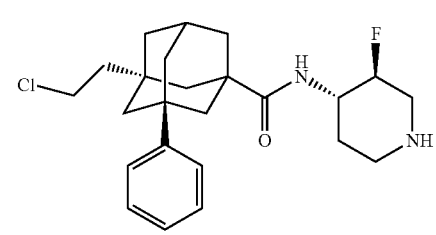
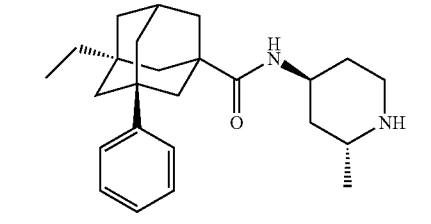
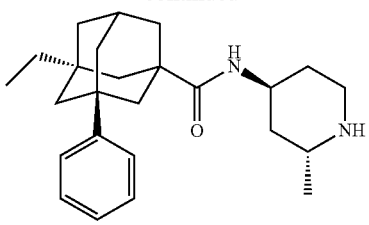
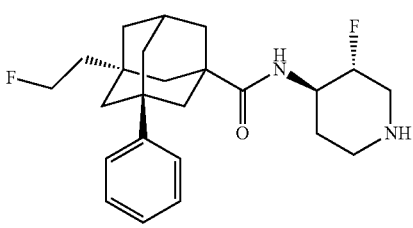
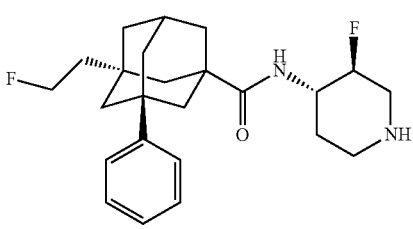
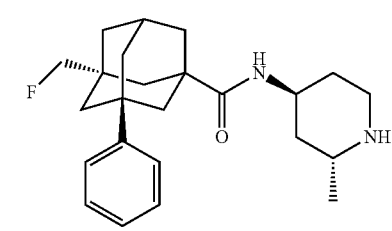
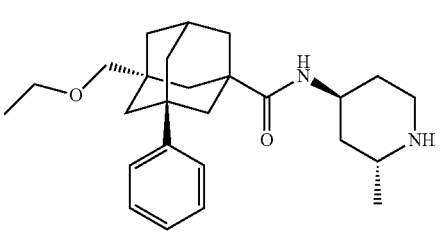
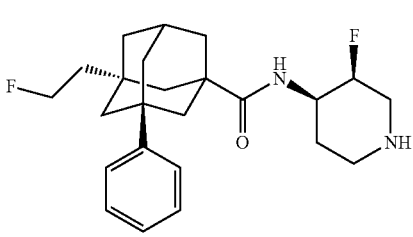
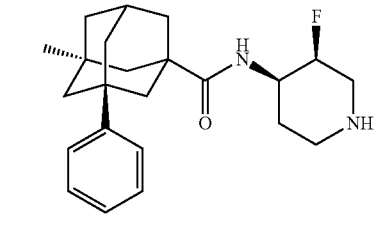

251
-continued
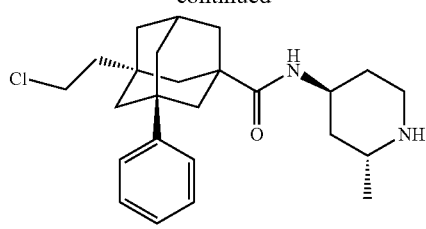
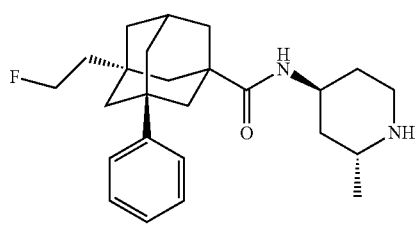
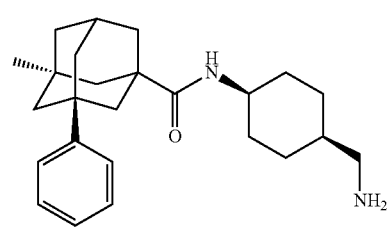
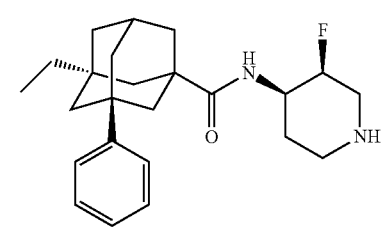
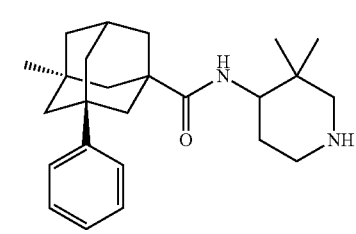
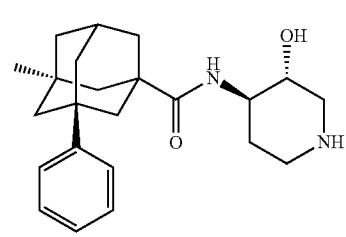
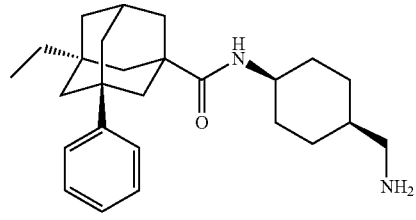
252
-continued
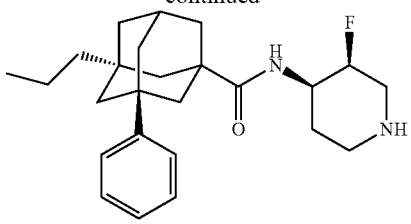
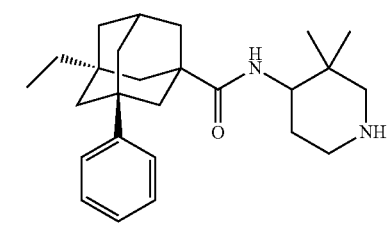
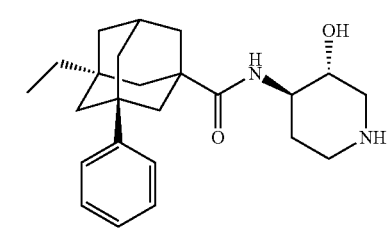
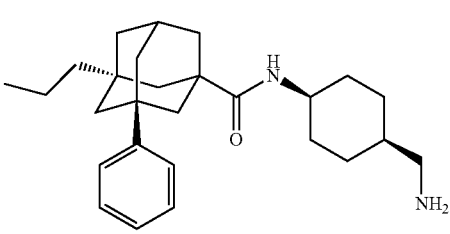
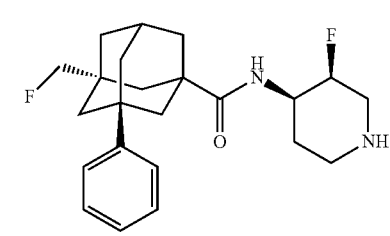
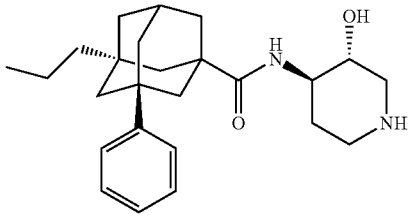

253
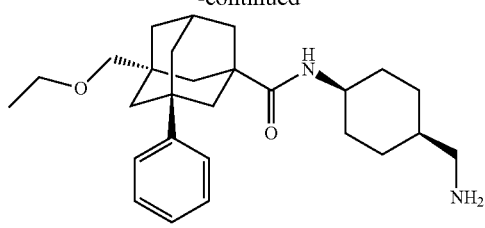
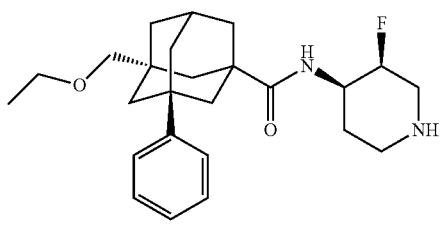
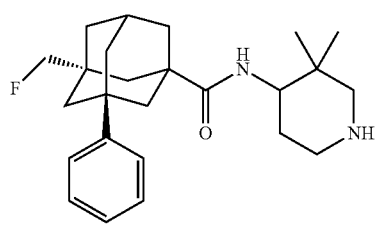
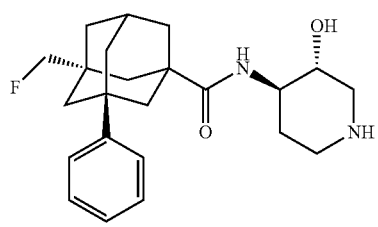
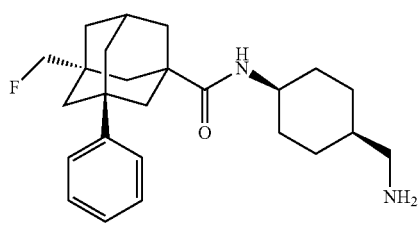
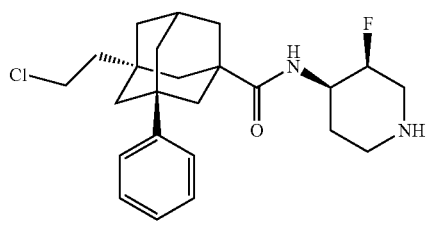
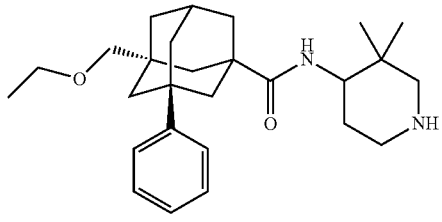
254
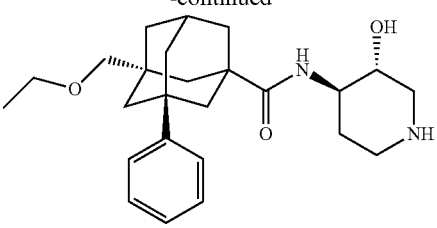
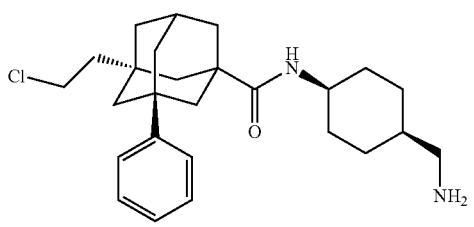
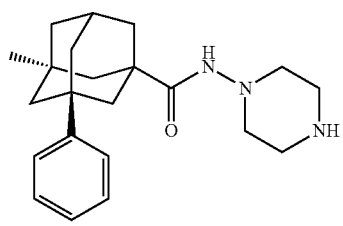
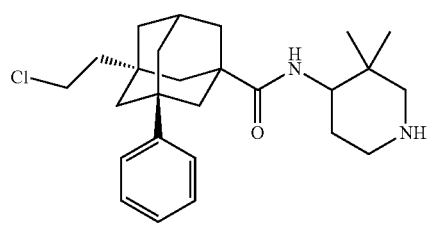
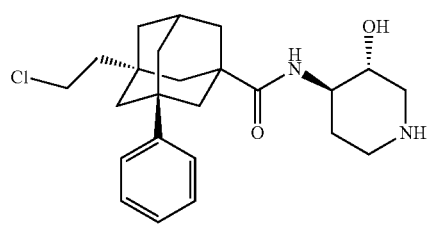
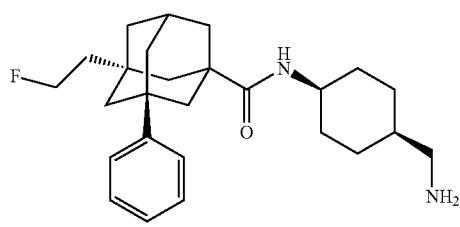
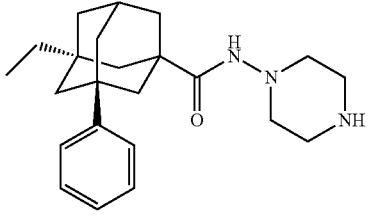

255
-continued
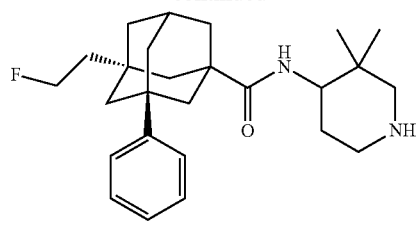
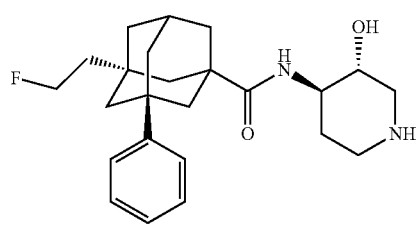
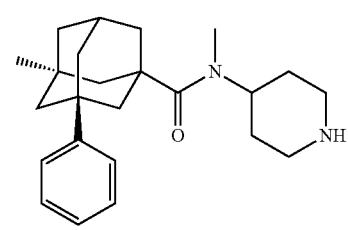
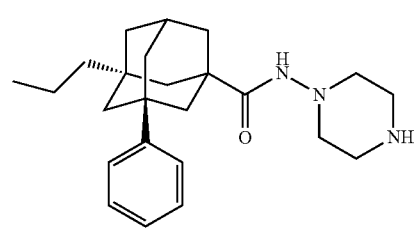
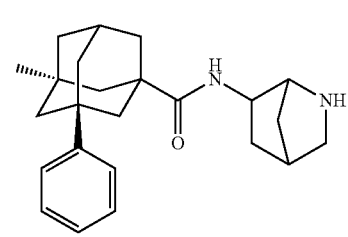
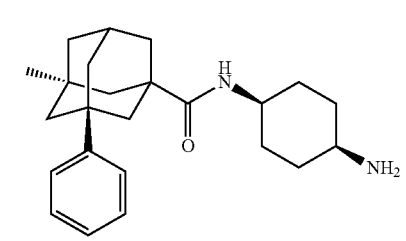
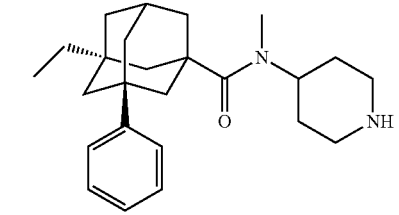
256
-continued
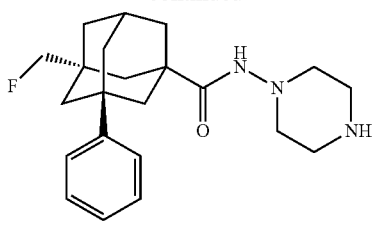
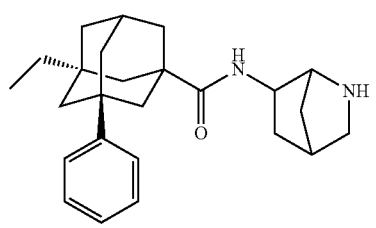
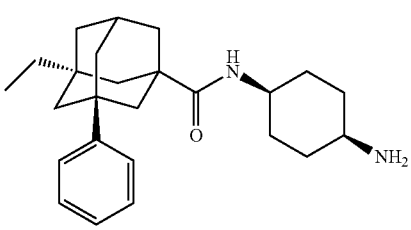
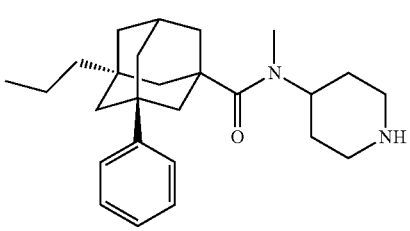
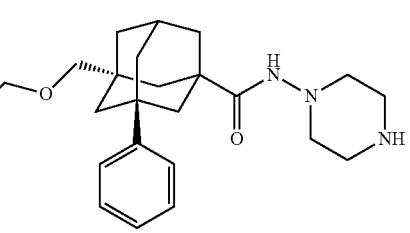
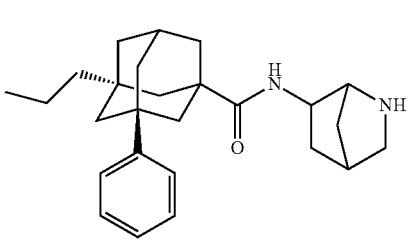
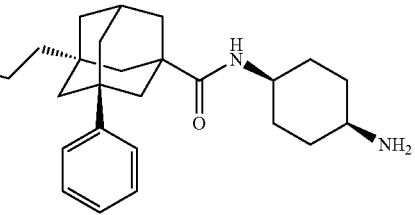

257
-continued
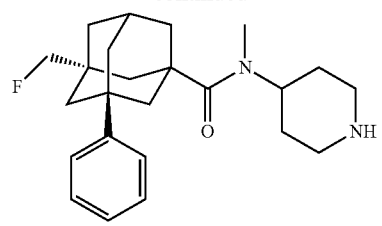
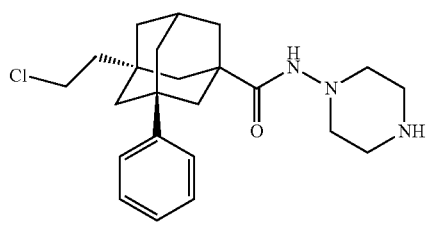
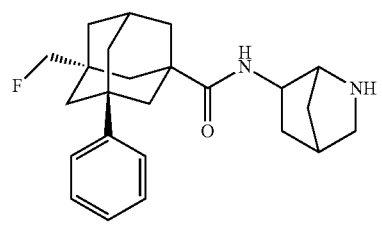
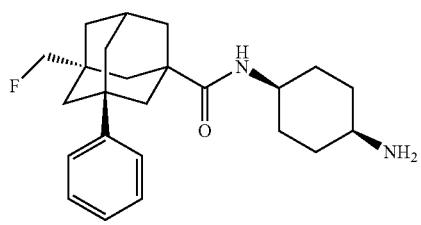
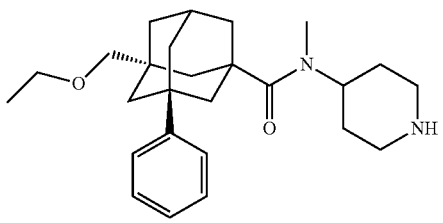
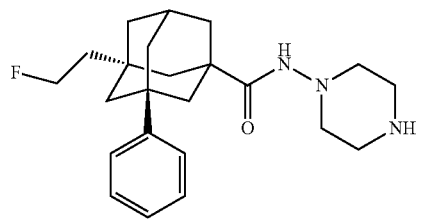
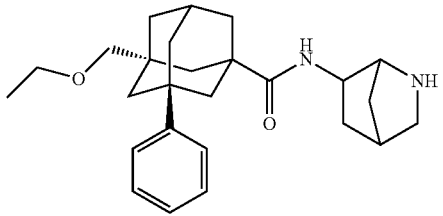
258
-continued
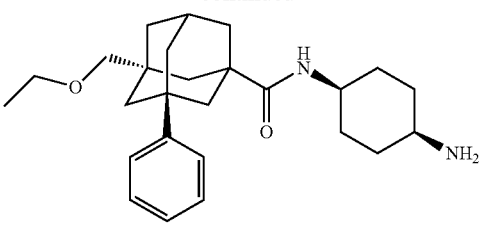
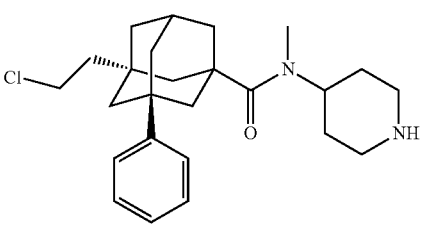
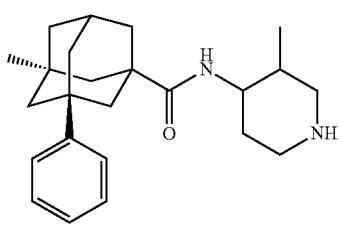
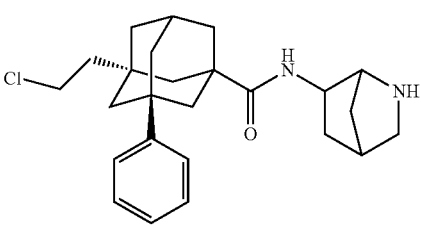
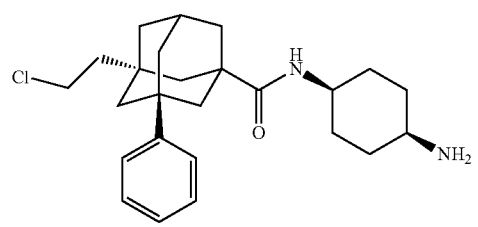
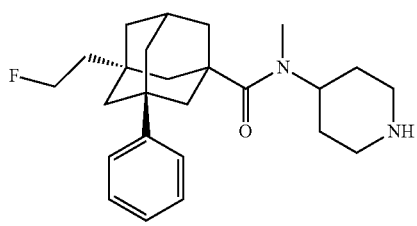
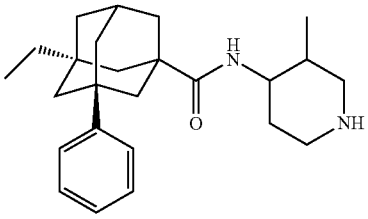

259
-continued
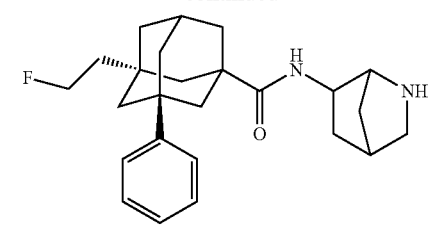
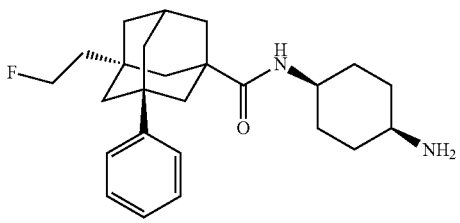
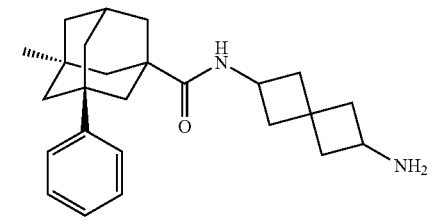
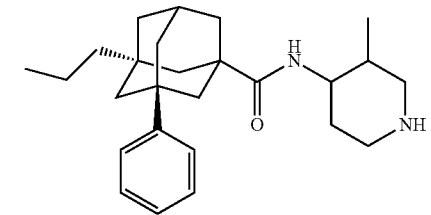
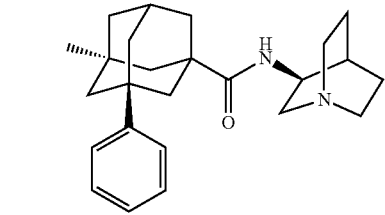
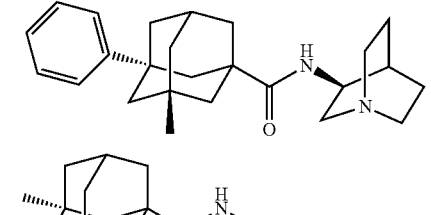
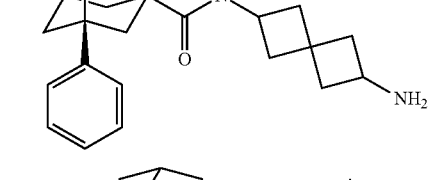
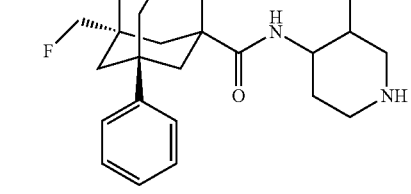
260
-continued
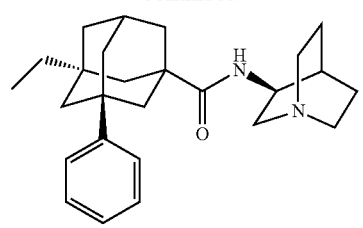
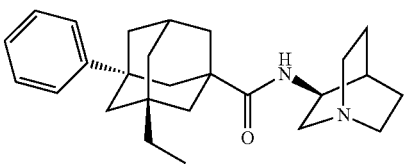
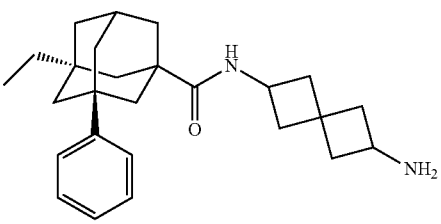
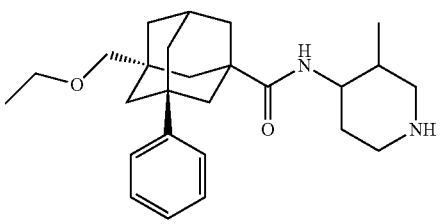
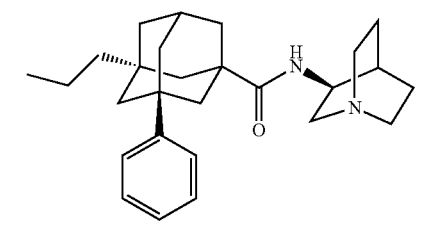
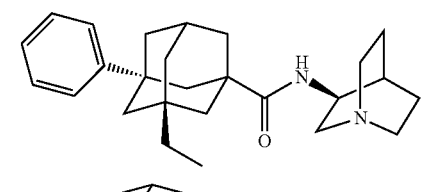
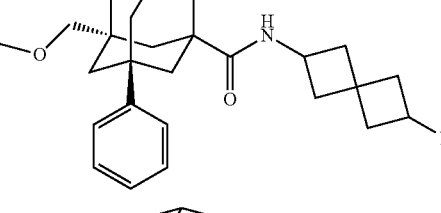
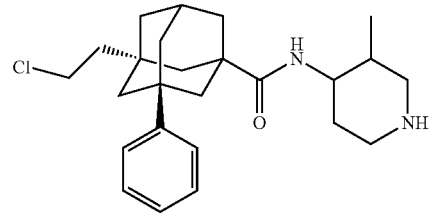

261
-continued
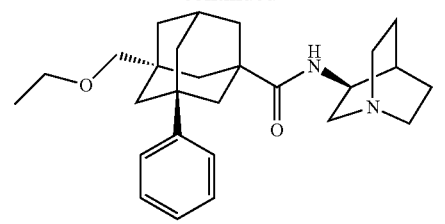
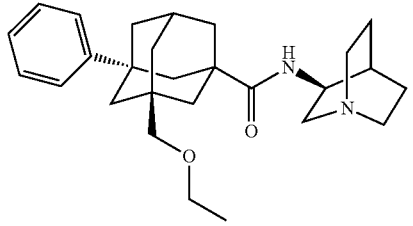
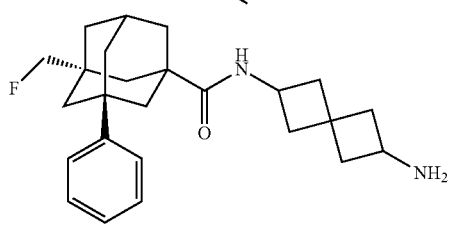
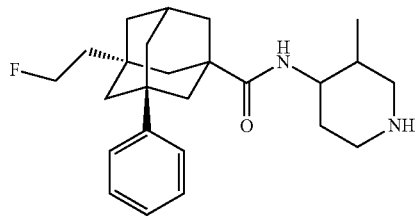
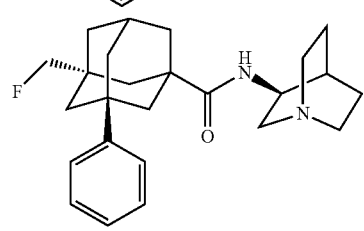
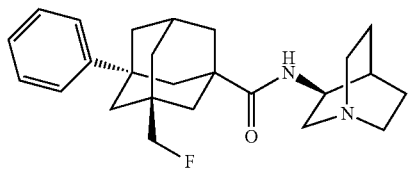
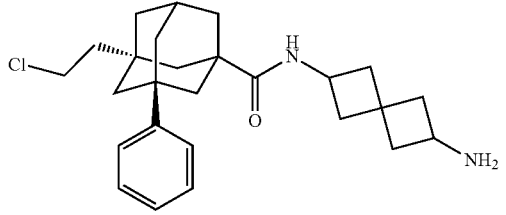
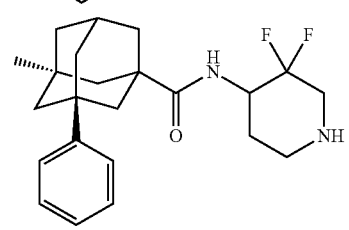
262
-continued
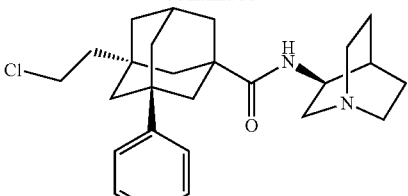
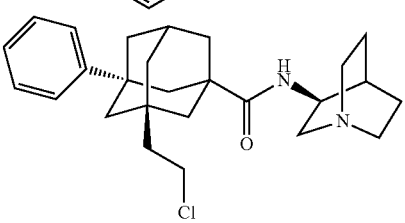
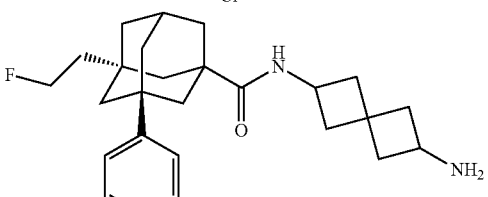
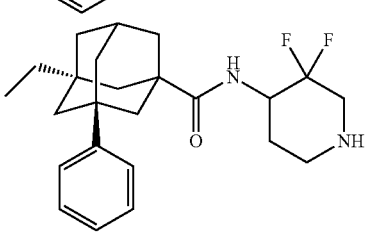
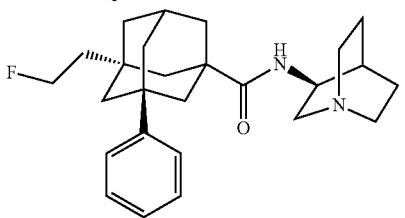
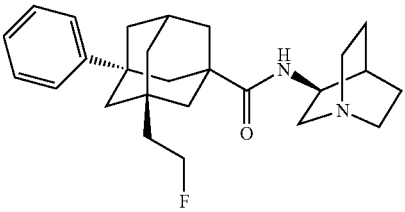
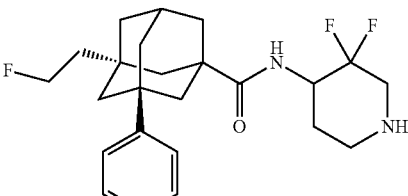
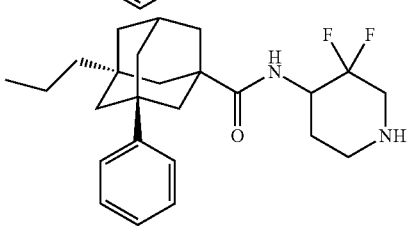

263
-continued
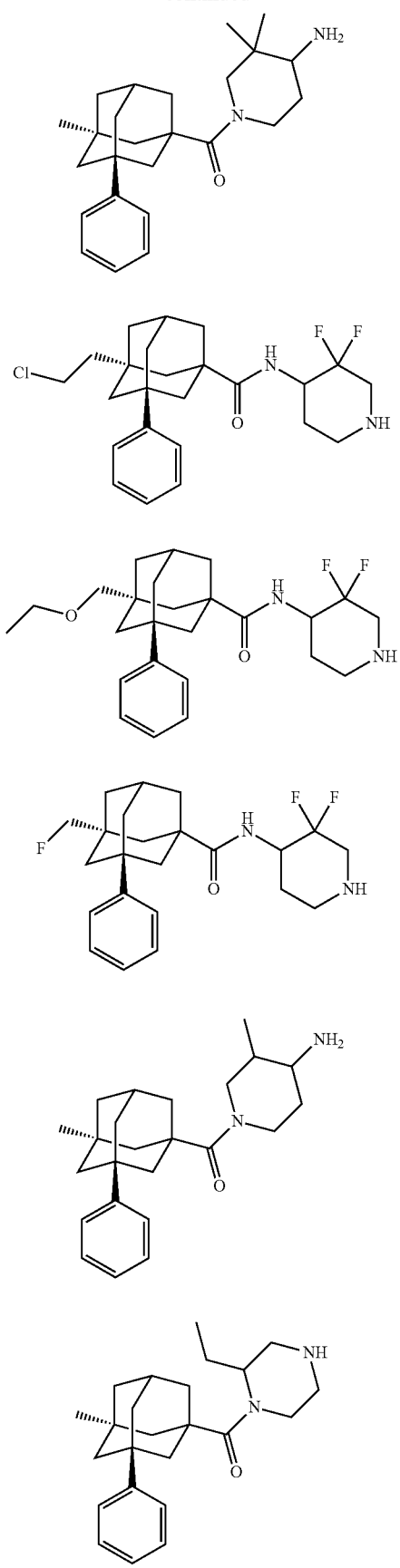
264
-continued
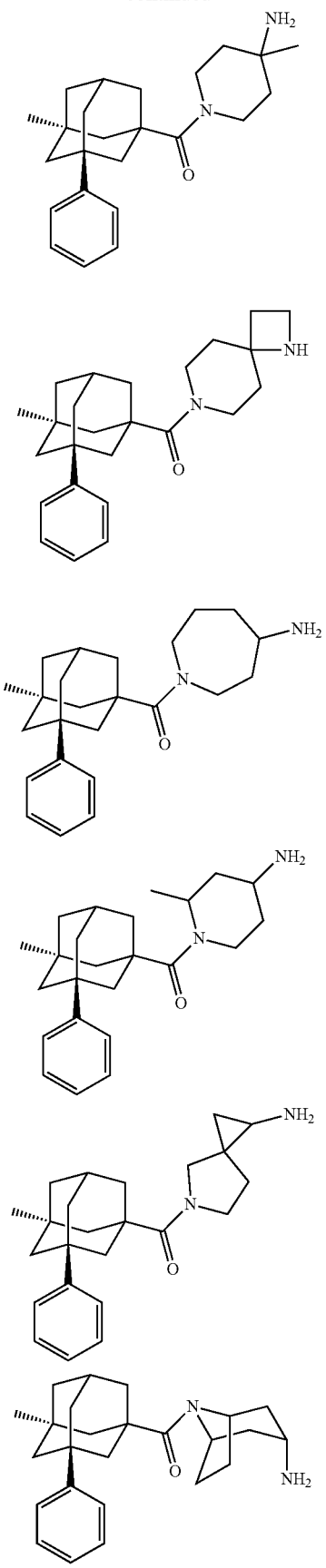

265
-continued
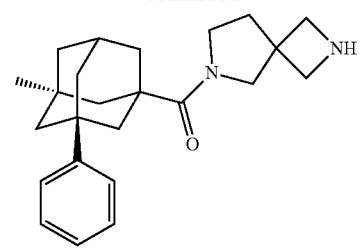
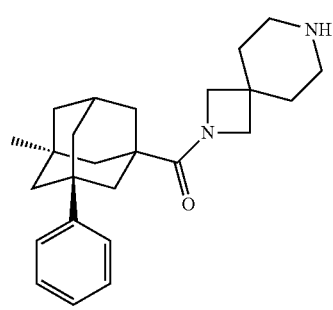
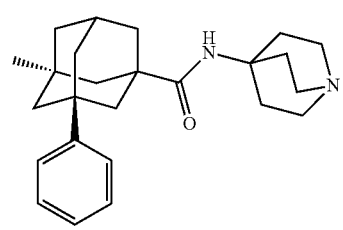
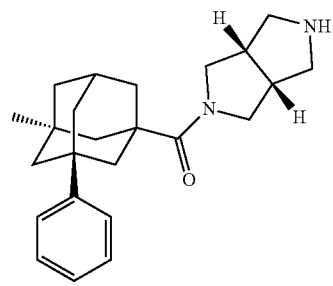
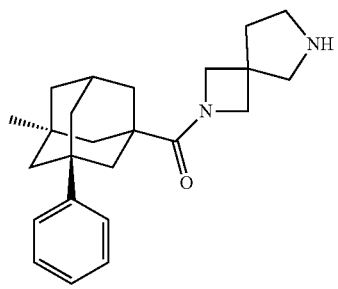
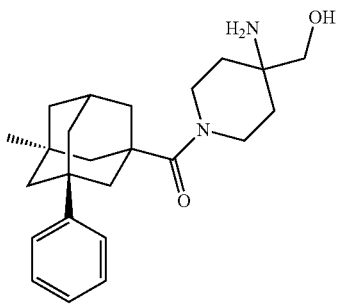
266
-continued
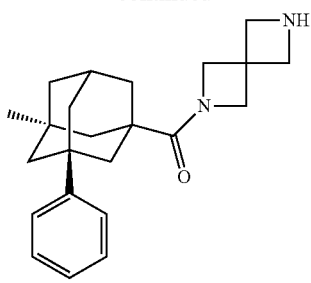
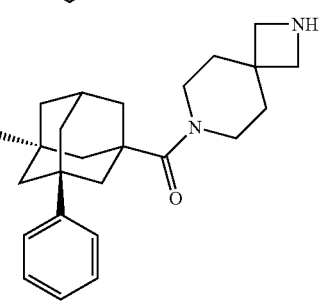
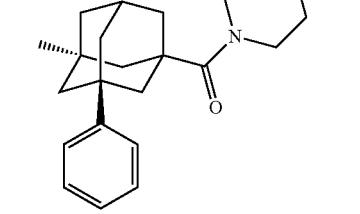
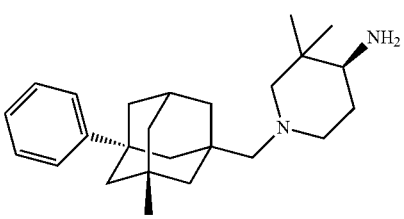
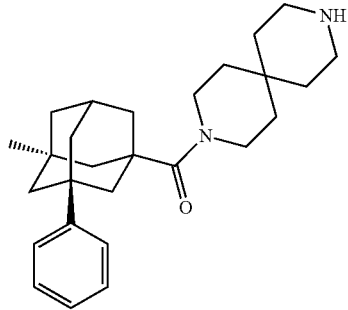
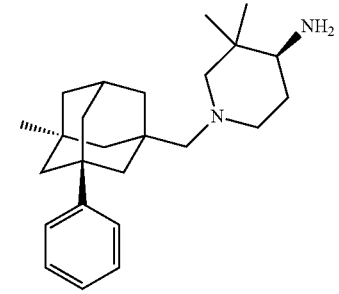
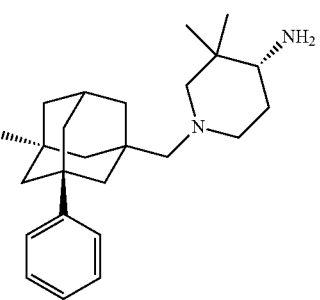

267
-continued
268
-continued
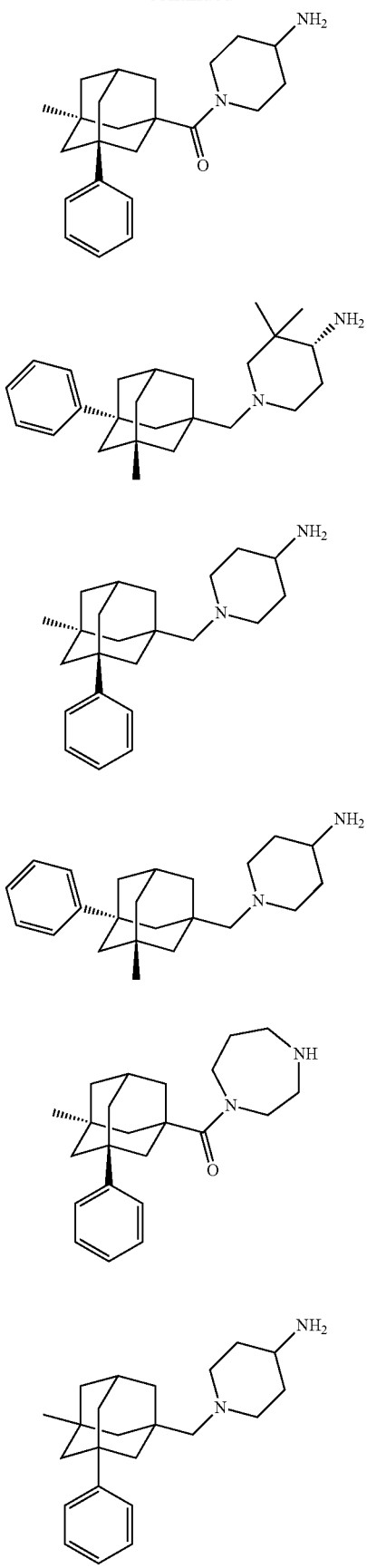
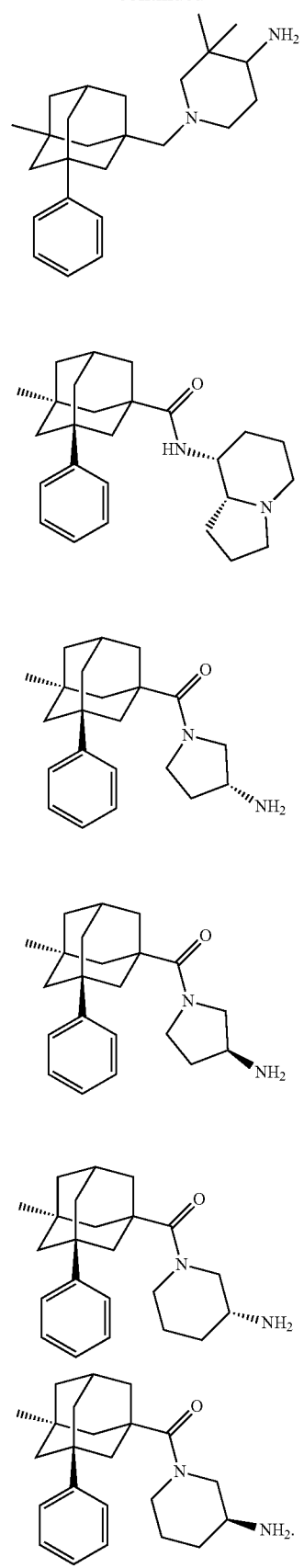

51. The compound of claim 50, selected from the group consisting of:
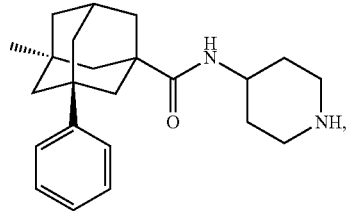
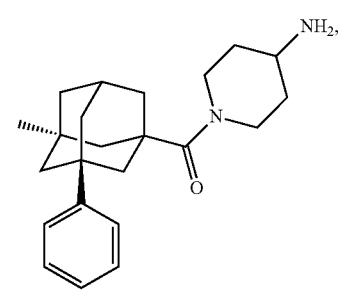
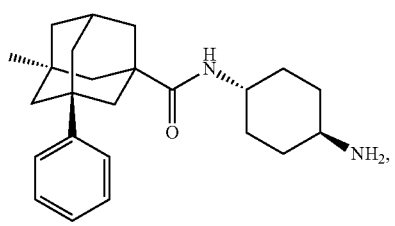
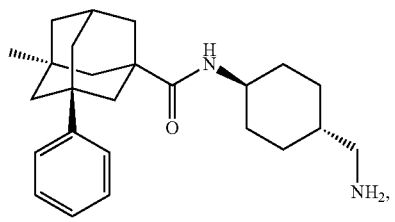
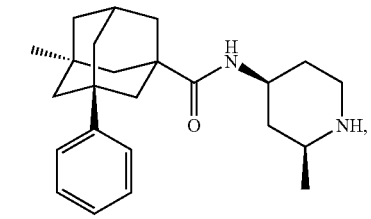
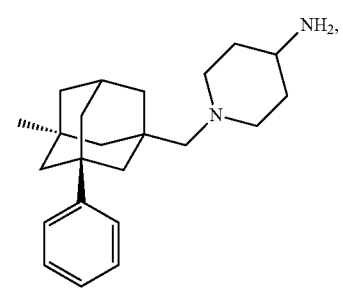
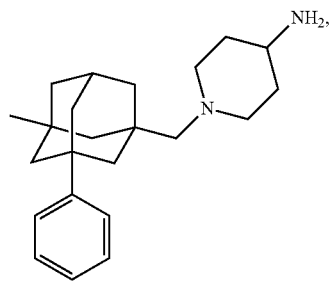
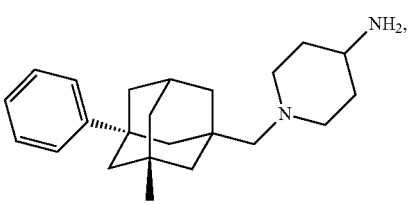
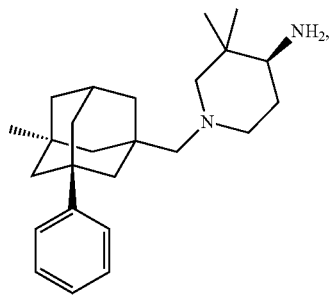
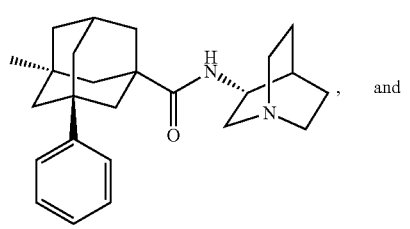
, and
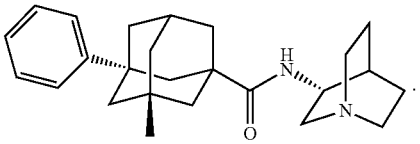
52. The compound of claim 51, selected from the group consisting of:
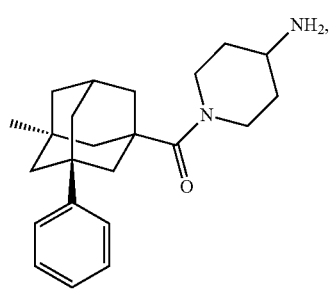

271
-continued
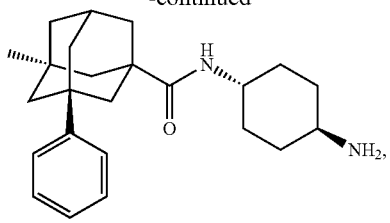
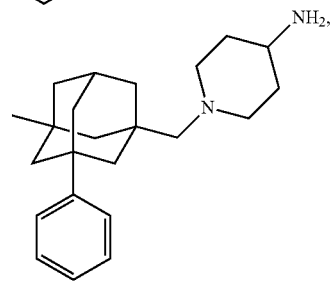
272
-continued
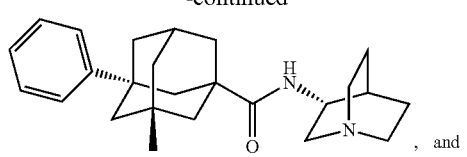, and
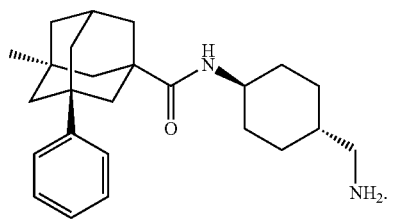
* * * * *